(12) United States Patent
Cole et al.

(10) Patent No.: US 8,747,866 B2
(45) Date of Patent: Jun. 10, 2014

(54) **IDENTIFICATION OF VIRULENCE ASSOCIATED REGIONS RD1 AND RD5 LEADING TO IMPROVE VACCINE OF *M. BOVIS* BCG AND *M. MICROTI***

(75) Inventors: Stewart Cole, Clamart (CH); Alexander S. Pym, London (GB); Roland Brosch, Paris (FR); Priscille Brodin, Paris (FR); Laleh Majlessi, Montigny le Bretonneux (FR); Caroline Demangel, Paris (FR); Claude LeClerc, Paris (FR)

(73) Assignee: Institut Pasteur, Paris (FR)

( * ) Notice: Subject to any disclaimer, the term of this patent is extended or adjusted under 35 U.S.C. 154(b) by 379 days.

(21) Appl. No.: 12/923,432

(22) Filed: Sep. 21, 2010

(65) Prior Publication Data

US 2012/0189662 A1    Jul. 26, 2012

Related U.S. Application Data

(62) Division of application No. 10/510,021, filed as application No. PCT/IB03/01789 on Apr. 1, 2003, now Pat. No. 7,883,712.

(51) Int. Cl.
*A61K 39/04*    (2006.01)
*C07H 21/02*    (2006.01)
*C07H 21/04*    (2006.01)

(52) U.S. Cl.
USPC ....... 424/248.1; 424/9.1; 424/9.2; 424/234.1; 536/23.1; 536/23.7

(58) Field of Classification Search
USPC ............. 424/9.1, 9.2, 234.1, 248.1; 536/23.1, 536/23.7
See application file for complete search history.

*Primary Examiner* — Rodney P Swartz
(74) *Attorney, Agent, or Firm* — Finnegan, Henderson, Farabow, Garrett & Dunner, L.L.P.

(57) ABSTRACT

The present invention relates to a strain of *M. bovis* BCG or *M. microti*, wherein said strain has integrated part or all of the RD1 region responsible for enhanced immunogenicity of the tubercle bacilli, especially the ESAT-6 and CFP-10 genes. These strains will be referred as the *M. bovis* BCG::RD1 or *M. microti*::RD1 strains and are useful as a new improved vaccine for preventing tuberculosis and as a therapeutical product enhancing the stimulation of the immune system for the treatment of bladder cancer.

48 Claims, 19 Drawing Sheets

BCG::RD1-2F9

BCG::pYUB412

BCG::RD3-I301

Figures 1A, 1B:
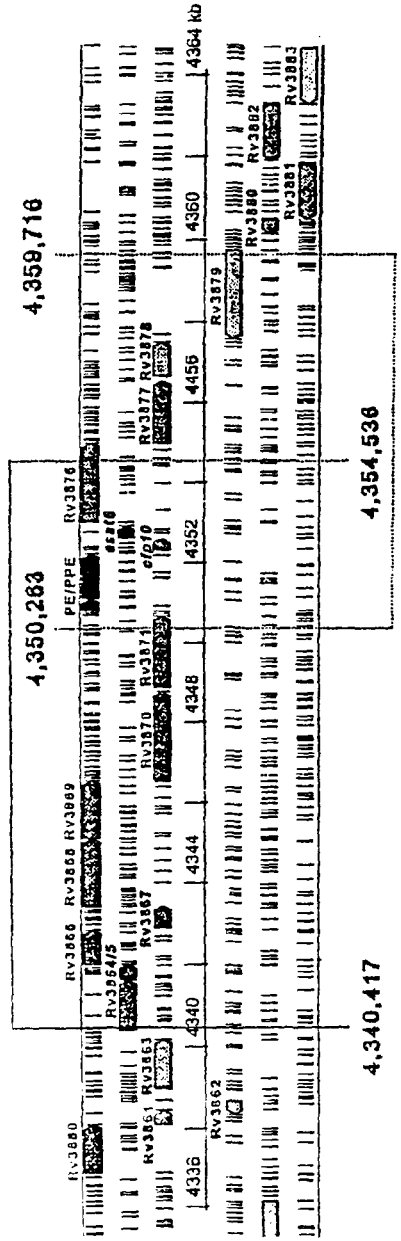

FIGURE 8A
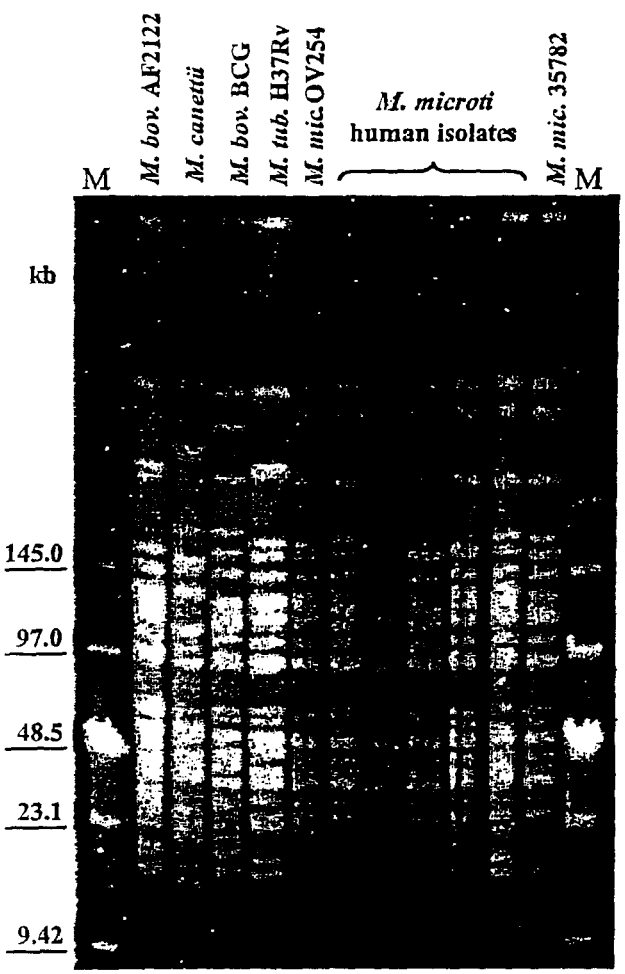
FIGURE 8B
FIGURE 8C
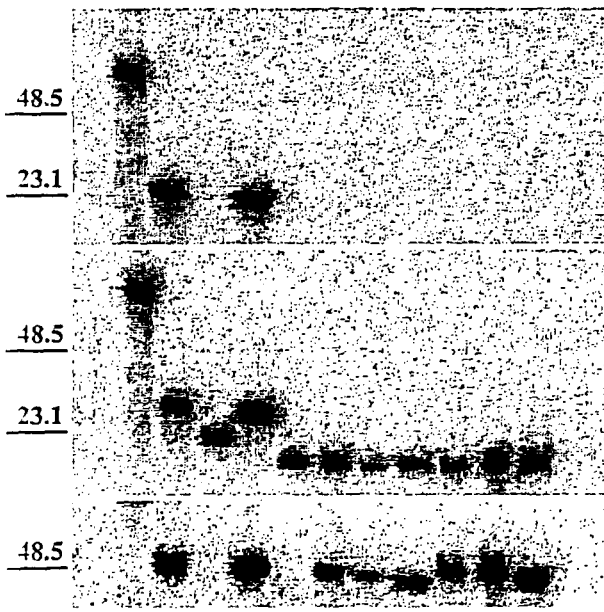
FIGURE 8D

SEQUENCE LISTING

<160> NUMBER OF SEQ ID NOS: 75

<210> SEQ ID NO 1
<211> LENGTH: 31808
<212> TYPE: DNA
<213> ORGANISM: Mycobacterium tuberculosis
<220> FEATURE:
<223> OTHER INFORMATION: Insert of cosmid RD1-2F9 corresponding to
      sequence in the genome of micybacterium tuberculosis H37Rv

<400> SEQUENCE: 1

| | | | | | |
|---|---|---|---|---|---|
| gatccgacca | caccagcccg | gcaccccgcg | gggatactcg | ccccgtccgc | cgtccggaga | 60 |
| tcgctgcccc | gcgccaccgc | ctggccggca | cgctgctgcc | gctacgccac | cagggccgcc | 120 |
| gcgcctgcct | tcagctccac | tgcgtccatt | gccggacccg | gcttggccac | gccagccgga | 180 |
| ggccccgcca | ccgagcacct | gggccgaccc | cgccctggcg | ccgatacgca | gtcggacgcg | 240 |
| acccggcgag | cgtggttggc | gacgcatggt | gcggctggtc | acctttggcc | ttgtcggcct | 300 |
| gggccggtcg | ggcatgcagc | gccaggaggc | ccaattcgaa | gcaacgatac | gaaccgtcct | 360 |
| gcatggcaac | cacaaggtcg | ccgtgctggg | caaaggaggt | gtgggaaaga | cgtcggttgc | 420 |
| ggcgtgcgtc | ggatcgatcc | ttgccgaact | gcgccagcag | gaccgtatcg | tcgggatcga | 480 |
| cgccgacacc | gccttcggca | ggctgagcag | ccgaatcgat | cctcgagcag | ctggttcgtt | 540 |
| ctgggagctg | accaccgaca | cgaatctgcg | gtccttcacc | gatatcaccg | cgcgcctggg | 600 |
| ccgaaattcc | gcgggactgt | acgtcctggc | aggccagccg | gcatccggtc | cgcgccgggt | 660 |
| gctcgatccg | gccatctacc | gcgaagccgc | cctaaggttg | gatcaccatt | tcgcaatctc | 720 |
| ggtgatcgac | tgcggttcct | ccatggaggc | ggcggtcacc | caggaagtat | tgcgcgatgt | 780 |
| ggatgctctg | atcgtggtgt | cctcgccctg | gcggatggt | gcctccgctg | ccgccaacac | 840 |
| catcgaatgg | ctgtcggatt | atggcctgac | aggtttgttg | cgacgcagca | tcgtggtgct | 900 |
| caacgattcg | gacggacacg | ccgacaagcg | caccaagtca | ttgctggccc | aggaattcat | 960 |
| cgaccacggg | cagcctgtgg | tcgaggtgcc | cttcgatccc | catttgcggc | cggggggggt | 1020 |
| catcgatatg | agccacgaaa | tggccccgac | gacgcggctg | aaaatcctgc | aggtcgccgc | 1080 |
| gacggtgacg | gcgtacttcg | cgtcgcgacc | cgccgacgca | cacggcagcc | cgccccggtg | 1140 |
| acctggctgg | ctgacccggt | cggcaacagc | aggatcgccc | gagcgcaggc | ctgcaaaacg | 1200 |
| tcaatctcgg | cgcccatcgt | cgaatcctgg | cgggcgcaac | gcggcgcgca | atgtggacag | 1260 |
| cgcgagaaat | cttgtcgatg | ttctcgcgct | gtccacatcc | agggcatctc | accgccactg | 1320 |
| ttccgcagac | ccctcgaacc | agcggtccga | gcggcggttg | cgtcatgccg | attgggcaga | 1380 |
| cacccggtgg | tcgcgcaccg | ggtaaccgtt | gcgctcggcc | agggatcgca | gctggcccaa | 1440 |
| cgcgaatgcc | cgcgcccggc | ctgattcggg | aattacgacc | cctgcccaca | gcccttccgc | 1500 |
| acccgcggac | tcgacggcgt | cgcgtgcaca | cagccaccgg | cgcgggcaag | cccggcacag | 1560 |
| ggtcttggcc | tcgtcgtcgg | gagtcgtcgt | ccaacgatcg | ggatcttgcg | tgcaaacgcc | 1620 |
| gagcgggacc | tcatacaggg | cggttactgt | catgtctacg | ttcctccaga | aagcgttgca | 1680 |
| ggttgtagcc | tctgccgcga | aagcgtatcg | cattaaccat | agcgatgcaa | cagtttcctc | 1740 |
| ctctgcctgc | ctagcggtgc | tgcggctccg | gttcggcgag | ctccgagctc | tagtgcgcgc | 1800 |
| accgccgagt | accagggcat | agatcctgtt | aatcagctgt | gtatctggcc | tcgccggcgc | 1860 |
| gtatccgacc | ccttcgggca | gatcttccag | gaaaagtgtt | ctgacatgcg | acagttcagg | 1920 |
| tgtgaagtga | actgtagcgg | cagttcggtt | tggctaggaa | actatttcca | tagcgggccg | 1980 |

```
tcgcgtcgct agatccaaaa tgtagcgaag tcatagcagt agaagggtgc aacggttagg    2040
atggcgggcg agcggaaagt ctgcccaccg tcccggctag tacccgcgaa taagggatca    2100
acgcagatgt ctaaagcagg gtcgactgtc ggaccggcgc cgctggtcgc gtgcagcggc    2160
ggcacatcag acgtgattga gccccgtcgc ggtgtcgcga tcattggcca ctcgtgccga    2220
gtcggcaccc agatcgacga ttctcgaatc tctcagacac atctgcgagc ggtatccgat    2280
gatggacggt ggcggatcgt cggcaacatc ccgagaggta tgttcgtcgg cggacgacgc    2340
ggcagctcgg tgaccgtcag cgataagacc ctaatccgat tcggcgatcc ccctggaggc    2400
aaggcgttga cgttcgaagt cgtcaggccg tcggattccg ctgcacagca cggccgcgta    2460
caaccatcag cggacctgtc ggacgacccg cgcacaacg ctgcgccggt cgcaccggac    2520
cccggcgtgt tcgcgcagg gcggccgcg gctgcgcgcc gtcgtgaact tgacatcagc    2580
caacgcagct tggcggccga cgggatcatc aacgcgggcg cgctcatcgc gttcgagaaa    2640
ggccgtagtt ggccccggga acggaccegg gcaaaactcg aagaagtgct gcagtggccc    2700
gctggaacca tcgcgcgaat ccgtcggggc gagcccaccg agcccgcaac aaaccccgac    2760 gcgtccccccg gactccggcc tgccgacggc ccggcgtcct tgatcgcgca ggctgtcacc    2820
gccgccgtag acggctgcag tctggctatc gcagcgttgc cggcgaccga ggaccccgag    2880
ttcaccgaac gtgccgcgcc gatccttgct gatttgcgcc agctcgaggc gattgccgtc    2940
caagcaaccc gcatcagccg gattacccccg gaattgatca aggcgttggg cgcggtacgt    3000
cgccaccacg acgaattaat gaggctggga gcaaccgccc ctggtgccac actggcgcag    3060
cgcttatatg ccgcacggcg gcgcgcgaac ctttccaccc tggagactgc ccaagcggcc    3120
ggcgtcgcag aagaaatgat cgtcggcgcc gaagccgagg aagagttgcc agccgaggcc    3180
accgaagcga tcgaagcact gatccgtcag atcaattgag gtcggctccg agcgtcccac    3240
aagtacaggc acgccgtaac gctcaagttc aacggtccgg ggaacgcgcg cgttctccgg    3300
cgtttgacgg tgcgttccat cgtgccgcga acttgaaaac gccagcgtca ccaaaaaatt    3360
cgtgcaccaa ccccccctccg agcgctgcta agctcaatgt gcagtgcaaa ggtgcagata    3420
atgatggcgc accggaacgg cgagcgtaag gaaacacata aatggcatcg ggtagcggtc    3480
tttgcaagac gacgagtaac tttatttggg gccagttact cttgcttgga gagggaatcc    3540
ccgacccagg cgacattttc aacaccggtt cgtcgctgtt caaacaaatc agcgacaaaa    3600
tgggactcgc cattccgggc accaactgga tcggccaagc ggcggaagct tacctaaacc    3660
agaacatcgc gcaacaactt cgcgcacagg tgatgggcga tctcgacaaa ttaaccggca    3720
acatgatctc gaatcaggcc aaatacgtct ccgatacgcg cgacgtcctg cgggccatga    3780
agaagatgat tgacggtgtc tacaaggttt gtaagggcct cgaaaagatt ccgctgctcg    3840
gccacttgtg gtcgtgggag ctcgcaatcc ctatgtccgg catcgcgatg ccgttgtcg    3900 gcggcgcatt gctctatcta acgattatga cgctgatgaa tgcgaccaac ctgaggggaa    3960
ttctcggcag gctgatcgag atgttgacga ccttgccaaa gttccccggc ctgcccgggt    4020
tgcccagcct gcccgacatc atcgacggcc tctggccgcc gaagttgccc gacattccga    4080
tccccggcct gcccgacatc ccgggcctac ccgacttcaa atggccgccc acccccggca    4140
gcccgttgtt ccccgacctc ccgtcgttcc cagggttccc cgggttcccg gagttccccg    4200
ccatccccgg gttccccgca ctgcccgggt tgcccagcat tcccaacttg ttccccggct    4260
tgccgggtct gggcgacctg ctgccccgcg taggcgattt gggcaagtta cccacctgga    4320
ctgagctggc cgctttgcct gacttcttgg gcggcttcgc cggcctgccc agcttgggtt    4380
```

```
ttggcaatct gctcagcttt gccagtttgc ccaccgtggg tcaggtgacc gccaccatgg    4440
gtcagctgca acagctcgtg gcggccggcg gtggccccag ccaactggcc agcatgggca    4500
gccaacaagc gcaactgatc tcgtcgcagg cccagcaagg aggccagcag cacgccaccc    4560
tcgtgagcga caagaaggaa gacgaggaag gcgtggccga ggcggagcgt gcacccatcg    4620
acgctggcac cgcggccagc caacgggggc aggaggggac cgtcctttga tcggacaccg    4680
agtcgccagc aggtctgtgc catagcgagt cgaagccata gcgagtagaa agttaaacgt    4740
agaggagggt tcaacccatg accggatttc tcggtgtcgt gccttcgttc ctgaaggtgc    4800
tggcgggcat gcacaacgag atcgtgggtg atatcaaaag ggcgaccgat acggtcgccg    4860
ggattagcgg acgagttcag cttacccatg gttcgttcac gtcgaaattc aatgacacgc    4920
tgcaagagtt tgagaccacc cgtagcagca cgggcacggg tttgcaggga gtcaccagcg    4980
gactggccaa taatctgctc gcagccgccg gcgcctacct caaggccgac gatggcctag    5040
ccggtgttat cgacaagatt ttcggttgat catgacgggt ccgtccgctg caggccgcgc    5100
gggcaccgcc gacaacgtgg tcggcgtcga ggtaaccatc gacggcatgt tggtgatcgc    5160
cgatcggtta cacctggttg atttccctgt cacgcttggg attcggccga atatcccgca    5220
agaggatctg cgagacatcg tctgggaaca ggtgcagcgt gacctcacag cgcaagggt    5280 gctcgacctc cacggggagc cccaaccgac ggtcgcggag atggtcgaaa ccctgggcag    5340
gccagatcgg accttggagg gtcgctggtg gcggcgcgac attggcggcg tcatggtgcg    5400
cttcgtcgtg tgccgcaggg gcgaccgcca tgtgatcgcg gcgcgcgacg gcgacatgct    5460
ggtgctgcag ttggtggcgc cgcaggtcgg cttggcgggc atggtgacag cggtgctggg    5520
gcccgccgaa cccgccaacg tcgaacccct gacgggtgtg gcaaccgagc tagccgaatg    5580
cacaaccgcg tcccaattga cgcaatacgg tatcgcaccg gcctcggccc gcgtctatgc    5640
cgagatcgtg ggtaacccga ccggctgggt ggagatcgtt gccagccaac gccaccccgg    5700
cggcaccacg acgcagaccg acgccgccgc tggcgtcctg gactccaagc tcggtaggct    5760
ggtgtcgctt ccccgccgtg ttggaggcga cctgtacgga agcttcctgc ccggcactca    5820
gcagaacttg gagcgtgcgc tggacggctt gctagagctg ctccctgcgg gcgcttggct    5880
agatcacacc tcagatcacg cacaagcctc ctcccgaggc tgaccccta catctccgct    5940 acgacttcag aaagggacgc catggtggac ccgccgggca acgacgacga ccacggtgat    6000
ctcgacgccc tcgatttctc cgccgccccac accaacgagg cgtcgccgct ggacgcctta    6060
gacgactatg cgccggtgca gaccgatgac gccgaaggcg acctggacgc cctccatgcg    6120
ctcaccgaac gcgacgagga gccggagctg gagttgttca cggtgaccaa ccctcaaggg    6180
tcggtgtcgt tctcaaccct gatggacggc agaatccagc acgtcgagct gacggacaag    6240
gcgaccagca tgtccgaagc gcagctggcc gacgagatct tcgttattgc cgatctggcc    6300
cgccaaaagg cgcgggcgtc gcagtacacg ttcatggtgg agaacatcgg tgaactgacc    6360
gacgaagacg cagaaggcag cgccctgctg cgggaattcg tggggatgac cctgaatctg    6420
ccgacgccgc aagaggctgc cgcagccgaa gccgaagtgt tcgccacccg ctacgatgtc    6480
gactacacct cccggtacaa ggccgatgac tgatcgcttg gccagtctgt tcgaaagcgc    6540
cgtcagcatg ttgccgatgt cggaggcgcg gtcgctagat ctgttcaccg agatcaccaa    6600
ctacgacgaa tccgcttgcg acgcatggat cggccggatc cggtgtgggg acaccgaccg    6660
ggtgacgctg tttcgcgcct ggtattgcgc ccgcaatttc ggacagttgt cgggatcggt    6720
ccagatctcg atgagcacgt taaacgccag gattgccatc gggggctgt acggcgatat    6780
```

```
cacctacccg gtcacctcgc cgctagcgat caccatgggc tttgccgcat gcgaggcagc      6840
gcaaggcaat tacgccgacg ccatggaggc cttagaggcc gccccggtcg cgggttccga      6900
gcacctggtg gcgtggatga aggcggttgt ctacggcgcg ccgaacgct ggaccgacgt       6960 gatcgaccag gtcaagagtg ctgggaaatg gccggacaag tttttggccg cgcggccgg      7020 tgtggcgcac ggggttgccg cggcaaacct ggccttgttc accgaagccg aacgccgact      7080
caccgaggcc aacgactcgc ccgccggtga ggcgtgtgcg cgcgccatcg cctggtatct      7140
ggcgatggca cggcgcagcc agggcaacga aagcgccgcg gtggcgctgc tggaatggtt      7200
acagaccact caccccgagc ccaaagtggc tgcggcgctg aaggatccct cctaccggct      7260
gaagacgacc accgccgaac agatcgcatc ccgcgccgat ccctgggatc cgggcagtgt      7320
cgtgaccgac aactccggcc gggagcggct gctcgccgag gcccaagccg aactcgaccg      7380
ccaaattggg ctcacccggg ttaaaaatca gattgaacgc taccgcgcgg cgacgctgat      7440
ggcccgggtc cgcgccgcca agggtatgaa ggtcgcccag cccagcaagc acatgatctt      7500
caccggaccg cccggtaccg gcaagaccac gatcgcgcgg gtggtggcca atatcctggc      7560
cggcttaggc gtcattgccg aacccaaact cgtcgagacg tcgcgcaagg acttcgtcgc      7620
cgagtacgag gggcaatcgg cggtcaagac cgctaagacg atcgatcagg cgctgggcgg      7680
ggtgcttttc atcgacgagg cttatgcgct ggtgcaggaa agagacgcc gcaccgatcc      7740 gttcggtcaa gaggcgctgg acacgctgct ggcgcggatg gagaacgacc gggaccggct      7800
ggtggtgatc atcgccgggt acagctccga catagatcgg ctgctggaaa ccaacgaggg      7860
tctgcggtcg cggttcgcca ctcgcatcga gttcgacacc tattcccccg aggaactcct      7920
cgagatcgcc aacgtcattg ccgctgctga tgattcggcg ttgaccgcag aggcggccga      7980
gaactttctt caggccgcca agcagttgga gcagcgcatg ttgcgcggcc ggcgcgccct      8040
ggacgtcgcc ggcaacggtc ggtatgcgcg ccagctggtg gaggcagcg agcaatgccg      8100 ggacatgcgt ctagcccagg tcctcgatat cgacaccctc gacgaagacc ggcttcgcga      8160
gatcaacggc tcagatatgg cggaggctat cgccgcggtg cacgcacacc tcaacatgag      8220
agaatgaact atggggcttc gcctcaccac caaggttcag gttagcggct ggcgttttct      8280
gctgcgccgg ctcgaacacg ccatcgtgcg ccgggacacc cggatgtttg acgacccgct      8340
gcagttctac agccgctcga tcgctcttgg catcgtcgtc gcggtcctga ttctggcggg      8400
tgccgcgctg ctggcgtact tcaaaccaca aggcaaactc ggcggcacca gcctgttcac      8460
cgaccgcgcg accaaccagc tttacgtgct gctgtccgga cagttgcatc cggtctacaa      8520
cctgacttcg gcgcggctgg tgctgggcaa tccggccaac ccgccaccg tgaagtcctc      8580 cgaactgagc aagctgccga tgggccagac cgttggaatc cccggcgccc cctacgccac      8640
gcctgtttcg gcgggcagca cctcgatctg gaccctatgc gacaccgtcg cccgagccga      8700
ctccacttcc ccggtagtgc agaccgcggt catcgcgatg ccgttggaga tcgatgcttc      8760
gatcgatccg ctccagtcac acgaagcggt gctggtgtcc taccagggcg aaacctggat      8820
cgtcacaact aagggacgcc acgccataga tctgaccgac cgcgccctca cctcgtcgat      8880
ggggataccg gtgacggcca ggccaacccc gatctcggag ggcatgttca acgcgctgcc      8940
tgatatgggg ccctggcagc tgccgccgat accggcggcg ggcgcgccca attgcttgg      9000 cctacctgat gatctagtga tcggatcggt cttccagatc cacaccgaca agggcccgca      9060
atactatgtg gtgctgcccg acggcatcgc gcaggtcaac gcgacaaccg ctgcggcgct      9120
gcgcgccacc caggcgcacg ggctggtcgc gccaccggca atggtgccca gtctggtcgt      9180
```

```
cagaatcgcc gaacgggtat accccctcacc gctaccgat gaaccgctca agatcgtgtc   9240
ccggccgcag gatcccgcgc tgtgctggtc atggcaacgc agcgccggcg accagtcgcc   9300
gcagtcaacg gtgctgtccg gccggcatct gccgatatcg ccctcagcga tgaacatggg   9360
gatcaagcag atccacggga cggcgaccgt ttacctcgac ggcggaaaat tcgtggcact   9420
gcaatccccc gatcctcgat acaccgaatc gatgtactac atcgatccac agggcgtgcg   9480
ttatggggtg cctaacgcgg agacagccaa gtcgctgggc ctgagttcac cccaaaacgc   9540
gccctgggag atcgttcgtc tcctggtcga cggtccggtg ctgtcgaaag atgccgcact   9600
gctcgagcac gacacgctgc ccgctgaccc tagcccccga aaagttcccg ccggagcctc   9660
cggagccccc tgatgacgac caagaagttc actcccacca ttacccgtgg ccccggttg    9720
accccgggcg agatcagcct cacgccgccc gatgacctgg gcatcgacat cccaccgtcg   9780
ggcgtccaaa agatccttcc ctacgtgatg ggtggcgcca tgctcggcat gatcgccatc   9840
atggtggccg gcggcaccag gcagctgtcg ccgtacatgt tgatgatgcc gctgatgatg   9900
atcgtgatga tggtcggcgg tctggccggt agcaccggtg gtggcggcaa gaaggtgccc   9960
gaaatcaacg ccgaccgcaa ggagtacctg cggtatttgg caggactacg cacccgagtg  10020
acgtcctcgg ccacctctca ggtggcgttc ttctcctacc acgcaccgca tcccgaggat  10080
ctgttgtcga tcgtcggcac ccaacggcag tggtcccggc cggccaacgc cgacttctat  10140
gcggccaccc gaatcggtat cggtgaccag ccggcggtgg atcgattatt gaagccggcc  10200
gtcggcgggg agttggccgc cgccagcgca gcacctcagc cgttcctgga gccggtcagt  10260
catatgtggg tggtcaagtt tctacgaacc catggattga tccatgactg cccgaaactg  10320
ctgcaactcc gtacctttcc gactatcgcg atcggcgggg acttggcggg ggcagccggc  10380
ctgatgacgg cgatgatctg tcacctagcc gtgttccacc caccggacct gctgcagatc  10440
cgggtgctca ccgaggaacc cgacgacccc gactggtcct ggctcaaatg gcttccgcac  10500
gtacagcacc agaccgaaac cgatgcgcc gggtccaccc ggctgatctt cacgcgccag   10560
gaaggtctgt cggacctggc cgcgcgcggg ccacacgcac ccgattcgct tcccggcggc  10620
ccctacgtag tcgtcgtcga cctgaccggc ggcaaggctg gattcccgcc cgacggtagg  10680
gccggtgtca cggtgatcac gttgggcaac catcgcggct cggcctaccg catcagggtg  10740
cacgaggatg ggacggctga tgaccggctc cctaaccaat cgtttcgcca ggtgacatcg  10800
gtcaccgatc ggatgtcgcc gcagcaagcc agccgtatcg cgcgaaagtt ggccggatgg  10860
tccatcacgg gcaccatcct cgacaagacg tcgcgggtcc agaagaaggt ggccaccgac  10920
tggcaccagc tggtcggtgc gcaaagtgtc gaggagataa caccttcccg ctggaggatg  10980
tacaccgaca ccgaccgtga ccggctaaag atcccgtttg gtcatgaact aaagaccggc  11040
aacgtcatgt acctggacat caaagagggc gcggaattcg gcgccggacc gcacggcatg  11100
ctcatcggga ccacggggtc tgggaagtcc gaattcctgc gcaccctgat cctgtcgctg  11160
gtggcaatga ctcatccaga tcaggtgaat ctcctgctca ccgacttcaa aggtggttca  11220
accttcctgg gaatggaaaa gcttccgcac actgccgctg tcgtcaccaa catggccgag  11280
gaagccgagc tcgtcagccg gatgggcgag gtgttgaccg gagaactcga tcggcgccag  11340
tcgatcctcc gacaggccgg gatgaaagtc ggcgcggccg gagccctgtc cggcgtggcc  11400
gaatacgaga agtaccgcga acgcggtgcc gacctacccc cgctgccaac gcttttcgtc  11460
gtcgtcgacg agttcgccga gctgttgcag agtcacccgg acttcatcgg gctgttcgac  11520
cggatctgcc gcgtcgggcg gtcgctgagg gtccatctgc tgctggctac ccagtcgctg  11580
```

```
cagaccggcg gtgttcgcat cgacaaactg gagccaaacc tgacatatcg aatcgcattg    11640
cgcaccacca gctctcatga atccaaggcg gtaatcggca caccggaggc gcagtacatc    11700
accaacaagg agagcggtgt cgggtttctc cgggtcggca tggaagaccc ggtcaagttc    11760
agcaccttct acatcagtgg gccatacatg ccgccggcgg caggcgtcga aaccaatggt    11820
gaagccggag ggcccggtca acagaccact agacaagccg cgcgcattca caggttcacc    11880
gcggcaccgg ttctcgagga ggcgccgaca ccgtgacccg cgccggcgac gatgcaaagc    11940
gcagcgatga ggaggagcgg cgccaacggc ccgcgccggc gacgatgcaa agcgcagcga    12000
tgaggaggag cggcgcgcat gactgctgaa ccggaagtac ggacgctgcg cgaggttgtg    12060
ctggaccagc tcggcactgc tgaatcgcgt gcgtacaaga tgtggctgcc gccgttgacc    12120
aatccggtcc cgctcaacga gctcatcgcc cgtgatcggc gacaacccct gcgatttgcc    12180
ctggggatca tggatgaacc gcgccgccat ctacaggatg tgtgggcgt  agacgtttcc    12240 ggggccggcg gcaacatcgg tattgggggc gcacctcaaa ccgggaagtc gacgctactg    12300
cagacgatgg tgatgtcggc cgccgccaca cactcaccgc gcaacgttca gttctattgc    12360
atcgacctag gtggcggcgg gctgatctat ctcgaaaacc ttccacacgt cggtggggta    12420
gccaatcggt ccgagcccga caaggtcaac cgggtggtcg cagagatgca agccgtcatg    12480
cggcaacggg aaaccacctt caaggaacac cgagtgggct cgatcgggat gtaccggcag    12540
ctgcgtgacg atccaagtca acccgttgcg tccgatccat acggcgacgt ctttctgatc    12600
atcgacggat ggcccggttt tgtcggcgag ttccccgacc ttgaggggca ggttcaagat    12660
ctggccgccc aggggctggc gttcggcgtc cacgtcatca tctccacgcc acgctggaca    12720
gagctgaagt cgcgtgttcg cgactacctc ggcaccaaga tcgagttccg gcttggtgac    12780
gtcaatgaaa cccagatcga ccggattacc cgcgagatcc cggcgaatcg tccgggtcgg    12840
gcagtgtcga tggaaaagca ccatctgatg atcggcgtgc ccaggttcga cggcgtgcac    12900
agcgccgata acctggtgga ggcgatcacc gcggggtga  cgcagatcgc ttcccagcac    12960
accgaacagg cacctccggt gcgggtcctg ccggagcgta tccacctgca cgaactcgac    13020
ccgaacccgc cgggaccaga gtccgactac cgcactcgct gggagattcc gatcggcttg    13080
cgcgagacgg acctgacgcc ggctcactgc cacatgcaca cgaacccgca cctactgatc    13140
ttcggtgcgg ccaaatcggg caagacgacc attgcccacg cgatcgcgcg cgccatttgt    13200
gcccgaaaca gtccccagca ggtgcggttc atgctcgcgg actaccgctc gggcctgctg    13260
gacgcggtgc cggacaccca tctgctgggc gccggcgcga tcaaccgcaa cagcgcgtcg    13320
ctagacgagg ccgttcaagc actggcggtc aacctgaaga agcggttgcc gccgaccgac    13380
ctgacgacgg cgcagctacg ctcgcgttcg tggtggagcg gatttgacgt cgtgcttctg    13440
gtcgacgatt ggcacatgat cgtgggtgcc gccgggggga tgccgccgat ggcaccgctg    13500
gccccgttat tgccggcggc ggcagatatc gggttgcaca tcattgtcac ctgtcagatg    13560
agccaggctt acaaggcaac catggacaag ttcgtcggcg ccgcattcgg gtcgggcgct    13620
ccgacaatgt tccttttcggg cgagaagcag gaattcccat ccagtgagtt caaggtcaag    13680
cggcgccccc ctggccaggc atttctcgtc tcgccagacg gcaaagaggt catccaggcc    13740
ccctacatcg agcctccaga agaagtgttc gcagcacccc caagcgccgg ttaagattat    13800
ttcattgccg gtgtagcagg acccgagctc agcccggtaa tcgagttcgg gcaatgctga    13860
ccatcgggtt tgtttccggc tataaccgaa cggtttgtgt acgggataca aatcagggga    13920
gggaagaagt aggcaaatgg aaaaaatgtc acatgatccg atcgctgccg acattggcac    13980
```

```
gcaagtgagc gacaacgctc tgcacggcgt gacggccggc tcgacggcgc tgacgtcggt    14040 gacccgggctg gttcccgcgg gggccgatga ggtctccgcc caagcggcga cggcgttcac   14100
atcggagggc atccaattgc tggcttccaa tgcatcggcc caagaccagc tccaccgtgc    14160
gggcgaagcg gtccaggacg tcgcccgcac ctattcgcaa atcgacgacg cgccgccgg    14220 cgtcttcgcc gaataggccc ccaacacatc ggagggagtg atcaccatgc tgtggcacgc    14280
aatgccaccg gagctaaata ccgcacggct gatggccggc gcgggtccgg ctccaatgct    14340
tgcggcggcc gcgggatggc agacgctttc ggcggctctg gacgctcagg ccgtcgagtt    14400
gaccgcgcgc ctgaactctc tgggagaagc ctggactgga ggtggcagcg acaaggcgct    14460
tgcggctgca acgccgatgg tggtctggct acaaaccgcg tcaacacagg ccaagacccg    14520
tgcgatgcag gcgacggcgc aagccgcggc atacacccag gccatggcca cgacgccgtc    14580
gctgccggag atcgccgcca accacatcac ccaggccgtc cttacggcca ccaacttctt    14640
cggtatcaac acgatcccga tcgcgttgac cgagatggat tatttcatcc gtatgtggaa    14700
ccaggcagcc ctggcaatgg aggtctacca ggccgagacc gcggttaaca cgcttttcga    14760
gaagctcgag ccgatggcgt cgatccttga tcccggcgcg agccagagca cgacgaaccc    14820
gatcttcgga atgccctccc ctggcagctc aacaccggtt ggccagttgc cgccggcggc    14880
tacccagacc ctcggccaac tgggtgagat gagcggcccg atgcagcagc tgacccagcc    14940
gctgcagcag gtgacgtcgt tgttcagcca ggtgggcggc accggcggcg caacccagc    15000 cgacgaggaa gccgcgcaga tgggcctgct cggcaccagt ccgctgtcga accatccgct    15060
ggctggtgga tcaggcccca gcgcgggcgc gggcctgctg cgcgcggagt cgctacctgg    15120
cgcaggtggg tcgttgaccc gcacgccgct gatgtctcag ctgatcgaaa agccggttgc    15180
cccctcggtg atgccggcgg ctgctgccgg atcgtcggcg acgggtggcg ccgctccggt    15240
gggtgcggga gcgatgggcc agggtgcgca atccggcggc tccaccaggc cgggtctggt    15300
cgcgccggca ccgctcgcgc aggagcgtga agaagacgac gaggacgact gggacgaaga    15360
ggacgactgg tgagctcccg taatgacaac agacttcccg gccacccggg ccggaagact    15420
tgccaacatt ttggcgagga aggtaaagag agaaagtagt ccagcatggc agagatgaag    15480
accgatgccg ctaccctcgc gcaggaggca ggtaatttcg agcggatctc cggcgacctg    15540
aaaacccaga tcgaccaggt gggagtcgacg gcaggttcgt tgcagggcca gtggcgcggc    15600
gcggcgggga cggccgccca ggccgcggtg gtgcgcttcc aagaagcagc caataagcag    15660
aagcaggaac tcgacgagat ctcgacgaat attcgtcagg ccggcgtcca atactcgagg    15720
gccgacgagg agcagcagca ggcgctgtcc tcgcaaatgg gcttctgacc cgctaatacg    15780
aaaagaaacg gagcaaaaac atgacagagc agcagtggaa tttcgcgggt atcgaggccg    15840
cggcaagcgc aatccaggga aatgtcacgt ccattcattc cctccttgac gaggggaagc    15900
agtccctgac caagctcgca gcggcctggg gcggtagcgg ttcggaggcg taccagggtg    15960
tccagcaaaa atgggacgcc acggctaccg agctgaacaa cgcgctgcag aacctggcgc    16020
ggacgatcag cgaagccggt caggcaatgg cttcgaccga aggcaacgtc actgggatgt    16080
tcgcataggg caacgccgag ttcgcgtaga atagcgaaac acgggatcgg gcgagttcga    16140
ccttccgtcg gtctcgccct ttctcgtgtt tatacgtttg agcgcactct gagaggttgt    16200
catggcggcc gactacgaca agctcttccg gccgcacgaa ggtatggaag ctccggacga    16260
tatggcagca cagccgttct tcgacccgag tgcttcgttt ccgccggcgc ccgcatcggc    16320
aaacctaccg aagcccaacg gccagactcc gcccccgacg tccgacgacc tgtcggagcg    16380
```

```
gttcgtgtcg gccccgccgc cgccaccccc accccacct ccgcctccgc caactccgat   16440
gccgatcgcc gcaggagagc cgccctcgcc ggaaccggcc gcatctaaac cacccacacc   16500
ccccatgccc atcgccggac ccgaaccggc cccacccaaa ccacccacac ccccatgcc    16560
catcgccgga cccgaaccgg ccccacccaa accacccaca cctccgatgc ccatcgccgg   16620
acctgcaccc accccaaccg aatcccagtt ggcgccccc agaccaccga caccacaaac    16680
gccaaccgga gcgccgcagc aaccggaatc accggcgccc cacgtaccct cgcacgggcc   16740
acatcaaccc cggcgcaccg caccagcacc gccctgggca agatgccaa tcggcgaacc    16800
cccgcccgct ccgtccagac cgtctgcgtc cccggccgaa ccaccgaccc ggcctgcccc   16860
ccaacactcc cgacgtgcgc gccggggtca ccgctatcgc acagacaccg aacgaaacgt   16920
cgggaaggta gcaactggtc catccatcca ggcgcggctg cgggcagagg aagcatccgg   16980
cgcgcagctc gcccccggaa cggagccctc gccagcgccg ttgggccaac cgagatcgta   17040
tctggctccg cccacccgcc ccgcgccgac agaacctccc cccagcccct cgccgcagcg   17100
caactccggt cggcgtgccg agcgacgcgt ccaccccgat ttagccgccc aacatgccgc   17160
ggcgcaacct gattcaatta cggccgcaac cactggcggt cgtcgccgca agcgtgcagc   17220
gccggatctc gacgcgacac agaaatcctt aaggccggcg gccaaggggc cgaaggtgaa   17280
gaaggtgaag ccccagaaac cgaaggccac gaagccgccc aaagtggtgt cgcagcgcgg   17340
ctggcgacat tgggtgcatg cgttgacgcg aatcaacctg ggcctgtcac ccgacgagaa   17400
gtacgagctg gacctgcacg ctcgagtccg ccgcaatccc cgcgggtcgt atcagatcgc   17460
cgtcgtcggt ctcaaaggtg gggctggcaa aaccacgctg acagcagcgt tggggtcgac   17520
gttggctcag gtgcgggccg accggatcct ggctctagac gcggatccag gcgccggaaa   17580
cctcgccgat cgggtagggc gacaatcggg cgcgaccatc gctgatgtgc ttgcagaaaa   17640
agagctgtcg cactacaacg acatccgcgc acacactagc gtcaatgcgg tcaatctgga   17700
agtgctgccg gcaccggaat acagctcggc gcagcgcgcg ctcagcgacg ccgactggca   17760
tttcatcgcc gatcctgcgt cgaggtttta caacctcgtc ttggctgatt gtggggccgg   17820
cttcttcgac ccgctgaccc gcggcgtgct gtccacggtg tccggtgtcg tggtcgtggc   17880
aagtgtctca atcgacggcg cacaacaggc gtcggtcgcg ttggactggt tgcgcaacaa   17940
cggttaccaa gatttggcga gccgcgcatg cgtggtcatc aatcacatca tgccgggaga   18000
acccaatgtc gcagttaaag acctggtgcg gcatttcgaa cagcaagttc aacccggccg   18060
ggtcgtggtc atgccgtggg acaggcacat tgccgccgga accgagattt cactcgactt   18120
gctcgaccct atctacaagc gcaaggtcct cgaattggcc gcagcgctat ccgacgattt   18180
cgagagggct ggacgtcgtt gagcgcacct gctgttgctg ctggtcctac cgccgcgggg   18240
gcaaccgctg cgcggcctgc caccacccgg gtgacgatcc tgaccggcag acggatgacc   18300
gatttggtac tgccagcggc ggtgccgatg gaaacttata ttgacgacac cgtcgcggtg   18360
ctttccgagg tgttggaaga cacgccggct gatgtactcg gcggcttcga ctttaccgcg   18420
caaggcgtgt gggcgttcgc tcgtcccgga tcgccgccgc tgaagctcga ccagtcactc   18480
gatgacgccg gggtggtcga cgggtcactg ctgactctgg tgtcagtcag tcgcaccgag   18540
cgctaccgac cgttggtcga ggatgtcatc gacgcgatcg ccgtgcttga cgagtcacct   18600
gagttcgacc gcacggcatt gaatcgcttt gtggggcgg cgatcccgct tttgaccgcg   18660
cccgtcatcg gatgcgcgat gcgggcgtgg tgggaaactg ggcgtagctt gtggtggccg   18720
ttggcgattg gcatcctggg gatcgctgtg ctggtaggca gcttcgtcgc gaacaggttc   18780
```

```
taccagagcg gccacctggc cgagtgccta ctggtcacga cgtatctgct gatcgcaacc   18840
gccgcagcgc tggccgtgcc gttgccgcgc ggggtcaact cgttgggggc gccacaagtt   18900
gccggcgccg ctacggccgt gctgtttttg accttgatga cgcggggcgg ccctcggaag   18960
cgtcatgagt tggcgtcgtt tgccgtgatc accgctatcg cggtcatcgc ggccgccgct   19020
gccttcggct atggatacca ggactgggtc cccgcggggg ggatcgcatt cgggctgttc   19080
attgtgacga atgcggccaa gctgaccgtc gcggtcgcgc ggatcgcgct gccgccgatt   19140
ccggtacccg gcgaaaccgt ggacaacgag gagttgctcg atcccgtcgc gaccccggag   19200
gctaccagcg aagaaacccc gacctggcag gccatcatcg cgtcggtgcc cgcgtccgcg   19260
gtccggctca ccgagcgcag caaactggcc aagcaacttc tgatcggata cgtcacgtcg   19320
ggcaccctga ttctggctgc cggtgccatc gcggtcgtgg tgcgcgggca cttctttgta   19380
cacagcctgg tggtcgcggg tttgatcacg accgtctgcg gatttcgctc gcggctttac   19440
gccgagcgct ggtgtgcgtg ggcgttgctg cggcgacgg tcgcgattcc gacgggtctg   19500
acggccaaac tcatcatctg gtacccgcac tatgcctggc tgttgttgag cgtctacctc   19560
acggtagccc tggttgcgct cgtggtggtc gggtcgatgg ctcacgtccg gcgcgtttca   19620
ccggtcgtaa aacgaactct ggaattgatc gacggcgcca tgatcgctgc catcattccc   19680
atgctgctgt ggatcaccgg ggtgtacgac acggtccgca atatccggtt ctgagccgga   19740
tcggctgatt ggcggttcct gacagaacat cgaggacacg gcgcaggttt gcataccttc   19800
ggcgcccgac aaattgctgc gattgagcgt gtggcgcgtc cggtaaaatt tgctcgatgg   19860
ggaacacgta taggagatcc ggcaatggct gaaccgttgg ccgtcgatcc caccggcttg   19920
agcgcagcgg ccgcgaaatt ggccggcctc gtttttccgc agcctccggc gccgatcgcg   19980
gtcagcggaa cggattcggt ggtagcagca atcaacgaga ccatgccaag catcgaatcg   20040
ctggtcagtg acgggctgcc cggcgtgaaa gccgccctga ctcgaacagc atccaacatg   20100
aacgcggcgg cggacgtcta tgcgaagacc gatcagtcac tgggaaccag tttgagccag   20160
tatgcattcg gctcgtcggg cgaaggcctg gctggcgtcg cctcggtcgg tggtcagcca   20220
agtcaggcta cccagctgct gagcacaccc gtgtcacagg tcacgaccca gctcggcgag   20280
acggccgctg agctggcacc ccgtgttgtt gcgacggtgc cgcaactcgt tcagctggct   20340
ccgcacgccg ttcagatgtc gcaaaacgca tcccccatcg ctcagacgat cagtcaaacc   20400
gcccaacagg ccgcccagag cgcgcagggc ggcagcggcc caatgccgc acagcttgcc   20460 agcgctgaaa aaccggccac cgagcaagcg gagccggtcc acgaagtgac aaacgacgat   20520
cagggcgacc agggcgacgt gcagccggcc gaggtcgttg ccgcggcacg tgacgaaggc   20580
gccggcgcat caccgggcca gcagcccggc ggggcgttc ccgcgcaagc catggatacc   20640
ggagccggtg cccgcccagc ggcgagtccg ctggcggccc ccgtcgatcc gtcgactccg   20700
gcaccctcaa caaccacaac gttgtagacc gggcctgcca gcggctccgt ctcgcacgca   20760
gcgcctgttg ctgtcctggc ctcgtcagca tgcggcggcc agggcccggt cgagcaaccc   20820
ggtgacgtat tgccagtaca gccagtccgc gacggccaca cgctgacgg ccgcgtcagt   20880 cgcagtgtgc gcttggtgca gggcaatctc ctgtgagtgg gcagcgtagg cccggaacgc   20940
ccgcagatga gcgcctcgc ggccggtagc ggtgctggtc atgggcttca tcagctcgaa   21000
ccacagcatg tgccgctcat cgcccggtgg attgacatcc accggcgccg gcggcaacaa   21060
gtcgagcaaa cgctgatcgg tagtgtcggc cagctgagcc gccgccgagg ggtcgacgac   21120
ctccagccgc gaccggcccg tcattttgcc gctctccgga atgtcatctg gctccagcac   21180
```

```
aatcttggcc acaccgggat ccgaactggc caactgctcc gcggtaccga tcaccgcccg  21240
cagcgtcatg tcgtggaaag ccgcccaggc ttgcacggcc aaaaccgggt aggtggcaca  21300
gcgtgcaatt tcgtcaaccg ggattgcgtg atccgcgctg ccaagtaca ccttattcgg   21360 caattccatc ccgtcgggta tgtaggccag cccatagctg ttggccacga cgatggaacc  21420
gtcggtggtc accgcggtga tccagaagaa cccgtagtcg cccgcgttgt tgtcggacgc  21480
gttgagcgcc gccgcgatgc gtcgcgccaa ccgcagcgca tcaccgcggc cacgctggcg  21540
ggcgctggca gctgcagtgg cggcgtcgcg tgccgcccga gccgccgaca ccgggatcat  21600
cgacaccggc gtaccgtcat ctgcagactc gctgcgatcg ggtttgtcga tgtgatcggt  21660
cgacggcggg cgggcaggag gtgccgtccg cgccgaggcc gcccgcgtgc tcggtgccgc  21720
cgccttgtcc gaggtagcca ccggcgcccc ccagtggca gcatgcgacc ccgcgcccga   21780
ggccgcggcc gtacccacgc tcgaacgcgc gcccgctccc acggcggtac cgctcggcgc  21840
ggcggccgcc gcccgtgcgc ccgggacacc ggacgccgca gccggcgtca ccgacgcggc  21900
ggattcgtcc gcatgggcag gccccgactg cgtccccccg cccgcatgct ggcccggcac  21960
accaggttgc tccgccaacg ccgcgggttt gacgtgcggc gccggctcgc cccctggggt  22020
gcccggtgtt gctggaccag acggaccggg agtggccggt gtaaccggct ggggcccagg  22080
cgatggcgcc ggtgccggag ccggctgcgg gtgtggagcg ggagctgggg taacgggcgt  22140
ggccggggtt gccggtgtgg ccggggcgac cgggggggtg accggcgtga tcggggttgg  22200
ctcgcctggt gtgccggtt tgaccggggt caccggggtg accggcttgc cggggtcac    22260 cggcgtgacg ggagtgccgg gcgttggtgt gatcggagtt accggcgctc ccgggatggg  22320
tgtgattggg gttcccgggg tgatcggggt tcccggggtg atcggggttc ccggtgtgcc  22380
cggtgtgccc ggggatggca cgaccagggt aggcacgtct gggggtggcg gcgacttctg  22440
ctgaagcaaa tcctcgagtg cgttcttcgg aggtttccaa ttcttggatt ccagcacccg  22500
ctcagcggtc tcggcgacca gactgacatt ggccccatgc gtcgccgtga ccaatgaatt  22560
gatggcggta tggcgctcat cagcatccag gctagggtca ttctccagga tatcgatctc  22620
ccgttgagcg ccatccacat tattgccgat atcggattta gcttgctcaa tcaacccggc  22680
aatatgcctg tgccaggtaa tcaccgtggc gagataatcc tgcagcgtca tcaattgatt  22740
gatgtttgca cccagggcgc cgttggcagc attggcggcg ccgccggacc ataggccgcc  22800
ttcgaagacg tggcctttct gctggcggca ggtgtccaat acatcggtga cccttgcaa   22860 aacctggcta tattcctggg cccggtcata gaaagtgtct tcatcggctt ccacccagcc  22920
gcccggatcc agcatctgtc tggcatagct gcccgtcggc ctggtaatac tcatccccta  22980
ctgccctccc caaccgcca gatcgcctcg cggatcaccg tccggttggc ctccggcatt   23040
tcacgccggc tcggccgctg gatccacccc gcgccggtat tcgcagtaac ccgttgaatc  23100
cgcgcgcatg atgcaccgct tgggcgatca gccgggtggt cacctcgctt gcgctggccg  23160
cgctgtcgca cggggcgctc ggtggtaacg gacgtcataa ttaaccagcg taaccgaacc  23220
taagaccagc tagctgcggc aatattggcg accaggacta tggcgccctc cgaacccggc  23280
cgatccatgt caaaacattg acaatgcgta ctcacgccgt gtcgggcgcg ctgaatgacc  23340
gcattgcggc gctcattcgg tgcgtagtcg ctaccaccgc aacaatgggc ttaggccatt  23400
ccttcgttca tcgcgcggga catggccgat aacgcagcgg tcagctgctc gcccgccgcg  23460
tcgttatacg cggacgccgc ggcctgcgca ttgtgcagcg cctcgttgac ccgctgagcc  23520
accgcctcgg cacccagctt cttcagcaaa ccatcttcga tgcgcaggcc ggtgagccac  23580
```

```
tggtgcccat tgatcgtcac ttcgacggtc tcggcttcgt cggtggcgcg aaggatccg    23640 ttgttcatct gattgagcgt cccgtctagg gccgactgaa accgcgccgc cagcgtcaac    23700
gcccgggcga catgcgggtc caattcgtcc atgctcactt cgactcctta ctgtcctggc    23760
gccgacggtt accaatgacg gcctcggtcc atgcccgatc ctcggtgtag agcgcctcgt    23820
cttcctgctg agaacccttg gacttggcgc cccttgtcc ctgatgcgcg gcacccatcg    23880
gcattcccat gccaccgccg cccagcgcgg cgccgccgcc ggcccttccc tggcctaagc    23940
cggcaatgtc accagcgcca gcgggccgca ccgattcggc gccccgatc gcggatccca    24000 acggcgccga cggcaccccg ccgcctccac cgccaccgag cgatgccgct ttgaccgcca    24060
cgtcgcccga cagcgctgcg gcttcccgcc cagccgacgt cagctgcgcc gccgtgtcag    24120
ccgggaggcc accacccggc gatccggtag gcggaaccat cggtgcggct ggcatcccgg    24180
taccgggagt cacaccggag ccgtcagacg gcggcatcag gaagccaggg atcaatccct    24240
gctcttgcgg aggcggggc gggtcgatct tgatggcggg gggaggcttc ggcgggttta    24300
ccggttccag ggctgccttg ttgttgtatt cggtcagcac cttctccgac ctctgctgat    24360
actccgcgta caccgggaga atttggtcgc gggccgaagg gttttccgcg taaagccgtt    24420
cgagcccgac tatgtcttca taagtcggat gttcccgcct agcccacacg tgcagctgcg    24480
cgacatattg agcctgcttg gccatcgcag cgctcaattt ggccatgtgg agtatccatt    24540
gccgttgttg atcgagcgaa gcctcgcaag cggtagccgc atcgccttcc cagttgtcaa    24600 accccggaa ccgcttgacg tcgccttgca gcgtcaggtt gaaagtgttc cacccatccg    24660
caaagtgcgc gagcgatgcg ccttggtcgc ccgtttcgag cttccttgcc gcttctttga    24720
gatccatgaa gttgggttca ccggccgtgg ccaccctcgg cgtatcggtt agttcggccg    24780
aactgtcccc tccgacggcc ccggccgatt ctgcctgcac agttccttcg ccgtcgttgt    24840
ccagcgcggt cgcagcctcc tcatcaacct cgccatacgc cttggccgcg ttgcgcagcg    24900
aggtcgccag acgctgccgc tctttggcac cggccgccag gtattcccgc atgttgtcgg    24960
cggacaatac cagctgttgg gcggcgtttt tagccgccgt gagttcgcac ggtgtgatgg    25020
ggacatcagt cggtgggtcc gccatcgggg cctccacctc gttggccctg ttcaaaatct    25080
cttgctgatc caccgtcacg gtctgcgact gcgtcatatc ggatcatcct ccttagtgct    25140
atagccatta tcgtcgctaa actgaaaggt tcctgcacta atttgatgcc gcccgttcat    25200
gccggcatcg cgaacggatc gccctacttc ggcagcgcca tctggtagcg gctttcctcg    25260 ggtgggaaa cccggcgaat cggcagctgc cgatgccgcg gggtaccgat cacattgtgc    25320
cgcagaatca cccggtcaat accgggatgc gggccgagat aggtcgtcgc attcggccac    25380
gccaccttta cctcctgccc gatgtgtgcg ccgatcaacc gggcaaattc ctcgaactgt    25440
ggcccgactg tgaccatcgc acctgccgcc gccgcacgca ccacgaactg ggtgaatgtc    25500
tgagcgtcac ccaggttgag ggcgatgtcg acatcgtcga agggcatgta gaccgggcat    25560
cggttcaccg tctcgccgac cagtacccca gctgacccga tcggcagctg gcagtggcgg    25620
ttggccacca gatgctggcc ttgcagcgcg ggccgctgcc cgccaaatag gcgggcgaag    25680
cccctgggtg tcttgggctt gtccgccgtg gtcagcaaca ccgtggactg cggggccatc    25740
cccgcgcgca cccggactct ggtgatggtg tggtccgcgc gcgccgacca ccatacatcc    25800
ggacctccgg gcgccgcgta ggcggcagtg taggcatcgc gccccttgat catcgaccat    25860
ttctcccgca caaagccgat gtcggtggcg tggtcgtagt catcgaagct gcggccacac    25920
accgcgtcga caccatggct agccagtcga tcggcaatgc gcgtcgcgga cgccaccaaa    25980
```

```
taccgggcca gtcctgcgac gccttcatcg cggcgctgcg ccgatttgcg ggtgcgttcc    26040
gggtcggcgc gcagcacgat ccaggtccgg cggttcgccg gcgccgggtc tgtcccgatc    26100
acctgctgat acagactcac cacgtccggc gctgcggtat tgccgacgcg gtagccggct    26160
gagacgatat cggcctccaa gtcgggacag tgcaccgaca ggagctcctc caccagtccg    26220
gtgtccagca tgtcgtcggt gtgggcttgc ccgtcgacga tgaccgtcgg cgtgaatggt    26280
cggggaatga gctcgattac ggcgaccaga aactcgcctt gccagcgcac cgcaacgtga    26340
tctcctggct tcacggtggc cccgaccaca ggttctgacg aggaatccgg gggccgtcgg    26400
cgccgccgca accacgcgta caccgccgcc acccagccgg tgatccggcg gccgtagaaa    26460
gtgaccgtgg ccacgatgac gcccaacgag gccagcgcaa tccccgccca ccagtagcgc    26520
gtctccaaga atgcgatgat gcatggcggg gccaacgcgg aggcaagcaa ggcgtgcccg    26580
gtgctgaacc gcagccctaa aggatttctc atcggcggct cagcgcccgt ctagccagcg    26640
cgcccaggcc cagggccaac gtaaggccga cggccaccaa cgccacagcc gtaatcgggc    26700
gacgatcggg accggctcc accaccgggg gtggaagtcg tctgacgttg tatggcgccg    26760
aagcagggcc gggcggaatg tcccacgtca gcgcggccac cgcatcgatg acgccggcgc    26820
cgaccaggtc gtcgaccccg cccccggggt gtctcgcggt ggcggtgatc cggtggatga    26880
tctgcgccgg cgtcaggtcg gggaaccgct gccgaagcag ggccgccaga cccgacacat    26940
atgccgcggc aaacgaggtg ccggcgatgg gtaccggccc ctcccggcct tgcagcgcat    27000
tcaccggttc accggtgtcg ccgagcgcga cgatgttttc tgcgggcgcg gccacgtcca    27060
cccacggtcc gtgcatcgag aacgagctgg gcatcccggt ctggccgata ccgccgacgc    27120
ttaacaccag cggtgcgtac cacgccgggg tgacaacggt ctgcacattg ttccagccgc    27180
gtgggtcgcc gggtgtggac gggtccggcg ccggattctg tacgcaatcg ccaccggtgt    27240
tgccggccgc gaccaccacc accacgcctt tgacgttgac cgcatagtcg atggatgcac    27300
ccagtgaggt ttcatcgatc ggcctgctca ccttgtagca ggcggcttca ctgatgttga    27360
tcacacccac gccgaggttg gcggcgtgca ccacggcgcg ggcaagactg cggatggaac    27420
cggcggccgg ggtggcgttg gggtcattcg ggttggcttg tgagccgacc ggttcgaagg    27480
cctcagacgt ctgacgtagc gagagcagtc gagcgtcggg cgcgacgccg acgaacccgt    27540
cggtgggcgc gggccggccc gcgatgatgg atgctgtgag agtcccatgg gcatcacagt    27600
cagacaggcc gttaccggcc tggtcgacga aatcgccgcc aggttccgcc gggacccgtg    27660
gcgaagcgtc gacaccggtg tcgatcaccg ccaccgtcac cccggcccg tcgcgaact     27720
tgtgggcatc ggccacgccc agatacgtgt tgctccacgg cggatcgtgg aacccggacc    27780
ccggcagcgt ggtgggcgac gcgcacaaaa cgcgctgttc ggtaggctga tccgggcccg    27840
tcacgtcggg cggcaacgcg cccggatcga tcggcggtgg cgtgatggcc gatgcgggcg    27900
acgcggtgag caacgccagc gccaccgtga tcagaaagat acggtgcact cccagaacac    27960
tccattcgtt gagattcatt gcgattcatt gagctgcgtt gctaccttgg gccacttgac    28020
ggacctgtgt gcattttaga cgtaacggct gggcaaacaa cgctgtcacg cctgggctgg    28080
tccgccgcgc cgaccagggc gcgtaggcgc tgtacctgga ccacgccggg actcaacggt    28140
tttgctaccg cactagccga tatgcggctg ctaccaaacg atcgcggcca tgtctcggtt    28200
gtctgagcac acgctgcgta tcgcggcatc gatgtcggtg gcggtgatga tctgcagatc    28260
ctgaaccgat accggttggc ccgcacgttt ttgcgcaacc accgggtgt cccggaaccc    28320
ttcggcgcgt tcgatcacgt tgcgggcgaa ccgaccgttt tgcatagcgt cgataccgtg    28380
```

```
ctgcccacta ggggtggtgt agttacggat ggtggtgacc gcgtcgagga atacctcccg   28440
tgcggcgtca tcgagctggc tggcgcgcgg tgtagcgtag cggtgtccaa tctcgacgat   28500
ctccaccggc gaataagact cgaaccgcag ctttcggttg aaccggccag ccaaacccgg   28560
gttcacggtg aggaattcat ccacctgatc ctcatagccg ccccgatga aacagaagtc    28620
gaatcggtgt gtttccaatt gaaccaggag ttgattgacc gcctccatgc cgatcatgtc   28680
cggtgttccg tcttgatgac gttcgatcag cgagtagaac tcgtccatga aaatgattcg   28740
cccgagtgac ttttcgatca gctcgttcgt cttgggtcct gactcccga tgtagtgccc    28800
acagaagtcc gatcggcgaa cttctcgaat ttcggggtga cgcacgatcc ccatgccggc   28860
gtagatcttg ccgagcgctt cagcggtggt tgtcttacct gtgcctggtg ccccaccag    28920
caacatgtgt tggtctgcc cctccaccgg taggccgtgc tctaggcgca tcatgcgcac    28980
ctcgagttgg tcttccagcg ccgataccgc ttgcttgacc gccgccaggc ccacctgttt   29040
ggccagcagt tccggccct cggctagcag ctcgccgcgc cgctgcgctg cattgtcgtc    29100
atcgagctgg tcgcggcttt tcgccgtcga agcatcccaa cggtcggagc ggctggcgat   29160
ggttcgttca tcggtaacaa tcaagcgcag gttcgggtcc gccagggctt ctttggcggc   29220
gtcggtgagc accccgttga tggtggcctt cgacagccag atctgggcct tgtcctcctc   29280
atgcagttgc cggtacacca tcccccgcac atacgccaag tcggcgacca gcagcggaat   29340
atcggccggt ccgatcgccg cggtgagcac gtcggcgccg aaccgctccg atgacctgct   29400
gtgtccgatc acgtccaccc ggtccagcca gtccagggcc actcgcccct gcccgagatg   29460
ggcggcggcg tgggctgcca gcgcacaaat cgacgcggtc accgccggca tgacgatcgc   29520
ctgtggcggc agatcctcgg cggccgtcga caacacgtcg ggccatcgct gcgtgacgta   29580
catcaggaac gcccgagcca gctgatgcca ctggtagttg cgccacgaat ccaatagctc   29640
gcggtttgct aacagggcat cggccttcgc atactccccc gcgatcgtca acgccgacga   29700
cagcgccagc cccacctgag atgcgtcggt caccgtgatc ccgatggatg gtcccagctg   29760
gacctcagcg gccaacgtcc ggccgatccg cgtggtctcg cggtgcagcc actcgctatg   29820
ggcgttgagc tgcttaagcg aggccagatc gcggtcaccg caggcgatac gacccagcca   29880
cgcgtcggcc atcgacggat cggcctcggt ggcagccaca aactcaggca acgccgccac   29940
gcatccctgg ccattcttga tcgtcatcgc ccgatcgaaa tgccggcgcg cagtgagtaa   30000
atcacccatc gtgtccacca ttctcgacat cgccgccgct gtcaccgcgg ttgcaacgtg   30060
tgtctgtcac tctgtgcctc aaattccgtt ggcaacgttc taccgcccta tcgacatcgt   30120
gaccggctca aggctgacat agcggttctc cgcacggaac atttccatct caaccagcca   30180
gttttgtcct gccgcaccga cttcaccgt tgcccgatcg atttgttcga tggtcacctc    30240
gaagccatgc cgatcgctct cggacagcga ggtaccgggt cgggcaatgg tgatgacact   30300
ggctggccgt ggcgtgggcg aaatcgcgac atcgacaccg ctgccttcag atttgccgtc   30360
atcgccgttc ttgcgccgcc gcacgtactc cacgacgccg acagtggtgc gcggcgcggg   30420
ccgtggtgtg ccgacgatgc tcaactgcgg catgcgtacg ctggcccaac gctcttggtc   30480
gcgagtgtgc acacacaccc gctcaccggc accgacgacg cgaatcacga tcctcttggc   30540
gatcgtgtcg tccgcggcca cgaagacgcg cgacagctca ccggcgtcgg taacgggaat   30600
catcagccgg tccccgttgc tcagcttgcc aatcaacacc cccgacggtc cgatctcggt   30660
gactagctgc gccggcaacg ggcagcgccg ctgtccgcgt aggtgtggac gtggccgca    30720
catgttggcc gcagccgcgg cggcttgctc accattgagc cgacgcaaga tcacactggg   30780
```

```
cggggtaggc gccggcgtcg gtgtgcgcac ggtgatggtc gcggtgcacg tcgcgtccgg  30840
atacaccgtt acgttctgga tgacctcatc ggcacgcagc gtccaggctt gcgagagaac  30900
ccgcgacgaa atcgcctcag ccgggtacgc atacgtcgtc atccacccgg cttcaccgcg  30960
gatagctttc cagcgctgcg cactcccggc taccgcgtcc gaccccagcc ggcgatcaag  31020
ctcagccaag tctgttgcgg tggccagttt ggcgcgcaag ccctgacagc gcagggagct  31080
ggcaacgcgt tgggcgaccg aaatggcagc ggccccaacg ctggtacgcc agcgtaaagc  31140
ttgggtgttg ccgatcaccg gaagccgcat gatcagccac gtttcgcgcc gcccggcata  31200
cggcggcgta ccgatctccg cgtcatacac ccgcgggtaa tcgccgacgg tgccggttcg  31260
cgagccgaag gtgacgacgc tgattgaatc gagttccagg tccagcgggt ggcgcagcaa  31320
cggcgcgagc tcaacgacgt caatcacgtt gtcgctttct acggtcaccg acccggtgac  31380
cgtagtcgcc cggtgcgctc ggccgagaag ttgcaccgcc accaccgcga caccgtcttg  31440
cacgcggacg ccacccccgg atcggttgtt ggccaaggta attgggtcat tccatttgac  31500
gggacgccga ccccgcagcc ccagtaccgc ccacgaccac gccggctgac cccaccactg  31560
tacgaacacc aaggcgacgc cgaccacgac agccatgacc gcacctagct ggccgcccag  31620
cgcccagccc gccgacgcga gcacgaacac tgtccacacc ccggcgaccc gcctcgcact  31680
gcgcgggctg aacccggtca gcttggacgt caacgcgccc tccgtagccg agccccgatt  31740
gccattgcca gcacaccggt ggccactgcg ccgacgaacc cgatagcgat attgcgcgcc  31800
cggtgatc                                                           31808
```
<210> SEQ ID NO 2
<211> LENGTH: 13773
<212> TYPE: DNA
<213> ORGANISM: mycobacterium tuberculosis
<220> FEATURE:
<223> OTHER INFORMATION: Complete DNA sequence of RD1 Rv3867-3877

<400> SEQUENCE: 2

```
atggtggacc cgccgggcaa cgacgacgac cacggtgatc tcgacgccct cgatttctcc     60
gccgcccaca ccaacgaggc gtcgccgctg gacgccttag acgactatgc gccggtgcag    120
accgatgacg ccgaaggcga cctggacgcc ctccatgcgc tcaccgaacg cgacgaggag    180
ccggagctgg agttgttcac ggtgaccaac cctcaagggt cggtgtcggt ctcaaccctg    240
atggacggca gaatccagca cgtcgagctg acggacaagg cgaccagcat gtccgaagcg    300
cagctggccg acgagatctt cgttattgcc gatctggccc gccaaaaggc gcgggcgtcg    360
cagtacacgt tcatggtgga gaacatcggt gaactgaccg acgaagacgc agaaggcagc    420
gccctgctgc gggaattcgt ggggatgacc ctgaatctgc cgacgccgga agaggctgcc    480
gcagccgaag ccgaagtgtt cgccacccgc tacgatgtcg actacacctc ccggtacaag    540
gccgatgact gatcgcttgg ccagtctgtt cgaaagcgcc gtcagcatgt tgccgatgtc    600
ggaggcgcgg tcgctagatc tgttcaccga gatcaccaac tacgacgaat ccgcttgcga    660
cgcatggatc ggccggatcc ggtgtgggga caccgaccgg gtgacgctgt ttcgcgcctg    720
gtattcgcgc cgcaatttcg gacagttgtc gggatcggtc cagatctcga tgagcacgtt    780
aaacgccagg attgccatcg gggggctgta cggcgatatc acctacccgg tcacctcgcc    840
gctagcgatc accatgggct ttgccgcatg cgaggcagcg caaggcaatt acgccgacgc    900
catggaggcc ttagaggccg ccccggtcgc gggttccgag cacctggtgg cgtggatgaa    960
ggcggttgtc tacggcgcgg ccgaacgctg gaccgacgtg atcgaccagg tcaagagtgc   1020
```

```
tgggaaatgg ccggacaagt ttttggccgg cgcggccggt gtggcgcacg gggttgccgc    1080
ggcaaacctg gccttgttca ccgaagccga acgccgactc accgaggcca acgactcgcc    1140
cgccggtgag gcgtgtgcgc gcgccatcgc ctggtatctg gcgatggcac ggcgcagcca    1200
gggcaacgaa agccgccgcgg tggcgctgct ggaatggtta cagaccactc accccgagcc    1260
caaagtggct gcggcgctga aggatccctc ctaccggctg aagacgacca ccgccgaaca    1320
gatcgcatcc cgccgcgatc cctgggatcc gggcagtgtc gtgaccgaca actccggccg    1380
ggagcggctg ctcgccgagg cccaagccga actcgaccgc caaattgggc tcacccgggt    1440
taaaaatcag attgaacgct accgcgcggc gacgctgatg gcccgggtcc gcgccgccaa    1500
gggtatgaag gtcgcccagc ccagcaagca catgatcttc accggaccgc ccggtaccgg    1560
caagaccacg atcgcgcggg tggtggccaa tatcctggcc ggcttaggcg tcattgccga    1620
acccaaactc gtcgagacgt cgcgcaagga cttcgtcgcc gagtacgagg gcaatcggc    1680 ggtcaagacc gctaagacga tcgatcaggc gctgggcggg gtgcttttca tcgacgaggc    1740
ttatgcgctg gtgcaggaaa gagacggccg caccgatccg ttcggtcaag aggcgctgga    1800
cacgctgctg gcgcggatgg agaacgaccg ggaccggctg gtggtgatca tcgccgggta    1860
cagctccgac atagatcggc tgctggaaac caacgagggt ctgcggtcgc ggttcgccac    1920
tcgcatcgag ttcgacacct attccccga ggaactcctc gagatcgcca acgtcattgc    1980
cgctgctgat gattcggcgt tgaccgcaga ggcggccgag aactttcttc aggccgccaa    2040
gcagttggag cagcgcatgt gcgcggccg gcgcgcccctg gacgtcgccg caacggtcg    2100 gtatgcgcgc cagctggtgg aggccagcga gcaatgccgg gacatgcgtc tagcccaggt    2160
cctcgatatc gacaccctcg acgaagaccg gcttcgcgag atcaacggct cagatatggc    2220
ggaggctatc gccgcggtgc acgcacacct caacatgaga gaatgaacta tggggcttcg    2280
cctcaccacc aaggttcagg ttagcggctg gcgttttctg ctgcgccggc tcgaacacgc    2340
catcgtgcgc cgggacaccc ggatgtttga cgacccgctg cagttctaca gccgctcgat    2400
cgctcttggc atcgtcgtcg cggtcctgat tctggcgggt gccgcgctgc tggcgtactt    2460
caaaccacaa ggcaaactcg gcggcaccag cctgttcacc gaccgcgcga ccaaccagct    2520
ttacgtgctg ctgtccggac agttgcatcc ggtctacaac ctgacttcgg cgcggctggt    2580
gctgggcaat ccgccaaacc cggccaccgt gaagtcctcc gaactgagca agctgccgat    2640
gggccagacc gttggaatcc ccggcgcccc ctacgccacg cctgtttcgg cgggcagcac    2700
ctcgatctgg accctatgcg acaccgtcgc ccgagccgac tccacttccc cggtagtgca    2760
gaccgcggtc atcgcgatgc cgttggagat cgatgcttcg atcgatccgc tccagtcaca    2820
cgaagcggtc ctggtgtcct accagggcga aacctggatc gtcacaacta agggacgcca    2880
cgccatagat ctgaccgacc gcgccctcac ctcgtcgatg gggataccgg tgacggccag    2940
gccaaccccg atctcggagg gcatgttcaa cgcgctgcct gatatggggc cctggcagct    3000
gccgccgata ccggcggcgg gcgcgcccaa ttcgcttggc ctacctgatg atctagtgat    3060
cggatcggtc ttccagatcc acaccgacaa gggcccgcaa tactatgtgg tgctgccga    3120 cggcatcgcg caggtcaacg cgacaaccgc tgcggcgctg cgcgccaccc aggcgcacgg    3180
gctggtcgcg ccaccggcaa tggtgcccag tctggtcgtc agaatcgccg aacgggtata    3240 ccccctcaccg ctacccgatg aaccgctcaa gatcgtgtcc cggccgcagg atcccgcgct    3300
gtgctggtca tggcaacgca gcgccggcga ccagtcgccg cagtcaacgg tgctgtccgg    3360
ccggcatctg ccgatatcgc cctcagcgat gaacatgggg atcaagcaga tccacgggac    3420
```

| | |
|---|---|
| ggcgaccgtt tacctcgacg gcggaaaatt cgtggcactg caatccccg atcctcgata | 3480 |
| caccgaatcg atgtactaca tcgatccaca gggcgtgcgt tatggggtgc ctaacgcgga | 3540 |
| gacagccaag tcgctgggcc tgagttcacc ccaaaacgcg ccctgggaga tcgttcgtct | 3600 |
| cctggtcgac ggtccggtgc tgtcgaaaga tgccgcactg ctcgagcacg acacgctgcc | 3660 |
| cgctgaccct agccccgaa aagttcccgc cggagcctcc ggagccccct gatgacgacc | 3720 |
| aagaagttca ctcccaccat tacccgtggc cccggttga ccccgggcga tcagcctc | 3780 |
| acgccgcccg atgacctggg catcgacatc ccaccgtcgg gcgtccaaaa gatccttccc | 3840 |
| tacgtgatgg gtgcgccat gctcggcatg atcgccatca tggtggccgg cggcaccagg | 3900 |
| cagctgtcgc cgtacatgtt gatgatgccg ctgatgatga tcgtgatgat ggtcggcggt | 3960 |
| ctggccggta gcaccggtgg tggcggcaag aaggtgcccg aaatcaacgc cgaccgcaag | 4020 |
| gagtacctgc ggtatttggc aggactacgc acccgagtga cgtcctcggc cacctctcag | 4080 |
| gtggcgttct tctcctacca cgcaccgcat cccgaggatc tgttgtcgat cgtcggcacc | 4140 |
| caacggcagt ggtcccggcc ggccaacgcc gacttctatg cggccacccg aatcggtatc | 4200 |
| ggtgaccagc cggcggtgga tcgattattg aagccggccg tcggcgggga gttggccgcc | 4260 |
| gccagcgcag cacctcagcc gttcctggag ccggtcagtc atatgtgggt ggtcaagttt | 4320 |
| ctacgaaccc atggattgat ccatgactgc ccgaaactgc tgcaactccg taccttccg | 4380 |
| actatcgcga tcggcgggga cttggcgggg gcagccggcc tgatgacggc gatgatctgt | 4440 |
| cacctagccg tgttccaccc accgacctg ctgcagatcc gggtgctcac cgaggaaccc | 4500 |
| gacgaccccg actggtcctg gctcaaatgg cttccgcacg tacagcacca gaccgaaacc | 4560 |
| gatgcggccg gtccacccg gctgatcttc acgcgccagg aaggtctgtc ggacctggcc | 4620 |
| gcgcgcgggc cacacgcacc cgattcgctt cccggcggcc cctacgtagt cgtcgtcgac | 4680 |
| ctgaccggcg gcaaggctgg attcccgccc gacggtaggg ccggtgtcac ggtgatcacg | 4740 |
| ttgggcaacc atcgcggctc ggcctaccgc atcagggtgc acgaggatgg gacggctgat | 4800 |
| gaccggctcc ctaaccaatc gtttcgccag gtgacatcgg tcaccgatcg gatgtcgccg | 4860 |
| cagcaagcca gccgtatcgc gcgaaagttg gccggatggt ccatcacggg caccatcctc | 4920 |
| gacaagacgt cgcgggtcca gaagaaggtg gccaccgact ggcaccagct ggtcggtgcg | 4980 |
| caaagtgtcg aggagataac accttcccgc tggaggatgt acaccgacac cgaccgtgac | 5040 |
| cggctaaaga tcccgtttgg tcatgaacta agaccggca acgtcatgta cctggacatc | 5100 |
| aaagagggcg cggaattcgg cgccggaccg cacggcatgc tcatcgggac cacggggtct | 5160 |
| gggaagtccg aattcctgcg caccctgatc ctgtcgctgg tggcaatgac tcatccagat | 5220 |
| caggtgaatc tcctgctcac cgacttcaaa ggtggttcaa ccttcctggg aatggaaaag | 5280 |
| cttccgcaca ctgccgctgt cgtcaccaac atggccgagg aagccgagct cgtcagccgg | 5340 |
| atgggcgagg tgttgaccgg agaactcgat cggcgccagt cgatcctccg acaggccggg | 5400 |
| atgaaagtcg gcgcggccgg agccctgtcc ggcgtggccg aatacgagaa gtaccgcgaa | 5460 |
| cgcggtgccg acctaccccc gctgccaacg cttttcgtcg tcgtcgacga gttcgccgag | 5520 |
| ctgttgcaga gtcacccgga cttcatcggg ctgttcgacc ggatctgccg cgtcgggcgg | 5580 |
| tcgctgaggg tccatctgct gctggctacc cagtcgctgc agaccggcgg tgttcgcatc | 5640 |
| gacaaactgg agccaaacct gacatatcga atcgcattgc gcaccaccag ctctcatgaa | 5700 |
| tccaaggcgt taatcggcac accgaggcg cagtacatca ccaacaagga gagcggtgtc | 5760 |
| gggtttctcc gggtcggcat ggaagacccg gtcaagttca gcaccttcta catcagtggg | 5820 |

```
ccatacatgc cgccggcggc aggcgtcgaa accaatggtg aagccggagg gcccggtcaa    5880
cagaccacta gacaagccgc gcgcattcac aggttcaccg cggcaccggt tctcgaggag    5940
gcgccgacac cgtgacccgc gccggcgacg atgcaaagcg cagcgatgag gaggagcggc    6000
gccaacggcc cgcgccggcg acgatgcaaa gcgcagcgat gaggaggagc ggcgcgcatg    6060
actgctgaac cggaagtacg gacgctgcgc gaggttgtgc tggaccagct cggcactgct    6120
gaatcgcgtg cgtacaagat gtggctgccg ccgttgacca atccggtccc gctcaacgag    6180
ctcatcgccc gtgatcggcg acaacccctg cgatttgccc tggggatcat ggatgaaccg    6240
cgccgccatc tacaggatgt gtggggcgta gacgtttccg gggccggcgg caacatcggt    6300
attggggggcg cacctcaaac cgggaagtcg acgctactgc agacgatggt gatgtcggcc    6360
gccgccacac actcaccgcg caacgttcag ttctattgca tcgacctagg tggcggcggg    6420
ctgatctatc tcgaaaacct tccacacgtc ggtggggtag ccaatcggtc cgagcccgac    6480
aaggtcaacc gggtggtcgc agagatgcaa gccgtcatgc ggcaacggga aaccaccttc    6540
aaggaacacc gagtgggctc gatcgggatg taccggcagc tgcgtgacga tccaagtcaa    6600
cccgttgcgt ccgatccata cggcgacgtc tttctgatca tcgacggatg gcccggtttt    6660
gtcggcgagt tccccgacct tgaggggcag gttcaagatc tggccgccca ggggctggcg    6720
ttcggcgtcc acgtcatcat ctccacgcca cgctggacag agctgaagtc gcgtgttcgc    6780
gactacctcg gcaccaagat cgagttccgg cttggtgacg tcaatgaaac ccagatcgac    6840
cggattaccc gcgagatccc ggcgaatcgt ccgggtcggg cagtgtcgat ggaaaagcac    6900
catctgatga tcggcgtgcc caggttcgac ggcgtgcaca gcgccgataa cctggtggag    6960
gcgatcaccg cggggggtgac gcagatcgct tcccagcaca ccgaacaggc acctccggtg    7020
cgggtcctgc cggagcgtat ccacctgcac gaactcgacc cgaacccgcc gggaccagag    7080
tccgactacc gcactcgctg ggagattccg atcggcttgc gcgagacgga cctgacgccg    7140
gctcactgcc acatgcacac gaacccgcac ctactgatct tcggtgcggc caaatcgggc    7200
aagacgacca ttgcccacgc gatcgcgcgc gccatttgtg cccgaaacag tccccagcag    7260
gtgcggttca tgctcgcgga ctaccgctcg ggcctgctgg acgcggtgcc ggacacccat    7320
ctgctgggcg ccggcgcgat caaccgcaac agcgcgtcgc tagacgaggc cgttcaagca    7380
ctggcggtca acctgaagaa gcggttgccg ccgaccgacc tgacgacggc gcagctacgc    7440
tcgcgttcgt ggtggagcgg atttgacgtc gtgcttctgg tcgacgattg gcacatgatc    7500
gtgggtgccg ccggggggat gccgccgatg gcaccgctgg ccccgttatt gccggcggcg    7560
gcagatatcg ggttgcacat cattgtcacc tgtcagatga gccaggctta caaggcaacc    7620
atggacaagt tcgtcggcgc cgcattcggg tcgggcgctc cgacaatgtt cctttcgggc    7680
gagaagcagg aattcccatc cagtgagttc aaggtcaagc ggcgcccccc tggccaggca    7740
tttctcgtct cgccagacgg caaagaggtc atccaggccc cctacatcga gcctccagaa    7800
gaagtgttcg cagcaccccc aagcgccggt taagattatt tcattgccgg tgtagcagga    7860
cccgagctca gccggtaat cgagttcggg caatgctgac catcgggttt gtttccggct    7920
ataccgaac ggtttgtgta cgggatacaa atacagggag ggaagaagta ggcaaatgga    7980
aaaaatgtca catgatccga tcgctgccga cattggcacg caagtgagcg acaacgctct    8040
gcacggcgtg acggccggct cgacggcgct gacgtcggtg accgggctgg ttcccgcggg    8100
ggccgatgag gtctccgccc aagcggcgac ggcgttcaca tcggagggca tccaattgct    8160
ggcttccaat gcatcggccc aagaccagct ccaccgtgcg ggcgaagcgg tccaggacgt    8220
```

```
cgcccgcacc tattcgcaaa tcgacgacgg cgccgccggc gtcttcgccg aataggcccc   8280
caacacatcg gagggagtga tcaccatgct gtggcacgca atgccaccgg agctaaatac   8340
cgcacggctg atggccggcg cgggtccggc tccaatgctt gcggcggccg cgggatggca   8400
gacgctttcg gcggctctgg acgctcaggc cgtcgagttg accgcgcgcc tgaactctct   8460
gggagaagcc tggactggag gtggcagcga caaggcgctt gcggctgcaa cgccgatggt   8520
ggtctggcta caaaccgcgt caacacaggc caagacccgt gcgatgcagg cgacggcgca   8580
agccgcggca tacacccagg ccatggccac gacgccgtcg ctgccggaga tcgccgccaa   8640
ccacatcacc caggccgtcc ttacggccac caacttcttc ggtatcaaca cgatcccgat   8700
cgcgttgacc gagatggatt atttcatccg tatgtggaac caggcagccc tggcaatgga   8760
ggtctaccag gccgagaccg cggttaacac gcttttcgag aagctcgagc cgatggcgtc   8820
gatccttgat cccggcgcga ccagagcac gacgaacccg atcttcggaa tgccctcccc   8880
tggcagctca acaccggttg ccagttgcc gccggcggct acccagaccc tcggccaact   8940
gggtgagatg agcggcccga tgcagcagct gacccagccg ctgcagcagg tgacgtcgtt   9000
gttcagccag gtgggcggca ccggcggcgg caacccagcc gacgaggaag ccgcgcagat   9060
gggcctgctc ggcaccagtc cgctgtcgaa ccatccgctg gctggtggat caggccccag   9120
cgcgggcgcg ggcctgctgc gcgcggagtc gctacctggc gcaggtgggt cgttgacccg   9180
cacgccgctg atgtctcagc tgatcgaaaa gccggttgcc ccctcggtga tgccggcggc   9240
tgctgccgga tcgtcggcga cgggtggcgc cgctccggtg ggtgcgggag cgatgggcca   9300
gggtgcgcaa tccggcggct ccaccaggcc gggtctggtc gcgccggcac cgctcgcgca   9360
ggagcgtgaa gaagacgacg aggacgactg ggacgaagag gacgactggt gagctcccgt   9420
aatgacaaca gacttcccgg ccacccgggc cggaagactt gccaacattt tggcgaggaa   9480
ggtaaagaga gaaagtagtc cagcatggca gagatgaaga ccgatgccgc taccctcgcg   9540
caggaggcag gtaatttcga gcggatctcc ggcgacctga aaacccagat cgaccaggtg   9600
gagtcgacgg caggttcgtt gcagggccag tggcgcggcg cggcggggac ggccgcccag   9660
gccgcggtgg tgcgcttcca agaagcagcc aataagcaga agcaggaact cgacgagatc   9720
tcgacgaata ttcgtcaggc cggcgtccaa tactcgaggg ccgacgagga gcagcagcag   9780
gcgctgtcct cgcaaatggg cttctgaccc gctaatacga aaagaaacgg agcaaaaaca   9840
tgacagagca gcagtggaat tcgcgggta tcgaggccgc ggcaagcgca atccagggaa   9900
atgtcacgtc cattcattcc ctccttgacg aggggaagca gtccctgacc aagctcgcag   9960
cggcctgggg cggtagcggt tcggaggcgt accagggtgt ccagcaaaaa tgggacgcca   10020
cggctaccga gctgaacaac gcgctgcaga acctggcgcg gacgatcagc gaagccggtc   10080
aggcaatggc ttcgaccgaa ggcaacgtca ctgggatgtt cgcatagggc aacgccgagt   10140
tcgcgtagaa tagcgaaaca cgggatcggg cgagttcgac cttccgtcgg tctcgccctt   10200
tctcgtgttt atacgtttga gcgcactctg agaggttgtc atggcggccg actacgacaa   10260
gctcttccgg ccgcacgaag gtatggaagc tccggacgat atggcagcgc agccgttctt   10320
cgaccccagt gcttcgtttc cgccggcgcc cgcatcggca aacctaccga agcccaacgg   10380
ccagactccg cccccgacgt ccgacgacct gtcggagcgg ttcgtgtcgg ccccgccgcc   10440 gccacccca ccccaccctc cgcctccgcc aactccgatg ccgatcgccg caggagagcc   10500
gccctcgccg gaaccggccg catctaaacc acccacaccc cccatgccca tcgcggacc    10560 cgaaccggcc ccacccaaac cacccacacc cccatgccca atcgccggac ccgaaccggc   10620
```

```
cccacccaaa ccacccacac ctccgatgcc catcgccgga cctgcaccca ccccaaccga   10680
atcccagttg gcgccccca gaccaccgac accacaaacg ccaaccggag cgccgcagca     10740
accggaatca ccggcgcccc acgtaccctc gcacgggcca catcaacccc ggcgcaccgc    10800
accagcaccg ccctgggcaa agatgccaat cggcgaaccc ccgcccgctc cgtccagacc    10860
gtctgcgtcc ccggccgaac caccgacccg gcctgccccc caacactccc gacgtgcgcg    10920
ccggggtcac cgctatcgca cagacaccga acgaaacgtc gggaaggtag caactggtcc    10980
atccatccag gcgcggctgc gggcagagga agcatccggc gcgcagctcg ccccggaac     11040
ggagccctcg ccagcgccgt tgggccaacc gagatcgtat ctggctccgc ccacccgccc    11100
cgcgccgaca gaacctcccc ccagcccctc gccgcagcgc aactccggtc ggcgtgccga    11160
gcgacgcgtc cacccgatt tagccgccca acatgccgcg gcgcaacctg attcaattac     11220
ggccgcaacc actggcggtc gtcgccgcaa gcgtgcagcg ccggatctcg acgcgacaca    11280
gaaatcctta aggccggcgg ccaagggcc gaaggtgaag aaggtgaagc cccagaaacc     11340
gaaggccacg aagccgccca aagtggtgtc gcagcgcggc tggcgacatt gggtgcatgc    11400
gttgacgcga atcaacctgg gcctgtcacc cgacgagaag tacgagctgg acctgcacgc    11460
tcgagtccgc cgcaatcccc gcgggtcgta tcagatcgcc gtcgtcggtc tcaaaggtgg    11520
ggctggcaaa accacgctga cagcagcgtt ggggtcgacg ttggctcagg tgcgggccga    11580
ccggatcctg gctctagacg cggatccagg cgccggaaac ctcgccgatc gggtagggcg    11640
acaatcgggc gcgaccatcg ctgatgtgct tgcagaaaaa gagctgtcgc actacaacga    11700
catccgcgca cacactagcg tcaatgcggt caatctggaa gtgctgccgg caccggaata    11760
cagctcggcg cagcgcgcgc tcagcgacgc cgactggcat ttcatcgccg atcctgcgtc    11820
gaggttttac aacctcgtct tggctgattg tggggccggc ttcttcgacc cgctgacccg    11880
cggcgtgctg tccacggtgt ccggtgtcgt ggtcgtggca agtgtctcaa tcgacgcgc     11940
acaacaggcg tcggtcgcgt tggactggtt gcgcaacaac ggttaccaag atttggcgag    12000
ccgcgcatgc gtggtcatca atcacatcat gccgggagaa cccaatgtcg cagttaaaga    12060
cctggtgcgg catttcgaac agcaagttca acccggccgg gtcgtggtca tgccgtggga    12120
caggcacatt gcggccggaa ccgagatttc actcgacttg ctcgacccta tctacaagcg    12180
caaggtcctc gaattggccg cagcgctatc cgacgatttc gagagggctg gacgtcgttg    12240
agcgcacctg ctgttgctgc tggtcctacc gccgcggggg caaccgctgc gcggcctgcc    12300
accacccggg tgacgatcct gaccggcaga cggatgaccg atttggtact gccagcggcc    12360
gtgccgatgg aaacttatat tgacgacacc gtcgcggtgc tttccgaggt gttggaagac    12420
acgccggctg atgtactcgg cggcttcgac tttaccgcgc aaggcgtgtg ggcgttcgct    12480
cgtcccggat cgccgccgct gaagctcgac cagtcactcg atgacgccgg ggtggtcgac    12540
gggtcactgc tgactctggt gtcagtcagt cgcaccgagc gctaccgacc gttggtcgag    12600
gatgtcatcg acgcgatcgc cgtgcttgac gagtcacctg agttcgaccg cacggcattg    12660
aatcgctttg tgggggcggc gatcccgctt ttgaccgcgc ccgtcatcgg gatgcgcatg    12720
cgggcgtggt gggaaactgg gcgtagcttg tggtggccgt tggcgattgg catcctgggg    12780
atcgctgtgc tggtaggcag cttcgtcgcg aacaggttct accagagcgg ccacctggcc    12840
gagtgcctac tggtcacgac gtatctgctg atcgcaaccg ccgcagcgct ggccgtgccg    12900
ttgccgcgcg gggtcaactc gttggggcg ccacaagttg ccggcgccgc tacgccgtg     12960
ctgttttga ccttgatgac gcggggcggc cctcggaagc gtcatgagtt ggcgtcgttt     13020
```

| | |
|---|---|
| gccgtgatca ccgctatcgc ggtcatcgcg ccgccgctg ccttcggcta tggataccag | 13080 |
| gactgggtcc ccgcgggggg gatcgcattc gggctgttca ttgtgacgaa tgcggccaag | 13140 |
| ctgaccgtcg cggtcgcgcg gatcgcgctg ccgccgattc cggtacccgg cgaaaccgtg | 13200 |
| gacaacgagg agttgctcga tcccgtcgcg accccggagg ctaccagcga agaaaccccg | 13260 |
| acctggcagg ccatcatcgc gtcggtgccc gcgtccgcgg tccggctcac cgagcgcagc | 13320 |
| aaactggcca agcaacttct gatcggatac gtcacgtcgg gcaccctgat tctggctgcc | 13380 |
| ggtgccatcg cggtcgtggt gcgcgggcac ttctttgtac acagcctggt ggtcgcgggt | 13440 |
| ttgatcacga ccgtctgcgg atttcgctcg ggctttacg ccgagcgctg gtgtgcgtgg | 13500 |
| gcgttgctgg cggcgacggt cgcgattccg acgggtctga cggccaaact catcatctgg | 13560 |
| tacccgcact atgcctggct gttgttgagc gtctacctca cggtagccct ggttgcgctc | 13620 |
| gtggtggtcg ggtcgatggc tcacgtccgg cgcgttcac cggtcgtaaa acgaactctg | 13680 |
| gaattgatcg acgcgccat gatcgctgcc atcattccca tgctgctgtg gatcaccggg | 13740 |
| gtgtacgaca cggtccgcaa tatccggttc tga | 13773 |

<210> SEQ ID NO 3
<211> LENGTH: 3909
<212> TYPE: DNA
<213> ORGANISM: Mycobacterium tuberculosis
<220> FEATURE:
<223> OTHER INFORMATION: RD1-AP34 (a 3909 bp fragment of the M.
tuberculosis H37Rv genome)

<400> SEQUENCE: 3

| | |
|---|---|
| gaattcccat ccagtgagtt caaggtcaag cggcgccccc ctggccaggc atttctcgtc | 60 |
| tcgccagacg gcaaagaggt catccaggcc ccctacatcg agcctccaga agaagtgttc | 120 |
| gcagcacccc caagcgccgg ttaagattat ttcattgccg gtgtagcagg acccgagctc | 180 |
| agcccggtaa tcgagttcgg gcaatgctga ccatcgggtt tgtttccggc tataaccgaa | 240 |
| cggtttgtgt acgggataca aatacaggga gggaagaagt aggcaaatgg aaaaaatgtc | 300 |
| acatgatccg atcgctgccg acattggcac gcaagtgagc gacaacgctc tgcacggcgt | 360 |
| gacggccggc tcgacggcgc tgacgtcggt gaccgggctg gttcccgcgg gggccgatga | 420 |
| ggtctccgcc caagcggcga cggcgttcac atcggagggc atccaattgc tggcttccaa | 480 |
| tgcatcggcc caagaccagc tccaccgtgc gggcgaagcg gtccaggacg tcgcccgcac | 540 |
| ctattcgcaa atcgacgacg gcgccgccgg cgtcttcgcc gaataggccc ccaacacatc | 600 |
| ggagggagtg atcaccatgc tgtggcacgc aatgccaccg gagctaaata ccgcacggct | 660 |
| gatggccggc gcgggtccgg ctccaatgct tgcggcggcc gcgggatggc agacgctttc | 720 |
| ggcggctctg gacgctcagg ccgtcgagtt gaccgcgcgc ctgaactctc tgggagaagc | 780 |
| ctggactgga ggtggcagcg acaaggcgct tgcggctgca acgccgatgg tggtctggct | 840 |
| acaaaccgcg tcaacacagg ccaagacccg tgcgatgcag cgacggcgc aagccgcggc | 900 |
| atacacccag gccatggcca cgacgccgtc gctgccggag atcgccgcca accacatcac | 960 |
| ccaggccgtc cttacggcca ccaacttctt cggtatcaac acgatcccga tcgcgttgac | 1020 |
| cgagatggat tatttcatcc gtatgtggaa ccaggcagcc ctggcaatgg aggtctacca | 1080 |
| ggccgagacc gcggttaaca cgcttttcga agctcgag ccgatggcgt cgatccttga | 1140 |
| tcccggcgcg agccagagca cgacgaaccc gatcttcgga atgccctccc ctggcagctc | 1200 |
| aacaccggtt ggccagttgc cgccggcggc tacccagacc ctcggccaac tgggtgagat | 1260 |
| gagcggcccg atgcagcagc tgacccagcc gctgcagcag gtgacgtcgt tgttcagcca | 1320 |

```
ggtgggcggc accggcggcg gcaacccagc cgacgaggaa gccgcgcaga tgggcctgct    1380
cggcaccagt ccgctgtcga accatccgct ggctggtgga tcaggcccca gcgcgggcgc    1440
gggcctgctg cgcgcggagt cgctacctgg cgcaggtggg tcgttgaccc gcacgccgct    1500
gatgtctcag ctgatcgaaa agccggttgc cccctcggtg atgccggcgg ctgctgccgg    1560
atcgtcggcg acgggtggcg ccgctccggt gggtgcggga gcgatgggcc agggtgcgca    1620
atccggcggc tccaccaggc cgggtctggt cgcgccggca ccgctcgcgc aggagcgtga    1680
agaagacgac gaggacgact gggacgaaga ggacgactgg tgagctcccg taatgacaac    1740
agacttcccg gccacccggg ccggaagact tgccaacatt ttggcgagga aggtaaagag    1800
agaaagtagt ccagcatggc agagatgaag accgatgccg ctaccctcgc gcaggaggca    1860
ggtaatttcg agcggatctc cggcgacctg aaaacccaga tcgaccaggt ggagtcgacg    1920
gcaggttcgt tgcagggcca gtggcgcggc gcgcgggga cggccgccca ggccgcggtg    1980
gtgcgcttcc aagaagcagc caataagcag aagcaggaac tcgacgagat ctcgacgaat    2040
attcgtcagg ccggcgtcca atactcgagg gccgacgagg agcagcagca ggcgctgtcc    2100
tcgcaaatgg gcttctgacc cgctaatacg aaaagaaacg gagcaaaaac atgacagagc    2160
agcagtggaa tttcgcgggt atcgaggccg cggcaagcgc aatccaggga aatgtcacgt    2220
ccattcattc cctccttgac gaggggaagc agtccctgac caagctcgca gcggcctggg    2280
gcggtagcgg ttcggaggcg taccaggtg tccagcaaaa atgggacgcc acggctaccg    2340
agctgaacaa cgcgctgcag aacctggcgc ggacgatcag cgaagccggt caggcaatgg    2400
cttcgaccga aggcaacgtc actgggatgt tcgcataggg caacgccgag ttcgcgtaga    2460
atagcgaaac acgggatcgg gcgagttcga ccttccgtcg gtctcgccct ttctcgtgtt    2520
tatacgtttg agcgcactct gagaggttgt catggcggcc gactacgaca agctcttccg    2580
gccgcacgaa ggtatggaag ctccggacga tatggcagcg cagccgttct tcgaccccag    2640
tgcttcgttt ccgccggcgc ccgcatcggc aaacctaccg aagcccaacg gccagactcc    2700
gcccccgacg tccgacgacc tgtcggagcg gttcgtgtcg gccccgccgc cgccaccccc    2760 accccccacct ccgcctccgc caactccgat gccgatcgcc gcaggagagc cgccctcgcc    2820
ggaaccggcc gcatctaaac cacccacacc ccccatgccc atcgccggac ccgaaccggc    2880
cccacccaaa ccacccacac cccccatgcc catcgccgga cccgaaccgg ccccacccaa    2940
accacccaca cctccgatgc ccatcgccgg acctgcaccc accccaaccg aatcccagtt    3000
ggcgcccccc agaccaccga caccacaaac gccaaccgga gcgccgcagc aaccggaatc    3060
accggcgccc cacgtacccct cgcacgggcc acatcaaccc cggcgcaccg caccagcacc    3120
gccctgggca agatgccaa tcggcgaacc cccgcccgct ccgtccagac cgtctgcgtc    3180 cccgccgaa ccaccgaccc ggcctgcccc ccaacactcc cgacgtgcgc gccgggtca    3240 ccgctatcgc acagacaccg aacgaaacgt cgggaaggta gcaactggtc catccatcca    3300
ggcgcggctg cgggcagagg aagcatccgg cgcgcagctc gccccggaa cggagccctc    3360 gccagcgccg ttgggccaac cgagatcgta tctggctccg cccacccgcc ccgcgccgac    3420
agaacctccc cccagcccct cgccgcagcg caactccggt cggcgtgccg agcgacgcgt    3480
ccaccccgat ttagccgccc aacatgccgc ggcgcaacct gattcaatta cggccgcaac    3540
cactggcggt cgtcgccgca agcgtgcagc gccggatctc gacgcgacac agaaatcctt    3600
aaggccggcg gccaagggc cgaaggtgaa gaaggtgaag ccccagaaac cgaaggccac    3660
gaagccgccc aaagtggtgt cgcagcgcgg ctggcgacat tgggtgcatg cgttgacgcg    3720
```

```
aatcaacctg ggcctgtcac ccgacgagaa gtacgagctg gacctgcacg ctcgagtccg    3780
ccgcaatccc cgcgggtcgt atcagatcgc cgtcgtcggt ctcaaaggtg gggctggcaa    3840
aaccacgctg acagcagcgt tggggtcgac gttggctcag gtgcgggccg accggatcct    3900
ggctctaga                                                            3909

<210> SEQ ID NO 4
<211> LENGTH: 324
<212> TYPE: DNA
<213> ORGANISM: Mycobacterium tuberculosis
<220> FEATURE:
<223> OTHER INFORMATION: DNA sequence Rv3861

<400> SEQUENCE: 4
gtgacctggc tggctgaccc ggtcggcaac agcaggatcg cccgagcgca ggcctgcaaa     60
acgtcaatct cggcgcccat cgtcgaatcc tggcgggcgc aacgcggcgc gcaatgtgga    120
cagcgcgaga aatcttgtcg atgttctcgc gctgtccaca tccagggcat ctcaccgcca    180
ctgttccgca gaccccctcga accagcggtc caggcggcgg ttgcgtcatg ccgattgggc    240 agacaccogg tggtcgcgca ccgggtaacc gttgcgctcg ccagggatc gcagctggcc    300 caacgcgaat gcccgcgccc ggcc                                           324

<210> SEQ ID NO 5
<211> LENGTH: 348
<212> TYPE: DNA
<213> ORGANISM: Mycobacterium tuberculosis
<220> FEATURE:
<223> OTHER INFORMATION: DNA sequence Rv3862c-whiB6

<400> SEQUENCE: 5
atgcgatacg ctttcgcggc agaggctaca acctgcaacg ctttctggag gaacgtagac     60
atgacagtaa ccgccctgta tgaggtcccg ctcggcgttt gcacgcaaga tcccgatcgt    120
tggacgacga ctcccgacga cgaggccaag accctgtgcc gggcttgccc cgcgccggtgg   180 ctgtgtgcac gcgacgccgt cgagtccgcg ggtgcggaag gctgtgggc aggggtcgta    240 attcccgaat caggccgggc gcgggcattc gcgttgggcc agctgcgatc cctggccgag    300
cgcaacggtt acccggtgcg cgaccaccgg gtgtctgccc aatcggca                 348

<210> SEQ ID NO 6
<211> LENGTH: 1176
<212> TYPE: DNA
<213> ORGANISM: Mycobacterium tuberculosis
<220> FEATURE:
<223> OTHER INFORMATION: DNA sequence RV3863

<400> SEQUENCE: 6
atggcgggcg agcggaaagt ctgcccaccg tcccggctag tacccgcgaa taagggatca     60
acgcagatgt ctaaagcagg gtcgactgtc ggaccggcgc cgctggtcgc gtgcagcggc    120
ggcacatcag acgtgattga gccccgtcgc ggtgtcgcga tcattggcca ctcgtgccga    180
gtcggcaccc agatcgacga ttctcgaatc tctcagacac atctgcgagc ggtatccgat    240
gatggacggt ggcggatcgt cggcaacatc ccgagaggta tgttcgtcgg cggacgacgc    300
ggcagctcgg tgaccgtcag cgataagacc ctaatccgat cggcgatcc cctggaggc     360 aaggcgttga cgttcgaagt cgtcaggcc tcggattccg ctgcacagca cggccgcgta    420
caaccatcag cggacctgtc ggacgacccg gcgcacaacg ctgcgccggt cgcaccggac    480
cccggcgtgg ttcgcgcagg ggcggccgcg gctgcgcgcc gtcgtgaact tgacatcagc    540
```

```
caacgcagct tggcggccga cgggatcatc aacgcgggcg cgctcatcgc gttcgagaaa      600
ggccgtagtt ggccccggga acggacccgg gcaaaactcg aagaagtgct gcagtggccc      660
gctggaacca tcgcgcgaat ccgtcggggc gagcccaccg agcccgcaac aaaccccgac      720
gcgtcccccg gactccggcc tgccgacggc ccggcgtcct tgatcgcgca ggctgtcacc      780
gccgccgtag acggctgcag tctggctatc gcagcgttgc cggcgaccga gaccccgag       840 ttcaccgaac gtgccgcgcc gatccttgct gatttgcgcc agctcgaggc gattgccgtc      900
caagcaaccc gcatcagccg gattaccccg gaattgatca aggcgttggg cgcggtacgt      960
cgccaccacg acgaattaat gaggctggga gcaaccgccc ctggtgccac actggcgcag     1020
cgcttatatg ccgcacggcg gcgcgcgaac ctttccaccc tggagactgc caagcggcc      1080 ggcgtcgcag aagaaatgat cgtcggcgcc gaagccgagg aagagttgcc agccgaggcc     1140
accgaagcga tcgaagcact gatccgtcag atcaat                               1176

<210> SEQ ID NO 7
<211> LENGTH: 1206
<212> TYPE: DNA
<213> ORGANISM: Mycobacterium tuberculosis
<220> FEATURE:
<223> OTHER INFORMATION: DNA sequence Rv3864

<400> SEQUENCE: 7
atggcatcgg gtagcggtct ttgcaagacg acgagtaact ttatttgggg ccagttactc       60
ttgcttggag agggaatccc cgacccaggc gacattttca acaccggttc gtcgctgttc      120
aaacaaatca gcgacaaaat gggactcgcc attccgggca ccaactggat cggccaagcg      180
gcggaagctt acctaaaacca gaacatcgcg caacaacttc gcgcacaggt gatgggcgat      240
ctcgacaaat taaccggcaa catgatctcg aatcaggcca aatacgtctc cgatacgcgc      300
gacgtcctgc gggccatgaa gaagatgatt gacggtgtct acaaggtttg taagggcctc      360
gaaaagattc cgctgctcgg ccacttgtgg tcgtgggagc tcgcaatccc tatgtccggc      420
atcgcgatgg ccgttgtcgg cggcgcattg ctctatctaa cgattatgac gctgatgaat      480
gcgaccaacc tgaggggaat tctcggcagg ctgatcgaga tgttgacgac cttgccaaag      540
ttccccggcc tgcccgggtt gcccagcctg cccgacatca tcgacggcct ctggccgccg      600
aagttgcccg acattccgat ccccggcctg cccgacatcc cgggcctacc cgacttcaaa      660
tggccgccca cccccggcag cccgttgttc ccgacctcc gtcgttccc agggttcccc        720 gggttcccgg agttccccgc catccccggg ttccccgcac tgcccgggtt gcccagcatt      780
cccaacttgt tccccggctt gccggtctg ggcgacctgc tgcccggcgt aggcgatttg       840
ggcaagttac ccacctggac tgagctggcc gctttgcctg acttcttggg cggcttcgcc      900
ggcctgccca gcttgggttt tggcaatctg ctcagctttg ccagtttgcc caccgtgggt      960
caggtgaccg ccaccatggg tcagctgcaa cagctcgtgg cggccggcgg tggccccagc     1020
caactggcca gcatgggcag ccaacaagcg caactgatct cgtcgcaggc ccagcaagga     1080
ggccagcagc acgccaccct cgtgagcgac aagaaggaag cgaggaagg cgtggccgag      1140 gcggagcgtg cacccatcga cgctggcacc gcggccagcc aacgggggca ggagggggacc    1200 gtccctt                                                               1206

<210> SEQ ID NO 8
<211> LENGTH: 309
<212> TYPE: DNA
<213> ORGANISM: Mycobacterium tuberculosis
```

<220> FEATURE:
<223> OTHER INFORMATION: DNA sequence Rv3865

<400> SEQUENCE: 8

| | | | | | |
|---|---|---|---|---|---|
| atgaccggat | ttctcggtgt | cgtgccttcg | ttcctgaagg | tgctggcggg | catgcacaac | 60 |
| gagatcgtgg | gtgatatcaa | aagggcgacc | gatacggtcg | ccgggattag | cggacgagtt | 120 |
| cagcttaccc | atggttcgtt | cacgtcgaaa | ttcaatgaca | cgctgcaaga | gtttgagacc | 180 |
| acccgtagca | gcacgggcac | gggttttgcag | ggagtcacca | gcggactggc | caataatctg | 240 |
| ctcgcagccg | ccggcgccta | cctcaaggcc | gacgatggcc | tagccggtgt | tatcgacaag | 300 |
| attttcggt | | | | | | 309 |

<210> SEQ ID NO 9
<211> LENGTH: 849
<212> TYPE: DNA
<213> ORGANISM: Mycobacterium tuberculosis
<220> FEATURE:
<223> OTHER INFORMATION: DNA sequence Rv3866

<400> SEQUENCE: 9

| | | | | | |
|---|---|---|---|---|---|
| atgacgggtc | cgtccgctgc | aggccgcgcg | ggcaccgccg | acaacgtggt | cggcgtcgag | 60 |
| gtaaccatcg | acggcatgtt | ggtgatcgcc | gatcggttac | acctggttga | tttccctgtc | 120 |
| acgcttggga | ttcggccgaa | tatcccgcaa | gaggatctgc | gagacatcgt | ctgggaacag | 180 |
| gtgcagcgtg | acctcacagc | gcaaggggtg | ctcgacctcc | acggggagcc | caaccgacg | 240 |
| gtcgcggaga | tggtcgaaac | cctgggcagg | ccagatcgga | ccttggaggg | tcgctggtgg | 300 |
| cggcgcgaca | ttggcggcgt | catggtgcgc | ttcgtcgtgt | gccgcagggg | cgaccgccat | 360 |
| gtgatcgcgg | cgcgcgacgg | cgacatgctg | gtgctgcagt | tggtggcgcc | gcaggtcggc | 420 |
| ttggcgggca | tggtgacagc | ggtgctgggg | cccgccgaac | ccgccaacgt | cgaacccctg | 480 |
| acgggtgtgg | caaccgagct | agccgaatgc | acaaccgcgt | cccaattgac | gcaatacgt | 540 |
| atcgcaccgg | cctcggcccg | cgtctatgcc | gagatcgtgg | gtaacccgac | cggctgggtg | 600 |
| gagatcgttg | ccagccaacg | ccaccccggc | ggcaccacga | cgcagaccga | cgccgccgct | 660 |
| ggcgtcctgg | actccaagct | cggtaggctg | gtgtcgcttc | cccgccgtgt | tggaggcgac | 720 |
| ctgtacggaa | gcttcctgcc | cggcactcag | cagaacttgg | agcgtgcgct | ggacggcttg | 780 |
| ctagagctgc | tccctgcggg | cgcttggcta | gatcacacct | cagatcacgc | acaagcctcc | 840 |
| tcccgaggc | | | | | | 849 |

<210> SEQ ID NO 10
<211> LENGTH: 552
<212> TYPE: DNA
<213> ORGANISM: mycobacterium tuberculosis
<220> FEATURE:
<223> OTHER INFORMATION: DNA sequence Rv3867

<400> SEQUENCE: 10

| | | | | | |
|---|---|---|---|---|---|
| atggtggacc | cgccgggcaa | cgacgacgac | cacggtgatc | tcgacgccct | cgatttctcc | 60 |
| gccgcccaca | ccaacgaggc | gtcgccgctg | gacgccttag | acgactatgc | gccggtgcag | 120 |
| accgatgacg | ccgaaggcga | cctggacgcc | ctccatgcgc | tcaccgaacg | cgacgaggag | 180 |
| ccggagctgg | agttgttcac | ggtgaccaac | cctcaagggt | cggtgtcggt | ctcaaccctg | 240 |
| atggacggca | gaatccagca | cgtcgagctg | acggacaagg | cgaccagcat | gtccgaagcg | 300 |
| cagctggccg | acgagatctt | cgttattgcc | gatctggccc | gccaaaaggc | gcgggcgtcg | 360 |
| cagtacacgt | tcatggtgga | gaacatcggt | gaactgaccg | acgaagacgc | agaaggcagc | 420 |

```
gccctgctgc gggaattcgt ggggatgacc ctgaatctgc cgacgccgga agaggctgcc    480
gcagccgaag ccgaagtgtt cgccacccgc tacgatgtcg actacacctc ccggtacaag    540
gccgatgact ga                                                        552
```

<210> SEQ ID NO 11
<211> LENGTH: 1722
<212> TYPE: DNA
<213> ORGANISM: mycobacterium tuberculosis
<220> FEATURE:
<223> OTHER INFORMATION: DNA sequence Rv3868

<400> SEQUENCE: 11

```
atgactgatc gcttggccag tctgttcgaa agcgccgtca gcatgttgcc gatgtcggag     60
gcgcggtcgc tagatctgtt caccgagatc accaactacg acgaatccgc ttgcgacgca    120
tggatcggcc ggatccggtg tggggacacc gaccgggtga cgctgtttcg cgcctggtat    180
tcgcgccgca atttcggaca gttgtcggga tcggtccaga tctcgatgag cacgttaaac    240
gccaggattg ccatcggggg gctgtacggc gatatcacct acccggtcac ctcgccgcta    300
gcgatcacca tgggctttgc cgcatgcgag gcagcgcaag gcaattacgc cgacgccatg    360
gaggccttag aggccgcccc ggtcgcgggt tccgagcacc tggtggcgtg gatgaaggcg    420
gttgtctacg gcgcggccga acgctggacc gacgtgatcg accaggtcaa gagtgctggg    480
aaatggccgg acaagttttt ggccggcgcg gccggtgtgg cgcacggggt tgccgcggca    540
aacctggcct tgttcaccga agccgaacgc cgactcaccg aggccaacga ctcgcccgcc    600
ggtgaggcgt gtgcgcgcgc catcgcctgg tatctggcga tggcacggcg cagccagggc    660
aacgaaagcg ccgcggtggc gctgctggaa tggttacaga ccactcaccc cgagcccaaa    720
gtggctgcgg cgctgaagga tccctcctac cggctgaaga cgaccaccgc cgaacagatc    780
gcatcccgcg ccgatccctg ggatccgggc agtgtcgtga ccgacaactc cggccgggag    840
cggctgctcg ccgaggccca agccgaactc gaccgccaaa ttgggctcac ccgggttaaa    900
aatcagattg aacgctaccg cgcggcgacg ctgatggccc gggtccgcgc cgccaagggt    960
atgaaggtcg cccagcccag caagcacatg atcttcaccg gaccgccggg taccggcaag   1020
accacgatcg cgcgggtggt ggccaatatc ctggccggct taggcgtcat tgccgaaccc   1080
aaactcgtcg agacgtcgcg caaggacttc gtcgccgagt acgaggggca atcggcggtc   1140
aagaccgcta agacgatcga tcaggcgctg ggcggggtgc ttttcatcga cgaggcttat   1200
gcgctggtgc aggaaagaga cggccgcacc gatccgttcg gtcaagaggc gctggacacg   1260
ctgctggcgc ggatggagaa cgaccgggac cggctggtgg tgatcatcgc cgggtacagc   1320
tccgacatag atcggctgct ggaaaccaac gagggtctgc ggtcgcggtt cgccactcgc   1380
atcgagttcg acacctattc ccccgaggaa ctcctcgaga tcgccaacgt cattgccgct   1440
gctgatgatt cggcgttgac cgcagaggcg gccgagaact tcttcaggc cgccaagcag   1500 ttggagcagc gcatgttgcg cggccggcgc gccctggacg tcgccggcaa cggtcggtat   1560
gcgcgccagc tggtggaggc cagcgagcaa tgccgggaca tgcgtctagc ccaggtcctc   1620
gatatcgaca ccctcgacga agaccggctt cgcgagatca acggctcaga tatggcggag   1680
gctatcgccg cggtgcacgc acacctcaac atgagagaat ga                      1722
```

<210> SEQ ID NO 12
<211> LENGTH: 1443
<212> TYPE: DNA
<213> ORGANISM: mycobacterium tuberculosis -continued
<220> FEATURE:
<223> OTHER INFORMATION: DNA sequence Rv3869

<400> SEQUENCE: 12

| | | | | | |
|---|---|---|---|---|---|
| atggggcttc | gcctcaccac | caaggttcag | gttagcggct | ggcgttttct | gctgcgccgg | 60 |
| ctcgaacacg | ccatcgtgcg | ccgggacacc | cggatgtttg | acgaccccgct | gcagttctac | 120 |
| agccgctcga | tcgctcttgg | catcgtcgtc | gcggtcctga | ttctggcggg | tgccgcgctg | 180 |
| ctggcgtact | tcaaaccaca | aggcaaactc | ggcggcacca | gcctgttcac | cgaccgcgcg | 240 |
| accaaccagc | tttacgtgct | gctgtccgga | cagttgcatc | cggtctacaa | cctgacttcg | 300 |
| gcgcggctgg | tgctgggcaa | tccggccaac | ccggccaccg | tgaagtcctc | cgaactgagc | 360 |
| aagctgccga | tgggccagac | cgttggaatc | cccggcgccc | cctacgccac | gcctgtttcg | 420 |
| gcgggcagca | cctcgatctg | gacccctatgc | gacaccgtcg | cccgagccga | ctccacttcc | 480 |
| ccggtagtgc | agaccgcggt | catcgcgatg | ccgttggaga | tcgatgcttc | gatcgatccg | 540 |
| ctccagtcac | acgaagcggt | gctggtgtcc | taccagggcg | aaacctggat | cgtcacaact | 600 |
| aagggacgcc | acgccataga | tctgaccgac | cgcgccctca | cctcgtcgat | ggggataccg | 660 |
| gtgacggcca | ggccaacccc | gatctcggag | ggcatgttca | acgcgctgcc | tgatatgggg | 720 |
| ccctggcagc | tgccgccgat | accggcggcg | ggcgcgccca | ttcgcttgg | cctacctgat | 780 |
| gatctagtga | tcggatcggt | cttccagatc | cacaccgaca | agggcccgca | atactatgtg | 840 |
| gtgctgcccg | acggcatcgc | gcaggtcaac | gcgacaaccg | ctgcggcgct | gcgcgccacc | 900 |
| caggcgcacg | gctggtcgc | gccaccggca | atggtgccca | gtctggtcgt | cagaatcgcc | 960 |
| gaacgggtat | accctcacc | gctacccgat | gaaccgctca | agatcgtgtc | ccggccgcag | 1020 |
| gatcccgcgc | tgtgctggtc | atggcaacg | agcgccggcg | accagtcgcc | gcagtcaacg | 1080 |
| gtgctgtccg | gccggcatct | gccgatatcg | ccctcagcga | tgaacatggg | gatcaagcag | 1140 |
| atccacggga | cggcgaccgt | ttacctcgac | ggcggaaaat | tcgtggcact | gcaatccccc | 1200 |
| gatcctcgat | acaccgaatc | gatgtactac | atcgatccac | agggcgtgcg | ttatggggtg | 1260 |
| cctaacgcgg | agacagccaa | gtcgctgggc | ctgagttcac | cccaaaacgc | gccctgggag | 1320 |
| atcgttcgtc | tcctggtcga | cggtccggtg | ctgtcgaaag | atgccgcact | gctcgagcac | 1380 |
| gacacgctgc | ccgctgaccc | tagccccga | aaagttcccg | ccggagcctc | cggagccccc | 1440 |
| tga | | | | | | 1443 |

<210> SEQ ID NO 13
<211> LENGTH: 2244
<212> TYPE: DNA
<213> ORGANISM: mycobacterium tuberculosis
<220> FEATURE:
<223> OTHER INFORMATION: DNA sequence Rv3870

<400> SEQUENCE: 13

| | | | | | |
|---|---|---|---|---|---|
| atgacgacca | agaagttcac | tcccaccatt | acccgtggcc | cccggttgac | cccgggcgag | 60 |
| atcagcctca | cgccgcccga | tgacctgggc | atcgacatcc | caccgtcggg | cgtccaaaag | 120 |
| atccttcccct | acgtgatggg | tggcgccatg | ctcggcatga | tcgccatcat | ggtggccggc | 180 |
| ggcaccaggc | agctgtcgcc | gtacatgttg | atgatgccgc | tgatgatgat | cgtgatgatg | 240 |
| gtcgcggtc | tggccggtag | caccggtggt | ggcggcaaga | aggtgcccga | aatcaacgcc | 300 |
| gaccgcaagg | agtacctgcg | gtatttggca | ggactacgca | cccgagtgac | gtcctcggcc | 360 |
| acctctcagg | tggcgttctt | ctcctaccac | gcaccgcatc | ccgaggatct | gttgtcgatc | 420 |
| gtcggcaccc | aacggcagtg | gtcccggccg | gccaacgccg | acttctatgc | ggccacccga | 480 |

| | |
|---|---:|
| atcggtatcg gtgaccagcc ggcggtggat cgattattga agccggccgt cggcggggag | 540 |
| ttggccgccg ccagcgcagc acctcagccg ttcctggagc cggtcagtca tatgtgggtg | 600 |
| gtcaagtttc tacgaaccca tggattgatc catgactgcc cgaaactgct gcaactccgt | 660 |
| acctttccga ctatcgcgat cggcggggac ttggcggggg cagccggcct gatgacggcg | 720 |
| atgatctgtc acctagccgt gttccaccca ccggacctgc tgcagatccg ggtgctcacc | 780 |
| gaggaacccg acgacccccga ctggtcctgg ctcaaatggc ttccgcacgt acagcaccag | 840 |
| accgaaaccg atgcggccgg gtccacccgg ctgatcttca cgcgccagga aggtctgtcg | 900 |
| gacctggccg cgcgcgggcc acacgcaccc gattcgcttc ccggcggccc ctacgtagtc | 960 |
| gtcgtcgacc tgaccggcgg caaggctgga ttcccgcccg acgtagggc cggtgtcacg | 1020 |
| gtgatcacgt tgggcaacca tcgcggctcg gcctaccgca tcagggtgca cgaggatggg | 1080 |
| acggctgatg accggctccc taaccaatcg tttcgccagg tgacatcggt caccgatcgg | 1140 |
| atgtcgccgc agcaagccag ccgtatcgcg cgaaagttgg ccggatggtc catcacgggc | 1200 |
| accatcctcg acaagacgtc gcgggtccag aagaaggtgg ccaccgactg gcaccagctg | 1260 |
| gtcggtgcgc aaagtgtcga ggagataaca ccttcccgct ggaggatgta caccgacacc | 1320 |
| gaccgtgacc ggctaaagat cccgtttggt catgaactaa agaccggcaa cgtcatgtac | 1380 |
| ctggacatca agagggcgc ggaattcggc gccggaccgc acggcatgct catcgggacc | 1440 |
| acggggtctg ggaagtccga attcctgcgc accctgatcc tgtcgctggt ggcaatgact | 1500 |
| catccagatc aggtgaatct cctgctcacc gacttcaaag gtggttcaac cttcctggga | 1560 |
| atggaaaagc ttccgcacac tgccgctgtc gtcaccaaca tggccgagga agccgagctc | 1620 |
| gtcagccgga tgggcgaggt gttgaccgga gaactcgatc ggcgccagtc gatcctccga | 1680 |
| caggccggga tgaaagtcgg cgcggccgga gccctgtccg gcgtggccga atacgagaag | 1740 |
| taccgcgaac gcggtgccga cctacccccg ctgccaacgc ttttcgtcgt cgtcgacgag | 1800 |
| ttcgccgagc tgttgcagag tcacccggac ttcatcgggc tgttcgaccg gatctgccgc | 1860 |
| gtcgggcggt cgctgagggt ccatctgctg ctggctaccc agtcgctgca gaccggcggt | 1920 |
| gttcgcatcg acaaactgga gccaaacctg acatatcgaa tcgcattgcg caccaccagc | 1980 |
| tctcatgaat ccaaggcggt aatcggcaca ccggaggcgc agtacatcac caacaaggag | 2040 |
| agcggtgtcg ggtttctccg ggtcggcatg gaagacccgg tcaagttcag caccttctac | 2100 |
| atcagtgggc catacatgcc gccggcggca ggcgtcgaaa ccaatggtga agccggaggg | 2160 |
| cccggtcaac agaccactag acaagccgcg cgcattcaca ggttcaccgc ggcaccggtt | 2220 |
| ctcgaggagg cgccgacacc gtga | 2244 |

```
<210> SEQ ID NO 14
<211> LENGTH: 1776
<212> TYPE: DNA
<213> ORGANISM: mycobacterium tuberculosis
<220> FEATURE:
<223> OTHER INFORMATION: DNA sequence Rv3871

<400> SEQUENCE: 14
```

| | |
|---|---:|
| atgactgctg aaccggaagt acggacgctg cgcgaggttg tgctggacca gctcggcact | 60 |
| gctgaatcgc gtgcgtacaa gatgtggctg ccgccgttga ccaatccggt cccgctcaac | 120 |
| gagctcatcg cccgtgatcg gcgacaaccc ctgcgatttg ccctggggat catggatgaa | 180 |
| ccgcgccgcc atctacagga tgtgtggggc gtagacgttt ccggggccgg cggcaacatc | 240 |
| ggtattgggg gcgcacctca aaccgggaag tcgacgctac tgcagacgat ggtgatgtcg | 300 |

```
gccgccgcca cacactcacc gcgcaacgtt cagttctatt gcatcgacct aggtggcggc    360
gggctgatct atctcgaaaa ccttccacac gtcggtgggg tagccaatcg gtccgagccc    420
gacaaggtca accgggtggt cgcagagatg caagccgtca tgcggcaacg ggaaaccacc    480
ttcaaggaac accgagtggg ctcgatcggg atgtaccggc agctgcgtga cgatccaagt    540
caacccgttg cgtccgatcc atacggcgac gtctttctga tcatcgacgg atggcccggt    600
tttgtcggcg agttccccga ccttgagggg caggttcaag atctggccgc ccaggggctg    660
gcgttcggcg tccacgtcat catctccacg ccacgctgga cagagctgaa gtcgcgtgtt    720
cgcgactacc tcggcaccaa gatcgagttc cggcttggtg acgtcaatga aacccagatc    780
gaccggatta cccgcgagat cccggcgaat cgtccgggtc gggcagtgtc gatggaaaag    840
caccatctga tgatcggcgt gcccaggttc gacggcgtgc acagcgccga taacctggtg    900
gaggcgatca ccgcggggt gacgcagatc gcttcccagc acaccgaaca ggcacctccg    960
gtgcgggtcc tgccggagcg tatccacctg cacgaactcg acccgaaccc gccgggacca   1020
gagtccgact accgcactcg ctgggagatt ccgatcggct tgcgcgagac ggacctgacg   1080
ccggctcact gccacatgca cacgaacccg cacctactga tcttcggtgc ggccaaatcg   1140
ggcaagacga ccattgccca cgcgatcgcg cgcgccattt gtgcccgaaa cagtccccag   1200
caggtgcggt tcatgctcgc ggactaccgc tcgggcctgc tggacgcggt gccggacacc   1260
catctgctgg gcgccggcgc gatcaaccgc aacagcgcgt cgctagacga ggccgttcaa   1320
gcactggcgg tcaacctgaa gaagcggttg ccgccgaccg acctgacgac ggcgcagcta   1380
cgctcgcgtt cgtggtggag cggatttgac gtcgtgcttc tggtcgacga ttggcacatg   1440
atcgtgggtg ccgccggggg gatgccgccg atggcaccgc tggccccgtt attgccggcg   1500
gcggcagata tcgggttgca catcattgtc acctgtcaga tgagccaggc ttacaaggca   1560
accatggaca agttcgtcgg cgccgcattc gggtcgggcg ctccgacaat gttcctttcg   1620
ggcgagaagc aggaattccc atccagtgag ttcaaggtca agcggcgccc ccctggccag   1680
gcatttctcg tctcgccaga cggcaaagag gtcatccagg cccctacat cgagcctcca   1740 gaagaagtgt tcgcagcacc cccaagcgcc ggttaa                             1776

<210> SEQ ID NO 15
<211> LENGTH: 297
<212> TYPE: DNA
<213> ORGANISM: Mycobacterium tuberculosis
<220> FEATURE:
<223> OTHER INFORMATION: PE coding sequence (Rv3872)

<400> SEQUENCE: 15
atggaaaaaa tgtcacatga tccgatcgct gccgacattg gcacgcaagt gagcgacaac     60
gctctgcacg gcgtgacggc cggctcgacg gcgctgacgt cggtgaccgg gctggttccc    120
gcgggggccg atgaggtctc cgcccaagcg gcgacggcgt tcacatcgga gggcatccaa    180
ttgctggctt ccaatgcatc ggcccaagac cagctccacc gtgcgggcga agcggtccag    240
gacgtcgccc gcacctattc gcaaatcgac gacggcgccg ccggcgtctt cgccgaa       297

<210> SEQ ID NO 16
<211> LENGTH: 1104
<212> TYPE: DNA
<213> ORGANISM: Mycobacterium tuberculosis
<220> FEATURE:
<223> OTHER INFORMATION: PPE coding sequence (Rv3873)

<400> SEQUENCE: 16
```

```
atgctgtggc acgcaatgcc accggagcta ataccgcac ggctgatggc cggcgcgggt      60
ccggctccaa tgcttgcggc ggccgcggga tggcagacgc tttcggcggc tctggacgct     120
caggccgtcg agttgaccgc cgcgcctgaac tctctgggag aagcctggac tggaggtggc    180
agcgacaagg cgcttgcggc tgcaacgccg atggtggtct ggctacaaac cgcgtcaaca    240
caggccaaga cccgtgcgat gcaggcgacg gcgcaagccg cggcatacac ccaggccatg    300
gccacgacgc cgtcgctgcc ggagatcgcc gccaaccaca tcacccaggc cgtccttacg    360
gccaccaact tcttcggtat caacacgatc ccgatcgcgt tgaccgagat ggattatttc    420
atccgtatgt ggaaccaggc agccctggca atggaggtct accaggccga gaccgcggtt    480
aacacgcttt tcgagaagct cgagccgatg gcgtcgatcc ttgatcccgg cgcgagccag    540
agcacgacga acccgatctt cggaatgccc tcccctggca gctcaacacc ggttggccag    600
ttgccgccgg cggctaccca gaccctcggc caactgggtg agatgagcgg cccgatgcag    660
cagctgaccc agccgctgca gcaggtgacg tcgttgttca gccaggtggg cggcaccggc    720
ggcggcaacc cagccgacga ggaagccgcg cagatgggcc tgctcggcac cagtccgctg    780
tcgaaccatc cgctggctgg tggatcaggc cccagcgcgg gcgcgggcct gctgcgcgcg    840
gagtcgctac ctggcgcagg tgggtcgttg accgcacgc cgctgatgtc tcagctgatc    900
gaaaagccgg ttgcccctc ggtgatgccg gcggctgctg ccggatcgtc ggcgacgggt     960
ggcgccgctc cggtgggtgc gggagcgatg ggccagggtg cgcaatccgg cggctccacc   1020
aggccgggtc tggtcgcgcc ggcaccgctc gcgcaggagc gtgaagaaga cgacgaggac   1080
gactgggacg aagaggacga ctgg                                          1104
```

<210> SEQ ID NO 17
<211> LENGTH: 300
<212> TYPE: DNA
<213> ORGANISM: Mycobacterium tuberculosis
<220> FEATURE:
<223> OTHER INFORMATION: CFP-10 coding sequence (Rv3874)

<400> SEQUENCE: 17

```
atggcagaga tgaagaccga tgccgctacc ctcgcgcagg aggcaggtaa tttcgagcgg     60
atctccggcg acctgaaaac ccagatcgac caggtggagt cgacggcagg ttcgttgcag    120
ggccagtggc gcggcgcggc ggggacggcc gcccaggccg cggtggtgcg cttccaagaa    180
gcagccaata agcagaagca ggaactcgac gagatctcga cgaatattcg tcaggccggc    240
gtccaatact cgagggccga cgaggagcag cagcaggcgc tgtcctcgca aatgggcttc    300
```

<210> SEQ ID NO 18
<211> LENGTH: 285
<212> TYPE: DNA
<213> ORGANISM: Mycobacterium tuberculosis
<220> FEATURE:
<223> OTHER INFORMATION: ESAT-6 coding sequence (Rv3875)

<400> SEQUENCE: 18

```
atgacagagc agcagtggaa tttcgcgggt atcgaggccg cggcaagcgc aatccaggga     60
aatgtcacgt ccattcattc cctccttgac gaggggaagc agtccctgac caagctcgca    120
gcggcctggg gcggtagcgg ttcggaggcg taccagggtg tccagcaaaa atgggacgcc    180
acggctaccg agctgaacaa cgcgctgcag aacctggcgc ggacgatcag cgaagccggt    240
caggcaatgg cttcgaccga aggcaacgtc actgggatgt tcgca                    285
```

```
<210> SEQ ID NO 19
<211> LENGTH: 2001
<212> TYPE: DNA
<213> ORGANISM: mycobacterium tuberculosis
<220> FEATURE:
<223> OTHER INFORMATION: DNA sequence Rv3876

<400> SEQUENCE: 19
atggcggccg actacgacaa gctcttccgg ccgcacgaag gtatggaagc tccggacgat     60
atggcagcgc agccgttctt cgaccccagt gcttcgtttc cgccggcgcc cgcatcggca    120
aacctaccga agcccaacgg ccagactccg cccccgacgt ccgacgacct gtcggagcgg    180
ttcgtgtcgg ccccgccgcc gccaccccca cccccacctc cgcctccgcc aactccgatg    240
ccgatcgccg caggagagcc gccctcgccg gaaccggccg catctaaacc acccacaccc    300
cccatgccca tcgccggacc cgaaccggcc cacccaaaac acccacaccc cccatgccc     360 atcgccggac ccgaaccggc cccacccaaa ccacccacac ctccgatgcc catcgccgga    420
cctgcaccca ccccaaccga atcccagttg gcgccccca gaccaccgac accacaaacg     480
ccaaccggag cgccgcagca accggaatca ccggcgcccc acgtaccctc gcacgggcca    540
catcaacccc ggcgcaccgc accagcaccg ccctgggcaa agatgccaat cggcgaaccc    600
ccgcccgctc cgtccagacc gtctgcgtcc ccggccgaac caccgacccg gcctgccccc    660
caacactccc gacgtgcgcg ccggggtcac cgctatcgca cagacaccga acgaaacgtc    720
gggaaggtag caactggtcc atccatccag gcgcggctgc gggcagagga agcatccggc    780
gcgcagctcg cccccggaac ggagccctcg ccagcgccgt tgggccaacc gagatcgtat    840
ctggctccgc ccaccgccc cgcgccgaca gaacctcccc ccagccctc gccgcagcgc    900 aactccggtc ggcgtgccga cgacgcgtc caccccgatt tagccgccca acatgccgcg    960
gcgcaacctg attcaattac ggccgcaacc actggcggtc gtcgccgcaa cgtgcagcg    1020 ccggatctcg acgcgacaca gaaatcctta aggccggcgg ccaaggggcc gaaggtgaag   1080
aaggtgaagc cccagaaacc gaaggccacg aagccgccca agtggtgtc gcagcgcggc   1140 tggcgacatt gggtgcatgc gttgacgcga atcaacctgg gcctgtcacc cgacgagaag   1200
tacgagctgg acctgcacgc tcgagtccgc cgcaatcccc gcgggtcgta tcagatcgcc   1260
gtcgtcggtc tcaaaggtgg ggctggcaaa accacgctga cagcagcgtt ggggtcgacg   1320
ttggctcagg tgcgggccga ccggatcctg gctctagacg cggatccagg cgccggaaac   1380
ctcgccgatc gggtagggcg acaatcgggc gcgaccatcg ctgatgtgct tgcagaaaaa   1440
gagctgtcgc actacaacga catccgcgca cacactagcg tcaatgcggt caatctggaa   1500
gtgctgccgg caccggaata cagctcggcg cagcgcgcgc tcagcgacgc cgactggcat   1560
ttcatcgccg atcctgcgtc gaggttttac aacctcgtct tggctgattg tggggccggc   1620
ttcttcgacc cgctgacccg cggcgtgctg tccacggtgt ccggtgtcgt ggtcgtggca   1680
agtgtctcaa tcgacggcgc acaacaggcg tcggtcgcgt tggactggtt gcgcaacaac   1740
ggttaccaag atttggcgag ccgcgcatgc gtggtcatca atcacatcat gccgggagaa   1800
cccaatgtcg cagttaaaga cctggtgcgg catttcgaac agcaagttca acccggccgg   1860
gtcgtggtca tgccgtggga caggcacatt gcggccggaa ccgagatttc actcgacttg   1920
ctcgacccta tctacaagcg caaggtcctc gaattggccg cagcgctatc cgacgatttc   1980
gagagggctg gacgtcgttg a                                             2001

<210> SEQ ID NO 20
<211> LENGTH: 1536
```

```
<212> TYPE: DNA
<213> ORGANISM: mycobacterium tuberculosis
<220> FEATURE:
<223> OTHER INFORMATION: DNA sequence Rv3877

<400> SEQUENCE: 20
ttgagcgcac ctgctgttgc tgctggtcct accgccgcgg gggcaaccgc tgcgcggcct      60
gccaccaccc gggtgacgat cctgaccggc agacggatga ccgatttggt actgccagcg     120
gcggtgccga tggaaactta tattgacgac accgtcgcgg tgctttccga ggtgttggaa     180
gacacgccgg ctgatgtact cggcggcttc gactttaccg cgcaaggcgt gtgggcgttc     240
gctcgtcccg gatcgccgcc gctgaagctc gaccagtcac tcgatgacgc cggggtggtc     300
gacgggtcac tgctgactct ggtgtcagtc agtcgcaccg agcgctaccg accgttggtc     360
gaggatgtca tcgacgcgat cgccgtgctt gacgagtcac ctgagttcga ccgcacggca     420
ttgaatcgct ttgtggggc ggcgatcccg cttttgaccg cgcccgtcat cgggatggcg      480
atgcgggcgt ggtgggaaac tgggcgtagc ttgtggtggc cgttggcgat ggcatcctg      540 gggatcgctg tgctggtagg cagcttcgtc gcgaacaggt tctaccagag cggccacctg     600
gccgagtgcc tactggtcac gacgtatctg ctgatcgcaa ccgccgcagc gctggccgtg     660
ccgttgccgc gcggggtcaa ctcgttgggg gcgccacaag ttgccggcgc cgctacggcc     720
gtgctgtttt tgaccttgat gacgcgggc ggccctcgga agcgtcatga gttggcgtcg      780
tttgccgtga tcaccgctat cgcggtcatc gcggccgccg ctgccttcgg ctatggatac     840
caggactggg tccccgcggg ggggatcgca ttcgggctgt tcattgtgac gaatgcggcc     900
aagctgaccg tcgcggtcgc gcggatcgcg ctgccgccga ttccggtacc cggcgaaacc     960
gtggacaacg aggagttgct cgatcccgtc gcgaccccgg aggctaccag cgaagaaacc    1020
ccgacctggc aggccatcat cgcgtcggtg cccgcgtccg cggtccggct caccgagcgc    1080
agcaaactgg ccaagcaact tctgatcgga tacgtcacgt cgggcaccct gattctggct    1140
gccggtgcca tcgcggtcgt ggtgcgcggg cacttctttg tacacagcct ggtggtcgcg    1200
ggtttgatca cgaccgtctg cggatttcgc tcgcggcttt acgccgagcg ctggtgtgcg    1260
tgggcgttgc tggcggcgac ggtcgcgatt ccgacgggtc tgacggccaa actcatcatc    1320
tggtacccgc actatgcctg gctgttgttg agcgtctacc tcacggtagc cctggttgcg    1380
ctcgtggtgg tcgggtcgat ggctcacgtc cggcgcgttt caccggtcgt aaaacgaact    1440
ctggaattga tcgacggcgc catgatcgct gccatcattc ccatgctgct gtggatcacc    1500
ggggtgtacg acacggtccg caatatccgg ttctga                              1536

<210> SEQ ID NO 21
<211> LENGTH: 840
<212> TYPE: DNA
<213> ORGANISM: Mycobacterium tuberculosis
<220> FEATURE:
<223> OTHER INFORMATION: DNA sequence Rv3878

<400> SEQUENCE: 21
atggctgaac cgttggccgt cgatcccacc ggcttgagcg cagcggccgc gaaattggcc      60
ggcctcgttt ttccgcagcc tccggcgccg atcgcggtca gcggaacgga ttcggtggta     120
gcagcaatca acgagaccat gccaagcatc gaatcgctgg tcagtgacgg gctgccggc      180 gtgaaagccg ccctgactcg aacagcatcc aacatgaacg cggcggcgga cgtctatgcg     240
aagaccgatc agtcactggg aaccagtttg agccagtatg cattcggctc gtcgggcgaa     300
ggcctggctg gcgtcgcctc ggtcggtggt cagccaagtc aggctaccca gctgctgagc     360
```

| | | |
|---|---|---|
| acacccgtgt cacaggtcac gacccagctc ggcgagacgg ccgctgagct ggcaccccgt | 420 | |
| gttgttgcga cggtgccgca actcgttcag ctggctccgc acgccgttca gatgtcgcaa | 480 | |
| aacgcatccc ccatcgctca gacgatcagt caaaccgccc aacaggccgc ccagagcgcg | 540 | |
| cagggcggca gcggcccaat gcccgcacag cttgccagcg ctgaaaaacc ggccaccgag | 600 | |
| caagcggagc cggtccacga agtgacaaac gacgatcagg gcgaccaggg cgacgtgcag | 660 | |
| ccggccgagg tcgttgccgc ggcacgtgac gaaggcgccg gcgcatcacc gggccagcag | 720 | |
| cccggcgggg gcgttcccgc gcaagccatg gataccggag ccggtgcccg cccagcggcg | 780 | |
| agtccgctgg cggcccccgt cgatccgtcg actccggcac cctcaacaac cacaacgttg | 840 | |

<210> SEQ ID NO 22
<211> LENGTH: 2187
<212> TYPE: DNA
<213> ORGANISM: Mycobacterium tuberculosis
<220> FEATURE:
<223> OTHER INFORMATION: DNA sequence Rv3879c

<400> SEQUENCE: 22

| | | |
|---|---|---|
| atgagtatta ccaggccgac gggcagctat gccagacaga tgctggatcc gggcggctgg | 60 | |
| gtggaagccg atgaagacac tttctatgac cgggcccagg aatatagcca ggttttgcaa | 120 | |
| agggtcaccg atgtattgga cacctgccgc cagcagaaag ccacgtcttc gaaggcggc | 180 | |
| ctatggtccg gcggcgccgc caatgctgcc aacggcgccc tgggtgcaaa catcaatcaa | 240 | |
| ttgatgacgc tgcaggatta tctcgccacg gtgattacct ggcacaggca tattgccggg | 300 | |
| ttgattgagc aagctaaatc cgatatcggc aataatgtgg atggcgctca acgggagatc | 360 | |
| gatatcctgg agaatgaccc tagcctggat gctgatgagc gccataccgc catcaattca | 420 | |
| ttggtcacgg cgacgcatgg ggccaatgtc agtctggtcg ccgagaccgc tgagcgggtg | 480 | |
| ctggaatcca agaattggaa acctccgaag aacgcactcg aggatttgct tcagcagaag | 540 | |
| tcgccgccac ccccagacgt gcctaccctg gtcgtgccat ccccgggcac accgggcaca | 600 | |
| ccgggaaccc cgatcacccc gggaaccccg atcaccccgg aaccccaat cacacccatc | 660 | |
| ccgggagcgc cggtaactcc gatcacacca acgcccggca ctcccgtcac gccggtgacc | 720 | |
| ccgggcaagc cggtcacccc ggtgacccccg gtcaaaccgg gcacccagg cgagccaacc | 780 | |
| ccgatcacgc cggtcacccc cccggtcgcc ccggccacac cggcaacccc ggccacgccc | 840 | |
| gttaccccag ctcccgctcc acacccgcag ccggctccgg caccggcgcc atcgcctggg | 900 | |
| ccccagccgg ttacaccggc cactcccggt ccgtctggtc cagcaacacc gggcacccca | 960 | |
| gggggcgagc cggcgccgca cgtcaaaccc gcggcgttgg cggagcaacc tggtgtgccg | 1020 | |
| ggccagcatg cgggcggggg gacgcagtcg gggcctgccc atgcggacga atccgccgcg | 1080 | |
| tcggtgacgc cggctgcggc gtccggtgtc ccgggcgcac gggcggcggc cgccgcgccg | 1140 | |
| agcggtaccg ccgtgggagc gggcgcgcgt tcgagcgtgg gtacgccgc ggcctcgggc | 1200 | |
| gcggggtcgc atgctgccac tgggcgggcg ccggtggcta cctcggacaa ggcggcggca | 1260 | |
| ccgagcacgc gggcggcctc ggcgcggacg gcacctcctg cccgcccgcc gtcgaccgat | 1320 | |
| cacatcgaca aacccgatcg cagcgagtct gcagatgacg gtacgccggt gtcgatgatc | 1380 | |
| ccggtgtcgc cggctcgggc ggcacgcgac ccgccactg cagctgccag cgcccgccag | 1440 | |
| cgtggccgcg gtgatgcgct gcggttggcg cgacgcatcg cggcggcgct caacgcgtcc | 1500 | |
| gacaacaacg cgggcgacta cggggttcttc tggatcaccg cggtgaccac cgacggttcc | 1560 | |
| atcgtcgtgg ccaacagcta tgggctggcc tacatacccg acgggatgga attgccgaat | 1620 | |

| | |
|---|---|
| aaggtgtact tggccagcgc ggatcacgca atcccggttg acgaaattgc acgctgtgcc | 1680 |
| acctacccgg ttttggccgt gcaagcctgg gcggctttcc acgacatgac gctgcgggcg | 1740 |
| gtgatcggta ccgcggagca gttggccagt tcggatcccg gtgtggccaa gattgtgctg | 1800 |
| gagccagatg acattccgga gagcggcaaa atgacgggcc ggtcgcggct ggaggtcgtc | 1860 |
| gacccctcgg cggcggctca gctggccgac actaccgatc agcgtttgct cgacttgttg | 1920 |
| ccgccggcgc cggtggatgt caatccaccg ggcgatgagc ggcacatgct gtggttcgag | 1980 |
| ctgatgaagc ccatgaccag caccgctacc ggccgcgagg ccgctcatct gcgggcgttc | 2040 |
| cgggcctacg ctgcccactc acaggagatt gccctgcacc aagcgcacac tgcgactgac | 2100 |
| gcggccgtcc agcgtgtggc cgtcgcggac tggctgtact ggcaatacgt caccgggttg | 2160 |
| ctcgaccggg ccctggccgc cgcatgc | 2187 |

<210> SEQ ID NO 23
<211> LENGTH: 345
<212> TYPE: DNA
<213> ORGANISM: Mycobacterium tuberculosis
<220> FEATURE:
<223> OTHER INFORMATION: DNA sequence Rv3880c

<400> SEQUENCE: 23

| | |
|---|---|
| gtgagcatgg acgaattgga cccgcatgtc gcccgggcgt tgacgctggc ggcgcggttt | 60 |
| cagtcggccc tagacgggac gctcaatcag atgaacaacg gatccttccg cgccaccgac | 120 |
| gaagccgaga ccgtcgaagt gacgatcaat gggcaccagt ggctcaccgg cctgcgcatc | 180 |
| gaagatggtt tgctgaagaa gctgggtgcc gaggcggtgg ctcagcgggt caacgaggcg | 240 |
| ctgcacaatg cgcaggccgc ggcgtccgcg tataacgacg cggcgggcga gcagctgacc | 300 |
| gctgcgttat cggccatgtc ccgcgcgatg aacgaaggaa tggcc | 345 |

<210> SEQ ID NO 24
<211> LENGTH: 1380
<212> TYPE: DNA
<213> ORGANISM: Mycobacterium tuberculosis
<220> FEATURE:
<223> OTHER INFORMATION: DNA sequence Rv3881c

<400> SEQUENCE: 24

| | |
|---|---|
| atgacgcagt cgcagaccgt gacggtggat cagcaagaga ttttgaacag ggccaacgag | 60 |
| gtggaggccc cgatggcgga cccaccgact gatgtcccca tcacaccgtg cgaactcacg | 120 |
| gcggctaaaa acgccgccca acagctggta ttgtccgccg acaacatgcg ggaatacctg | 180 |
| gcggccggtg ccaaagagcg gcagcgtctg gcgacctcgc tgcgcaacgc ggccaaggcg | 240 |
| tatggcgagg ttgatgagga ggctgcgacc cgctggacaa cgacggcga aggaactgtg | 300 |
| caggcagaat cggccggggc cgtcggaggg gacagttcgg ccgaactaac cgatacgccg | 360 |
| agggtggcca cggccggtga acccaacttc atggatctca agaagcggc aaggaagctc | 420 |
| gaaacgggcg accaaggcgc atcgctcgcg cactttgcgg atgggtggaa cactttcaac | 480 |
| ctgacgctgc aaggcgacgt caagcggttc cgggggtttg acaactggga aggcgatgcg | 540 |
| gctaccgctt gcgaggcttc gctcgatcaa caacggcaat ggatactcca catggccaaa | 600 |
| ttgacgctgc cgatggccaa gcaggctcaa tatgtcgcgc agctgcacgt gtgggctagg | 660 |
| cgggaacatc cgacttatga agacatagtc gggctcgaac ggctttacgc ggaaaaccct | 720 |
| tcggcccgcg accaaattct cccggtgtac gcggagtatc agcagaggtc ggagaaggtg | 780 |
| ctgaccgaat acaacaacaa ggcagccctg gaaccggtaa accccgccgaa gcctcccccc | 840 |

-continued

```
gccatcaaga tcgacccgcc cccgcctccg caagagcagg gattgatccc tggcttcctg    900
atgccgccgt ctgacggctc cggtgtgact cccggtaccg ggatgccagc cgcaccgatg    960
gttccgccta ccggatcgcc gggtggtggc ctcccggctg acacggcggc gcagctgacg   1020
tcggctgggc gggaagccgc agcgctgtcg ggcgacgtgg cggtcaaagc ggcatcgctc   1080
ggtggcggtg gaggcggcgg ggtgccgtcg gcgccgttgg gatccgcgat cggggggcgcc  1140 gaatcggtgc ggcccgctgg cgctggtgac attgccggct taggccaggg aagggccggc   1200
ggcggcgccg cgctgggcgg cggtggcatg ggaatgccga tgggtgccgc gcatcaggga   1260 caaggggggcg ccaagtccaa gggttctcag caggaagacg aggcgctcta caccgaggat  1320
cgggcatgga ccgaggccgt cattggtaac cgtcggcgcc aggacagtaa ggagtcgaag   1380
```

<210> SEQ ID NO 25
<211> LENGTH: 1386
<212> TYPE: DNA
<213> ORGANISM: Mycobacterium tuberculosis
<220> FEATURE:
<223> OTHER INFORMATION: DNA sequence Rv3882c

<400> SEQUENCE: 25

```
atgagaaatc ctttagggct gcggttcagc accgggcacg ccttgcttgc ctccgcgttg     60
gccccgccat gcatcatcgc attcttggag acgcgctact ggtgggcggg gattgcgctg    120
gcctcgttgg gcgtcatcgt ggccacggtc actttctacg ccgccggat caccggctgg    180 gtggcggcgg tgtacgcgtg gttgcggcgg cgccgacggc ccccggattc ctcgtcagaa    240
cctgtggtcg gggccaccgt gaagccagga gatcacgttg cggtgcgctg gcaaggcgag    300
tttctggtcg ccgtaatcga gctcattccc cgaccattca cgccgacggt catcgtcgac    360
gggcaagccc acaccgacga catgctggac accggactgg tggaggagct cctgtcggtg    420
cactgtcccg acttggaggc cgatatcgtc tcagccggct accgcgtcgg caataccgca    480
gcgccggacg tggtgagtct gtatcagcag gtgatcggga cagacccggc gccggcgaac    540
cgccggacct ggatcgtgct gcgcgccgac ccggaacgca cccgcaaatc ggcgcagcgc    600
cgcgatgaag gcgtcgcagg actggcccgg tatttggtgg cgtccgcgac gcgcattgcc    660
gatcgactgg ctagccatgg tgtcgacgcg gtgtgtggcc gcagcttcga tgactacgac    720
cacgccaccg acatcggctt tgtgcgggag aaatggtcga tgatcaaggg gcgcgatgcc    780
tacactgccg cctacgcggc gcccggaggt ccggatgtat ggtggtcggc gcgcgcggac    840
cacaccatca ccagagtccg ggtcgcgccg gggatggccc cgcagtccac ggtgttgctg    900
accacggcgg acaagcccaa gacacccagg ggcttcgccc gcctatttgg cgggcagcgg    960
cccgcgctgc aaggccagca tctggtggcc aaccgccact gccagctgcc gatcgggtca   1020
gctggggtac tggtcggcga cacggtgaac cgatgcccgg tctacatgcc cttcgacgat   1080
gtcgacatcg ccctcaacct gggtgacgct cagacattca cccagttcgt ggtgcgtgcg   1140
gcggcggcag gtgcgatggt cacagtcggg ccacagttcg aggaatttgc ccggttgatc   1200
ggcgcacaca tcgggcagga ggtaaaggtg gcgtggccga atgcgacgac ctatctcggc   1260
ccgcatcccg gtattgaccg ggtgattctg cggcacaatg tgatcggtac cccgcggcat   1320
cggcagctgc cgattcgccg ggtttcccca cccgaggaaa gccgctacca gatggcgctg   1380
ccgaag                                                              1386
```

<210> SEQ ID NO 26
<211> LENGTH: 1338

```
<212> TYPE: DNA
<213> ORGANISM: Mycobacterium tuberculosis
<220> FEATURE:
<223> OTHER INFORMATION: DNA sequence Rv3883c

<400> SEQUENCE: 26
gtgcaccgta tctttctgat cacggtggcg ctggcgttgc tcaccgcgtc gcccgcatcg      60
gccatcacgc caccgccgat cgatccgggc gcgttgccgc ccgacgtgac gggcccggat     120
cagcctaccg aacagcgcgt tttgtgcgcg tcgcccacca cgctgccggg gtccgggttc     180
cacgatccgc cgtggagcaa cacgtatctg ggcgtggccg atgcccacaa gttcgcgacc     240
ggggccgggg tgacggtggc ggtgatcgac accggtgtcg acgcttcgcc acgggtcccg     300
gcggaacctg gcggcgattt cgtcgaccag gccggtaacg gcctgtctga ctgtgatgcc     360
catgggactc tcacagcatc catcatcgcg ggccggcccg cgcccaccga cgggttcgtc     420
ggcgtcgcgc ccgacgctcg actgctctcg ctacgtcaga cgtctgaggc cttcgaaccg     480
gtcggctcac aagccaaccc gaatgacccc aacgccaccc cggccgccgg ttccatccgc     540
agtcttgccc gcgccgtggt gcacgccgcc aacctcggcg tgggtgtgat caacatcagt     600
gaagccgcct gctacaaggt gagcaggccg atcgatgaaa cctcactggg tgcatccatc     660
gactatgcgg tcaacgtcaa aggcgtggtg gtggtggtcg cggccggcaa caccggtggc     720
gattgcgtac agaatccggc gccggacccg tccacacccg cgacccacg cggctggaac      780 aatgtgcaga ccgttgtcac cccggcgtgg tacgcaccgc tggtgttaag cgtcggcggt     840
atcggccaga ccgggatgcc cagctcgttc tcgatgcacg accgtgggt ggacgtggcc      900 gcgcccgcag aaaacatcgt cgcgctcggc gacaccggtg aaccggtgaa tgcgctgcaa     960
ggccgggagg ggccggtacc catcgccggc acctcgtttg ccgcggcata tgtgtcgggt    1020
ctggcggccc tgcttcggca gcggttcccc gacctgacgc cggcgcagat catccaccgg    1080
atcaccgcca ccgcgagaca ccccgggggc ggggtcgacg acctggtcgg cgccggcgtc    1140
atcgatgcgg tggccgcgct gacgtgggac attccgcccg gcctgcttc ggcgccatac     1200 aacgtcagac gacttccacc cccggtggtg gagccgggtc ccgatcgtcg cccgattacg    1260
gctgtggcgt tggtggccgt cggccttacg ttggccctgg gctgggcgc gctggctaga     1320 cgggcgctga gccgccga                                                  1338

<210> SEQ ID NO 27
<211> LENGTH: 1857
<212> TYPE: DNA
<213> ORGANISM: Mycobacterium tuberculosis
<220> FEATURE:
<223> OTHER INFORMATION: DNA sequence Rv3884c

<400> SEQUENCE: 27
atgtcgagaa tggtggacac gatgggtgat ttactcactg cgcgccggca tttcgatcgg      60
gcgatgacga tcaagaatgg ccagggatgc gtggcggcgt tgcctgagtt tgtggctgcc     120
accgaggccg atccgtcgat ggccgacgcg tggctgggtc gtatcgcctg cggtgaccgc     180
gatctggcct cgcttaagca gctcaacgcc catagcgagt ggctgcaccg cgagaccacg     240
cggatcggcc ggacgttggc cgctgaggtc cagctgggac catccatcgg gatcacggtg     300
accgacgcat ctcaggtggg gctggcgctg tcgtcggcgt tgacgatcgc ggggagtat     360 gcgaaggccg atgcccctgtt agcaaaccgc gagctattgg attcgtggcg caactaccag     420
tggcatcagc tggctcgggc gttcctgatg tacgtcacgc agcgatgcc cgacgtgttg     480 tcgacggccg ccgaggatct gccgccacag gcgatcgtca tgccggcggt gaccgcgtcg     540
```

```
atttgtgcgc tggcagccca cgccgccgcc catctcgggc aggggcgagt ggccctggac    600
tggctggacc gggtggacgt gatcggacac agcaggtcat cggagcggtt cggcgccgac    660
gtgctcaccg cggcgatcgg accgccgat attccgctgc tggtcgccga cttggcgtat    720
gtgcggggga tggtgtaccg gcaactgcat gaggaggaca aggcccagat ctggctgtcg    780
aaggccacca tcaacggggt gctcaccgac gccgccaaag aagccctggc ggacccgaac    840
ctgcgcttga ttgttaccga tgaacgaacc atcgccagcc gctccgaccg ttgggatgct    900
tcgacggcga aaagccgcga ccagctcgat gacgacaatg cagcgcagcg gcgcggcgag    960
ctgctagccg agggccggga actgctggcc aaacaggtgg gcctggcggc ggtcaagcaa    1020
gcggtatcgg cgctggaaga ccaactcgag gtgcgcatga tgcgcctaga gcacggccta    1080
ccggtggagg ggcagaccaa ccacatgttg ctggtggggc caccaggcac aggtaagaca    1140
accaccgctg aagcgctcgg caagatctac gccggcatgg ggatcgtgcg tcaccccgaa    1200
attcgagaag ttcgccgatc ggacttctgt gggcactaca tcggggagtc aggacccaag    1260
acgaacgagc tgatcgaaaa gtcactcggg cgaatcattt tcatggacga gttctactcg    1320
ctgatcgaac gtcatcaaga cggaacaccg gacatgatcg gcatggaggc ggtcaatcaa    1380
ctcctggttc aattggaaac acaccgattc gacttctgtt tcatcggggc cggctatgag    1440
gatcaggtgg atgaattcct caccgtgaac ccgggtttgg ctggccggtt caaccgaaag    1500
ctgcggttcg agtcttattc gccggtggag atcgtcgaga ttggacaccg ctacgctaca    1560
ccgcgcgcca gccagctcga tgacgccgca cgggaggtat tcctcgacgc ggtcaccacc    1620
atccgtaact acaccacccc tagtgggcag cacggtatcg acgctatgca aaacggtcgg    1680
ttcgcccgca acgtgatcga acgcgccgaa gggttccggg acaccgggt ggttgcgcaa    1740 aaacgtgcgg gccaaccggt atcggttcag gatctgcaga tcatcaccgc caccgacatc    1800
gatgccgcga tacgcagcgt gtgctcagac aaccgagaca tggccgcgat cgtttgg    1857
```

<210> SEQ ID NO 28
<211> LENGTH: 1611
<212> TYPE: DNA
<213> ORGANISM: Mycobacterium tuberculosis
<220> FEATURE:
<223> OTHER INFORMATION: DNA sequence Rv3885c

<400> SEQUENCE: 28

```
ttgacgtcca agctgaccgg gttcagcccg cgcagtgcga ggcgggtcgc cggggtgtgg    60
acagtgttcg tgctcgcgtc ggcgggctgg gcgctgggcg gccagctagg tgcggtcatg    120
gctgtcgtgg tcggcgtcgc cttggtgttc gtacagtggt ggggtcagcc ggcgtggtcg    180
tgggcggtac tggggctgcg gggtcggcgt cccgtcaaat ggaatgaccc aattaccttg    240
gccaacaacc gatccggggg tggcgtccgc gtgcaagacg gtgtcgcggt ggtggcggtg    300
caacttctcg gccgagcgca ccgggcgact acggtcaccg ggtcggtgac cgtagaaagc    360
gacaacgtga ttgacgtcgt tgagctcgcg ccgttgctgc cgaccccgct ggacctggaa    420
ctcgattcaa tcagcgtcgt caccttcggc tcgcgaaccg gcaccgtcgg cgattacccg    480
cgggtgtatg acgcggagat cggtacgccg ccgtatgccg ggcggcgcga acgtggctg    540 atcatgcggc ttccggtgat cggcaacacc caagctttac gctggcgtac cagcgttggg    600
gccgctgcca tttcggtcgc ccaacgcgtt gccagctccc tgcgctgtca gggcttgcgc    660
gccaaactgg ccaccgcaac agacttggct gagcttgatc gccggctggg gtcggacgcg    720
gtagccggga gtgcgcagcg ctggaaagct atccgcggtg aagccgggtg gatgacgacg    780
```

| | |
|---|---|
| tatgcgtacc cggctgaggc gatttcgtcg cgggttctct cgcaagcctg gacgctgcgt | 840 |
| gccgatgagg tcatccagaa cgtaacggtg tatccggacg cgacgtgcac cgcgaccatc | 900 |
| accgtgcgca caccgacgcc ggcgcctacc ccgcccagtg tgatcttgcg tcggctcaat | 960 |
| ggtgagcaag ccgccgcggc tgcggccaac atgtgcgggc cacgtccaca cctacgcgga | 1020 |
| cagcggcgct gcccgttgcc ggcgcagcta gtcaccgaga tcggaccgtc gggggtgttg | 1080 |
| attggcaagc tgagcaacgg ggaccggctg atgattcccg ttaccgacgc cggtgagctg | 1140 |
| tcgcgcgtct tcgtggccgc ggacgacacg atcgccaaga ggatcgtgat tcgcgtcgtc | 1200 |
| ggtgccggtg agcgggtgtg tgtgcacact cgcgaccaag agcgttgggc cagcgtacgc | 1260 |
| atgccgcagt tgagcatcgt cggcacacca cggcccgcgc cgcgcaccac tgtcggcgtc | 1320 |
| gtggagtacg tgcggcggcg caagaacggc gatgacggca aatctgaagg cagcggtgtc | 1380 |
| gatgtcgcga tttcgcccac gccacggcca gccagtgtca tcaccattgc ccgacccggt | 1440 |
| acctcgctgt ccgagagcga tcggcatggc ttcgaggtga ccatcgaaca aatcgatcgg | 1500 |
| gcaacggtga agtcggtgc ggcaggacaa aactggctgg ttgagatgga aatgttccgt | 1560 |
| gcggagaacc gctatgtcag ccttgagccg gtcacgatgt cgataggccg g | 1611 |

<210> SEQ ID NO 29
<211> LENGTH: 620
<212> TYPE: DNA
<213> ORGANISM: Mycobacterium tuberculosis
<220> FEATURE:
<223> OTHER INFORMATION: CFP-10 + ESAT-6

<400> SEQUENCE: 29

```
atggcagaga tgaagaccga tgccgctacc ctcgcgcagg aggcaggtaa tttcgagcgg     60
atctccggcg acctgaaaac ccagatcgac caggtggagt cgacggcagg ttcgttgcag    120
ggccagtggc gcggcgcggc ggggacggcc gcccaggccg cggtggtgcg cttccaagaa    180
gcagccaata agcagaagca ggaactcgac gagatctcga cgaatattcg tcaggccggc    240
gtccaatact cgagggccga cgaggagcag cagcaggcgc tgtcctcgca aatgggcttc    300
tgacccgcta atacgaaaag aaacggagca aaaacatgac agagcagcag tggaatttcg    360
cgggtatcga ggccgcggca agcgcaatcc agggaaatgt cacgtccatt cattccctcc    420
ttgacgaggg gaagcagtcc ctgaccaagc tcgcagcggc ctggggcggt agcggttcgg    480
aggcgtacca gggtgtccag caaaaatggg acgccacggc taccgagctg aacaacgcgc    540
tgcagaacct ggcgcggacg atcagcgaag ccggtcaggc aatggcttcg accgaaggca    600
acgtcactgg gatgttcgca                                                620
```

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Primer
      SP6-BAC1

<400> SEQUENCE: 30

```
agttagctca ctcattaggc a                                               21
```

<210> SEQ ID NO 31
<211> LENGTH: 21
<212> TYPE: DNA
<213> ORGANISM: Artificial Sequence
<220> FEATURE:

<223> OTHER INFORMATION: Description of Artificial Sequence: Primer
      T7-BAC1

<400> SEQUENCE: 31
ggatgtgctg caaggcgatt a                                              21

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer
      esat-6F

<400> SEQUENCE: 32
gtcacgtcca ttcattccct                                                20

<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Primer
      esat-6R

<400> SEQUENCE: 33
atcccagtga cgttgcctt                                                 19

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer
      RD1mic flanking region F

<400> SEQUENCE: 34
gcagtgcaaa ggtgcagata                                                20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer
      RD1mic flanking region R

<400> SEQUENCE: 35
gattgagaca cttgccacga                                                20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer
      plcA.int.F

<400> SEQUENCE: 36
caagttgggt ctggtcgaat                                                20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer
      plcA.int.R

<400> SEQUENCE: 37
gctacccaag gtctcctggt                                                   20

<210> SEQ ID NO 38
<211> LENGTH: 153
<212> TYPE: DNA
<213> ORGANISM: Mycobacterium tuberculosis
<220> FEATURE:
<223> OTHER INFORMATION: Sequences at the junction RD1mic

<400> SEQUENCE: 38
caagacgagg ttgtaaaacc tcgacgcagg atcggcgatg aaatgccagt cggcgtcgct      60
gagcgcgcgc tgcgccgagt cccattttgt cgctgatttg tttgaacagc gacgaaccgg     120
tgttgaaaat gtcgcctggg tcggggattc cct                                  153

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence: Primer
      RD5mic flanking region F

<400> SEQUENCE: 39
gaatgccgac gtcatatcg                                                    19

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer
      RD5mic flanking region R

<400> SEQUENCE: 40
cggccactga gttcgattat                                                   20

<210> SEQ ID NO 41
<211> LENGTH: 152
<212> TYPE: DNA
<213> ORGANISM: Mycobacterium tuberculosis
<220> FEATURE:
<223> OTHER INFORMATION: Sequence at the junction RD5mic

<400> SEQUENCE: 41
cctcgatgaa ccacctgaca tgaccccatc ctttccaaga actggagtct ccggacatgc      60
cggggcggtt cactgcccca ggtgtcctgg gtcgttccgt tgaccgtcga gtccgaacat     120
ccgtcattcc cggtggcagt cggtgcggtg ac                                   152

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Primer MiD1
      flanking region F

<400> SEQUENCE: 42
cagccaacac caagtagacg                                                   20

<210> SEQ ID NO 43
<211> LENGTH: 20
<212> TYPE: DNA

```
<213> ORGANISM: Artificial Sequence
<220> FEATURE:
<223> OTHER INFORMATION: Description of Artificial Sequence: Primer MiD1
      flanking region R

<400> SEQUENCE: 43
tctacctgca gtcgcttgtg                                                    20

<210> SEQ ID NO 44
<211> LENGTH: 123
<212> TYPE: DNA
<213> ORGANISM: Mycobacterium tuberculosis
<220> FEATURE:
<223> OTHER INFORMATION: Sequence at the junction MiD1

<400> SEQUENCE: 44
cacctgacat gaccccatcc tttccaagaa ctggagtctc cggacatgcc ggggcggttc        60
agggacattc atgtccatct tctggcagat cagcagatcg cttgttctca gtgcaggtga      120
gtc                                                                     123

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer MiD2
      flanking region R

<400> SEQUENCE: 45
gtccatcgag gatgtcgagt                                                    20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer MiD2
      flanking region L

<400> SEQUENCE: 46
ctaggccatt ccgttgtctg                                                    20

<210> SEQ ID NO 47
<211> LENGTH: 151
<212> TYPE: DNA
<213> ORGANISM: Mycobacterium tuberculosis
<220> FEATURE:
<223> OTHER INFORMATION: Sequence at the junction MiD2

<400> SEQUENCE: 47
gctgcctact acgctcaacg ccagagacca gccgccggct gaggtctcag atcagagagt        60
ctccggactc accggggcgg ttcataaagg cttcgagacc ggacgggctg taggttcctc      120
aactgtgtgg cggatggtct gagcacttaa c                                     151

<210> SEQ ID NO 48
<211> LENGTH: 15
<212> TYPE: DNA
<213> ORGANISM: Artificial Sequence
<220> FEATURE:
<223> OTHER INFORMATION: Description of Artificial Sequence: Primer MiD3
      flanking region R

<400> SEQUENCE: 48
ggcgacgcca tttcc                                                         15
```

```
<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Primer MiD3
      flanking region L

<400> SEQUENCE: 49
aactgtcggg cttgctctt                                                    19

<210> SEQ ID NO 50
<211> LENGTH: 181
<212> TYPE: DNA
<213> ORGANISM: Mycobacterium tuberculosis
<220> FEATURE:
<223> OTHER INFORMATION: Sequence at the junction MiD3

<400> SEQUENCE: 50
tggcgccggc acctccgttg ccaccgttgc cgccgctggt gggcgcggtg ccgttcgccc        60
cggccgaacc gttcagggcc gggttcgccc tcagccgcta acacgccga ccaagatcaa       120 cgagctacct gcccggtcaa ggttgaagag cccccatatc agcaagggcc cggtgtcggc      180
g                                                                     181

<210> SEQ ID NO 51
<211> LENGTH: 108
<212> TYPE: PRT
<213> ORGANISM: Mycobacterium tuberculosis
<220> FEATURE:
<223> OTHER INFORMATION: RV3861 - hypothetical protein

<400> SEQUENCE: 51

Val Thr Trp Leu Ala Asp Pro Val Gly Asn Ser Arg Ile Ala Arg Ala
1               5                   10                  15

Gln Ala Cys Lys Thr Ser Ile Ser Ala Pro Ile Val Glu Ser Trp Arg
            20                  25                  30

Ala Gln Arg Gly Ala Gln Cys Gly Gln Arg Glu Lys Ser Cys Arg Cys
        35                  40                  45

Ser Arg Ala Val His Ile Gln Gly Ile Ser Pro Pro Leu Phe Arg Arg
    50                  55                  60

Pro Leu Glu Pro Ala Val Gln Ala Val Ala Ser Cys Arg Leu Gly
65                  70                  75                  80

Arg His Pro Val Val Ala His Arg Val Thr Val Ala Leu Gly Gln Gly
                85                  90                  95

Ser Gln Leu Ala Gln Arg Glu Cys Pro Arg Pro Ala
            100                 105

<210> SEQ ID NO 52
<211> LENGTH: 116
<212> TYPE: PRT
<213> ORGANISM: Mycobacterium tuberculosis
<220> FEATURE:
<223> OTHER INFORMATION: WHIB6 - Possible transcriptional regulatory
      protein WHIB-like WHIB6

<400> SEQUENCE: 52

Met Arg Tyr Ala Phe Ala Ala Glu Ala Thr Thr Cys Asn Ala Phe Trp
1               5                   10                  15

Arg Asn Val Asp Met Thr Val Thr Ala Leu Tyr Glu Val Pro Leu Gly
            20                  25                  30

Val Cys Thr Gln Asp Pro Asp Arg Trp Thr Thr Thr Pro Asp Asp Glu
```

```
                35                  40                  45
Ala Lys Thr Leu Cys Arg Ala Cys Pro Arg Arg Trp Leu Cys Ala Arg
 50                  55                  60

Asp Ala Val Glu Ser Ala Gly Ala Glu Gly Leu Trp Ala Gly Val Val
 65                  70                  75                  80

Ile Pro Glu Ser Gly Arg Ala Arg Ala Phe Ala Leu Gly Gln Leu Arg
                 85                  90                  95

Ser Leu Ala Glu Arg Asn Gly Tyr Pro Val Arg Asp His Arg Val Ser
            100                 105                 110

Ala Gln Ser Ala
        115

<210> SEQ ID NO 53
<211> LENGTH: 392
<212> TYPE: PRT
<213> ORGANISM: Mycobacterium tuberculosis
<220> FEATURE:
<223> OTHER INFORMATION: Rv3863 - hypothetical alanine rich protein

<400> SEQUENCE: 53

Met Ala Gly Glu Arg Lys Val Cys Pro Ser Arg Leu Val Pro Ala
 1               5                  10                  15

Asn Lys Gly Ser Thr Gln Met Ser Lys Ala Gly Ser Thr Val Gly Pro
                 20                  25                  30

Ala Pro Leu Val Ala Cys Ser Gly Gly Thr Ser Asp Val Ile Glu Pro
                 35                  40                  45

Arg Arg Gly Val Ala Ile Ile Gly His Ser Cys Arg Val Gly Thr Gln
 50                  55                  60

Ile Asp Asp Ser Arg Ile Ser Gln Thr His Leu Arg Ala Val Ser Asp
 65                  70                  75                  80

Asp Gly Arg Trp Arg Ile Val Gly Asn Ile Pro Arg Gly Met Phe Val
                 85                  90                  95

Gly Gly Arg Arg Gly Ser Ser Val Thr Val Ser Asp Lys Thr Leu Ile
            100                 105                 110

Arg Phe Gly Asp Pro Pro Gly Lys Ala Leu Thr Phe Glu Val Val
            115                 120                 125

Arg Pro Ser Asp Ser Ala Ala Gln His Gly Arg Val Gln Pro Ser Ala
130                 135                 140

Asp Leu Ser Asp Pro Ala His Asn Ala Ala Pro Val Ala Pro Asp
145                 150                 155                 160

Pro Gly Val Val Arg Ala Gly Ala Ala Ala Arg Arg Arg Glu
                165                 170                 175

Leu Asp Ile Ser Gln Arg Ser Leu Ala Ala Asp Gly Ile Ile Asn Ala
            180                 185                 190

Gly Ala Leu Ile Ala Phe Glu Lys Gly Arg Ser Trp Pro Arg Glu Arg
            195                 200                 205

Thr Arg Ala Lys Leu Glu Glu Val Leu Gln Trp Pro Ala Gly Thr Ile
        210                 215                 220

Ala Arg Ile Arg Arg Gly Glu Pro Thr Glu Pro Ala Thr Asn Pro Asp
225                 230                 235                 240

Ala Ser Pro Gly Leu Arg Pro Ala Asp Gly Pro Ala Ser Leu Ile Ala
                245                 250                 255

Gln Ala Val Thr Ala Ala Val Asp Gly Cys Ser Leu Ala Ile Ala Ala
            260                 265                 270

Leu Pro Ala Thr Glu Asp Pro Glu Phe Thr Glu Arg Ala Ala Pro Ile
        275                 280                 285
```

```
Leu Ala Asp Leu Arg Gln Leu Glu Ala Ile Ala Val Gln Ala Thr Arg
    290                 295                 300

Ile Ser Arg Ile Thr Pro Glu Leu Ile Lys Ala Leu Gly Ala Val Arg
305                 310                 315                 320

Arg His His Asp Glu Leu Met Arg Leu Gly Ala Thr Ala Pro Gly Ala
                325                 330                 335

Thr Leu Ala Gln Arg Leu Tyr Ala Ala Arg Arg Ala Asn Leu Ser
            340                 345                 350

Thr Leu Glu Thr Ala Gln Ala Ala Gly Val Ala Glu Glu Met Ile Val
            355                 360                 365

Gly Ala Glu Ala Glu Glu Leu Pro Ala Glu Ala Thr Glu Ala Ile
370                 375                 380

Glu Ala Leu Ile Arg Gln Ile Asn
385                 390

<210> SEQ ID NO 54
<211> LENGTH: 402
<212> TYPE: PRT
<213> ORGANISM: Mycobacterium tuberculosis
<220> FEATURE:
<223> OTHER INFORMATION: Rv3864 - conserved hypothetical protein

<400> SEQUENCE: 54

Met Ala Ser Gly Ser Gly Leu Cys Lys Thr Thr Ser Asn Phe Ile Trp
1               5                   10                  15

Gly Gln Leu Leu Leu Leu Gly Glu Gly Ile Pro Asp Pro Gly Asp Ile
            20                  25                  30

Phe Asn Thr Gly Ser Ser Leu Phe Lys Gln Ile Ser Asp Lys Met Gly
            35                  40                  45

Leu Ala Ile Pro Gly Thr Asn Trp Ile Gly Gln Ala Ala Glu Ala Tyr
50                  55                  60

Leu Asn Gln Asn Ile Ala Gln Gln Leu Arg Ala Gln Val Met Gly Asp
65                  70                  75                  80

Leu Asp Lys Leu Thr Gly Asn Met Ile Ser Asn Gln Ala Lys Tyr Val
            85                  90                  95

Ser Asp Thr Arg Asp Val Leu Arg Ala Met Lys Lys Met Ile Asp Gly
            100                 105                 110

Val Tyr Lys Val Cys Lys Gly Leu Glu Lys Ile Pro Leu Leu Gly His
            115                 120                 125

Leu Trp Ser Trp Glu Leu Ala Ile Pro Met Ser Gly Ile Ala Met Ala
            130                 135                 140

Val Val Gly Gly Ala Leu Leu Tyr Leu Thr Ile Met Thr Leu Met Asn
145                 150                 155                 160

Ala Thr Asn Leu Arg Gly Ile Leu Gly Arg Leu Ile Glu Met Leu Thr
                165                 170                 175

Thr Leu Pro Lys Phe Pro Gly Leu Pro Gly Leu Pro Ser Leu Pro Asp
            180                 185                 190

Ile Ile Asp Gly Leu Trp Pro Pro Lys Leu Pro Asp Ile Pro Ile Pro
            195                 200                 205

Gly Leu Pro Asp Ile Pro Gly Leu Pro Asp Phe Lys Trp Pro Pro Thr
210                 215                 220

Pro Gly Ser Pro Leu Phe Pro Asp Leu Pro Ser Phe Pro Gly Phe Pro
225                 230                 235                 240

Gly Phe Pro Glu Phe Pro Ala Ile Pro Gly Pro Ala Leu Pro Gly
                245                 250                 255
```

```
Leu Pro Ser Ile Pro Asn Leu Phe Pro Gly Leu Pro Gly Leu Gly Asp
            260                 265                 270

Leu Leu Pro Gly Val Gly Asp Leu Gly Lys Leu Pro Thr Trp Thr Glu
        275                 280                 285

Leu Ala Ala Leu Pro Asp Phe Leu Gly Gly Phe Ala Gly Leu Pro Ser
    290                 295                 300

Leu Gly Phe Gly Asn Leu Leu Ser Phe Ala Ser Leu Pro Thr Val Gly
305                 310                 315                 320

Gln Val Thr Ala Thr Met Gly Gln Leu Gln Gln Leu Val Ala Ala Gly
                325                 330                 335

Gly Gly Pro Ser Gln Leu Ala Ser Met Gly Ser Gln Ala Gln Leu
            340                 345                 350

Ile Ser Ser Gln Ala Gln Gln Gly Gln Gln His Ala Thr Leu Val
    355                 360                 365

Ser Asp Lys Lys Glu Asp Glu Glu Val Ala Glu Ala Glu Arg Ala
    370                 375                 380

Pro Ile Asp Ala Gly Thr Ala Ala Ser Gln Arg Gly Gln Glu Gly Thr
385                 390                 395                 400

Val Leu

<210> SEQ ID NO 55
<211> LENGTH: 103
<212> TYPE: PRT
<213> ORGANISM: Mycobacterium tuberculosis
<220> FEATURE:
<223> OTHER INFORMATION: Rv3865 - conserved hypothetical protein

<400> SEQUENCE: 55

Met Thr Gly Phe Leu Gly Val Val Pro Ser Phe Leu Lys Val Leu Ala
1               5                   10                  15

Gly Met His Asn Glu Ile Val Gly Asp Ile Lys Arg Ala Thr Asp Thr
                20                  25                  30

Val Ala Gly Ile Ser Gly Arg Val Gln Leu Thr His Gly Ser Phe Thr
            35                  40                  45

Ser Lys Phe Asn Asp Thr Leu Gln Glu Phe Glu Thr Thr Arg Ser Ser
        50                  55                  60

Thr Gly Thr Gly Leu Gln Gly Val Thr Ser Gly Leu Ala Asn Asn Leu
65                  70                  75                  80

Leu Ala Ala Ala Gly Ala Tyr Leu Lys Ala Asp Asp Gly Leu Ala Gly
                85                  90                  95

Val Ile Asp Lys Ile Phe Gly
            100

<210> SEQ ID NO 56
<211> LENGTH: 283
<212> TYPE: PRT
<213> ORGANISM: Mycobacterium tuberculosis
<220> FEATURE:
<223> OTHER INFORMATION: Rv3866 - conserved hypothetical protein

<400> SEQUENCE: 56

Met Thr Gly Pro Ser Ala Ala Gly Arg Ala Gly Thr Ala Asp Asn Val
1               5                   10                  15

Val Gly Val Glu Val Thr Ile Asp Gly Met Leu Val Ile Ala Asp Arg
                20                  25                  30

Leu His Leu Val Asp Phe Pro Val Thr Leu Gly Ile Arg Pro Asn Ile
            35                  40                  45

Pro Gln Glu Asp Leu Arg Asp Ile Val Trp Glu Gln Val Gln Arg Asp
```

```
                    50                  55                  60
Leu Thr Ala Gln Gly Val Leu Asp Leu His Gly Glu Pro Gln Pro Thr
 65                  70                  75                  80

Val Ala Glu Met Val Glu Thr Leu Gly Arg Pro Asp Arg Thr Leu Glu
                     85                  90                  95

Gly Arg Trp Arg Arg Asp Ile Gly Gly Val Met Val Arg Phe Val
                100                 105                 110

Val Cys Arg Arg Gly Asp Arg His Val Ile Ala Ala Arg Asp Gly Asp
                115                 120                 125

Met Leu Val Leu Gln Leu Val Ala Pro Gln Val Gly Leu Ala Gly Met
                130                 135                 140

Val Thr Ala Val Leu Gly Pro Ala Glu Pro Ala Asn Val Glu Pro Leu
145                 150                 155                 160

Thr Gly Val Ala Thr Glu Leu Ala Glu Cys Thr Thr Ala Ser Gln Leu
                    165                 170                 175

Thr Gln Tyr Gly Ile Ala Pro Ala Ser Ala Arg Val Tyr Ala Glu Ile
                180                 185                 190

Val Gly Asn Pro Thr Gly Trp Val Glu Ile Val Ala Ser Gln Arg His
                195                 200                 205

Pro Gly Gly Thr Thr Gln Thr Asp Ala Ala Ala Gly Val Leu Asp
210                 215                 220

Ser Lys Leu Gly Arg Leu Val Ser Leu Pro Arg Arg Val Gly Gly Asp
225                 230                 235                 240

Leu Tyr Gly Ser Phe Leu Pro Gly Thr Gln Gln Asn Leu Glu Arg Ala
                    245                 250                 255

Leu Asp Gly Leu Leu Glu Leu Pro Ala Gly Ala Trp Leu Asp His
                260                 265                 270

Thr Ser Asp His Ala Gln Ala Ser Ser Arg Gly
                275                 280

<210> SEQ ID NO 57
<211> LENGTH: 183
<212> TYPE: PRT
<213> ORGANISM: mycobacterium tuberculosis
<220> FEATURE:
<223> OTHER INFORMATION: Protein sequence Rv3867

<400> SEQUENCE: 57

Met Val Asp Pro Pro Gly Asn Asp Asp His Gly Asp Leu Asp Ala
  1               5                  10                  15

Leu Asp Phe Ser Ala Ala His Thr Asn Glu Ala Ser Pro Leu Asp Ala
                 20                  25                  30

Leu Asp Asp Tyr Ala Pro Val Gln Thr Asp Asp Ala Glu Gly Asp Leu
             35                  40                  45

Asp Ala Leu His Ala Leu Thr Glu Arg Asp Glu Glu Pro Glu Leu Glu
         50                  55                  60

Leu Phe Thr Val Thr Asn Pro Gln Gly Ser Val Ser Val Ser Thr Leu
 65                  70                  75                  80

Met Asp Gly Arg Ile Gln His Val Glu Leu Thr Asp Lys Ala Thr Ser
                 85                  90                  95

Met Ser Glu Ala Gln Leu Ala Asp Glu Ile Phe Val Ile Ala Asp Leu
            100                 105                 110

Ala Arg Gln Lys Ala Arg Ala Ser Gln Tyr Thr Phe Met Val Glu Asn
        115                 120                 125

Ile Gly Glu Leu Thr Asp Glu Asp Ala Glu Gly Ser Ala Leu Leu Arg
    130                 135                 140
```

```
Glu Phe Val Gly Met Thr Leu Asn Leu Pro Thr Pro Glu Ala Ala
145                 150                 155                 160

Ala Ala Glu Ala Glu Val Phe Ala Thr Arg Tyr Asp Val Asp Tyr Thr
            165                 170                 175

Ser Arg Tyr Lys Ala Asp Asp
            180

<210> SEQ ID NO 58
<211> LENGTH: 573
<212> TYPE: PRT
<213> ORGANISM: mycobacterium tuberculosis
<220> FEATURE:
<223> OTHER INFORMATION: Protein sequence Rv3868

<400> SEQUENCE: 58

Met Thr Asp Arg Leu Ala Ser Leu Phe Glu Ser Ala Val Ser Met Leu
1               5                   10                  15

Pro Met Ser Glu Ala Arg Ser Leu Asp Leu Phe Thr Glu Ile Thr Asn
            20                  25                  30

Tyr Asp Glu Ser Ala Cys Asp Ala Trp Ile Gly Arg Ile Arg Cys Gly
        35                  40                  45

Asp Thr Asp Arg Val Thr Leu Phe Arg Ala Trp Tyr Ser Arg Arg Asn
    50                  55                  60

Phe Gly Gln Leu Ser Gly Ser Val Gln Ile Ser Met Ser Thr Leu Asn
65                  70                  75                  80

Ala Arg Ile Ala Ile Gly Gly Leu Tyr Gly Asp Ile Thr Tyr Pro Val
                85                  90                  95

Thr Ser Pro Leu Ala Ile Thr Met Gly Phe Ala Ala Cys Glu Ala Ala
            100                 105                 110

Gln Gly Asn Tyr Ala Asp Ala Met Glu Ala Leu Glu Ala Ala Pro Val
        115                 120                 125

Ala Gly Ser Glu His Leu Val Ala Trp Met Lys Ala Val Val Tyr Gly
    130                 135                 140

Ala Ala Glu Arg Trp Thr Asp Val Ile Asp Gln Val Lys Ser Ala Gly
145                 150                 155                 160

Lys Trp Pro Asp Lys Phe Leu Ala Gly Ala Ala Gly Val Ala His Gly
                165                 170                 175

Val Ala Ala Ala Asn Leu Ala Leu Phe Thr Glu Ala Glu Arg Arg Leu
            180                 185                 190

Thr Glu Ala Asn Asp Ser Pro Ala Gly Glu Ala Cys Ala Arg Ala Ile
        195                 200                 205

Ala Trp Tyr Leu Ala Met Ala Arg Arg Ser Gln Gly Asn Glu Ser Ala
    210                 215                 220

Ala Val Ala Leu Leu Glu Trp Leu Gln Thr Thr His Pro Glu Pro Lys
225                 230                 235                 240

Val Ala Ala Ala Leu Lys Asp Pro Ser Tyr Arg Leu Lys Thr Thr Thr
                245                 250                 255

Ala Glu Gln Ile Ala Ser Arg Ala Asp Pro Trp Asp Pro Gly Ser Val
            260                 265                 270

Val Thr Asp Asn Ser Gly Arg Glu Arg Leu Leu Ala Glu Ala Gln Ala
        275                 280                 285

Glu Leu Asp Arg Gln Ile Gly Leu Thr Arg Val Lys Asn Gln Ile Glu
    290                 295                 300

Arg Tyr Arg Ala Ala Thr Leu Met Ala Arg Val Arg Ala Ala Lys Gly
305                 310                 315                 320
```

-continued

```
Met Lys Val Ala Gln Pro Ser Lys His Met Ile Phe Thr Gly Pro Pro
            325                 330                 335

Gly Thr Gly Lys Thr Thr Ile Ala Arg Val Val Ala Asn Ile Leu Ala
            340                 345                 350

Gly Leu Gly Val Ile Ala Glu Pro Lys Leu Val Glu Thr Ser Arg Lys
            355                 360                 365

Asp Phe Val Ala Glu Tyr Glu Gly Gln Ser Ala Val Lys Thr Ala Lys
            370                 375                 380

Thr Ile Asp Gln Ala Leu Gly Gly Val Leu Phe Ile Asp Glu Ala Tyr
385                 390                 395                 400

Ala Leu Val Gln Glu Arg Asp Gly Arg Thr Asp Pro Phe Gly Gln Glu
            405                 410                 415

Ala Leu Asp Thr Leu Leu Ala Arg Met Glu Asn Asp Arg Asp Arg Leu
            420                 425                 430

Val Val Ile Ile Ala Gly Tyr Ser Ser Asp Ile Asp Arg Leu Leu Glu
            435                 440                 445

Thr Asn Glu Gly Leu Arg Ser Arg Phe Ala Thr Arg Ile Glu Phe Asp
            450                 455                 460

Thr Tyr Ser Pro Glu Glu Leu Leu Glu Ile Ala Asn Val Ile Ala Ala
465                 470                 475                 480

Ala Asp Asp Ser Ala Leu Thr Ala Glu Ala Glu Asn Phe Leu Gln
            485                 490                 495

Ala Ala Lys Gln Leu Glu Gln Arg Met Leu Arg Gly Arg Arg Ala Leu
            500                 505                 510

Asp Val Ala Gly Asn Gly Arg Tyr Ala Arg Gln Leu Val Glu Ala Ser
            515                 520                 525

Glu Gln Cys Arg Asp Met Arg Leu Ala Gln Val Leu Asp Ile Asp Thr
            530                 535                 540

Leu Asp Glu Asp Arg Leu Arg Glu Ile Asn Gly Ser Asp Met Ala Glu
545                 550                 555                 560

Ala Ile Ala Ala Val His Ala His Leu Asn Met Arg Glu
            565                 570

<210> SEQ ID NO 59
<211> LENGTH: 480
<212> TYPE: PRT
<213> ORGANISM: mycobacterium tuberculosis
<220> FEATURE:
<223> OTHER INFORMATION: Protein sequence Rv3869

<400> SEQUENCE: 59

Met Gly Leu Arg Leu Thr Thr Lys Val Gln Val Ser Gly Trp Arg Phe
1               5                   10                  15

Leu Leu Arg Arg Leu Glu His Ala Ile Val Arg Arg Asp Thr Arg Met
            20                  25                  30

Phe Asp Asp Pro Leu Gln Phe Tyr Ser Arg Ser Ile Ala Leu Gly Ile
            35                  40                  45

Val Val Ala Val Leu Ile Leu Ala Gly Ala Leu Leu Ala Tyr Phe
            50                  55                  60

Lys Pro Gln Gly Lys Leu Gly Gly Thr Ser Leu Phe Thr Asp Arg Ala
65                  70                  75                  80

Thr Asn Gln Leu Tyr Val Leu Ser Gly Gln Leu His Pro Val Tyr
            85                  90                  95

Asn Leu Thr Ser Ala Arg Leu Val Leu Gly Asn Pro Ala Asn Pro Ala
            100                 105                 110

Thr Val Lys Ser Ser Glu Leu Ser Lys Leu Pro Met Gly Gln Thr Val
```

```
            115                 120                 125
Gly Ile Pro Gly Ala Pro Tyr Ala Thr Pro Val Ser Ala Gly Ser Thr
    130                 135                 140

Ser Ile Trp Thr Leu Cys Asp Thr Val Ala Arg Ala Asp Ser Thr Ser
145                 150                 155                 160

Pro Val Val Gln Thr Ala Val Ile Ala Met Pro Leu Glu Ile Asp Ala
                165                 170                 175

Ser Ile Asp Pro Leu Gln Ser His Glu Ala Val Leu Val Ser Tyr Gln
            180                 185                 190

Gly Glu Thr Trp Ile Val Thr Thr Lys Gly Arg His Ala Ile Asp Leu
        195                 200                 205

Thr Asp Arg Ala Leu Thr Ser Ser Met Gly Ile Pro Val Thr Ala Arg
210                 215                 220

Pro Thr Pro Ile Ser Glu Gly Met Phe Asn Ala Leu Pro Asp Met Gly
225                 230                 235                 240

Pro Trp Gln Leu Pro Pro Ile Pro Ala Ala Gly Ala Pro Asn Ser Leu
                245                 250                 255

Gly Leu Pro Asp Asp Leu Val Ile Gly Ser Val Phe Gln Ile His Thr
            260                 265                 270

Asp Lys Gly Pro Gln Tyr Tyr Val Val Leu Pro Asp Gly Ile Ala Gln
        275                 280                 285

Val Asn Ala Thr Thr Ala Ala Leu Arg Ala Thr Gln Ala His Gly
290                 295                 300

Leu Val Ala Pro Pro Ala Met Val Pro Ser Leu Val Val Arg Ile Ala
305                 310                 315                 320

Glu Arg Val Tyr Pro Ser Pro Leu Pro Asp Glu Pro Leu Lys Ile Val
                325                 330                 335

Ser Arg Pro Gln Asp Pro Ala Leu Cys Trp Ser Trp Gln Arg Ser Ala
            340                 345                 350

Gly Asp Gln Ser Pro Gln Ser Thr Val Leu Ser Gly Arg His Leu Pro
        355                 360                 365

Ile Ser Pro Ser Ala Met Asn Met Gly Ile Lys Gln Ile His Gly Thr
370                 375                 380

Ala Thr Val Tyr Leu Asp Gly Gly Lys Phe Val Ala Leu Gln Ser Pro
385                 390                 395                 400

Asp Pro Arg Tyr Thr Glu Ser Met Tyr Tyr Ile Asp Pro Gln Gly Val
                405                 410                 415

Arg Tyr Gly Val Pro Asn Ala Glu Thr Ala Lys Ser Leu Gly Leu Ser
            420                 425                 430

Ser Pro Gln Asn Ala Pro Trp Glu Ile Val Arg Leu Leu Val Asp Gly
        435                 440                 445

Pro Val Leu Ser Lys Asp Ala Ala Leu Leu Glu His Asp Thr Leu Pro
450                 455                 460

Ala Asp Pro Ser Pro Arg Lys Val Pro Ala Gly Ala Ser Gly Ala Pro
465                 470                 475                 480

<210> SEQ ID NO 60
<211> LENGTH: 747
<212> TYPE: PRT
<213> ORGANISM: mycobacterium tuberculosis
<220> FEATURE:
<223> OTHER INFORMATION: Protein sequence Rv3870

<400> SEQUENCE: 60

Met Thr Thr Lys Lys Phe Thr Pro Thr Ile Thr Arg Gly Pro Arg Leu
1               5                   10                  15
```

Thr Pro Gly Glu Ile Ser Leu Thr Pro Pro Asp Asp Leu Gly Ile Asp
            20                  25                  30

Ile Pro Pro Ser Gly Val Gln Lys Ile Leu Pro Tyr Val Met Gly Gly
            35                  40                  45

Ala Met Leu Gly Met Ile Ala Ile Met Val Ala Gly Gly Thr Arg Gln
50                  55                  60

Leu Ser Pro Tyr Met Leu Met Met Pro Leu Met Met Ile Val Met Met
65                  70                  75                  80

Val Gly Gly Leu Ala Gly Ser Thr Gly Gly Gly Lys Lys Val Pro
                85                  90                  95

Glu Ile Asn Ala Asp Arg Lys Glu Tyr Leu Arg Tyr Leu Ala Gly Leu
                100                 105                 110

Arg Thr Arg Val Thr Ser Ser Ala Thr Ser Gln Val Ala Phe Phe Ser
            115                 120                 125

Tyr His Ala Pro His Pro Glu Asp Leu Leu Ser Ile Val Gly Thr Gln
            130                 135                 140

Arg Gln Trp Ser Arg Pro Ala Asn Ala Asp Phe Tyr Ala Ala Thr Arg
145                 150                 155                 160

Ile Gly Ile Gly Asp Gln Pro Ala Val Asp Arg Leu Leu Lys Pro Ala
                165                 170                 175

Val Gly Gly Glu Leu Ala Ala Ala Ser Ala Ala Pro Gln Pro Phe Leu
                180                 185                 190

Glu Pro Val Ser His Met Trp Val Val Lys Phe Leu Arg Thr His Gly
            195                 200                 205

Leu Ile His Asp Cys Pro Lys Leu Leu Gln Leu Arg Thr Phe Pro Thr
210                 215                 220

Ile Ala Ile Gly Gly Asp Leu Ala Gly Ala Ala Gly Leu Met Thr Ala
225                 230                 235                 240

Met Ile Cys His Leu Ala Val Phe His Pro Pro Asp Leu Leu Gln Ile
                245                 250                 255

Arg Val Leu Thr Glu Glu Pro Asp Asp Pro Asp Trp Ser Trp Leu Lys
            260                 265                 270

Trp Leu Pro His Val Gln His Gln Thr Glu Thr Asp Ala Ala Gly Ser
            275                 280                 285

Thr Arg Leu Ile Phe Thr Arg Gln Glu Gly Leu Ser Asp Leu Ala Ala
            290                 295                 300

Arg Gly Pro His Ala Pro Asp Ser Leu Pro Gly Gly Pro Tyr Val Val
305                 310                 315                 320

Val Val Asp Leu Thr Gly Gly Lys Ala Gly Phe Pro Pro Asp Gly Arg
                325                 330                 335

Ala Gly Val Thr Val Ile Thr Leu Gly Asn His Arg Gly Ser Ala Tyr
                340                 345                 350

Arg Ile Arg Val His Glu Asp Gly Thr Ala Asp Arg Leu Pro Asn
            355                 360                 365

Gln Ser Phe Arg Gln Val Thr Ser Val Thr Asp Arg Met Ser Pro Gln
            370                 375                 380

Gln Ala Ser Arg Ile Ala Arg Lys Leu Ala Gly Trp Ser Ile Thr Gly
385                 390                 395                 400

Thr Ile Leu Asp Lys Thr Ser Arg Val Gln Lys Lys Val Ala Thr Asp
                405                 410                 415

Trp His Gln Leu Val Gly Ala Gln Ser Val Glu Glu Ile Thr Pro Ser
            420                 425                 430

Arg Trp Arg Met Tyr Thr Asp Thr Asp Arg Asp Arg Leu Lys Ile Pro

```
                435                 440                 445
Phe Gly His Glu Leu Lys Thr Gly Asn Val Met Tyr Leu Asp Ile Lys
            450                 455                 460

Glu Gly Ala Glu Phe Gly Ala Gly Pro His Gly Met Leu Ile Gly Thr
465                 470                 475                 480

Thr Gly Ser Gly Lys Ser Glu Phe Leu Arg Thr Leu Ile Leu Ser Leu
                485                 490                 495

Val Ala Met Thr His Pro Asp Gln Val Asn Leu Leu Thr Asp Phe
            500                 505                 510

Lys Gly Gly Ser Thr Phe Leu Gly Met Glu Lys Leu Pro His Thr Ala
            515                 520                 525

Ala Val Val Thr Asn Met Ala Glu Glu Ala Glu Leu Val Ser Arg Met
            530                 535                 540

Gly Glu Val Leu Thr Gly Glu Leu Asp Arg Arg Gln Ser Ile Leu Arg
545                 550                 555                 560

Gln Ala Gly Met Lys Val Gly Ala Gly Ala Leu Ser Gly Val Ala
                565                 570                 575

Glu Tyr Glu Lys Tyr Arg Glu Arg Gly Ala Asp Leu Pro Pro Leu Pro
            580                 585                 590

Thr Leu Phe Val Val Asp Glu Phe Ala Glu Leu Leu Gln Ser His
            595                 600                 605

Pro Asp Phe Ile Gly Leu Phe Asp Arg Ile Cys Arg Val Gly Arg Ser
            610                 615                 620

Leu Arg Val His Leu Leu Leu Ala Thr Gln Ser Leu Gln Thr Gly Gly
625                 630                 635                 640

Val Arg Ile Asp Lys Leu Glu Pro Asn Leu Thr Tyr Arg Ile Ala Leu
                645                 650                 655

Arg Thr Thr Ser Ser His Glu Ser Lys Ala Val Ile Gly Thr Pro Glu
            660                 665                 670

Ala Gln Tyr Ile Thr Asn Lys Glu Ser Gly Val Gly Phe Leu Arg Val
            675                 680                 685

Gly Met Glu Asp Pro Val Lys Phe Ser Thr Phe Tyr Ile Ser Gly Pro
690                 695                 700

Tyr Met Pro Pro Ala Ala Gly Val Glu Thr Asn Gly Glu Ala Gly Gly
705                 710                 715                 720

Pro Gly Gln Gln Thr Thr Arg Gln Ala Ala Arg Ile His Arg Phe Thr
                725                 730                 735

Ala Ala Pro Val Leu Glu Glu Ala Pro Thr Pro
            740                 745

<210> SEQ ID NO 61
<211> LENGTH: 591
<212> TYPE: PRT
<213> ORGANISM: mycobacterium tuberculosis
<220> FEATURE:
<223> OTHER INFORMATION: Protein sequence Rv3871

<400> SEQUENCE: 61

Met Thr Ala Glu Pro Glu Val Arg Thr Leu Arg Glu Val Val Leu Asp
1               5                   10                  15

Gln Leu Gly Thr Ala Glu Ser Arg Ala Tyr Lys Met Trp Leu Pro Pro
            20                  25                  30

Leu Thr Asn Pro Val Pro Leu Asn Glu Leu Ile Ala Arg Asp Arg Arg
        35                  40                  45

Gln Pro Leu Arg Phe Ala Leu Gly Ile Met Asp Glu Pro Arg Arg His
    50                  55                  60
```

```
Leu Gln Asp Val Trp Gly Val Asp Val Ser Gly Ala Gly Asn Ile
 65                  70                  75                  80

Gly Ile Gly Gly Ala Pro Gln Thr Gly Lys Ser Thr Leu Leu Gln Thr
                 85                  90                  95

Met Val Met Ser Ala Ala Ala Thr His Ser Pro Arg Asn Val Gln Phe
                100                 105                 110

Tyr Cys Ile Asp Leu Gly Gly Gly Leu Ile Tyr Leu Glu Asn Leu
            115                 120                 125

Pro His Val Gly Gly Val Ala Asn Arg Ser Glu Pro Asp Lys Val Asn
        130                 135                 140

Arg Val Val Ala Glu Met Gln Ala Val Met Arg Gln Arg Glu Thr Thr
145                 150                 155                 160

Phe Lys Glu His Arg Val Gly Ser Ile Gly Met Tyr Arg Gln Leu Arg
                165                 170                 175

Asp Asp Pro Ser Gln Pro Val Ala Ser Asp Pro Tyr Gly Asp Val Phe
            180                 185                 190

Leu Ile Ile Asp Gly Trp Pro Gly Phe Val Gly Glu Phe Pro Asp Leu
        195                 200                 205

Glu Gly Gln Val Gln Asp Leu Ala Ala Gln Gly Leu Ala Phe Gly Val
210                 215                 220

His Val Ile Ile Ser Thr Pro Arg Trp Thr Glu Leu Lys Ser Arg Val
225                 230                 235                 240

Arg Asp Tyr Leu Gly Thr Lys Ile Glu Phe Arg Leu Gly Asp Val Asn
                245                 250                 255

Glu Thr Gln Ile Asp Arg Ile Thr Arg Glu Ile Pro Ala Asn Arg Pro
            260                 265                 270

Gly Arg Ala Val Ser Met Glu Lys His His Leu Met Ile Gly Val Pro
        275                 280                 285

Arg Phe Asp Gly Val His Ser Ala Asp Asn Leu Val Glu Ala Ile Thr
290                 295                 300

Ala Gly Val Thr Gln Ile Ala Ser Gln His Thr Glu Gln Ala Pro Pro
305                 310                 315                 320

Val Arg Val Leu Pro Glu Arg Ile His Leu His Glu Leu Asp Pro Asn
                325                 330                 335

Pro Pro Gly Pro Glu Ser Asp Tyr Arg Thr Arg Trp Glu Ile Pro Ile
            340                 345                 350

Gly Leu Arg Glu Thr Asp Leu Thr Pro Ala His Cys His Met His Thr
        355                 360                 365

Asn Pro His Leu Leu Ile Phe Gly Ala Ala Lys Ser Gly Lys Thr Thr
370                 375                 380

Ile Ala His Ala Ile Ala Arg Ala Ile Cys Ala Arg Asn Ser Pro Gln
385                 390                 395                 400

Gln Val Arg Phe Met Leu Ala Asp Tyr Arg Ser Gly Leu Leu Asp Ala
                405                 410                 415

Val Pro Asp Thr His Leu Leu Gly Ala Gly Ala Ile Asn Arg Asn Ser
            420                 425                 430

Ala Ser Leu Asp Glu Ala Val Gln Ala Leu Ala Val Asn Leu Lys Lys
        435                 440                 445

Arg Leu Pro Pro Thr Asp Leu Thr Thr Ala Gln Leu Arg Ser Arg Ser
450                 455                 460

Trp Trp Ser Gly Phe Asp Val Val Leu Leu Val Asp Asp Trp His Met
465                 470                 475                 480

Ile Val Gly Ala Ala Gly Gly Met Pro Pro Met Ala Pro Leu Ala Pro
```

```
                    485                 490                 495
Leu Leu Pro Ala Ala Ala Asp Ile Gly Leu His Ile Ile Val Thr Cys
            500                 505                 510

Gln Met Ser Gln Ala Tyr Lys Ala Thr Met Asp Lys Phe Val Gly Ala
            515                 520                 525

Ala Phe Gly Ser Gly Ala Pro Thr Met Phe Leu Ser Gly Glu Lys Gln
            530                 535                 540

Glu Phe Pro Ser Ser Glu Phe Lys Val Lys Arg Arg Pro Pro Gly Gln
545                 550                 555                 560

Ala Phe Leu Val Ser Pro Asp Gly Lys Glu Val Ile Gln Ala Pro Tyr
                565                 570                 575

Ile Glu Pro Pro Glu Glu Val Phe Ala Ala Pro Pro Ser Ala Gly
            580                 585                 590

<210> SEQ ID NO 62
<211> LENGTH: 99
<212> TYPE: PRT
<213> ORGANISM: Mycobacterium tuberculosis
<220> FEATURE:
<223> OTHER INFORMATION: Rv3872-PE35 - PE family-related protein

<400> SEQUENCE: 62

Met Glu Lys Met Ser His Asp Pro Ile Ala Ala Asp Ile Gly Thr Gln
1               5                   10                  15

Val Ser Asp Asn Ala Leu His Gly Val Thr Ala Gly Ser Thr Ala Leu
            20                  25                  30

Thr Ser Val Thr Gly Leu Val Pro Ala Gly Ala Asp Glu Val Ser Ala
        35                  40                  45

Gln Ala Ala Thr Ala Phe Thr Ser Glu Gly Ile Gln Leu Leu Ala Ser
    50                  55                  60

Asn Ala Ser Ala Gln Asp Gln Leu His Arg Ala Gly Glu Ala Val Gln
65                  70                  75                  80

Asp Val Ala Arg Thr Tyr Ser Gln Ile Asp Asp Gly Ala Ala Gly Val
                85                  90                  95

Phe Ala Glu

<210> SEQ ID NO 63
<211> LENGTH: 368
<212> TYPE: PRT
<213> ORGANISM: Mycobacterium tuberculosis
<220> FEATURE:
<223> OTHER INFORMATION: Rv3873-PPE68 - PPE family protein

<400> SEQUENCE: 63

Met Leu Trp His Ala Met Pro Pro Glu Leu Asn Thr Ala Arg Leu Met
1               5                   10                  15

Ala Gly Ala Gly Pro Ala Pro Met Leu Ala Ala Ala Gly Trp Gln
            20                  25                  30

Thr Leu Ser Ala Ala Leu Asp Ala Gln Ala Val Glu Leu Thr Ala Arg
        35                  40                  45

Leu Asn Ser Leu Gly Glu Ala Trp Thr Gly Gly Ser Asp Lys Ala
    50                  55                  60

Leu Ala Ala Ala Thr Pro Met Val Val Trp Leu Gln Thr Ala Ser Thr
65                  70                  75                  80

Gln Ala Lys Thr Arg Ala Met Gln Ala Thr Ala Gln Ala Ala Tyr
                85                  90                  95

Thr Gln Ala Met Ala Thr Thr Pro Ser Leu Pro Glu Ile Ala Ala Asn
            100                 105                 110
```

His Ile Thr Gln Ala Val Leu Thr Ala Thr Asn Phe Phe Gly Ile Asn
            115                 120                 125

Thr Ile Pro Ile Ala Leu Thr Glu Met Asp Tyr Phe Ile Arg Met Trp
        130                 135                 140

Asn Gln Ala Ala Leu Ala Met Glu Val Tyr Gln Ala Glu Thr Ala Val
145                 150                 155                 160

Asn Thr Leu Phe Glu Lys Leu Glu Pro Met Ala Ser Ile Leu Asp Pro
                165                 170                 175

Gly Ala Ser Gln Ser Thr Thr Asn Pro Ile Phe Gly Met Pro Ser Pro
            180                 185                 190

Gly Ser Ser Thr Pro Val Gly Gln Leu Pro Pro Ala Ala Thr Gln Thr
        195                 200                 205

Leu Gly Gln Leu Gly Glu Met Ser Gly Pro Met Gln Gln Leu Thr Gln
    210                 215                 220

Pro Leu Gln Gln Val Thr Ser Leu Phe Ser Gln Val Gly Gly Thr Gly
225                 230                 235                 240

Gly Gly Asn Pro Ala Asp Glu Glu Ala Ala Gln Met Gly Leu Leu Gly
                245                 250                 255

Thr Ser Pro Leu Ser Asn His Pro Leu Ala Gly Gly Ser Gly Pro Ser
            260                 265                 270

Ala Gly Ala Gly Leu Leu Arg Ala Glu Ser Leu Pro Gly Ala Gly Gly
        275                 280                 285

Ser Leu Thr Arg Thr Pro Leu Met Ser Gln Leu Ile Glu Lys Pro Val
    290                 295                 300

Ala Pro Ser Val Met Pro Ala Ala Ala Gly Ser Ser Ala Thr Gly
305                 310                 315                 320

Gly Ala Ala Pro Val Gly Ala Gly Ala Met Gly Gln Gly Ala Gln Ser
                325                 330                 335

Gly Gly Ser Thr Arg Pro Gly Leu Val Ala Pro Ala Pro Leu Ala Gln
            340                 345                 350

Glu Arg Glu Glu Asp Asp Glu Asp Asp Trp Asp Glu Glu Asp Asp Trp
        355                 360                 365

<210> SEQ ID NO 64
<211> LENGTH: 100
<212> TYPE: PRT
<213> ORGANISM: Mycobacterium tuberculosis
<220> FEATURE:
<223> OTHER INFORMATION: Rv3874-esxB - 10kDa culture filtrate antigen
      CFP10

<400> SEQUENCE: 64

Met Ala Glu Met Lys Thr Asp Ala Ala Thr Leu Ala Gln Glu Ala Gly
1               5                   10                  15

Asn Phe Glu Arg Ile Ser Gly Asp Leu Lys Thr Gln Ile Asp Gln Val
                20                  25                  30

Glu Ser Thr Ala Gly Ser Leu Gln Gly Gln Trp Arg Gly Ala Ala Gly
            35                  40                  45

Thr Ala Ala Gln Ala Ala Val Val Arg Phe Gln Glu Ala Ala Asn Lys
        50                  55                  60

Gln Lys Gln Glu Leu Asp Glu Ile Ser Thr Asn Ile Arg Gln Ala Gly
65                  70                  75                  80

Val Gln Tyr Ser Arg Ala Asp Glu Glu Gln Gln Gln Ala Leu Ser Ser
                85                  90                  95

Gln Met Gly Phe
            100

```
<210> SEQ ID NO 65
<211> LENGTH: 95
<212> TYPE: PRT
<213> ORGANISM: Mycobacterium tuberculosis
<220> FEATURE:
<223> OTHER INFORMATION: Rv3875-Esat6 - 6 kDa early secretory antigenic
      target Esat6 (Esat-6)

<400> SEQUENCE: 65

Met Thr Glu Gln Gln Trp Asn Phe Ala Gly Ile Glu Ala Ala Ala Ser
1               5                   10                  15

Ala Ile Gln Gly Asn Val Thr Ser Ile His Ser Leu Leu Asp Glu Gly
            20                  25                  30

Lys Gln Ser Leu Thr Lys Leu Ala Ala Ala Trp Gly Gly Ser Gly Ser
        35                  40                  45

Glu Ala Tyr Gln Gly Val Gln Gln Lys Trp Asp Ala Thr Ala Thr Glu
    50                  55                  60

Leu Asn Asn Ala Leu Gln Asn Leu Ala Arg Thr Ile Ser Glu Ala Gly
65                  70                  75                  80

Gln Ala Met Ala Ser Thr Glu Gly Asn Val Thr Gly Met Phe Ala
                85                  90                  95

<210> SEQ ID NO 66
<211> LENGTH: 666
<212> TYPE: PRT
<213> ORGANISM: mycobacterium tuberculosis
<220> FEATURE:
<223> OTHER INFORMATION: Protein sequence Rv3876

<400> SEQUENCE: 66

Met Ala Ala Asp Tyr Asp Lys Leu Phe Arg Pro His Glu Gly Met Glu
1               5                   10                  15

Ala Pro Asp Asp Met Ala Ala Gln Pro Phe Phe Asp Pro Ser Ala Ser
            20                  25                  30

Phe Pro Pro Ala Pro Ala Ser Ala Asn Leu Pro Lys Pro Asn Gly Gln
        35                  40                  45

Thr Pro Pro Pro Thr Ser Asp Asp Leu Ser Glu Arg Phe Val Ser Ala
    50                  55                  60

Pro Pro Pro Pro Pro Pro Pro Pro Pro Pro Pro Thr Pro Met
65                  70                  75                  80

Pro Ile Ala Ala Gly Glu Pro Pro Ser Pro Glu Pro Ala Ala Ser Lys
                85                  90                  95

Pro Pro Thr Pro Pro Met Pro Ile Ala Gly Pro Glu Pro Ala Pro Pro
            100                 105                 110

Lys Pro Pro Thr Pro Pro Met Pro Ile Ala Gly Pro Glu Pro Ala Pro
        115                 120                 125

Pro Lys Pro Pro Thr Pro Pro Met Pro Ile Ala Gly Pro Ala Pro Thr
    130                 135                 140

Pro Thr Glu Ser Gln Leu Ala Pro Pro Arg Pro Pro Thr Pro Gln Thr
145                 150                 155                 160

Pro Thr Gly Ala Pro Gln Gln Pro Glu Ser Pro Ala Pro His Val Pro
                165                 170                 175

Ser His Gly Pro His Gln Pro Arg Arg Thr Ala Pro Ala Pro Pro Trp
            180                 185                 190

Ala Lys Met Pro Ile Gly Glu Pro Pro Ala Pro Ser Arg Pro Ser
        195                 200                 205

Ala Ser Pro Ala Glu Pro Pro Thr Arg Pro Ala Pro Gln His Ser Arg
    210                 215                 220
```

-continued

Arg Ala Arg Arg Gly His Arg Tyr Arg Thr Asp Thr Glu Arg Asn Val
225                 230                 235                 240

Gly Lys Val Ala Thr Gly Pro Ser Ile Gln Ala Arg Leu Arg Ala Glu
            245                 250                 255

Glu Ala Ser Gly Ala Gln Leu Ala Pro Gly Thr Glu Pro Ser Pro Ala
        260                 265                 270

Pro Leu Gly Gln Pro Arg Ser Tyr Leu Ala Pro Thr Arg Pro Ala
    275                 280                 285

Pro Thr Glu Pro Pro Ser Pro Ser Pro Gln Arg Asn Ser Gly Arg
290                 295                 300

Arg Ala Glu Arg Arg Val His Pro Asp Leu Ala Ala Gln His Ala Ala
305                 310                 315                 320

Ala Gln Pro Asp Ser Ile Thr Ala Ala Thr Thr Gly Arg Arg
                325                 330                 335

Lys Arg Ala Ala Pro Asp Leu Asp Ala Thr Gln Lys Ser Leu Arg Pro
            340                 345                 350

Ala Ala Lys Gly Pro Lys Val Lys Val Lys Pro Gln Lys Pro Lys
        355                 360                 365

Ala Thr Lys Pro Pro Lys Val Val Ser Gln Arg Gly Trp Arg His Trp
370                 375                 380

Val His Ala Leu Thr Arg Ile Asn Leu Gly Leu Ser Pro Asp Glu Lys
385                 390                 395                 400

Tyr Glu Leu Asp Leu His Ala Arg Val Arg Arg Asn Pro Arg Gly Ser
                405                 410                 415

Tyr Gln Ile Ala Val Val Gly Leu Lys Gly Ala Gly Lys Thr Thr
            420                 425                 430

Leu Thr Ala Ala Leu Gly Ser Thr Leu Ala Gln Val Arg Ala Asp Arg
        435                 440                 445

Ile Leu Ala Leu Asp Ala Asp Pro Gly Ala Gly Asn Leu Ala Asp Arg
    450                 455                 460

Val Gly Arg Gln Ser Gly Ala Thr Ile Ala Asp Val Leu Ala Glu Lys
465                 470                 475                 480

Glu Leu Ser His Tyr Asn Asp Ile Arg Ala His Thr Ser Val Asn Ala
                485                 490                 495

Val Asn Leu Glu Val Leu Pro Ala Pro Glu Tyr Ser Ser Ala Gln Arg
            500                 505                 510

Ala Leu Ser Asp Ala Asp Trp His Phe Ile Ala Asp Pro Ala Ser Arg
        515                 520                 525

Phe Tyr Asn Leu Val Leu Ala Asp Cys Gly Ala Gly Phe Phe Asp Pro
    530                 535                 540

Leu Thr Arg Gly Val Leu Ser Thr Val Ser Gly Val Val Val Ala
545                 550                 555                 560

Ser Val Ser Ile Asp Gly Ala Gln Gln Ala Ser Val Ala Leu Asp Trp
                565                 570                 575

Leu Arg Asn Asn Gly Tyr Gln Asp Leu Ala Ser Arg Ala Cys Val Val
            580                 585                 590

Ile Asn His Ile Met Pro Gly Glu Pro Asn Val Ala Val Lys Asp Leu
        595                 600                 605

Val Arg His Phe Glu Gln Gln Val Gln Pro Gly Arg Val Val Val Met
    610                 615                 620

Pro Trp Asp Arg His Ile Ala Ala Gly Thr Glu Ile Ser Leu Asp Leu
625                 630                 635                 640

```
Leu Asp Pro Ile Tyr Lys Arg Lys Val Leu Glu Leu Ala Ala Ala Leu
            645                 650                 655

Ser Asp Asp Phe Glu Arg Ala Gly Arg Arg
            660                 665

<210> SEQ ID NO 67
<211> LENGTH: 511
<212> TYPE: PRT
<213> ORGANISM: mycobacterium tuberculosis
<220> FEATURE:
<223> OTHER INFORMATION: Protein sequence Rv3877

<400> SEQUENCE: 67

Met Ser Ala Pro Ala Val Ala Ala Gly Pro Thr Ala Gly Ala Thr
1               5                   10                  15

Ala Ala Arg Pro Ala Thr Thr Arg Val Thr Ile Leu Thr Gly Arg Arg
            20                  25                  30

Met Thr Asp Leu Val Leu Pro Ala Ala Val Pro Met Glu Thr Tyr Ile
            35                  40                  45

Asp Asp Thr Val Ala Val Leu Ser Glu Val Leu Glu Asp Thr Pro Ala
        50                  55                  60

Asp Val Leu Gly Gly Phe Asp Phe Thr Ala Gln Gly Val Trp Ala Phe
65                  70                  75                  80

Ala Arg Pro Gly Ser Pro Leu Lys Leu Asp Gln Ser Leu Asp Asp
            85                  90                  95

Ala Gly Val Val Asp Gly Ser Leu Leu Thr Leu Val Ser Val Ser Arg
            100                 105                 110

Thr Glu Arg Tyr Arg Pro Leu Val Glu Asp Val Ile Asp Ala Ile Ala
            115                 120                 125

Val Leu Asp Glu Ser Pro Glu Phe Asp Arg Thr Ala Leu Asn Arg Phe
        130                 135                 140

Val Gly Ala Ala Ile Pro Leu Leu Thr Ala Pro Val Ile Gly Met Ala
145                 150                 155                 160

Met Arg Ala Trp Trp Glu Thr Gly Arg Ser Leu Trp Trp Pro Leu Ala
            165                 170                 175

Ile Gly Ile Leu Gly Ile Ala Val Leu Val Gly Ser Phe Val Ala Asn
            180                 185                 190

Arg Phe Tyr Gln Ser Gly His Leu Ala Glu Cys Leu Leu Val Thr Thr
            195                 200                 205

Tyr Leu Leu Ile Ala Thr Ala Ala Ala Leu Ala Val Pro Leu Pro Arg
        210                 215                 220

Gly Val Asn Ser Leu Gly Ala Pro Gln Val Ala Gly Ala Ala Thr Ala
225                 230                 235                 240

Val Leu Phe Leu Thr Leu Met Thr Arg Gly Gly Pro Arg Lys Arg His
            245                 250                 255

Glu Leu Ala Ser Phe Ala Val Ile Thr Ala Ile Ala Val Ile Ala Ala
            260                 265                 270

Ala Ala Ala Phe Gly Tyr Gly Tyr Gln Asp Trp Val Pro Ala Gly Gly
            275                 280                 285

Ile Ala Phe Gly Leu Phe Ile Val Thr Asn Ala Ala Lys Leu Thr Val
        290                 295                 300

Ala Val Ala Arg Ile Ala Leu Pro Pro Ile Pro Val Pro Gly Glu Thr
305                 310                 315                 320

Val Asp Asn Glu Glu Leu Leu Asp Pro Val Ala Thr Pro Glu Ala Thr
            325                 330                 335
```

```
Ser Glu Glu Thr Pro Thr Trp Gln Ala Ile Ile Ala Ser Val Pro Ala
            340                 345                 350

Ser Ala Val Arg Leu Thr Glu Arg Ser Lys Leu Ala Lys Gln Leu Leu
            355                 360                 365

Ile Gly Tyr Val Thr Ser Gly Thr Leu Ile Leu Ala Ala Gly Ala Ile
        370                 375                 380

Ala Val Val Val Arg Gly His Phe Phe Val His Ser Leu Val Val Ala
385                 390                 395                 400

Gly Leu Ile Thr Thr Val Cys Gly Phe Arg Ser Arg Leu Tyr Ala Glu
                405                 410                 415

Arg Trp Cys Ala Trp Ala Leu Leu Ala Ala Thr Val Ala Ile Pro Thr
            420                 425                 430

Gly Leu Thr Ala Lys Leu Ile Ile Trp Tyr Pro His Tyr Ala Trp Leu
        435                 440                 445

Leu Leu Ser Val Tyr Leu Thr Val Ala Leu Val Ala Leu Val Val Val
    450                 455                 460

Gly Ser Met Ala His Val Arg Arg Val Ser Pro Val Val Lys Arg Thr
465                 470                 475                 480

Leu Glu Leu Ile Asp Gly Ala Met Ile Ala Ala Ile Pro Met Leu
                485                 490                 495

Leu Trp Ile Thr Gly Val Tyr Asp Thr Val Arg Asn Ile Arg Phe
            500                 505                 510

<210> SEQ ID NO 68
<211> LENGTH: 280
<212> TYPE: PRT
<213> ORGANISM: Mycobacterium tuberculosis
<220> FEATURE:
<223> OTHER INFORMATION: Rv3878 - conserved hypothetical alanine rich
      protein

<400> SEQUENCE: 68

Met Ala Glu Pro Leu Ala Val Asp Pro Thr Gly Leu Ser Ala Ala Ala
1               5                   10                  15

Ala Lys Leu Ala Gly Leu Val Phe Pro Gln Pro Pro Ala Pro Ile Ala
            20                  25                  30

Val Ser Gly Thr Asp Ser Val Ala Ala Ile Asn Glu Thr Met Pro
        35                  40                  45

Ser Ile Glu Ser Leu Val Ser Asp Gly Leu Pro Gly Val Lys Ala Ala
    50                  55                  60

Leu Thr Arg Thr Ala Ser Asn Met Asn Ala Ala Ala Asp Val Tyr Ala
65                  70                  75                  80

Lys Thr Asp Gln Ser Leu Gly Thr Ser Leu Ser Gln Tyr Ala Phe Gly
                85                  90                  95

Ser Ser Gly Glu Gly Leu Ala Gly Val Ala Ser Val Gly Gly Gln Pro
            100                 105                 110

Ser Gln Ala Thr Gln Leu Leu Ser Thr Pro Val Ser Gln Val Thr Thr
        115                 120                 125

Gln Leu Gly Glu Thr Ala Ala Glu Leu Ala Pro Arg Val Val Ala Thr
    130                 135                 140

Val Pro Gln Leu Val Gln Leu Ala Pro His Ala Val Gln Met Ser Gln
145                 150                 155                 160

Asn Ala Ser Pro Ile Ala Gln Thr Ile Ser Gln Thr Ala Gln Ala
                165                 170                 175

Ala Gln Ser Ala Gln Gly Gly Ser Gly Pro Met Pro Ala Gln Leu Ala
            180                 185                 190
```

```
Ser Ala Glu Lys Pro Ala Thr Glu Gln Ala Glu Pro Val His Glu Val
        195                 200                 205

Thr Asn Asp Asp Gln Gly Asp Gln Gly Asp Val Gln Pro Ala Glu Val
    210                 215                 220

Val Ala Ala Ala Arg Asp Glu Gly Ala Gly Ala Ser Pro Gly Gln Gln
225                 230                 235                 240

Pro Gly Gly Gly Val Pro Ala Gln Ala Met Asp Thr Gly Ala Gly Ala
                245                 250                 255

Arg Pro Ala Ala Ser Pro Leu Ala Ala Pro Val Asp Pro Ser Thr Pro
                260                 265                 270

Ala Pro Ser Thr Thr Thr Thr Leu
                275                 280

<210> SEQ ID NO 69
<211> LENGTH: 729
<212> TYPE: PRT
<213> ORGANISM: Mycobacterium tuberculosis
<220> FEATURE:
<223> OTHER INFORMATION: Rv3879c - hypothetical alanine and proline rich
      protein

<400> SEQUENCE: 69

Met Ser Ile Thr Arg Pro Thr Gly Ser Tyr Ala Arg Gln Met Leu Asp
1               5                   10                  15

Pro Gly Gly Trp Val Glu Ala Asp Glu Asp Thr Phe Tyr Asp Arg Ala
                20                  25                  30

Gln Glu Tyr Ser Gln Val Leu Gln Arg Val Thr Asp Val Leu Asp Thr
            35                  40                  45

Cys Arg Gln Gln Lys Gly His Val Phe Glu Gly Gly Leu Trp Ser Gly
    50                  55                  60

Gly Ala Ala Asn Ala Ala Asn Gly Ala Leu Gly Ala Asn Ile Asn Gln
65                  70                  75                  80

Leu Met Thr Leu Gln Asp Tyr Leu Ala Thr Val Ile Thr Trp His Arg
                85                  90                  95

His Ile Ala Gly Leu Ile Glu Gln Ala Lys Ser Asp Ile Gly Asn Asn
                100                 105                 110

Val Asp Gly Ala Gln Arg Glu Ile Asp Ile Leu Glu Asn Asp Pro Ser
            115                 120                 125

Leu Asp Ala Asp Glu Arg His Thr Ala Ile Asn Ser Leu Val Thr Ala
    130                 135                 140

Thr His Gly Ala Asn Val Ser Leu Val Ala Glu Thr Ala Glu Arg Val
145                 150                 155                 160

Leu Glu Ser Lys Asn Trp Lys Pro Pro Lys Asn Ala Leu Glu Asp Leu
                165                 170                 175

Leu Gln Gln Lys Ser Pro Pro Pro Asp Val Pro Thr Leu Val Val
                180                 185                 190

Pro Ser Pro Gly Thr Pro Gly Thr Pro Gly Thr Pro Ile Thr Pro Gly
            195                 200                 205

Thr Pro Ile Thr Pro Gly Thr Pro Ile Thr Pro Ile Pro Gly Ala Pro
    210                 215                 220

Val Thr Pro Ile Thr Pro Thr Pro Gly Thr Pro Val Thr Pro Val Thr
225                 230                 235                 240

Pro Gly Lys Pro Val Thr Pro Val Thr Pro Val Lys Pro Gly Thr Pro
                245                 250                 255

Gly Glu Pro Thr Pro Ile Thr Pro Val Thr Pro Pro Val Ala Pro Ala
                260                 265                 270
```

```
Thr Pro Ala Thr Pro Ala Thr Pro Val Thr Pro Ala Pro Ala Pro His
        275                 280                 285

Pro Gln Pro Ala Pro Ala Pro Ala Pro Ser Pro Gly Pro Gln Pro Val
    290                 295                 300

Thr Pro Ala Thr Pro Gly Pro Ser Gly Pro Ala Thr Pro Gly Thr Pro
305                 310                 315                 320

Gly Gly Glu Pro Ala Pro His Val Lys Pro Ala Ala Leu Ala Glu Gln
                325                 330                 335

Pro Gly Val Pro Gly Gln His Ala Gly Gly Thr Gln Ser Gly Pro
            340                 345                 350

Ala His Ala Asp Glu Ser Ala Ala Ser Val Thr Pro Ala Ala Ala Ser
            355                 360                 365

Gly Val Pro Gly Ala Arg Ala Ala Ala Ala Pro Ser Gly Thr Ala
370                 375                 380

Val Gly Ala Gly Ala Arg Ser Ser Val Gly Thr Ala Ala Ala Ser Gly
385                 390                 395                 400

Ala Gly Ser His Ala Ala Thr Gly Arg Ala Pro Val Ala Thr Ser Asp
                405                 410                 415

Lys Ala Ala Ala Pro Ser Thr Arg Ala Ala Ser Ala Arg Thr Ala Pro
                420                 425                 430

Pro Ala Arg Pro Pro Ser Thr Asp His Ile Asp Lys Pro Asp Arg Ser
            435                 440                 445

Glu Ser Ala Asp Asp Gly Thr Pro Val Ser Met Ile Pro Val Ser Ala
    450                 455                 460

Ala Arg Ala Ala Arg Asp Ala Ala Thr Ala Ala Ala Ser Ala Arg Gln
465                 470                 475                 480

Arg Gly Arg Gly Asp Ala Leu Arg Leu Ala Arg Arg Ile Ala Ala Ala
                485                 490                 495

Leu Asn Ala Ser Asp Asn Asn Ala Gly Asp Tyr Gly Phe Phe Trp Ile
            500                 505                 510

Thr Ala Val Thr Thr Asp Gly Ser Ile Val Val Ala Asn Ser Tyr Gly
        515                 520                 525

Leu Ala Tyr Ile Pro Asp Gly Met Glu Leu Pro Asn Lys Val Tyr Leu
    530                 535                 540

Ala Ser Ala Asp His Ala Ile Pro Val Asp Glu Ile Ala Arg Cys Ala
545                 550                 555                 560

Thr Tyr Pro Val Leu Ala Val Gln Ala Trp Ala Ala Phe His Asp Met
                565                 570                 575

Thr Leu Arg Ala Val Ile Gly Thr Ala Glu Gln Leu Ala Ser Ser Asp
            580                 585                 590

Pro Gly Val Ala Lys Ile Val Leu Glu Pro Asp Asp Ile Pro Glu Ser
        595                 600                 605

Gly Lys Met Thr Gly Arg Ser Arg Leu Glu Val Val Asp Pro Ser Ala
    610                 615                 620

Ala Ala Gln Leu Ala Asp Thr Thr Asp Gln Arg Leu Leu Asp Leu Leu
625                 630                 635                 640

Pro Pro Ala Pro Val Asp Val Asn Pro Gly Asp Glu Arg His Met
                645                 650                 655

Leu Trp Phe Glu Leu Met Lys Pro Met Thr Ser Thr Ala Thr Gly Arg
            660                 665                 670

Glu Ala Ala His Leu Arg Ala Phe Arg Ala Tyr Ala Ala His Ser Gln
        675                 680                 685

Glu Ile Ala Leu His Gln Ala His Thr Ala Thr Asp Ala Ala Val Gln
    690                 695                 700
```

```
Arg Val Ala Val Ala Asp Trp Leu Tyr Trp Gln Tyr Val Thr Gly Leu
705                 710                 715                 720

Leu Asp Arg Ala Leu Ala Ala Ala Cys
                725

<210> SEQ ID NO 70
<211> LENGTH: 115
<212> TYPE: PRT
<213> ORGANISM: Mycobacterium tuberculosis
<220> FEATURE:
<223> OTHER INFORMATION: Rv3880c - conserved hypothetical protein

<400> SEQUENCE: 70

Val Ser Met Asp Glu Leu Asp Pro His Val Ala Arg Ala Leu Thr Leu
1               5                   10                  15

Ala Ala Arg Phe Gln Ser Ala Leu Asp Gly Thr Leu Asn Gln Met Asn
                20                  25                  30

Asn Gly Ser Phe Arg Ala Thr Asp Glu Ala Glu Thr Val Glu Val Thr
            35                  40                  45

Ile Asn Gly His Gln Trp Leu Thr Gly Leu Arg Ile Glu Asp Gly Leu
        50                  55                  60

Leu Lys Lys Leu Gly Ala Glu Ala Val Ala Gln Arg Val Asn Glu Ala
65                  70                  75                  80

Leu His Asn Ala Gln Ala Ala Ser Ala Tyr Asn Asp Ala Ala Gly
                85                  90                  95

Glu Gln Leu Thr Ala Ala Leu Ser Ala Met Ser Arg Ala Met Asn Glu
                100                 105                 110

Gly Met Ala
        115

<210> SEQ ID NO 71
<211> LENGTH: 460
<212> TYPE: PRT
<213> ORGANISM: Mycobacterium tuberculosis
<220> FEATURE:
<223> OTHER INFORMATION: Rv3881c - conserved hypothetical alanine and
      glycine rich protein

<400> SEQUENCE: 71

Met Thr Gln Ser Gln Thr Val Thr Val Asp Gln Gln Glu Ile Leu Asn
1               5                   10                  15

Arg Ala Asn Glu Val Glu Ala Pro Met Ala Asp Pro Pro Thr Asp Val
                20                  25                  30

Pro Ile Thr Pro Cys Glu Leu Thr Ala Ala Lys Asn Ala Ala Gln Gln
            35                  40                  45

Leu Val Leu Ser Ala Asp Asn Met Arg Glu Tyr Leu Ala Ala Gly Ala
        50                  55                  60

Lys Glu Arg Gln Arg Leu Ala Thr Ser Leu Arg Asn Ala Ala Lys Ala
65                  70                  75                  80

Tyr Gly Glu Val Asp Glu Ala Ala Thr Ala Leu Asp Asn Asp Gly
                85                  90                  95

Glu Gly Thr Val Gln Ala Glu Ser Ala Gly Ala Val Gly Gly Asp Ser
                100                 105                 110

Ser Ala Glu Leu Thr Asp Thr Pro Arg Val Ala Thr Ala Gly Glu Pro
            115                 120                 125

Asn Phe Met Asp Leu Lys Glu Ala Ala Arg Lys Leu Glu Thr Gly Asp
        130                 135                 140

Gln Gly Ala Ser Leu Ala His Phe Ala Asp Gly Trp Asn Thr Phe Asn
145                 150                 155                 160
```

```
Leu Thr Leu Gln Gly Asp Val Lys Arg Phe Arg Gly Phe Asp Asn Trp
            165                 170                 175

Glu Gly Asp Ala Ala Thr Ala Cys Glu Ala Ser Leu Asp Gln Gln Arg
            180                 185                 190

Gln Trp Ile Leu His Met Ala Lys Leu Ser Ala Ala Met Ala Lys Gln
            195                 200                 205

Ala Gln Tyr Val Ala Gln Leu His Val Trp Ala Arg Arg Glu His Pro
            210                 215                 220

Thr Tyr Glu Asp Ile Val Gly Leu Glu Arg Leu Tyr Ala Glu Asn Pro
225                 230                 235                 240

Ser Ala Arg Asp Gln Ile Leu Pro Val Tyr Ala Glu Tyr Gln Gln Arg
            245                 250                 255

Ser Glu Lys Val Leu Thr Glu Tyr Asn Asn Lys Ala Ala Leu Glu Pro
            260                 265                 270

Val Asn Pro Pro Lys Pro Pro Ala Ile Lys Ile Asp Pro Pro
            275                 280                 285

Pro Pro Gln Glu Gln Gly Leu Ile Pro Gly Phe Leu Met Pro Pro Ser
            290                 295                 300

Asp Gly Ser Gly Val Thr Pro Gly Thr Gly Met Pro Ala Ala Pro Met
305                 310                 315                 320

Val Pro Pro Thr Gly Ser Pro Gly Gly Gly Leu Pro Ala Asp Thr Ala
            325                 330                 335

Ala Gln Leu Thr Ser Ala Gly Arg Glu Ala Ala Ala Leu Ser Gly Asp
            340                 345                 350

Val Ala Val Lys Ala Ala Ser Leu Gly Gly Gly Gly Gly Val
            355                 360                 365

Pro Ser Ala Pro Leu Gly Ser Ala Ile Gly Gly Ala Glu Ser Val Arg
370                 375                 380

Pro Ala Gly Ala Gly Asp Ile Ala Gly Leu Gly Gln Gly Arg Ala Gly
385                 390                 395                 400

Gly Gly Ala Ala Leu Gly Gly Gly Met Gly Met Pro Met Gly Ala
                    405                 410                 415

Ala His Gln Gly Gln Gly Gly Ala Lys Ser Lys Gly Ser Gln Gln Glu
            420                 425                 430

Asp Glu Ala Leu Tyr Thr Glu Asp Arg Ala Trp Thr Glu Ala Val Ile
            435                 440                 445

Gly Asn Arg Arg Arg Gln Asp Ser Lys Glu Ser Lys
450                 455                 460

<210> SEQ ID NO 72
<211> LENGTH: 462
<212> TYPE: PRT
<213> ORGANISM: Mycobacterium tuberculosis
<220> FEATURE:
<223> OTHER INFORMATION: Rv3882c - possible conserved membrane protein

<400> SEQUENCE: 72

Met Arg Asn Pro Leu Gly Leu Arg Phe Ser Thr Gly His Ala Leu Leu
1               5                   10                  15

Ala Ser Ala Leu Ala Pro Pro Cys Ile Ile Ala Phe Leu Glu Thr Arg
            20                  25                  30

Tyr Trp Trp Ala Gly Ile Ala Leu Ala Ser Leu Gly Val Ile Val Ala
            35                  40                  45

Thr Val Thr Phe Tyr Gly Arg Arg Ile Thr Gly Trp Val Ala Ala Val
            50                  55                  60
```

-continued

```
Tyr Ala Trp Leu Arg Arg Arg Arg Pro Pro Asp Ser Ser Ser Glu
 65                  70                  75                  80

Pro Val Val Gly Ala Thr Val Lys Pro Gly Asp His Val Ala Val Arg
                 85                  90                  95

Trp Gln Gly Glu Phe Leu Val Ala Val Ile Glu Leu Ile Pro Arg Pro
            100                 105                 110

Phe Thr Pro Thr Val Ile Val Asp Gly Gln Ala His Thr Asp Asp Met
        115                 120                 125

Leu Asp Thr Gly Leu Val Glu Glu Leu Leu Ser Val His Cys Pro Asp
130                 135                 140

Leu Glu Ala Asp Ile Val Ser Ala Gly Tyr Arg Val Gly Asn Thr Ala
145                 150                 155                 160

Ala Pro Asp Val Val Ser Leu Tyr Gln Gln Val Ile Gly Thr Asp Pro
                165                 170                 175

Ala Pro Ala Asn Arg Arg Thr Trp Ile Val Leu Arg Ala Asp Pro Glu
            180                 185                 190

Arg Thr Arg Lys Ser Ala Gln Arg Asp Glu Gly Val Ala Gly Leu
        195                 200                 205

Ala Arg Tyr Leu Val Ala Ser Ala Thr Arg Ile Ala Asp Arg Leu Ala
210                 215                 220

Ser His Gly Val Asp Ala Val Cys Gly Arg Ser Phe Asp Asp Tyr Asp
225                 230                 235                 240

His Ala Thr Asp Ile Gly Phe Val Arg Glu Lys Trp Ser Met Ile Lys
                245                 250                 255

Gly Arg Asp Ala Tyr Thr Ala Ala Tyr Ala Ala Pro Gly Gly Pro Asp
            260                 265                 270

Val Trp Trp Ser Ala Arg Ala Asp His Thr Ile Thr Arg Val Arg Val
        275                 280                 285

Ala Pro Gly Met Ala Pro Gln Ser Thr Val Leu Leu Thr Thr Ala Asp
290                 295                 300

Lys Pro Lys Thr Pro Arg Gly Phe Ala Arg Leu Phe Gly Gly Gln Arg
305                 310                 315                 320

Pro Ala Leu Gln Gly Gln His Leu Val Ala Asn Arg His Cys Gln Leu
                325                 330                 335

Pro Ile Gly Ser Ala Gly Val Leu Val Gly Glu Thr Val Asn Arg Cys
            340                 345                 350

Pro Val Tyr Met Pro Phe Asp Val Asp Ile Ala Leu Asn Leu Gly
        355                 360                 365

Asp Ala Gln Thr Phe Thr Gln Phe Val Val Arg Ala Ala Ala Gly
370                 375                 380

Ala Met Val Thr Val Gly Pro Gln Phe Glu Glu Phe Ala Arg Leu Ile
385                 390                 395                 400

Gly Ala His Ile Gly Gln Glu Val Lys Val Ala Trp Pro Asn Ala Thr
                405                 410                 415

Thr Tyr Leu Gly Pro His Pro Gly Ile Asp Arg Val Ile Leu Arg His
            420                 425                 430

Asn Val Ile Gly Thr Pro Arg His Arg Gln Leu Pro Ile Arg Arg Val
        435                 440                 445

Ser Pro Pro Glu Glu Ser Arg Tyr Gln Met Ala Leu Pro Lys
450                 455                 460

<210> SEQ ID NO 73
<211> LENGTH: 446
<212> TYPE: PRT
<213> ORGANISM: Mycobacterium tuberculosis
```

<220> FEATURE:
<223> OTHER INFORMATION: Rv3883c - possible secreted protease

<400> SEQUENCE: 73

```
Val His Arg Ile Phe Leu Ile Thr Val Ala Leu Ala Leu Leu Thr Ala
1               5                   10                  15

Ser Pro Ala Ser Ala Ile Thr Pro Pro Ile Asp Pro Gly Ala Leu
            20                  25                  30

Pro Pro Asp Val Thr Gly Pro Asp Gln Pro Thr Glu Gln Arg Val Leu
        35                  40                  45

Cys Ala Ser Pro Thr Thr Leu Pro Gly Ser Gly Phe His Asp Pro Pro
    50                  55                  60

Trp Ser Asn Thr Tyr Leu Gly Val Ala Asp Ala His Lys Phe Ala Thr
65              70                  75                  80

Gly Ala Gly Val Thr Val Ala Val Ile Asp Thr Gly Val Asp Ala Ser
                85                  90                  95

Pro Arg Val Pro Ala Glu Pro Gly Gly Asp Phe Val Asp Gln Ala Gly
            100                 105                 110

Asn Gly Leu Ser Asp Cys Asp Ala His Gly Thr Leu Thr Ala Ser Ile
        115                 120                 125

Ile Ala Gly Arg Pro Ala Pro Thr Asp Gly Phe Val Gly Val Ala Pro
130                 135                 140

Asp Ala Arg Leu Leu Ser Leu Arg Gln Thr Ser Glu Ala Phe Glu Pro
145                 150                 155                 160

Val Gly Ser Gln Ala Asn Pro Asn Asp Pro Asn Ala Thr Pro Ala Ala
                165                 170                 175

Gly Ser Ile Arg Ser Leu Ala Arg Ala Val Val His Ala Ala Asn Leu
            180                 185                 190

Gly Val Gly Val Ile Asn Ile Ser Glu Ala Ala Cys Tyr Lys Val Ser
        195                 200                 205

Arg Pro Ile Asp Glu Thr Ser Leu Gly Ala Ser Ile Asp Tyr Ala Val
    210                 215                 220

Asn Val Lys Gly Val Val Val Val Ala Ala Gly Asn Thr Gly Gly
225                 230                 235                 240

Asp Cys Val Gln Asn Pro Ala Pro Asp Pro Ser Thr Pro Gly Asp Pro
                245                 250                 255

Arg Gly Trp Asn Asn Val Gln Thr Val Val Thr Pro Ala Trp Tyr Ala
            260                 265                 270

Pro Leu Val Leu Ser Val Gly Gly Ile Gly Gln Thr Gly Met Pro Ser
        275                 280                 285

Ser Phe Ser Met His Gly Pro Trp Val Asp Val Ala Ala Pro Ala Glu
    290                 295                 300

Asn Ile Val Ala Leu Gly Asp Thr Gly Glu Pro Val Asn Ala Leu Gln
305                 310                 315                 320

Gly Arg Glu Gly Pro Val Pro Ile Ala Gly Thr Ser Phe Ala Ala Ala
                325                 330                 335

Tyr Val Ser Gly Leu Ala Ala Leu Leu Arg Gln Arg Phe Pro Asp Leu
            340                 345                 350

Thr Pro Ala Gln Ile Ile His Arg Ile Thr Ala Thr Ala Arg His Pro
        355                 360                 365

Gly Gly Gly Val Asp Asp Leu Val Gly Ala Val Ile Asp Ala Val
    370                 375                 380

Ala Ala Leu Thr Trp Asp Ile Pro Pro Gly Pro Ala Ser Ala Pro Tyr
385                 390                 395                 400
```

-continued

Asn Val Arg Arg Leu Pro Pro Val Val Glu Gly Pro Asp Arg
                405             410             415

Arg Pro Ile Thr Ala Val Ala Leu Val Ala Val Gly Leu Thr Leu Ala
            420                 425                 430

Leu Gly Leu Gly Ala Leu Ala Arg Arg Ala Leu Ser Arg Arg
435                 440                 445

<210> SEQ ID NO 74
<211> LENGTH: 619
<212> TYPE: PRT
<213> ORGANISM: Mycobacterium tuberculosis
<220> FEATURE:
<223> OTHER INFORMATION: Rv3884c - probable CBXX/CFQX family protein

<400> SEQUENCE: 74

Met Ser Arg Met Val Asp Thr Met Gly Asp Leu Leu Thr Ala Arg Arg
1               5                   10                  15

His Phe Asp Arg Ala Met Thr Ile Lys Asn Gly Gln Gly Cys Val Ala
                20                  25                  30

Ala Leu Pro Glu Phe Val Ala Thr Glu Ala Asp Pro Ser Met Ala
            35                  40                  45

Asp Ala Trp Leu Gly Arg Ile Ala Cys Gly Asp Arg Asp Leu Ala Ser
50                  55                  60

Leu Lys Gln Leu Asn Ala His Ser Glu Trp Leu His Arg Glu Thr Thr
65                  70                  75                  80

Arg Ile Gly Arg Thr Leu Ala Ala Glu Val Gln Leu Gly Pro Ser Ile
                85                  90                  95

Gly Ile Thr Val Thr Asp Ala Ser Gln Val Gly Leu Ala Leu Ser Ser
                100                 105                 110

Ala Leu Thr Ile Ala Gly Glu Tyr Ala Lys Ala Asp Ala Leu Leu Ala
            115                 120                 125

Asn Arg Glu Leu Leu Asp Ser Trp Arg Asn Tyr Gln Trp His Gln Leu
130                 135                 140

Ala Arg Ala Phe Leu Met Tyr Val Thr Gln Arg Trp Pro Asp Val Leu
145                 150                 155                 160

Ser Thr Ala Ala Glu Asp Leu Pro Pro Gln Ala Ile Val Met Pro Ala
                165                 170                 175

Val Thr Ala Ser Ile Cys Ala Leu Ala Ala His Ala Ala His Leu
            180                 185                 190

Gly Gln Gly Arg Val Ala Leu Asp Trp Leu Asp Arg Val Asp Val Ile
            195                 200                 205

Gly His Ser Arg Ser Ser Glu Arg Phe Gly Ala Asp Val Leu Thr Ala
210                 215                 220

Ala Ile Gly Pro Ala Asp Ile Pro Leu Leu Val Ala Asp Leu Ala Tyr
225                 230                 235                 240

Val Arg Gly Met Val Tyr Arg Gln Leu His Glu Glu Asp Lys Ala Gln
                245                 250                 255

Ile Trp Leu Ser Lys Ala Thr Ile Asn Gly Val Leu Thr Asp Ala Ala
            260                 265                 270

Lys Glu Ala Leu Ala Asp Pro Asn Leu Arg Leu Ile Val Thr Asp Glu
        275                 280                 285

Arg Thr Ile Ala Ser Arg Ser Asp Arg Trp Asp Ala Ser Thr Ala Lys
    290                 295                 300

Ser Arg Asp Gln Leu Asp Asp Asn Ala Ala Gln Arg Arg Gly Glu
305                 310                 315                 320

-continued

```
Leu Leu Ala Glu Gly Arg Glu Leu Leu Ala Lys Gln Val Gly Leu Ala
            325                 330                 335

Ala Val Lys Gln Ala Val Ser Ala Leu Glu Asp Gln Leu Glu Val Arg
        340                 345                 350

Met Met Arg Leu Glu His Gly Leu Pro Val Glu Gly Gln Thr Asn His
    355                 360                 365

Met Leu Leu Val Gly Pro Pro Gly Thr Gly Lys Thr Thr Ala Glu
370                 375                 380

Ala Leu Gly Lys Ile Tyr Ala Gly Met Gly Ile Val Arg His Pro Glu
385                 390                 395                 400

Ile Arg Glu Val Arg Arg Ser Asp Phe Cys Gly His Tyr Ile Gly Glu
            405                 410                 415

Ser Gly Pro Lys Thr Asn Glu Leu Ile Glu Lys Ser Leu Gly Arg Ile
        420                 425                 430

Ile Phe Met Asp Glu Phe Tyr Ser Leu Ile Glu Arg His Gln Asp Gly
    435                 440                 445

Thr Pro Asp Met Ile Gly Met Glu Ala Val Asn Gln Leu Leu Val Gln
450                 455                 460

Leu Glu Thr His Arg Phe Asp Phe Cys Phe Ile Gly Ala Gly Tyr Glu
465                 470                 475                 480

Asp Gln Val Asp Glu Phe Leu Thr Val Asn Pro Gly Leu Ala Gly Arg
            485                 490                 495

Phe Asn Arg Lys Leu Arg Phe Glu Ser Tyr Ser Pro Val Glu Ile Val
        500                 505                 510

Glu Ile Gly His Arg Tyr Ala Thr Pro Arg Ala Ser Gln Leu Asp Asp
    515                 520                 525

Ala Ala Arg Glu Val Phe Leu Asp Ala Val Thr Thr Ile Arg Asn Tyr
530                 535                 540

Thr Thr Pro Ser Gly Gln His Gly Ile Asp Ala Met Gln Asn Gly Arg
545                 550                 555                 560

Phe Ala Arg Asn Val Ile Glu Arg Ala Glu Gly Phe Arg Asp Thr Arg
            565                 570                 575

Val Val Ala Gln Lys Arg Ala Gly Gln Pro Val Ser Val Gln Asp Leu
        580                 585                 590

Gln Ile Ile Thr Ala Thr Asp Ile Asp Ala Ala Ile Arg Ser Val Cys
    595                 600                 605

Ser Asp Asn Arg Asp Met Ala Ala Ile Val Trp
610                 615
```

<210> SEQ ID NO 75
<211> LENGTH: 537
<212> TYPE: PRT
<213> ORGANISM: Mycobacterium tuberculosis
<220> FEATURE:
<223> OTHER INFORMATION: Rv3885c - possible conserved membrane protein

<400> SEQUENCE: 75

```
Leu Thr Ser Lys Leu Thr Gly Phe Ser Pro Arg Ser Ala Arg Arg Val
1               5                   10                  15

Ala Gly Val Trp Thr Val Phe Val Leu Ala Ser Ala Gly Trp Ala Leu
            20                  25                  30

Gly Gly Gln Leu Gly Ala Val Met Ala Val Val Gly Val Ala Leu
        35                  40                  45

Val Phe Val Gln Trp Trp Gly Gln Pro Ala Trp Ser Trp Ala Val Leu
    50                  55                  60
```

```
Gly Leu Arg Gly Arg Arg Pro Val Lys Trp Asn Asp Pro Ile Thr Leu
 65                  70                  75                  80

Ala Asn Asn Arg Ser Gly Gly Val Arg Val Gln Asp Gly Val Ala
                 85                  90                  95

Val Val Ala Val Gln Leu Leu Gly Arg Ala His Arg Ala Thr Thr Val
            100                 105                 110

Thr Gly Ser Val Thr Val Glu Ser Asp Asn Val Ile Asp Val Val Glu
            115                 120                 125

Leu Ala Pro Leu Leu Arg His Pro Leu Asp Leu Glu Leu Asp Ser Ile
130                 135                 140

Ser Val Val Thr Phe Gly Ser Arg Thr Gly Thr Val Gly Asp Tyr Pro
145                 150                 155                 160

Arg Val Tyr Asp Ala Glu Ile Gly Thr Pro Tyr Ala Gly Arg Arg
                165                 170                 175

Glu Thr Trp Leu Ile Met Arg Leu Pro Val Ile Gly Asn Thr Gln Ala
            180                 185                 190

Leu Arg Trp Arg Thr Ser Val Gly Ala Ala Ile Ser Val Ala Gln
        195                 200                 205

Arg Val Ala Ser Ser Leu Arg Cys Gln Gly Leu Arg Ala Lys Leu Ala
210                 215                 220

Thr Ala Thr Asp Leu Ala Glu Leu Asp Arg Arg Leu Gly Ser Asp Ala
225                 230                 235                 240

Val Ala Gly Ser Ala Gln Arg Trp Lys Ala Ile Arg Gly Glu Ala Gly
                245                 250                 255

Trp Met Thr Thr Tyr Ala Tyr Pro Ala Glu Ala Ile Ser Ser Arg Val
            260                 265                 270

Leu Ser Gln Ala Trp Thr Leu Arg Ala Asp Glu Val Ile Gln Asn Val
        275                 280                 285

Thr Val Tyr Pro Asp Ala Thr Cys Thr Ala Thr Ile Thr Val Arg Thr
            290                 295                 300

Pro Thr Pro Ala Pro Thr Pro Pro Ser Val Ile Leu Arg Arg Leu Asn
305                 310                 315                 320

Gly Glu Gln Ala Ala Ala Ala Ala Asn Met Cys Gly Pro Arg Pro
                325                 330                 335

His Leu Arg Gly Gln Arg Arg Cys Pro Leu Pro Ala Gln Leu Val Thr
            340                 345                 350

Glu Ile Gly Pro Ser Gly Val Leu Ile Gly Lys Leu Ser Asn Gly Asp
        355                 360                 365

Arg Leu Met Ile Pro Val Thr Asp Ala Gly Glu Leu Ser Arg Val Phe
            370                 375                 380

Val Ala Ala Asp Asp Thr Ile Ala Lys Arg Ile Val Ile Arg Val Val
385                 390                 395                 400

Gly Ala Gly Glu Arg Val Cys Val His Thr Arg Asp Gln Glu Arg Trp
                405                 410                 415

Ala Ser Val Arg Met Pro Gln Leu Ser Ile Val Gly Thr Pro Arg Pro
            420                 425                 430

Ala Pro Arg Thr Thr Val Gly Val Val Glu Tyr Val Arg Arg Arg Lys
            435                 440                 445

Asn Gly Asp Asp Gly Lys Ser Glu Gly Ser Gly Val Asp Val Ala Ile
            450                 455                 460

Ser Pro Thr Pro Arg Pro Ala Ser Val Ile Thr Ile Ala Arg Pro Gly
465                 470                 475                 480

Thr Ser Leu Ser Glu Ser Asp Arg His Gly Phe Glu Val Thr Ile Glu
                485                 490                 495
```

```
Gln Ile Asp Arg Ala Thr Val Lys Val Gly Ala Ala Gly Gln Asn Trp
            500                 505                 510

Leu Val Glu Met Glu Met Phe Arg Ala Glu Asn Arg Tyr Val Ser Leu
        515                 520                 525

Glu Pro Val Thr Met Ser Ile Gly Arg
        530                 535
```

IDENTIFICATION OF VIRULENCE ASSOCIATED REGIONS RD1 AND RD5 LEADING TO IMPROVE VACCINE OF M. BOVIS BCG AND M. MICROTI

This is a division of application Ser. No. 10/510,021, filed Oct. 1, 2004, no U.S. Pat. No. 7,883,712, which is a National Stage of International Application No. PCT/IB03/01789 under 35 U.S.C. §371, all of which are incorporated herein by reference.

Virulence associated regions have been sought for a long time in *Mycobacterium*. The present invention concerns the identification of 2 genomic regions which are shown to be associated with a virulent phenotype in *Mycobacteria* and particularly in *M. tuberculosis*. It concerns also the fragments of said regions.

One of these two regions known as RD5 is disclosed in Molecular Microbiology (1999), vol. 32, pages 643 to 655 (Gordon S. V. et al.). The other region named RD1-2F9 spans the known region RD1 as disclosed in Molecular Microbiology (1999), vol. 32, pages 643 to 655 (Gordon S. V. et al.). Both of the regions RD1 and RD5 or at least one of them are absent from the vaccine strains of *M. bovis* BCG and in *M. microti*, strains found involved and used as live vaccines in the 1960's.

Other applications which are encompassed by the present invention are related to the use of all or part of the said regions to detect virulent strains of *Mycobacteria* and particularly *M. tuberculosis* in humans and animals. The region RD1-2F9 and RD5 are considered as virulence markers under the present invention.

The recombinant *Mycobacteria* and particularly *M. bovis* BCG after modification of their genome by introduction of all or part of RD1-2F9 region and/or RD5 region in said genome can be used for the immune system of patients affected with a cancer as for example a bladder cancer.

The present invention relates to a strain of *M. bovis* BOG or *M. microti*, wherein said strain has integrated all or part of the region RD1-2F9 responsible for enhanced immunogenicity to the tubercle bacilli, especially the genes encoding the ESAT-6 and CFP-10 antigens. These strains will be referred to as the *M. bovis* BCG::RD1 or *M. microti*::RD1 strains and are useful as a new improved vaccine for prevention of tuberculosis infections and for treating superficial bladder cancer.

*Mycobacterium bovis* BCG (bacille Calmette-Guérin) has been used since 1921 to prevent tuberculosis although it is of limited efficacy against adult pulmonary disease in highly endemic areas. *Mycobacterium microti*, another member of the *Mycobacterium tuberculosis* complex, was originally described as the infective agent of a tuberculosis-like disease in voles (*Microtus agrestis*) in the 1930's (Wells, A. Q. 1937. Tuberculosis in wild voles. Lancet 1221 and Wells, A. Q. 1946. The murine type of tubercle bacillus. Medical Research council special report series 259:1-42.). Until recently, *M. microti* strains were thought to be pathogenic only for voles, but not for humans and some were even used as a live-vaccine. In fact, the vole bacillus proved to be safe and effective in preventing clinical tuberculosis in a trial involving roughly 10,000 adolescents in the UK in the 1950's (Hart, P. D. a., and I. Sutherland: 1977. BCG and vole bacillus vaccines in the prevention of tuberculosis in adolescence and early adult life. British Medical Journal 2:293-295). At about the same time, another strain, OV166, was successfully administered to half a million newborns in Prague, former Czechoslovakia, without any serious complications (Sula, L., and I. Radkovsky 1976. Protective effects of *M. microti* vaccine against tuberculosis. J. Hyg. Epid. Microbiol. Immunol. 20:1-6). *M. microti* vaccination has since been discontinued because it was no more effective than the frequently employed BCG vaccine. As a result, improved vaccines are needed for preventing and treating tuberculosis.

The problem for attempting to ameliorate this live vaccine is that the molecular mechanism of both the attenuation and the immunogenicity of BCG is still poorly understood. Comparative genomic studies of all six members of the *M. tuberculosis* complex have identified more than 140 genes, whose presence is facultative, that may confer differences in phenotype, host range and virulence. Relative to the genome of the paradigm strain, *M. tuberculosis* H37Rv (S. T. Cole, et al., Nature 393, 537 (1998)), many of these genes occur in chromosomal regions that have been deleted from certain species (RD1-16, RvD1-5), M. A. Behr, et al., Science 284, 1520 (1999); R. Brosch, et al., Infection Immun. 66, 2221 (1998); S. V. Gordon, et al., Molec Microbiol 32, 643 (1999); H. Salmon, et al, Genome Res 10, 2044 (2000), G. G. Mahairas et al, J. Bacteriol. 178, 1274 (1996) and R. Brosch, et al., Proc Natl Acad Sci USA 99, 3684 (2002).

In connection with the invention and based on their distribution among tubercle bacilli and potential to encode virulence functions, RD1, RD7 and RD9 (FIG. 1A, B) were accorded highest priority for functional genomic analysis using "knock-ins" of *M. bovis* BCG to assess their potential contribution to the attenuation process. Clones spanning these RD regions were selected from an ordered *M. tuberculosis* H37Rv library of integrating shuttle cosmids T. Cole, et al, Nature 393, 537 (1998) and W. R. Bange, et al, Tuber. Lung Dis. 79, 171 (1999)), and individually electroporated into BCG Pasteur, where they inserted stably into the attB site (M. H. Lee, at al, Proc. Natl. Acad. Sci. USA 88, 3111 (1991)).

We have uncovered that only reintroduction of all or part of RD1-2F9 led to profound phenotypic alteration. Strikingly, the BCG::RD1 "knock-in" grew more vigorously than BCG controls in immuno-deficient mice, inducing extensive splenomegaly and granuloma formation.

RD1 is restricted to the avirulent strains *M. bovis* BCG and *M. microti*. Although the endpoints are not identical, the deletions have removed from both vaccine strains a cluster of six genes (Rv3871-Rv3876) that are part of the ESAT-6 locus (FIG. 1A (S. T. Cole, et al., Nature 393, 537 (1998) and F. Tekaia, et al., Tubercle Lung Disease 79, 329 (1999)).

Among the missing products are members of the mycobacterial PE (Rv3872), PPE (Rv3873), and ESAT-6 (Rv3874, Rv3875) protein families. Despite lacking obvious secretion signals, ESAT-6 (Rv3875) and the related protein CFP-10 (Rv3874), are abundant components of short term culture filtrate, acting as immunodominant T-cell antigens that induce potent Th1 responses (F. Tekaia, et al., Tubercle Lung Disease 79, 329 (1999); A. L. Sorensen, et al, infect Immun. 63, 1710 (1995) and R. Colangelli, et al., Infect. Immun. 68, 990 (2000)).

In summary, we have discovered that the restoration of RD1-2F9 to *M. bovis* BCG leads to increased persistence in immunocompetent mice. The *M. bovis* BCG::RD1 strain includes RD1-specific immune responses of the Th1-type, has enhanced immunogenicity and confers better protection than *M. bovis* BCG alone in animal models of tuberculosis. The *M. bovis* BCG::RD1 vaccine is significantly more virulent than *M. bovis* BCG in immunodeficient mice but considerably less virulent than *M. tuberculosis*.

In addition, we show that *M. microti* lacks a different but overlapping part of the RD1 region (RD1$^{mic}$) to *M. bovis* BCG and our results indicate that reintroduction of RD1-2F9 confers increased virulence of BCG::RD1 in immunodeficient mice. The rare strains of *M. microti* that are associated with human disease contain a region referred to as RD5$^{mic}$ whereas those from voles do not.

*M. bovis* BCG vaccine could be improved by reintroducing other genes encoding ESAT-6 family members that have been lost, notably, those found in the RD8 and RD5 loci of *M. tuberculosis*. These regions also code for additional T-cell antigens.

*M. bovis* BCG::RD1 could be improved by reintroducing the RD8 and RD5 loci of *M. tuberculosis*.

*M. bovis* BCG vaccine could be improved by reintroducing and overexpressing the genes contained in the RD1, RD5 and RD8 regions.

Accordingly, these new strains, showing greater persistence and enhanced immunogenicity, represent an improved vaccine for preventing tuberculosis and treating bladder cancer.

In addition, the greater persistence of these recombinant strains is an advantage for the presentation of other antigens, for instance from HIV in humans and in order to induce protection immune responses. Those improved strains may also be of use in veterinary medicine, for instance in preventing bovine tuberculosis.

DESCRIPTION

Therefore, the present invention is aimed at a strain of *M. bovis* BCG or *M. microti*, wherein said strain has integrated all or part of the RD1-2F9 region as shown in SEQ ID No 1 responsible for enhanced immunogenicity to the tubercle bacilli. These strains will be referred to as the *M. bovis* BCG::RD1 or *M. microti*::RD1 strains.

In connection with the invention, "part or all of the RD1-2F9 region" means that the strain has integrated a portion of DNA originating from *Mycobacterium tuberculosis* or any virulent member of the *Mycobacterium tuberculosis* complex (*M. africanum*, *M. bovis*, *M. canettii*), which comprises at least one, two, three, four, five, or more gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28). The expression "a portion of DNA" means also a nucleotide sequence or a nucleic acid or a polynucleotide. The expression "gene" is referred herein as the coding is sequence in frame with its natural promoter as well as the coding sequence which has been isolated and framed with an exogenous promoter, for example a promoter capable of directing high level of expression of said coding sequence.

In a specific aspect, the invention relates to a strain of *M. bovis* BCG or *M. microti* wherein said strain has integrated at least one, two, three or more gene(s) selected from Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19) and Rv3877 (SEQ ID No 20).

In another specific aspect, the invention relates to a strain of *M. bovis* BCG or *M. microti* herein said strain has integrated at least one, two, three or more gene(s) selected from Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6) and Rv3876 (SEQ ID No 19).

Preferably, a strain according to the invention is one which has integrated a portion of DNA originating from *Mycobacterium tuberculosis* or any virulent member of the *Mycobacterium tuberculosis* complex (*M. africanum*, *M. bovis*, *M. canetti*), which comprises at least four genes selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18; ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28), provided that it comprises Rv3874 (SEQ ID No 17, CFP-10) and/or Rv3875 (SEQ ID No 18, ESAT-6).

Strains which have integrated a portion of DNA originating from *Mycobacterium tuberculosis* or any virulent member of the *Mycobacterium tuberculosis* complex (*M. africanum*, *M. bovis*, *M. canettii*) comprising at least Rv3871 (SEQ ID No 14), Rv3875 (SEQ ID No 18, ESAT-6) and Rv3876 (SEQ ID No 19) or at least Rv3871 (SEQ ID No 14), Rv3875 (SEQ ID No 18, ESAT-6) and Rv3877 (SEQ ID No 20) or at least Rv3871 (SEQ ID No 14), Rv3875 (SEQ ID No 18, ESAT-6), Rv3876 (SEQ ID No 19) and Rv3877 (SEQ ID No 20) are of particular interest.

The above strains according to the invention may further comprise Rv3874 (SEQ ID No 17, CFP-10), Rv3872 (SEQ ID No 15, mycobacterial PE) and/or Rv3873 (SEQ ID No 16, PPE). In addition, it may further comprise at least one, two, three or four gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28).

The invention encompasses strains which have integrated a portion of DNA originating from *Mycobacterium tuberculosis* or any virulent member of the *Mycobacterium tuberculosis* complex (*M. africanum*, *M. bovis*, *M. canettii*), which comprises Rv3875 (SEQ ID No 18, ESAT-6) or Rv3874 (SEQ ID No 17, CFP-10) or both Rv3875 (SEQ ID No 18, ESAT-6) and Rv3874 (SEQ ID No 17, CFP-10).

These genes can be mutated (deletion, insertion or base modification) so as to maintain the improved immunogenicity while decreasing the virulence of the strains. Using routine procedure, the man skilled in the art can select the *M. bovis* BCG::RD1 or *M. microti*::RD1 strains, in which a mutated gene has been integrated, showing improved immunogenicity and lower virulence.

We have shown here that introduction of the RD1-2F9 region makes the vaccine strains induce a more effective immune response against a challenge with *M. tuberculosis*. However, this first generation of constructs can be followed by other, more fine-tuned generations of constructs as the complemented BCG::RD1 vaccine strain also showed a more virulent phenotype in severely immune-compromised (SCID) mice. Therefore, the BCG::RD1 constructs may be modified so as to be applicable as vaccine strains while being safe for immune-compromised individuals. The term "construct" means an engineered gene unit, usually involving a gene of interest that has been fused to a promoter.

In this perspective, the man skilled in the art can adapt the BCG::RD1 strain by the conception of BCG vaccine strains that only early parts of the genes coding for ESAT-6 or CFP-10 in a mycobacterial expression vector (for example pSM81) tinder the control of a promoter, more particularly an hsp60 promoter. For example, at least one portion of the esat-6 gene that codes for immunogenic 20-mer peptides of ESAT-6 active as T-cell epitopes (Mustafa A S, Oftung F, Amoudy H A, Madi N M, Abal A T, Shaban F, Rosen Krands I, & Andersen P. (2000) Multiple epitopes from the Mycobacterium tuberculosis ESAT-6 antigen are recognized by antigen-specific human T cell lines. Clin Infect Dis. 30 Suppl 3:S201-5, peptides P1 to P8 are incorporated herein in the description) could to be cloned into this vector and electroporated into BCG, resulting in a BCG strain that produces these epitopes.

Alternatively, the ESAT-6 and CFP-10 encoding genes (for example on plasmid RD1-AP34 and or RD1-2F9) could be altered by directed mutagenesis (using for example QuikChange Site-Directed Mutagenesis Kit from Stratagen) in a way that most of the immunogenic peptides of ESAT-6 remain intact, but the biological functionality of ESAT-6 is lost.

This approach could result in a more protective BCG vaccine without increasing the virulence of the recombinant BCG strain.

Therefore, the invention is also aimed at a method for preparing and selecting M. bovis BCG or M. microti recombinant, strains comprising a step consisting of modifying the M. bovis BCG::RD1 or M. microti::RD1 strains as defined above by insertion, deletion or mutation in the integrated RD1 region, more particularly in the esat-6 or CFP-10 gene, said method leading to strains that are less virulent for immunodepressed individuals. Together, these methods would allow to explain what causes the effect that we see with our BCG::RD1 strain (the presence of additional T-cell epitopes from ESAT-6 and CFP10 resulting in increased immunogenicity) or whether the effect is caused by better fitness of the recombinant BCG::RD1 clones resulting in longer exposure time of the immune system to the vaccine—or—by a combinatorial effect of both factors.

In a preferred embodiment, the invention is aimed at the M. bovis BCG::RD1 strains, which have integrated a cosmid herein referred to as the RD1-2F9 and RD1-AP34 contained in the E. coli strains deposited on Apr. 2, 2002 at the CNCM (Institut Pasteur, 25, rue du Docteur Roux, 75724 Paris cedex 15, France) under the accession number I-2831 and I-2832 respectively. The RD1-2F9 is a cosmid comprising the portion of the Mycobacterium tuberculosis H37Rv genome previously named RD1-2F9 that spans the RD1 region and contains a gene conferring resistance to Kanamycin. The RD1-AP34 is a cosmid comprising a portion of the Mycobacterium tuberculosis H37Rv genome containing two genes coding for ESAT-6 and CFP-10 as well as a gene conferring resistance to Kinamycin.

The cosmid RD1-AP34 contains a 3909 bp fragment of the M. tuberculosis H37Rv genome from region 4350459 bp to 4354367 bp that has been cloned into an integrating vector pKint in order to be integrated in the genome of Mycobacterium bovis BCG and Mycobacterium microti strains (SEQ II) No 3). The Accession No. of the segment 160 of the M. tuberculosis H37Rv genome that contains this region is AL022120.

```
SEQ ID No 3:
    1 - gaattcccat ccagtgagtt caaggtcaag cggcgccccc ctggccaggc atttctcgtc
   61 - tcgccagacg gcaaagaggt catccaggcc ccctacatcg agcctccaga agaagtgttc
  121 - gcagcacccc caagcgccgg ttaagattat ttcattgccg gtgtagcagg acccgagctc
  181 - agcccggtaa tcagagttcgg gcaatgcta ccatcgggtt tgtttccggc tataaccgaa
  241 - cggtttgtgt acgggataca aatacaggga gggaagaagt aggcaaatgg aaaaaatgtc
  301 - acatgatccg atcgctgccg acattggcac gcaagtgagc gacaacgctc tgcacggcgt
  361 - gacggccggc tcgacggcgc tgacgtcggt gaccgggctg gttcccgcgg gggccgatga
  421 - ggtctccgcc caagcggcga cggcgttcac atcggaggc atccaattgc tggcttccaa
  481 - tgcatcggcc caagaccagc tccaccgtgc gggcgaagcg gtccaggacg tcgcccgcac
  541 - ctattcgcaa atcgacacg gcgccgccgg cgtcttcgcc gaataggccc ccaacacatc
  601 - ggagggagtg atcaccatgc tgtggcacgc aatgccaccg gagctaaata ccgcacggct
  661 - gatggccggc gcgggtccgg ctccaatgct tgcggcggcc gcgggatggc agacgctttc
  721 - ggcggctctg gacgctcagg ccgtcgagtt gaccgcgcgc ctgaactctc taggagaagc
  781 - ctggactgga ggtggcagcg acaaggcgct tgcggctgca acgccgatgg tggtctggct
  841 - acaaaccgcg tcaacacagg ccaagacccg tgcgatgcag gcgacggcgc aagccgcggc
  901 - atacacccag gccatggcca cgacgccgtc gctgccggag atcgccgcca accacatcac
  961 - ccaggccgtc cttacggcca ccaacttctt cggtatcaac acgatcccga tcgcgttgac
```

-continued

1021 - cgagatggat tatttcatcc gtatgtggaa ccaggcagcc ctggcaatgg aggtctacca

1081 - ggccgagacc gcggttaaca cgcttttcga gaagctcgag ccgatggcgt cgatccttga

1141 - tcccggcgcg agccagagca cgacgaaccc gatcttcgga atgccctccc ctggcagctc

1201 - aacaccggtt ggccagttgc cgccggcggc tacccagacc ctcggccaac tgggtgagat

1261 - gagcggcccg atgcagcagc tgacccagcc gctgcagcag gtgacgtcgt tgttcagcca

1321 - ggtgggcggc accggcggcg gcaacccagc cgacgaggaa gccgcgcaga tgggcctgct

1381 - cggcaccagt ccgctgtcga accatccgct ggctggtgga tcaggcccca gcgcgggcgc

1441 - gggcctgctg cgcgcggagt cgctacctgg cgcaggtggg tcgttgaccc gcacgccgct

1501 - gatgtctcag ctgatcgaaa agccggttgc ccctcggtg atgccggcgg ctgctgccgg

1561 - atcgtcggcg acggtggcg ccgctccggt gggtgcggga gcgatgggcc aggtgcgca

1621 - atccggcggc tccaccaggc cgggtctggt cgcgccggca ccgctcgcgc aggagcgtga

1681 - agaagacgac gaggacgact gggacgaaga ggacgactgg tgagctcccg taatgacaac

1741 - agacttcccg gccaccgggg ccggaagact tgccaacatt ttggcgagga aggtaaagag

1801 - agaaagtagt ccagcatggc agagatgaag accgatgccg ctaccctcgc gcaggaggca

1861 - ggtaatttcg agcggatctc cggcgacctg aaaacccaga tcgaccaggt ggagtcgacg

1921 - gcaggttcgt tgcagggcca gtggcgcggc gcggcgggga cggccgccca ggccgcggtg

1981 - gtgcgcttcc aagaagcagc caataagcag aagcaggaac tcgacgagat ctcgacgaat

2041 - attcgtcagg ccggcgtcca atactcgagg gccgacgagg agcagcagca ggcgctgtcc

2101 - tcgcaaatgg gcttctgacc cgctaatacg aaaagaaacg gagcaaaaac atgacagagc

2161 - agcagtggaa tttcgcgggt atcgaggccg cggcaagcgc aatccagga aatgtcacgt

2221 - ccattcattc cctccttgac gagggaagc agtccctgac caagctcgca gcggcctggg

2281 - gcggtagcgg ttcggaggcg taccagggtg tccagcaaaa atgggacgcc acggctaccg

2341 - agctgaacaa cgcgctgcag aacctggcgc ggacgatcag cgaagccggt caggcaatgg

2401 - cttcgaccga aggcaacgtc actgggatgt tcgcataggg caacgccgag ttcgcgtaga

2461 - atagcgaaac acgggatcgg gcgagttcga ccttccgtcg gtctcgccct ttctcgtgtt

2521 - tatacgtttg agcgcactct gagaggttgt catggcggcc gactacgaca agctcttccg

2581 - gccgcacgaa ggtatggaag ctccggacga tatggcagcg cagccgttct tcgaccccag

2641 - tgcttcgttt ccgccggcgc ccgcatcggc aaacctaccg aagcccaacg gccagactcc

2701 - gccccgacg tccgacgacc tgtcggagcg gttcgtgtcg gccccgccgc cgccacccc

2761 - accccccacct ccgcctccgc caactccgat gccgatcgcc gcaggagagc cgccctcgcc

2821 - ggaaccggcc gcatctaaac cacccacacc cccatgccc atcgccggac ccgaaccggc

2881 - cccacccaca ccacccacac ccccatgcc catcgccgga cccgaaccgg ccccacccaa

2941 - accacccaca cctccgatgc ccatcgccgg acctgcaccc accccaaccg aatcccagtt

3001 - ggcgcccccc agaccaccga caccacaaac gccaaccgga gcgccgcagc aaccggaatc

3061 - accggcgccc cacgtaccct cgcacgggcc acatcaaccc cggcgcaccg caccagcacc

3121 - gccctgggca aagatgccaa tcggcgaacc cccgcccgct ccgtccagac cgtctgcgtc

3181 - cccggccgaa ccaccgaccc ggcctgcccc caacactcc cgacgtgcgc gccggggtca

3241 - ccgctatcgc acagacaccg aacgaaacgt cgggaaggta gcaactggtc catccatcca

3301 - ggcgcggctg cgggcagagg aagcatccgg cgcgcagctc gcccccggaa cggagccctc

3361 - gccagcgccg ttgggccaac cgagatcgta tctggctccg cccaccccgcc ccgcgccgac

3421 - agaacctccc cccagccct cggcgcaccg caactccggt cggcgtgccg agcgacgcgt

-continued

```
3481 - ccacccgat ttagccgccc aacatgccgc ggcgcaacct gattcaatta cggccgcaac

3541 - cactggcggt cgtcgccgca agcgtgcagc gccggatctc gacgcgacac agaaatcctt

3601 - aaggccggcg gccaagggc cgaaggtgaa gaaggtgaag ccccagaaac cgaaggccac

3661 - gaagccgccc aaagtggtgt cgcagcgcgg ctggcgacat tgggtgcatg cgttgacgcg

3721 - aatcaacctg ggcctgtcac ccgacgagaa gtacgagctg gacctgcacg ctcgagtccg

3781 - ccgcaatccc cgcgggtcgt atcagatcgc cgtcgtcggt ctcaaaggtg gggctggcaa

3841 - aaccacgctg acagcagcgt tggggtcgac gttggctcag gtgcgggccg accggatcct

3901 - ggctctaga
``` pos. 0001-0006 EcoRI-restriction site
pos. 0286-0583 Rv3872 coding for a PE-Protein (SEQ ID No 15)
pos. 0616-1720 Rv3873 coding for a PPE-Protein (SEQ ID No 16)
pos. 1816-2115 Rv3874 coding for Culture Filtrat protein 10 kD (CFP10) (SEQ ID No 17)
pos. 2151-2435 Rv3875 coding for Early Secreted Antigen Target 6 kD (ESAT6) (SEQ ID No 18)
pos. 3903-3609 XbaI-restriction site
pos. 1816-2435 CFP-10 gene+esat-6 gene (SEQ ID No 29).

These sequences can be completed with the Rv3861 to Rv3871, and Rv3876 to Rv3885 as referred in Table 1 below.

| Gene Name | Gene length | Protein length | Gene type | Accesion number in NCBI Bank NC = gene NP = protein | Loc (kb) in M. tuberculosis H37Rv | Coordinates in Mycobacterium tuberculosis H37Rv | Molecular mass of protein (Dalton) | Description |
|---|---|---|---|---|---|---|---|---|
| Rv3861 | 324 | 108 | CDS | | 4337.95 | 4337946 . . . 4338269 | 11643.42 | hypothetical protein |
| Rv3862 c-whiB6 | 348 | 116 | CDS | | 4338.52 | compl 4338174 . . . 4338521 | 12792.38 | possible transcriptional regulatory protein whiB-like WhiB6 |
| Rv3863 | 1176 | 392 | CDS | | 4338.85 | 4338849 . . . 4340024 | 41087.44 | hypothetical alanine rich protein |
| Rv3864 | 1206 | 402 | CDS | | 4340.27 | 4340270 . . . 4341475 | 42068.66 | conserved hypothetical protein |
| Rv3865 | 309 | 103 | CDS | | 4341.57 | 4341566 . . . 4341874 | 10618.01 | conserved hypothetical protein |
| Rv3866 | 849 | 283 | CDS | | 4341.88 | 4341880 . . . 4342728 | 30064.04 | conserved hypothetical protein |
| Rv3867 | 549 | 183 | CDS | NC_000962 NP_218384 | 4342.77 | 4342767 . . . 4343318 | 19945.52 | conserved protein |
| Rv3868 | 1719 | 573 | CDS | NC_000962 NP_218385 | 4343.3 | 4343311 . . . 4345032 | 62425.40 | conserved protein |
| Rv3869 | 1440 | 480 | CDS | NC_000962 NP_218386 | 4345.04 | 4345036 . . . 4346478 | 51092.58 | possible conserved membrane protein |
| Rv3870 | 2241 | 747 | CDS | NC_000962 NP_218387 | 4346.48 | 4346478 . . . 4348721 | 80912.76 | possible conserved membrane protein |
| Rv3871 | 1773 | 591 | CDS | NC_000962 NP_218388 | 4348.83 | 4348824 . . . 4350599 | 64560.65 | conserved protein |
| Rv3876 | 1998 | 666 | CDS | NC_000962 NP_218393 | 4353.01 | 4353007 . . . 4355007 | 70644.92 | conserved proline and alanine rich protein |
| Rv3877 | 1533 | 511 | CDS | NC_000962 NP_218394 | 4355.01 | 4355004 . . . 4356539 | 53981.12 | probable conserved transmembrane protein |
| Rv3878 | 840 | 280 | CDS | NC_000962 | 4356.69 | 4356693 . . . 4357532 | 27395.23 | conserved hypothetical alanine rich protein |

-continued

| Gene Name | Gene length | Protein length | Gene type | Accesion number in NCBI Bank NC = gene NP = protein | Loc (kb) in M. tuberculosis H37Rv | Coordinates in Mycobacterium tuberculosis H37Rv | Molecular mass of protein (Dalton) | Description |
|---|---|---|---|---|---|---|---|---|
| Rv3879c | 2187 | 729 | CDS | NC_000962 | 4359.78 | compl. 4357596 . . . 4359782 | 74492.13 | hypothetical alanine and proline rich protein |
| Rv3880c | 345 | 115 | CDS | NC_000962 | 4360.55 | compl. 4360202 . . . 4360546 | 12167.51 | conserved hypothetical protein |
| Rv3881c | 1380 | 460 | CDS | NC_000962 | 4361.92 | compl. 4360546 . . . 4361925 | 47593.62 | conserved hypothetical alanine and glycine rich protein |
| Rv3882c | 1386 | 462 | CDS | NC_000962 | 4363.42 | compl. 4362035 . . . 4363420 | 50396.58 | possible conserved membrane protein |
| Rv3883c | 1338 | 446 | CDS | NC_000962 | 4364.76 | compl. 4363420 . . . 4364757 | 45085.89 | possible secreted protease |
| Rv3884c | 1857 | 619 | CDS | NC_000962 | 4366.84 | compl. 4364982 . . . 4366838 | 68040.97 | probable CBXX/CFQX family protein |
| Rv3885c | 1611 | 537 | CDS | NC_000962 | 4368.52 | compl. 4366911 . . . 4368521 | 57637.95 | possible conserved membrane protein |

The sequence of the fragment RD1-2F9 (~32 kb) covers the region of the *M. tuberculosis* genome AL123456 from ca 4337 kb to ca. 4369 kb, and also contains the sequence described in SEQ ID No 1. Therefore, the invention also embraces *M. bovis* BCG::RD1 strain and *M. microti*::RD1 strain which have integrated the sequence as shown in SEQ ID No 1.

The above described strains fulfill the aim of the invention which is to provide an improved tuberculosis vaccine or *M. bovis* BCG-based prophylactic or therapeutic agent, or a recombinant *M. microti* derivative for these purposes.

The above described *M. bovis* BCG::RD1 strains are better tuberculosis vaccines than *M. bovis* BCG. These strains can also be improved by reintroducing other genes found in the RD8 and RD5 loci of *M. tuberculosis* or any virulent member of the *Mycobacterium tuberculosis* complex (*M. africanum, M. bovis, M. canettii*). These regions code for additional T-cell antigens.

As indicated, overexpressing the genes contained in the RD1, RD5 and RD8 regions by means of exogenous promoters is encompassed by the invention. The same applies regarding *M. microti*:RD1 strains. *M. microti* strains could also be improved by reintroducing the RD8 locus of *M. tuberculosis* or any virulent member of the *Mycobacterium tuberculosis* complex (*M. africanum, M. bovis, M. canettii*).

In a second embodiment, the invention is directed to a cosmid or a plasmid, more commonly named vectors, comprising all or part of the RD1-2F9 region originating from *Mycobacterium tuberculosis* or any virulent member of the *Mycobacterium tuberculosis* complex (*M. africanum, M. bovis, M. canettii*), said region comprising at least one, two, three or more gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28). The term "vector" refers to a DNA molecule originating from a virus a bacteria, or the cell of a higher organism into which another DNA fragment of appropriate size can be integrated without loss of the vectors Capacity for self-replication; a vector introduces foreign DNA into host cells, where it can be reproduced in large quantities. Examples are plasmids, cosmids, and yeast artificial chromosomes; vectors are often recombinant molecules containing DNA sequences from several sources.

Preferably, a cosmid or a plasmid of the invention comprises a part of the RD1-2F9 region originating from *Mycobacterium tuberculosis* or any virulent member of the *Mycobacterium tuberculosis* complex (*M. africanum, M. bovis, M. canettii*), said part comprising at least one, two, three or more gene(s) selected from Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19) and Rv3877 (SEQ ID No 20).

Preferably, a cosmid or a plasmid of the invention comprises a part of the RD1-2F9 region originating from *Mycobacterium tuberculosis* or any virulent member of the *Mycobacterium tuberculosis* complex (*M. africanum, M. bovis, M. canettii*), said part comprising at least one, two, three or more gene(s) selected from Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6) and Rv3876 (SEQ ID No 19).

Preferably, a cosmid or a plasmid of the invention comprises CFP-10, ESAT-6 or both or a part of them. It may also comprise a mutated gene selected CFP-10, ESAT-6 or both, said mutated gene being responsible for the improved immunogenicity and decreased virulence.

A cosmid or a plasmid as mentioned above may comprise at least four genes selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18; ESAT-6), Rv3876 (SEQ ID No 19), Rv3877 (SEQ ID No 20), Rv3878 (SEQ ID No 24), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28), provided that it comprises Rv3874 (SEQ ID No 17, CFP-10) and/or Rv3875 (SEQ ID No 18, ESAT-6)

Advantageously, a cosmid or a plasmid of the invention comprises a portion of DNA originating from *Mycobacterium tuberculosis* or any virulent member of the *Mycobacterium tuberculosis* complex (*M. africanum, M. bovis, M. canettii*), which comprises at least Rv3871 (SEQ ID No 14), Rv3875 (SEQ ID No 18, ESAT-6) and Rv3876 (SEQ ID No 19) or at least Rv3871 (SEQ ID No 14), Rv3875 (SEQ ID No 18, ESAT-6) and Rv3877 (SEQ ID No 20) or at least Rv3871 (SEQ ID No 14), Rv3875 (SEQ ID No 18, ESAT-6), Rv3876 (SEQ ID No 19) and Rv3877 (SEQ ID No 20).

The above cosmids or plasmids may, further comprise Rv3872 (SEQ ID No 15, mycobacterial PE) Rv3873 (SEQ ID No 16, PPE) Rv3874 (SEQ ID No 17, CFP-10). It may also further comprise at least one, two, three or four gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28).

Two particular cosmids of the invention are the cosmids herein referred as RD1-2F9 and RD1-AP34 contained in the *E. coli* strains deposited at the CNCM (Institut Pasteur, 25, rue du DocteUr Roux, 75724 Paris cedex 15, France) under the accession number 1-2831 and 1-2832 respectively.

A particular plasmid or cosmid of the invention is one which has integrated the complete RD1-2F9 region as shown in SEQ ID No 1.

The invention also relates to the use of these cosmids or plasmids for transforming *M. bovis* BCG or *M. microti* strains.

As indicated above, these cosmids or plasmids may comprise a mutated gene selected from Rv3861 to Rv3885, said mutated gene being responsible for the improved immunogenicity and decreased virulence.

In another embodiment, the invention embraces a pharmaceutical composition comprising a strain as depicted above and a pharmaceutically acceptable carrier.

In addition to the strains, these pharmaceutical compositions may contain suitable pharmaceutically-acceptable carriers comprising excipients and auxiliaries which facilitate processing of the living vaccine into preparations which can be used pharmaceutically. Further details on techniques for formulation and administration may be found in the latest edition of Remington's Pharmaceutical Sciences (Maack Publishing Co., Easton, Pa.).

Preferably, such composition is suitable for oral, intravenous or subcutaneous administration.

The determination of the effective dose is well within the capability of those skilled in the art. A therapeutically effective dose refers to that amount of active ingredient, i.e the number of strains administered, which ameliorates the symptoms or condition. Therapeutic efficacy and toxicity may be determined by standard pharmaceutical procedures in experimental animals, e.g., ED50 (the dose therapeutically effective in 50% of the population) and LD50 (the dose lethal to 50% of the population). The dose ratio of toxic to therapeutic effects is the therapeutic index, and it can be expressed as the ratio, LD50/ED50. Pharmaceutical compositions which exhibit large therapeutic indices are preferred. Of course, ED50 is to be modulated according to the mammal to be treated or vaccinated. In this regard, the invention contemplates a composition suitable for human administration as well as veterinary composition.

The invention is also aimed at a vaccine comprising a *M. bovis* BCG::RD1 or *M. microti*::RD1 strain as depicted above and a suitable carrier. This vaccine is especially useful for preventing tuberculosis. It can also be used for treating bladder cancer.

The *M. bovis* BCG::RD1 or *M. microti*::RD1 strains are also useful as a carrier for the expression and presentation of foreign antigens or molecules of interest that are of therapeutic or prophylactic interest. Owing to its greater persistence, BCG::RD1 will present antigens to the immune system over a longer period thereby inducing stronger, more robust immune responses and notably protective responses. Examples of such foreign antigens can be found in patents and patent applications U.S. Pat. No. 6,191,270 for antigen LSA3, U.S. Pat. No. 6,096,879 and U.S. Pat. No. 5,314,808 for HBV antigens, EP 201,540 for HIV-1 antigens, U.S. Pat. No. 5,986,051 for *H. pylori* antigens and FR 2,744,724 for *P. falciparum* MSP-1 antigen.

The invention also concerns a product comprising a strain as depicted above and at least one protein selected from ESAT-6 and CFP-10 or epitope derived thereof for a separate, simultaneous or sequential use for treating tuberculosis.

In still another embodiment, the invention concerns the use of a *M. bovis* BCG::RD1 or *M. microti*::RD1 strain as depicted above for preventing or treating tuberculosis. It also concerns the use of a *M. bovis* BCG::RD1 or *M. microti*::RD1 strain as a powerful adjuvant/immunomodulator used in the treatment of superficial bladder cancer.

The invention also contemplates the identification at the species level of members of the *M. tuberculosis* complex by means of an RD-based molecular diagnostic test. Inclusion of markers for $RD1^{mic}$ and $RD5^{mic}$ would improve the tests and act as predictors of virulence, especially in humans.

In this regard, the invention concerns a diagnostic kit for the identification at the species level of members of the *M. tuberculosis* complex comprising DNA probes and primers specifically hybridizing to a DNA portion of the RD1 or RD5 region of *M. tuberculosis*, more particularly probes hybridizing under stringent conditions to a gene selected from Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), and Rv3876 (SEQ ID No 19), preferably CFP-10 and ESAT-6.

As used herein, the term "stringent conditions" refers to conditions which permit hybridization between the probe sequences and the polynucleotide sequence to be detected. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature. The temperature range corresponding to a particular level of stringency can be further narrowed by calculating the purine to pyrimidine ratio of the nucleic acid of interest and adjusting the temperature accordingly. Variations on the above ranges and conditions are well known in the art.

Among the preferred primers, we can cite:

```
primer esat-6F
                                           (SEQ ID No 32)
GTCACGTCCATTCATTCCCT, primer esat-6R
                                           (SEQ ID No 33)
ATCCCAGTGACGTTGCCTT), primer RD1mic flanking region F
                                           (SEQ ID No 34)
GCAGTGCAAAGGTGCAGATA, primer RD1mic flanking region R
                                           (SEQ ID No 35)
GATTGAGACACTTGCCACGA, primer RD5mic flanking region F
                                           (SEQ ID No 39)
GAATGCCGACGTCATATCG, primer RD5mic flanking region R
                                           (SEQ ID NO 40)
CGGCCACTGAGTTCGATTAT.
```

The present invention covers also the complementary nucleotide sequences of said above primers as well as the nucleotide sequences hybridizing under stringent conditions with them and having at least 20 nucleotides and less than 500 nucleotides.

Diagnostic fits for the identification at the species level of members of the *M. tuberculosis* complex comprising at least one, two, three or more antibodies directed to mycobacterial PE, PPE, CFP-10, ESAT-6, are also embraced by the invention.

Preferably, such kit comprises antibodies directed to CFP-10 and ESAT-6.

As used herein, the term "antibody" refers to intact molecules as well as fragments thereof, such as Fab, F(ab').sub.2, and Fv, which are capable of binding the epitopic determinant. Probes or antibodies can be labeled with isotopes, fluorescent or phosphorescent molecules or by any other means known in the art.

The invention also relates to virulence markers associated with RD1 and/or RD5 regions of the genome of *M. tuberculosis* or a part of these regions.

The invention is further detailed below and will be illustrated with the following figures.

FIGURE LEGENDS

Figures 1C, 1D:
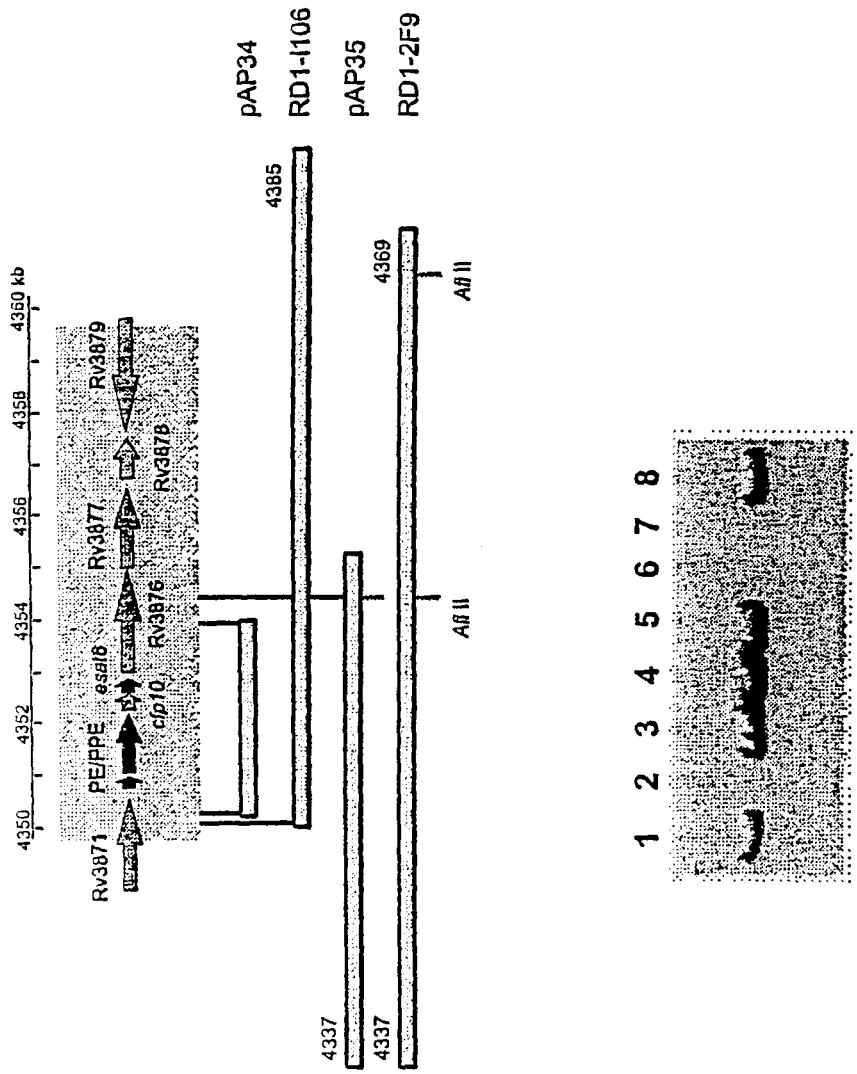
Figure 2A:
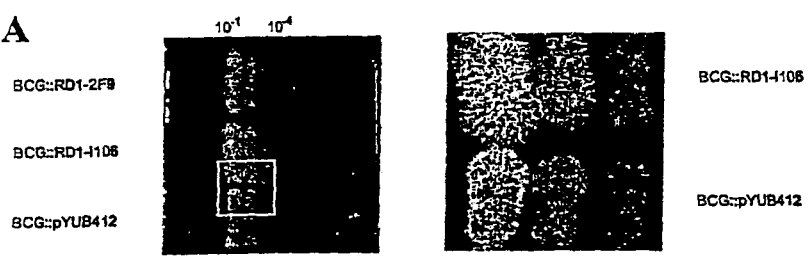
Figure 2B:
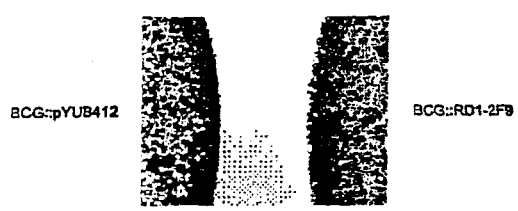
Figure 2C:
Figure 2D:
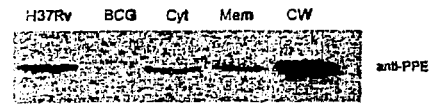

FIG. 1: *M. bovis* BCG and *M. microti* have a chromosomal deletion, RD1, spanning the cfp10-esat6 locus.

(A) Map of the cfp10-esat6 region showing the six possible reading frames and the *M. tuberculosis* H37Rv gene predictions. This map is also available at: genolist.pasteur.fr/TuberculList/.

The deleted regions are shown for BCG and *M. microti* with their respective H37Rv genome coordinates and the extent of the conserved ESAT-6 locus (F. Tekaia, et al., *Tubercle Lung Disease* 79, 329 (1999)), is indicated by the gray bar.

(B) Table showing characteristics of deleted regions selected for complementation analysis. Potential virulence factors and their putative functions disrupted by each deletion are shown. The coordinates are for the *M. tuberculosis* H37Rv genome.

(C) Clones used to complement BCG. Individual clones spanning RD1 regions (RD1-1106 and RD1-2F9) were selected from an ordered *M. tuberculosis* genomic library (R.B. unpublished) in pYUB412 (S. T. Cole, et al., *Nature* 393, 537 (1998) and W. R. Bange, F. M. Collins, W. R. Jacobs, Jr., *Tuber. Lung Dis.* 79, 171 (1999)) and electroporated into *M. bovis* BCG strains, or *M. microti*. Hygromycin-resistant transformants were verified using PCR specific for the corresponding genes. pAP35 was derived from RD1-2F9 by excision of an AA fragment pAP34 was constructed by subcloning an EcoRI-XbaI fragment into the integrative vector pKINT. The ends of each fragment are related to the BCG RD1 deletion (shaded box) with black lines and the H37Rv coordinates for the other fragment ends given in kilobases.

(D) Immunoblot analysis, using an ESAT-6 monoclonal antibody, of whole cell protein extracts from log-phase cultures of (well n° 1) H37Rv (S. T. Cole, et al., *Nature* 393, 537 (1998)), (n° 2) BCG::pYUB412 (M. A. Behr, et al., *Science* 284, 1520 (1999)), (n° 3) BCG::RD14106 (R. Brosch; et al., *Infection Immun.* 66, 2221 (1998)), (n° 4) BCG::RD1-2F9 (S. V. Gordon, et al., *Molec Microbiol* 32, 643 (1999)), (n° 5) *M. bovis* (H. Salamon et al, *Genome Res* 10, 2044 (2000)), (n° 6) *Mycobacterium smegmatis* (G. G. Mahairas, et al, *J. Bacteriol.* 178, 1274 (1996)), (n° 7) *M. smegmatis*::pYUB412, and (n° 8) *M. smegmatis*::RD1-2F9 (R. Brosch, et al., *Proc Natl Acad Sci USA* 99, 3684. (2002)).

FIG. 2: Complementation of BCG Pasteur with the RD1 region alters the colony morphology and leads to accumulation of Rv3873 and ESAT-6 in the cell wall.

(A) Serial dilutions of 3 week old cultures of BCG::pYUB412, BCG:1106 or BCG::RD1-2F9 growing on Middlebrook 7H10 agar plates. The white square shows the area of the plate magnified in the image to the right.

(B) Light microscope image at fifty fold magnification of BCG::pYUB412 and BCG::RD1-2F9 colonies. 5 µl drops of bacterial suspensions of each strain were spotted adjacently onto 7H10 plates and imaged after 10 days growth, illuminating the colonies through the agar.

(C) Immunoblot analysis of different cell fractions of H37Rv obtained from cvmbs.colostate.edu/microbiology/tb/ResearchMA.html using either an anti-ESAT6 antibody or (D) anti-Rv3873 (PPE) rabbit serum. H37Rv and BOG signify whole cell extracts from the respective bacteria and Cyt, Mem and CW correspond to the cytosolic, membrane and cell wall fractions of *M. tuberculosis* H37Rv.

FIG. 3: Complementation of BCG Pasteur with the RD1 region increases bacterial persistence and pathogenicity in mice.

(A) Bacteria in the spleen and lungs of BALB/c mice following intravenous (i.v.) infection via the lateral tail vein with $10^6$ colony forming units (cfu) of *M. tuberculosis* H37Rv (black) or $10^7$ cfu of either BCG::pYUB412 (light grey) or BCG::RD1-I106 (grey).

(B) Bacterial persistence in the spleen and lungs of C57BL/6 mice following infection with $10^5$ cfu of BCG::pYUB412 (light grey), BCG::RD1-I106 (middle grey) or BCG::RD1-2F9 (dark grey):

(C) Bacterial multiplication after i.v. infection with $10^6$ cfu of BCG::pYUB412 (light grey) and BCG::RD1-2F9 (grey) in severe combined immunodeficiency mice (SCID). For A, B, and C each timepoint is the mean of 3 to 4 mice and the error bars represent standard deviations.

(D) Spleens from SCID mice three weeks after i.v. infection with 10⁶ cfu of either BCG::pYUB412, BCG::RD1-2F9 or BCG::I301 (an RD3 "knock-in", FIG. 1B). The scale is in cm.

FIG. 4: Immunization of mice with BCG::RD1 generates marked ESAT-6 specific T-cell responses and enhanced protection to a challenge with *M. tuberculosis*.

(A) Proliferative response of splenocytes of C57BL/6 mice immunized subcutaneously (s.c.) with 10⁶ CFU of BCG::pYUB412 (open squares) or BCG::RD1-2F9 (solid squares) to in vitro stimulation with various concentrations of synthetic peptides from poliovirus type 1 capsid protein VP1, ESAT-6 or Ag85A (K. Huygen, et al., *Infect. Immun.* 62, 363 (1994), L. Brandt, *J. Immunol.* 157, 3527 (1996) and C. Leclerc et al, *J. Virol.* 65, 711 (1991)).

(B) Proliferation of splenocytes from BCG::RD1-2F9-immunised mice in the absence or presence of 10 µg/ml of ESAT-6 1-20 peptide, with or without 1 µg/ml of anti-CD4 (GK1.5) or anti-CD8 (H35-17-2) monoclonal antibody. Results are expressed as mean and standard deviation of ³H-thymidine incorporation from duplicate wells.

(C) Concentration of IFN-γ in culture supernatants of splenocytes of C57BL/6 mice stimulated for 72 h with peptides or PPD after s.c. or i.v. immunization with either BCG::pYUB412 (middle grey and white) or BCG::RD1-2F9 (light grey and black). Mice were inoculated with either 10⁶ (white and light grey) or 10⁷ (middle grey and black) cfu. Levels of IFN-γ were quantified using a sandwich ELISA (detection limit of 500 pg/ml) with the mAbs R4-6A2 and biotin-conjugated XMG1.2. Results are expressed as the mean and standard deviation of duplicate culture wells.

(D) Bacterial counts in the spleen and lungs of vaccinated and unvaccinated BALB/c mice 2 months after an i.v. challenge with *M. tuberculosis* H37Rv. The mice were challenged 2 months after i.v. inoculation with 10⁶ cfu of either BCG::pYUB412 or BCG::RD1-2F9. Organ homogenates for bacterial enumeration were plated on 7H11 medium, with or without hygromycin, to differentiate *M. tuberculosis* from residual BCG colonies. Results are expressed as the mean and standard deviation of 4 to 5 mice and the levels of significance derived using the Wilcoxon rank sum test.

FIG. 5: *Mycobacterium microti* strain OV254 BAC map (BAC clones named MIXXX, where XXX is the identification number of the clone), overlaid on the *M. tuberculosis* H37Rv (BAC clones named RvXXX, where XXX is the identification number of the clone) and *M. bovis* AF2122/97 (BAC clones named MbXXX, where XXX is the identification number of the clone) BAC maps. The scale bars indicate the position on the *M. tuberculosis* genome.

FIG. 6: Difference in the region 4340-4360 kb between the deletion in BCG RD1$^{bcg}$ (A) and in *M. microti* RD1$^{mic}$ (C) relative to *M. tuberculosis* H37Rv (B).

FIG. 7: Difference in the region 3121-3127 kb between *M. tuberculosis* H37Rv. (A) and *M. microti* OV254 (B). Gray boxes picture the direct repeats (DR), black ones the unique numbered spacer sequences. * spacer sequence identical to the one of spacer 58 reported by van Embden et al. (42). Note that spacers 33-36 and 20-22 are not shown because H37Rv lacks these spacers.

FIG. 8: A) AseI PFGE profiles of various *M. microti* strains; Hybridization with a radiolabeled B) esat-6 probe; C) probe of the RD1$^{mic}$ flanking region; D) plcA probe. 1. *M. bovis* AF2122/97, 2. *M. canetti,* 3. *M. bovis* BCG Pasteur, 4. *M. tuberculosis* H37Rv, 5. *M. microti* OV254, 6. *M. microti* Myc 94-2272, 7. *M. microti* B3 type mouse, 8. *M. microti* B4 type mouse, 9. *M. microti* B2 type llama, 10. *M. microti* B1 type llama, 11. *M. microti* ATCC 35782. M: Low range PFGE marker (NEB).

FIG. 9: PCR products obtained from various *M. microti* strains using primers that flank the RD1$^{mic}$ region, for amplifying ESAT-6 antigen, that flank the MiD2 region. 1. *M. microti* B1 type llama, 2. *M. microti* B4 type mouse, 3. *M. microti* B3 type mouse, 4. *M. microti* B2 type llama, 5. *M. microti* ATCC 35782, 6. *M. microti* OV254, 7. *M. microti* Myc 94-2272; 8. *M. tuberculosis* H37Rv.

FIG. 10: Map of the *M. tuberculosis* H37Rv RD1 genomic region. Map of the fragments used to complement BCG and *M. microti* (black) and the genomic regions deleted from different mycobacterial strains (grey). The middle part show key genes, putative promoters (P) and transcripts, the various proteins from RD1 region, their sites (number of amino acid residues), InterPro domains ebi.ac.uk/interpro/, membership of *M. tuberculosis* protein families from TubercuList genolist.pasteur.fr/TubercuList/. The dashed lines mark the extent of the RD1 deletion in BCG, *M. microti* and *M. tuberculosis* clinical isolate MT56 (Brosch, R., et al. A new evolutionary scenario for the *Mycobacterium tuberculosis* complex. *Proc Natl Aced Sci USA* 99, 3684-9. (2002)). *M. bovis* AF2122/97 is shown because it contains a frameshift mutation in Rv3881, a gene flanking the RD1 region of BCG. The fragments are drawn to show their ends in relation to the genetic map, unless they extend beyond the genomic region indicated. pRD1-2F9, pRD1-I106 and pAP35 are based on pYUB312; pAP34 on pKINT; pAP47 and pAP48 on pSM81.

FIG. 11: Western blot analysis of various RD1 knock-ins of *M. bovis* BCG and *M. microti*. The left panel sows results of immunodetection of ESAT-6, CFP-10 and PPE68 (Rv3873) in whole cells lysates (WCL) and culture supernatants of BCG; the center panel displays the equivalent findings from *M. microti* and the right panel contains *M. tuberculosis* H37Rv control samples. Samples from mycobacteria transformed with the following plasmids were present in lanes: –, pYUB412 vector control; 1, pAP34; 2, pAP35; 3, RD1-I106, 4, RD1-2F9. The positions of the nearest molecular weight markers are indicated.

FIG. 12: Analysis of immune responses induced by BCG recombinants. A, The upper three panels display the results of splenocyte proliferation assays in response to stimulation in vitro with a peptide from MalE (negative control), to PPD or to a peptide containing an immunodominant CD4-epitope from ESAT-6. B, The lower panel shows IFN-(production by splenocytes in response to the same antigens. Symbols indicate the nature of the various BCG transformants. Samples were taken from C57BL16 mice immunized subcutaneously.

FIG. 13: Further immunological characterization of responses to BCG::RD1-2F9 A, Proliferative response of splenocytes of C57BL/6 mice immunized subcutaneously (s.c.) with $10^6$ CFU of BCG::pYUB412 or BCG::RD1-2F9 to in vitro stimulation with various concentrations of synthetic peptides from poliovirus type 1 capsid protein VP1 (negative control), ESAT-6 or Ag85A (see Methods for details). B, Proliferation of splenocytes from BCG::RD1-2F9 immunized mice in the absence or presence of ESAT-6 1-20 peptide, with or without anti-CD4 or anti-CD8 monoclonal antibody. Results are expressed as mean and standard deviation of $^3$H-thymidine incorporation from duplicate wells. C, Concentration of IFN-(in culture supernatants of splenocytes of C57BL/6 mice stimulated for 72 h with peptides or PPD after s.c. or i.v. immunization with either BCG::pYUB412 or BCG::RD1-2F9. Mice were inoculated with either $10^6$ or $10^7$ CFU. Results are expressed as the mean and standard deviation of duplicate culture wells.

FIG. 14: Mouse protection studies. A, Bacterial counts in the spleen and lungs of vaccinated and unvaccinated C57BU6 mice 2 months after an i.v. challenge with *M. tuberculosis* H37Rv. The mice were challenged 2 months after i.v. inoculation with $10^6$ cfu of either BCG::pYUB412 or BCG::RD1-2F9. Organ homogenates for bacterial enumeration were plated on 7H11 medium, with or without hygromycin, to differentiate *M. tuberculosis* from residual BCG colonies. Results are expressed as the mean and standard deviation of 4 mice. Hatched columns correspond to the cohort of unvaccinated mice, while white and black columns correspond to mice vaccinated with BCG::pYUB412 and BCG::RD1-2F9, respectively. B, Bacterial counts in the spleen and lungs of vaccinated and unvaccinated C57BL6 mice after an aerosol challenge with 1000 CFUs of *M. tuberculosis*. All mice were treated with antibiotics for three weeks prior to infection with *M. tuberculosis*. Data are the mean and SE measured on groups of three animals, and differences between groups were analyzed using ANOVA (*p<0.05, **p<0.01).

Figure 15A:
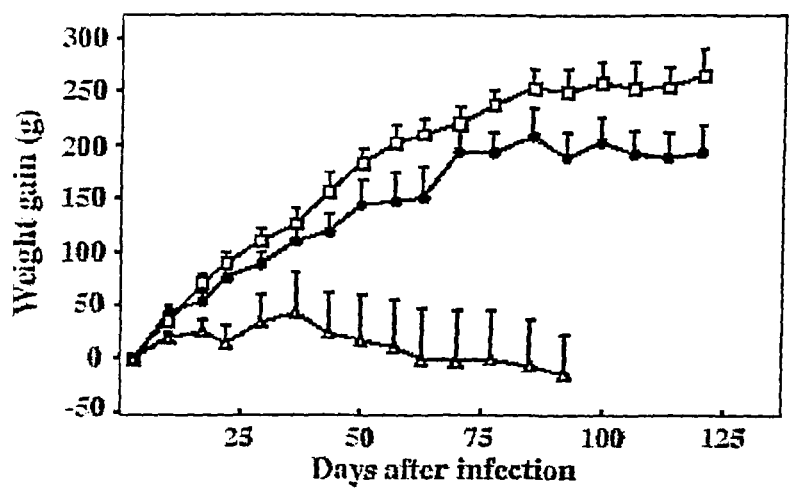
Figure 15B:
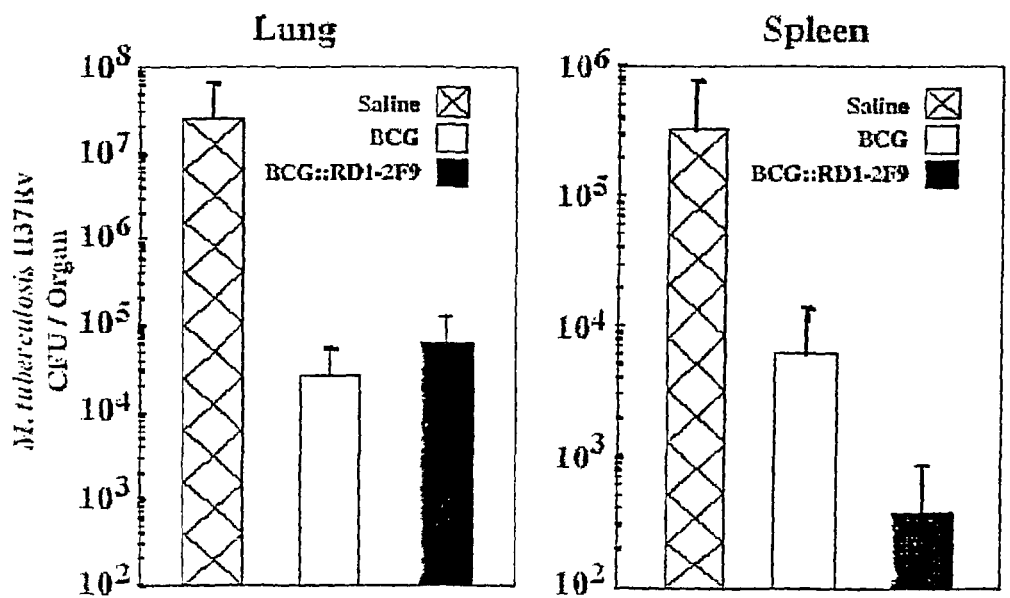
Figure 15C:

FIG. 15: Guinea pig protection studies. A, Mean weight gain of vaccinated and unvaccinated guinea pigs following aerosol infection with *M. tuberculosis* H37Rv. Guinea pigs were vaccinated with either saline (triangles), BCG (squares) or BCG:RD1-2F9 (filled circles). The error bars are the standard error of the mean. Each time point represents the mean weight of six guinea pigs. For the saline vaccinated group the last live weight was used for calculating the means as the animals were killed on signs of severe tuberculosis which occurred after 50, 59, 71, 72, 93 and 93 days. B, Mean bacterial counts in the spleen and lungs of vaccinated and unvaccinated guinea pigs after an aerosol challenge with *M. tuberculosis* H37Rv. Groups of 6 guinea pigs were vaccinated subcutaneously with either saline, BCG or BCG::RD1-2F9 and infected 56 days later. Vaccinated animals were killed 120 days following infection and unvaccinated ones on signs of suffering or significant weight loss. The error bars represent the standard error of the mean of six observations. C, Spleens of vaccinated guinea pigs 120 days after infection with *M. tuberculosis* H37Rv; left, animal immunized with BCG; right, animal immunized with BCG::RD1-2F9.

Figure 16:
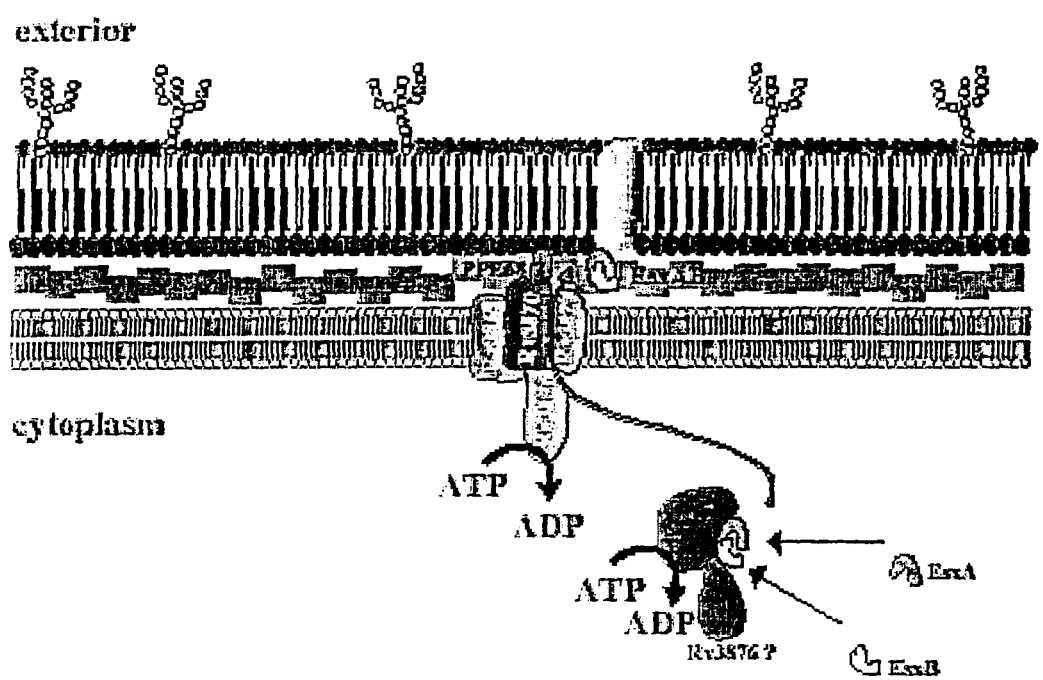

FIG. 16: Diagram of the *M. tuberculosis* H37Rv genomic region showing a working model for biogenesis and export of ESAT-6 proteins. It presents a possible functional model indicating predicted subcellular localization and potential interactions within the mycobacterial cell envelope. Rosetta stone analysis indicates direct interaction between proteins Rv3870 and Rv3871, and the sequence similarity between the N-terminal domains of Rv3868 and Rv3876 suggests that these putative chaperones might also interact. Rv3868 is a member of the AAA-family of ATPases that perform chaperone-like functions by assisting in the assembly, and disassembly of protein complexes (Neuwald, A. F., Aravind, L., Spouge, J. L. & Koonin, E N. AAA+; A class of chaperone-like ATPases associated with the assembly, operation, and disassembly of protein complexes. *Genome Res* 9, 27-43. (1999).). It is striking that many type III secretion systems require chaperones for stabilization of the effector proteins that they secrete and for prevention of premature protein-protein interactions (Page, A. L. & Parsot, C. Chaperones of the type III secretion pathway: jacks of all trades. *Mol Microbiol* 46, 1-11. (2002).). Thus, Rv3868, and possibly Rv3876, may be required for the folding and/or dimerization of ESAT-6/CFP-10 proteins (Renshaw, P. S., et al. Conclusive evidence that the major T-cell antigens of the *M. tuberculosis* complex ESAT-6 and CFP-10 form a tight, 1:1 complex and characterization of the structural properties of ESAT-6, CFP-10 and the ESAT-6-CFP-10 complex: implications for pathogenesis and virulence. *J Biol Chem* 8, 8 (2002).), or even to prevent premature dimerization. ESAT-6/CFP-10 are predicted to be exported through a transmembrane channel, consisting of at least Rv3870, Rv3871, and Rv3877, and possibly Rv3869, in a process catalyzed by ATP-hydrolysis. Rv3873 (PPE 68) is known to occur in the cell envelope and may also be involved as shown herein.

EXAMPLE 1

Figure 3A:
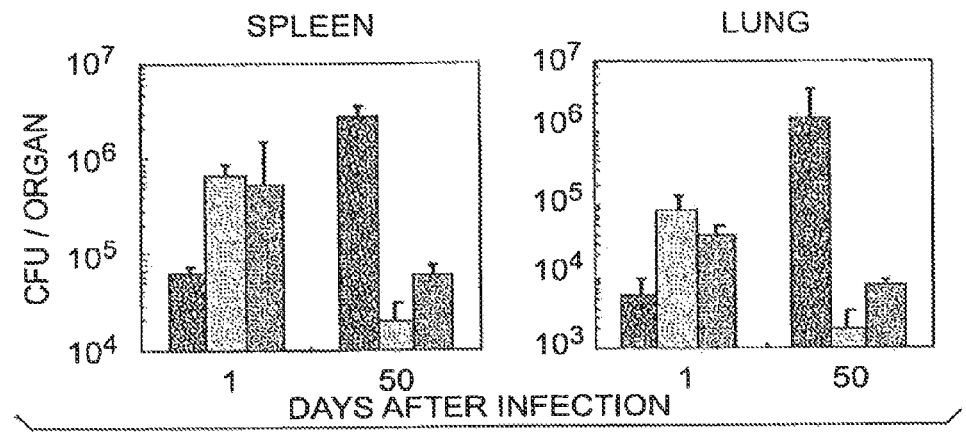
Figure 3B:
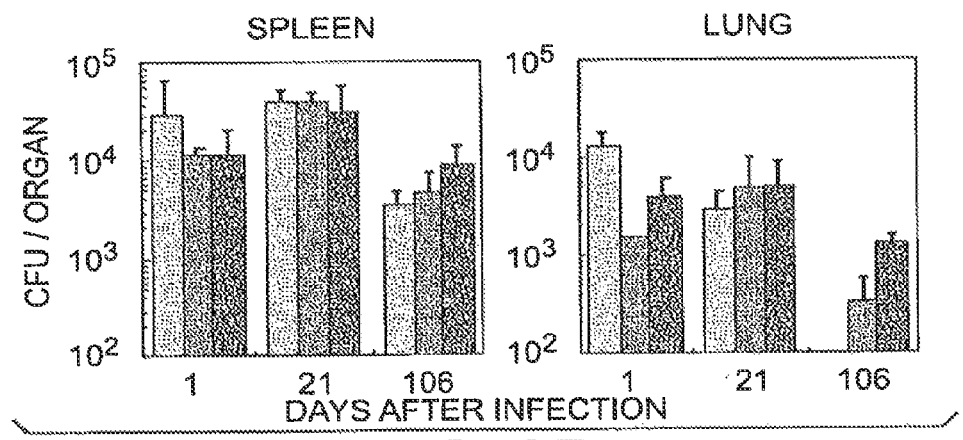
Figure 3C:
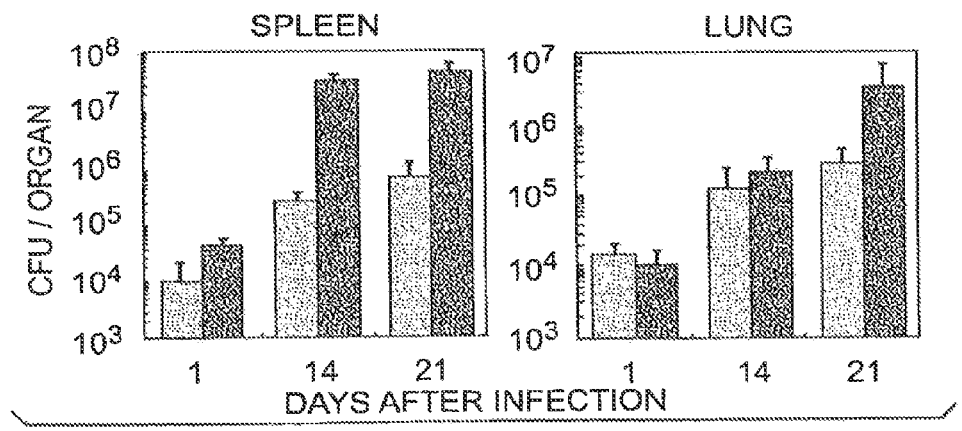
Figure 3D:
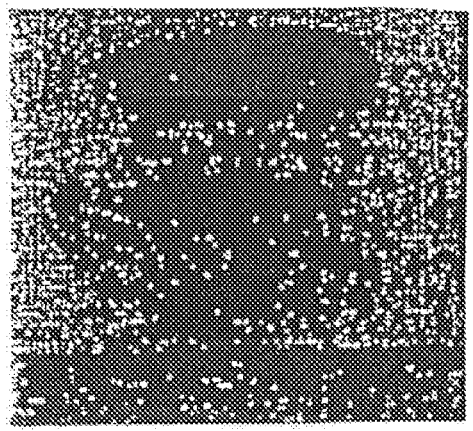

Preparation and Assessment of *M. bovis* BCG::RD1 Strains as a Vaccine for Treating or Preventing Tuberculosis As mentioned above, we have found that complementation with RD1 was accompanied by a change in colonial appearance as the BCG Pasteur "knock-in" strains developed a strikingly different morphotype (FIG. 2A). The RD1 complemented strains adopted a spreading, less-rugose morphology, that is characteristic of *M. bovis*, and this was more apparent when the colonies were inspected by light microscopy (FIG. 2B). Maps of the clones used are shown (FIG. 1C). These changes were seen following complementation with all of the RD1 constructs (FIG. 1C) and on complementing *M. microti* (data not shown). Pertinently, Calmette and Guérin (A. Calmette, *La vaccination preventive contre la tuberculose*. (Masson et cie., Paris, 1927)) observed a change in colony morphology during their initial passaging of *M. bovis*, and our experiments now demonstrate that this change, corresponding to loss of RD1, directly contributed to attenuating this virulent strain. The integrity of the cell wall is known to be a key virulence determinant for *M. tuberculosis* (C. E. Barry, *Trends Microbiol* 9, 237 (2001)), and changes in both cell wall lipids (M. S. Glickman, J. S. Cox, W. R. Jacobs, Jr., *Mol Cell* 5, 717 (2000)) and protein (F. X. Berthet, et al., *Science* 282, 759 (1998)) have been shown to alter colony morphology and diminish persistence in animal models.

To determine which genes were implicated in these morphological changes, antibodies recognising three RD1 proteins (Rv3873, CFP10 and ESAT-6) were used in immunocytological and subcellular fractionation analysis. When the different cell fractions from *M. tuberculosis* were immunoblotted all three proteins were localized in the cell wall fraction (FIG. 2C) though significant quantities of Rv3873, a PPE protein, were also detected in the membrane and cytosolic fractions (FIG. 2D). Using immunogold staining and electron Microscopy the presence of ESAT-6 in the envelope of *M. tuberculosis* was confirmed but no alteration in capsular ultrastructure could be detected (data not shown). Previously, CFP-10 and ESAT-6 have been considered as secreted proteins (F. X. Berthet et al, *Microbiology* 144, 3195 (1998)) but our results suggest that their biological functions are linked directly with the cell wall:

Changes in colonial morphology are often accompanied by altered bacterial virulence. Initial assessment of the growth of different BCG::RD1 "knock-ins" in C57BL/6 or BALB/c mice following intravenous infection revealed that complementation did not restore levels of virulence to those of the reference strain *M. tuberculosis* H37Rv (FIG. 3A). In longer-term experiments, modest yet significant differences were detected in the persistence of the BCG::RD1 "knock-ins" in comparison to BCG controls. Following intravenous infection of C57B116 mice, only the RD1 "knock-ins" were still detectable in the lungs after 106 days (FIG. 3B). This difference in virulence between the RD1 recombinants and the BCG vector control was more pronounced in severe combined immunodeficiency (SCID) mice (FIG. 3C). The BCG::

RD1-2F9 "knock-in" was markedly more virulent, as evidenced by the growth rate in lungs and spleen and also by an increased degree of splenomegaly (FIG. 3D). Cytological examination revealed numerous bacilli, extensive cellular infiltration and granuloma formation. These increases in virulence following complementation with the RD1 region, demonstrate that the loss of this genomic locus contributed to the attenuation of BCG.

The inability to restore full virulence to BCG Pasteur was not due to instability of our constructs nor to the strain used (data not shown). Essentially identical results were obtained on complementing BCG Russia, a strain less passaged than BCG Pasteur and presumed, therefore, to be closer to the original ancestor (M. A. Behr, et al., Science 284, 1520 (1999)). This indicates that the attenuation of BCG was a polymutational process and loss of residual virulence for animals was documented in, the late 1920s (T. Oettinger, et al, Tuber Lung Dis 79, 243 (1999)). Using the same experimental strategy, we also tested the effects of complementing with RD3-5, RD7 and RD9 (S. T. Cole, et al., Nature 393, 537 (1998); M. A. Behr, et al., Science 284, 1520 (1999); Brosch, et al., Infection Immun. 66, 2221 (1998) and S. V. Gordon et al., Molec Microbial 32, 643 (1999)) encoding putative virulence factors (FIG. 1B). Reintroduction of these regions, which are not restricted to avirulent strains, did not affect virulence in immuno-competent mice. Although it is possible that deletion effects act synergistically it seems more plausible that other attenuating mechanisms are at play.

Figure 4A:
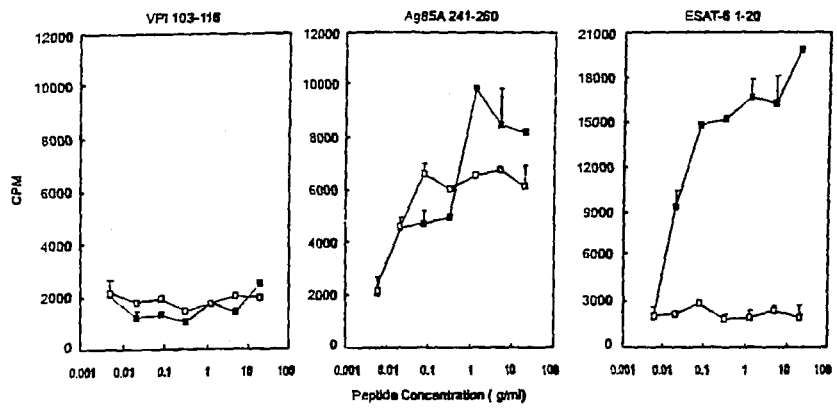
Figure 4B:
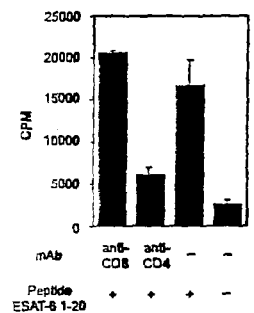
Figure 4C:
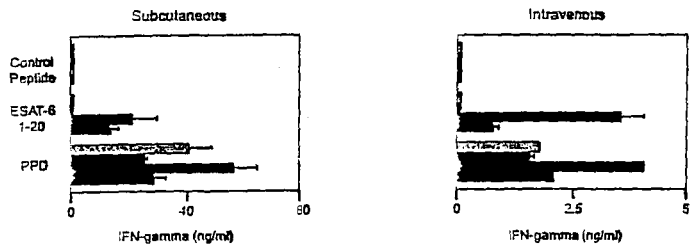
Figure 4D:
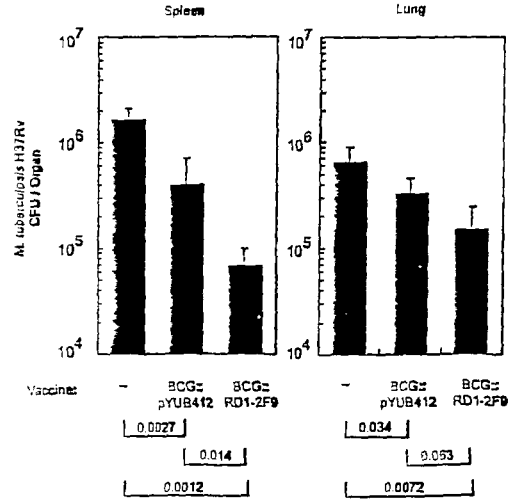
Figure 4B:
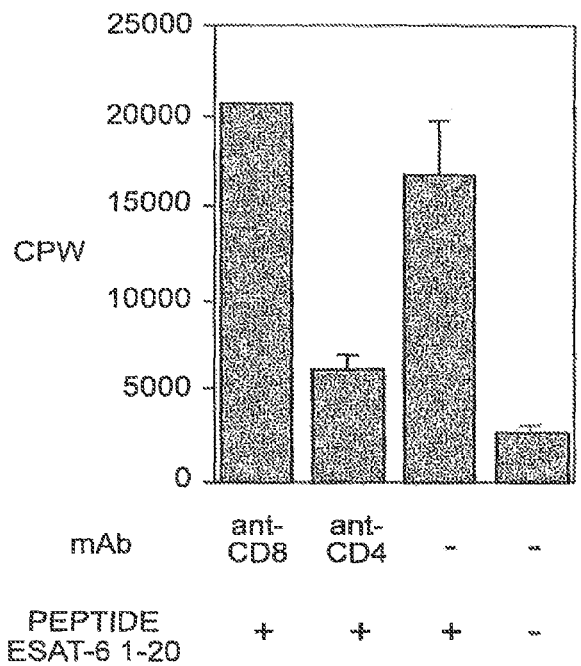
Figure 4C:
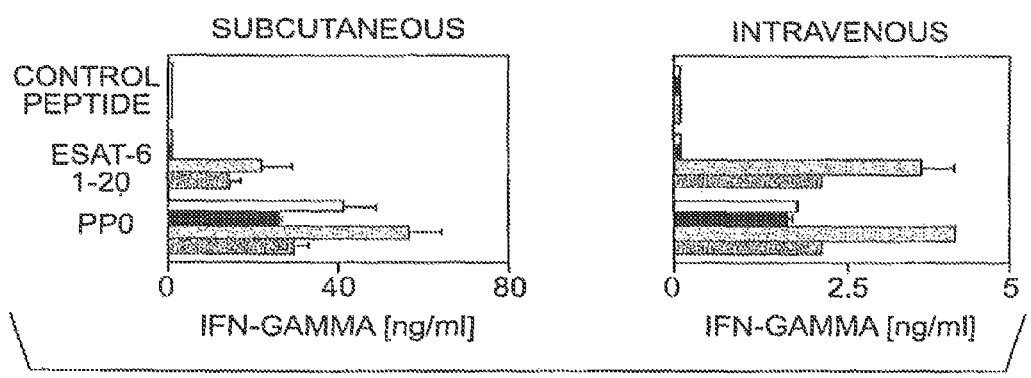
Figure 4D:
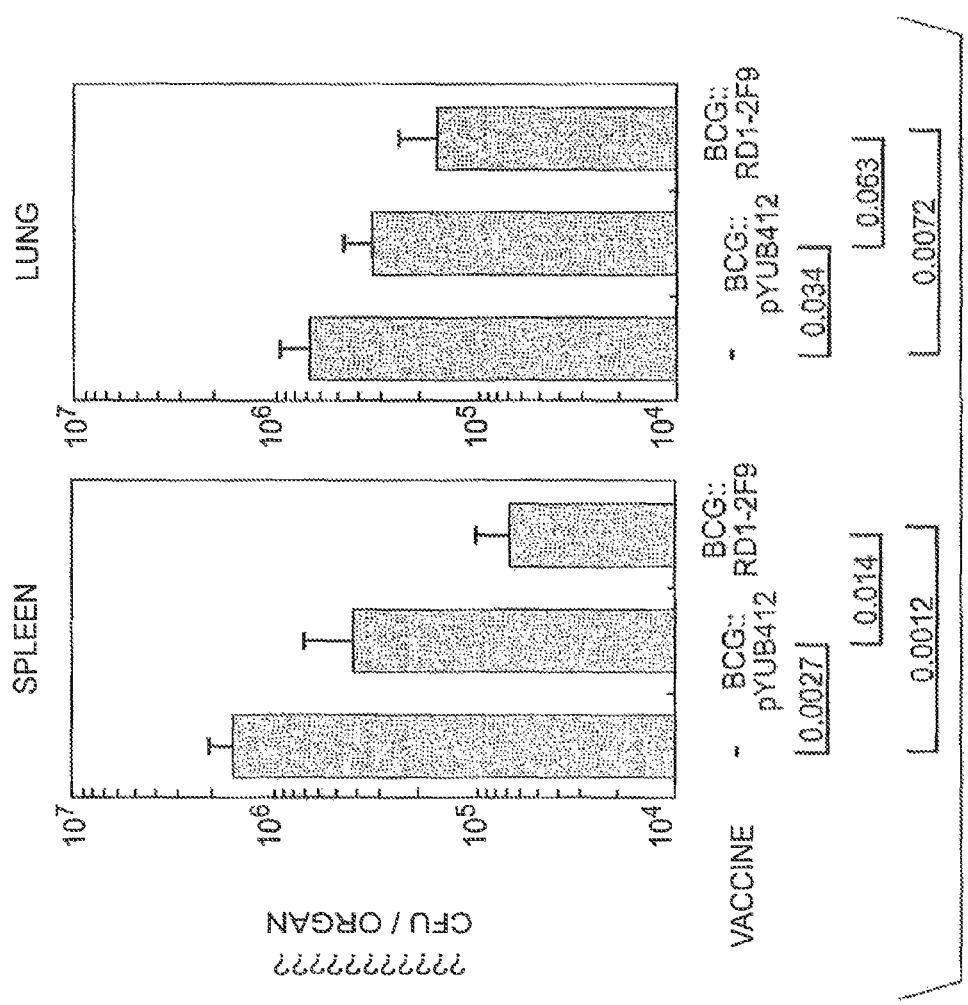

Since RD1 encodes at least two potent T-cell antigens (R. Colangelli, et al., Infect. Immun. 68, 990 (2000), M. Harboe, et al., Infect. Immun. 66, 717 (1998) and R. L. V. Skjøt, et al., Infect. Immun. 68, 214 (2000)), we investigated whether its restoration induced immune responses to these antigens or even improved the protective capacity of BCG. Three weeks following either intravenous or subcutaneous inoculation with BCG::RD1 or BCG controls, we observed similar proliferation of splenocytes to an Ag85A (an antigenic BCG protein) peptide (K. Huygen, et al., Infect. Immun. 62, 363 (1994)), but not against a control viral peptide (FIG. 4A). Moreover, BCG::RD1 generated powerful CD4$^+$ T-cell responses against the ESAT-6 peptide as shown by splenocyte proliferation (FIG. 4A, B) and strong IFN-γ production (FIG. 4C). In contrast, the BCG::pYUB412 control did not stimulate ESAT-6 specific T-cell responses thus indicating that these were mediated by the RD1 locus. ESAT-6 is, therefore, highly immunogenic in mice in the context of recombinant BCG.

When used as a subunit vaccine, ESAT-6 elicits T-cell responses and induces levels of protection weaker than but akin to those of BCG (L. Brandt et al, Infect. Immun. 68, 791 (2000)). Challenge experiments were conducted to determine if induction of immune responses to BCG::RD1-encoded antigens, such as ESAT-6, could improve protection against infection with M. tuberculosis. Groups of mice inoculated with either BCG::pYUB412 or BCG::RD1 were subsequently infected intravenously with M. tuberculosis H37Rv. These experiments showed that immunization with the BCG::RD1 "knock-in" inhibited the growth of M. tuberculosis within both BALB/c (FIG. 4D) and C57BL/6 mice when compared to inoculation with BCG alone.

Although the increases in protection induced by BCG::RD1 and the BCG control are modest they demonstrate convincingly that genetic differences have developed between the live vaccine and the pathogen which have weakened the protective capacity of BCG. This study therefore defines the genetic basis of a compromise that has occurred, during the attenuation process, between loss of virulence and reduced protection (M. A. Behr, P. M. Small, Nature 389, 133 (1997)). The strategy of reintroducing, or even overproducing (M. A. Horwitz et al, Proc Natl Acad Sci USA 91, 13853 (2000)), the missing immunodominant antigens of M. tuberculosis in BCG, could be combined with an immuno-neutral attenuating mutation to create a more efficacious tuberculosis vaccine.

EXAMPLE 2

BAC Based Comparative Genomics Identifies Mycobacterium microti as a Natural ESAT-6 Deletion Mutant We searched for any genetic differences between human and vole isolates that might explain their different degree of virulence and host preference and what makes the vole isolates harmless for humans. In this regard, comparative genomics methods were employed in connection with the present invention to identify major differences that may exist between the M. microti reference strain OV254 and the entirely sequenced strains of M. tuberculosis H37Rv (10) or M. bovis AF2122/97 (14). An ordered Bacterial Artificial Chromosome (BAC) library of M. microti OV254 was constructed and individual BAC to BAC comparison of a minimal set of these clones with BAC clones from previously constructed libraries of M. tuberculosis H37Rv and M. bovis AF2122/97 was undertaken.

Ten regions were detected in M. microti that were different to the corresponding genomic regions in M. tuberculosis and M. bovis. To investigate if these regions were associated with the ability of M. microti strains to infect humans, their genetic organization was studied in 8 additional M. microti strains; including those isolated recently from patients with pulmonary tuberculosis. This analysis identified some regions that were specifically absent from all tested M. microti strains, but present in all other members of the M. tuberculosis complex and other regions that were only absent from vole isolates of M. microti.

2.1 Materials and Methods

Bacterial Strains and Plasmids.

M. microti OV254 which was originally isolated from voles in the UK in the 1930's was kindly supplied by M J Colston (45). DNA from M. microti OV216 and OV183 were included in a set of strains used during a multicenter study (26). M. microti Myc 94-2272 was isolated in 1988 from the perfusion fluid of a 41-year-old dialysis patient (43) and was kindly provided by L. M. Parsons. M. microti. 35782 was purchased from American Type Culture Collection (designation TMC 1608 (M. P. Prague)). M. microti B1 type llama, B2 type llama, B3 type mouse and B4 type mouse were obtained from the collection of the National Reference Center for Mycobacteria, Forschungszentrum Borstel, Germany. M. bovis strain AF2122/97, spoligotype 9 was responsible for a herd outbreak in Devon in the UK and has been isolated from lesions in both cattle and badgers. Typically, mycobacteria were grown on 7H9 Middlebrook liquid medium (Difco) containing 10% oleic-acid-dextrose-catalase (Difco), 0.2% pyruvic acid and 0.05% Tween 80.

Library Construction, Preparation of BAC DNA and Sequencing Reactions.

Preparation of agarose-embedded genomic DNA from M. microti strain OV254, M. tuberculosis H37Rv, M. bovis BCG was performed as described by Brosch et al. (5). The M. microti library was constructed by ligation of partially digested HindIII fragments (50-125 kb) into pBeloBAC11. From the 10,000 clones that were obtained, 2,000 were picked into 96 well plates and stored at −80° C. Plasmid preparations of recombinant clones for sequencing reactions were obtained by pooling eight copies of 96 well plates, with each well containing an overnight culture in 250 µl 2YT medium with 12.5 µg·ml$^{-1}$ chloramphenicol. After 5 min centrifugation at 3000 rpm; the bacterial pellets were resuspended in 25 µl of solution A (25 mM Tris, pH 8.0, 50 mM glucose and 10 mM EDTA), cells were lysed by adding 25 µl of buffer B (NaOH 0.2 M, SDS 0.2%). Then 20 µl of cold 3 M sodium acetate pH 4.8 were added and kept on ice for 30 min. After centrifugation at 3000 rpm for 30 min, the pooled supernatants (140 µl) were transferred to new plates. 130 µl of isopropanol were added, and after 30 min on ice, DNA was pelleted by centrifugation at 3500 rpm for IS min. The supernatant was discarded and the pellet resuspended in 50 µl of a 10 µg/ml RNAse A solution (in Tris 10 mM pH 7.5/EDTA 10 mM) and incubated at 64° C. for 15 min. After precipitation (2.5 µl of sodium acetate 3 M pH 7 and 200 µl of absolute ethanol) pellets were rinsed with 200 µl of 70% ethanol, air dried and finally suspended in 20 µl of TE buffer.

End-sequencing reactions were performed with a Taq DyeDeoxy Terminator cycle sequencing kit (Applied Biosystems) using a mixture of 13 µl of DNA solution, 2 µl of Primer (2 µM) (SP6-BAC1, AGTTAGCTCACTCATTAGGCA (SEQ ID No 15), or T7-BAC1, GGATGTGCTGCAAGGC-GATTA (SEQ ID No 16)). 2.5 µl of Big Dye and 2.5 µl of a 5× buffer (50 mM MgCl$_2$, 50 mM Tris). Thermal cycling was performed on a PTC-100 amplifier (MJ Inc.) with an initial denaturation step of 60 s at 95° C., followed by 90 cycles of 15 s at 95° C., 15 s at 56° C., 4 min at 60° C. DNA was then precipitated with 80 µl of 76% ethanol and centrifuged at 3000 rpm for 30 min. After discarding the supernatant, DNA was finally rinsed with 80 µl of 70% ethanol and resuspended in appropriate buffers depending on the type of automated sequencer used (ABI 377 or ABI 3700). Sequence data were transferred to Digital workstations and edited using the TED software from the Staden package (37). Edited sequences were compared against the *M. tuberculosis* H37Rv database genolist.pasteur.fr/TuberculList/, the *M. bovis* BLAST server sanger.ac.uk/Projects/M bovis/blast, and in-house databases to determine the relative positions of the *M. microti* OV254 BAC end-sequences.

Preparation of BAC DNA from Recombinants and BAC Digestion Profile Comparison.

DNA for digestion was prepared as previously described (4). DNA (1 µg) was digested with HindIII (Boehringer) and restriction products separated by pulsed-field gel electrophoresis (PFGE) on a Biorad CHEF-DR III system using a 1% (w/v) agarose gel and a pulse of 3.5 s for 17 h at 6 V·cm$^{-1}$. Low-range PFGE markers (NEB) were used as size standards. Insert sizes were estimated after ethidium bromide staining and visualization with UV light. Different comparisons were made with overlapping clones from the *M. microti* OV254, *M. bovis* AF2122/97, and *M. tuberculosis* H37Rv pBeloBAC11 libraries.

PCR Analysis to Determine Presence of Genes in Different *M. microti* Strains.

Reactions contained 5 µl of 10×PCR buffer (100 mM β-mercaptoethanol, 600 mM Tris-HCl, pH 8.8, 20 mM MgCl$_2$, 170 mM (NH$_4$)$_2$SO$_4$, 20 mM nucleotide mix dNTP), 2.5 µl of each primer at 2 µM, 10 ng of template DNA, 10% DMSO and 0.5 unit of Taq polymerase in a final volume of 12.5 µl. Thermal cycling was performed on a PTC-100 amplifier (MJ Inc.) with an initial denaturation step of 90 s at 95° C., followed by 35 cycles of 45 s at 95° C., 1 min at 60° C. and 2 min at 72° C.

RFLP Analysis.

In brief, agarose plugs of genomic DNA prepared as previously described (5) were digested with either AseI, DraI or XbaI (NEB), then electrophoresed on a 1% agarose gel, and finally transferred to Hybond-C extra nitrocellulose membranes (Amersham). Different probes were amplified by PCR from the *M. microti* strain OV254 or *M. tuberculosis* H37Rv using primers for:
esat-6 (esat-6F GTCACGTCCATTCATTCCCT (SEQ ID No 17);
esat-6R ATCCCAGTGACGTTGCCTT) (SEQ ID No 18),
the RD1$^{mic}$ flanking region (4340, 209F GCAGTGCAAAG-GTGCAGATA (SEQ ID No 19); 4354,701R GATTGAGA-CACTTGCCACGA (SEQ ID No 20)), or
plcA (plcA.int.F CAAGTTGGGTCTGGTCGAAT (SEQ No 21); plcA.int.R GCTACCCAAGGTCTCCTGGT (SEQ ID No 22)). Amplification products were radio-labeled by using the Stratagene Prime-It II kit (Stratagene). Hybridizations were performed at 65° C. in a solution containing NaCl 0.8 M, EDTA pH 8, 5 mM, sodium phosphate 50 mM pH 8, 2% SDS, 1×Denhardt's reagent and 100 µg/ml salmon sperm DNA (Genaxis). Membranes Were exposed to phosphorimager screens and images were digitalized by using a STORM phospho-imager.

DNA Sequence Accession Numbers.

The nucleotide sequences that flank MID1, MiD2, MiD3 as well as the junction sequence of RD1$^{mic}$ have been deposited in the EMBL database. Accession numbers are AJ345005, AJ345006, AJ315556 and AJ315557, respectively.

2.2 Results

Establishment of a Complete Ordered BAC Library of *M. microti* OV254.

Figure 5:
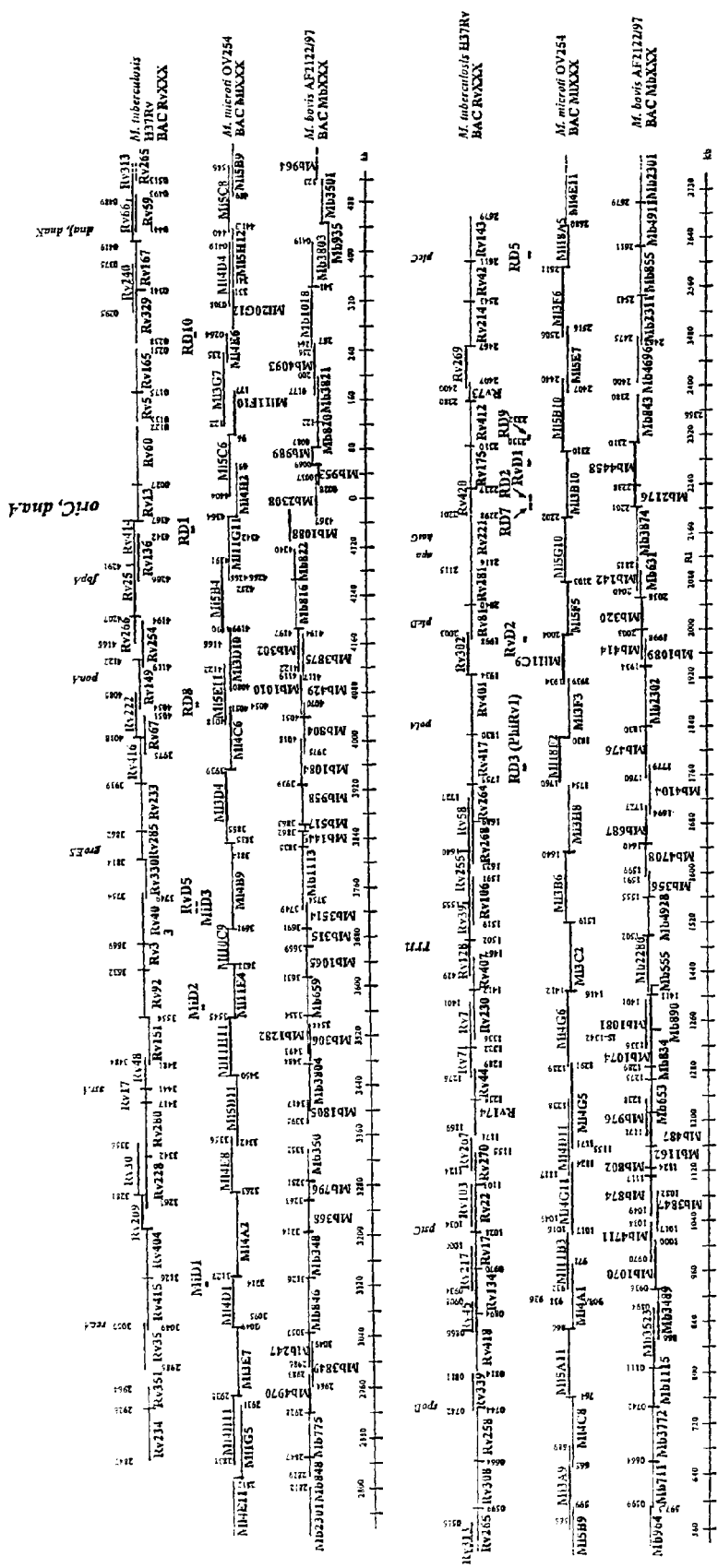

Electroporation of pBeloBAC11 containing partial HindIII digests of *M. microti* OV254 DNA into *Escherichia coli* DH10B yielded about 10,000 recombinant clones, from which 2,000 were isolated and stored in 96-well plates. Using the complete sequence of the *M. tuberculosis* H37Rv genome as a scaffold, end-sequencing of 384 randomly chosen *M. microti* BAC clones allowed us to select enough clones to cover almost all of the 4.4 Mb chromosome. A few rare clones that spanned regions that were not covered by this approach were identified by PCR screening of pools as previously described (4). This resulted in a minimal set of 50 BACs, covering over 99.9% of the *M. microti* OV254 genome, whose positions relative to *M. tuberculosis* H37Rv are shown in FIG. 5. The insert size ranged between 50 and 125 kb, and the recombinant clones were stable. Compared with other BAC libraries from tubercle bacilli (4, 13) the *M. microti* OV254 BAC library contained clones that were generally larger than those obtained previously, which facilitated the comparative genomics approach, described below.

Identification of DNA Deletions in *M. microti* OV254 Relative to *M. tuberculosis* H37Rv by Comparative Genomics.

The minimal overlapping set of 50 BAC clones, together with the availability of three other ordered BAC libraries from *M. tuberculosis* H37Rv, *M. bovis* BCG Pasteur 1173P2 (5, 13) and *M. bovis* AF2122/97 (14) allowed us to carry out direct BAC to BAC comparison of clones spanning the same genomic regions. Size differences of PFGE-separated HindIII restriction fragments from *M. microti* OV254 BACs, relative to restriction fragments from *M. bovis* and/or *M. tuberculosis* BAC clones, identified loci that differed among the tested strains. Size variations of at least 2 kb were easily detectable and 10 deleted regions, evenly distributed around the genome, and containing more than 60 open reading frames (ORFs), were identified. These regions represent over 60 kb that are missing from *M. microti* OV254 strain compared to *M. tuberculosis* H37Rv. First, it was found that phiRv2 (RD11), one of the two *M. tuberculosis* H37Rv prophages was present in *M. microti* OV254, whereas phiRv1, also referred to as RD3 (29) was absent. Second, it was found that *M. microti* lacks four of the genomic regions that were also absent from *M. bovis* BCG. In fact, these four regions of difference named RD7, RD8, RD9 and RD10 are absent from all members of the *M. tuberculosis* complex with the exception of *M. tuberculosis* and *M. canettii*, and seem to have been lost from a common progenitor strain of *M. africanum*, *M. microti* and *M. bovis* (3). As such, our results obtained with individual BAC to BAC comparisons show that *M. microti* is part of this non-*M. tuberculosis* lineage of the tubercle bacilli, and this assumption was further confirmed by sequencing the junction regions of RD7-RD10 in *M. microti* OV254. The sequences obtained were identical to those from *M. africanum*, *M. bovis* and *M. bovis* BCG strains. Apart from these four conserved regions of difference, and phiRv1 (RD3) *M. microti* OV254 did not show any other RDs with identical junction regions to *M. bovis* BCG Pasteur, which misses at least 17 RDs relative to *M. tuberculosis* H37Rv (1, 13, 35). However, five other regions missing from the genome of *M. microti* OV254 relative to *M. tuberculosis* H37Rv were identified (RD1$^{mic}$, RD5$^{mic}$, MiD1, MiD2, MiD3). Such regions are specific either for strain OV254 or for *M. microti* strains in general. Interestingly, two of these regions, RD1$^{mic}$, RD5$^{mic}$ partially overlap RDs from the *M. bovis* BCG.

Antigens ESAT-6 and CFP-10 are Absent from *M. microti*.

Figures 6A, 6B, 6C:
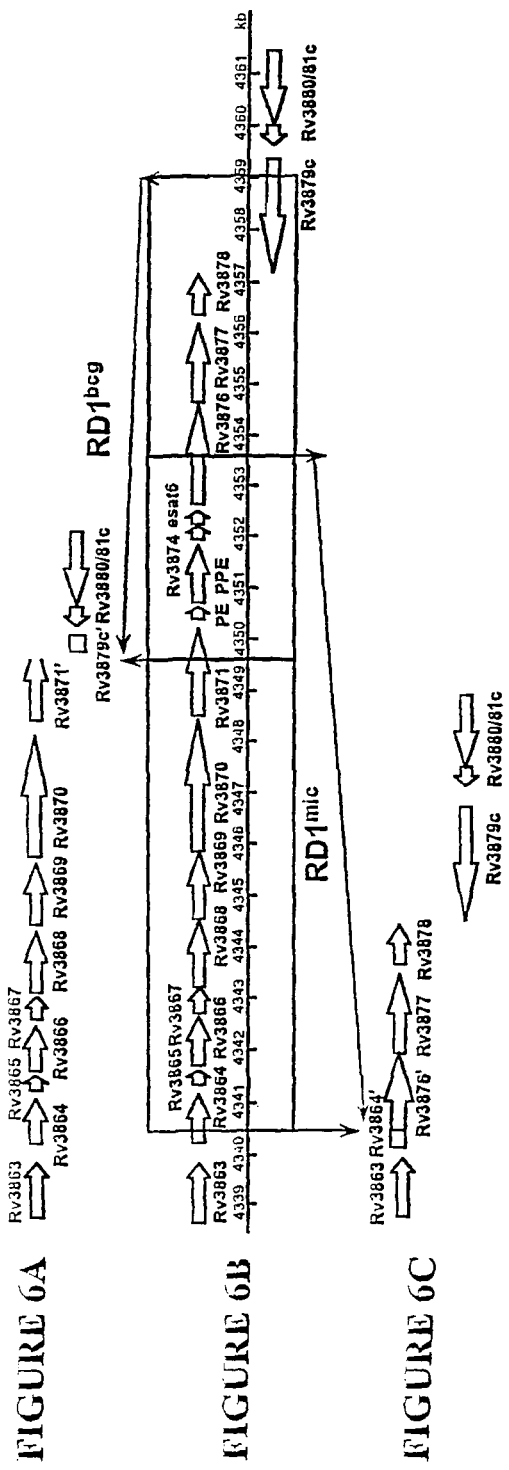

One of the most interesting findings of the BAC to BAC comparison was a novel deletion in a genomic region close to the origin of replication (FIG. 5). Detailed PCR and sequence analysis of this region in *M. microti* OV254 showed a segment of 14 kb to be missing (equivalent to *M. tuberculosis* H37Rv from 4340.4 to 4354.5 kb) that partly overlapped RD1$^{bcg}$ absent from *M. bovis* BCG. More precisely, ORFs Rv3864 and Rv3876 are truncated in *M. microti* OV254 and ORFs Rv3865 to Rv3875 are absent (FIG. 6). This observation is particularly interesting as previous comparative genomic analysis identified RD1$^{bcg}$ as the only RD region that is specifically absent from all BCG sub-strains but present in all other members of the *M. tuberculosis* complex (1, 4, 13, 29, 35). As shown in FIG. 6, in *M. microti* OV254 the RD1$^{mic}$ deletion is responsible for the loss of a large portion of the conserved ESAT-6 family core region (40) including the genes coding for the major T-cell antigens ESAT-6 and CFP-10 (2, 15). The fact that previous deletion screening protocols employed primer sequences that were designed for the right hand portion of the RD1$^{bcg}$ region (i.e. gene Rv3878) (6, 39) explains why the RD1$^{mic}$ deletion was not detected earlier by these investigations. FIG. 6 shows that RD1$^{mic}$ does not affect genes Rv3877, Rv3878 and Rv3879 which are part of the RD1$^{bcg}$ deletion.

Deletion of Phospholipase-C Genes in *M. microti* OV254.

RD5$^{mic}$, the other region absent from *M. microti* OV254, that partially overlapped an RD region from BCG, was revealed by comparison of BAC clone Mi18A5 with BAC Rv143 (FIG. 5). PCR analysis and sequencing of the junction region revealed that RD5$^{mic}$ was smaller than the RD5 deletion in BCG (Table 2 and 3 below).

TABLE 2

Description of the putative function of the deleted and truncated ORFs in *M. microti* OV254

| Region | Start-End | overlapping ORF | Putative Function or family |
|---|---|---|---|
| RD 10 | 264.5-266.5 | Rv0221-Rv0223 | echA1 |
| RD 3 | 1779.5-1788.5 | Rv1573-Rv1586 | bacteriophage proteins |
| RD 7 | 2207.5-2220.5 | Rv1964-Rv1977 | yrbE3A-3B; mce3A-F; unknown |
| RD 9 | 2330-2332 | Rv2072-Rv2075 | cobL; probable oxidoreductase; unknown |
| RD5$^{mic}$ | 2627.6-2633.4 | Rv2348-Rv2352 | plc A-C; member of PPE family |
| MiD1 | 3121.8-3126.6 | Rv2816-Rv2819 | IS6110 transposase; unknown |
| MiD2 | 3554.0-3755.2 | Rv3187-Rv3190 | IS6110 transposase; unknown |
| MiD3 | 3741.1-3755.7 | Rv3345-Rv3349 | members of the PE-PGRS and PPE families; insertion elements |
| RD8 | 4056.8-4062.7 | Rv3617-Rv3618 | ephA; lpqG; member of the PE-PGRS family |
| RD1$^{mic}$ | 4340.4-4354.5 | Rv3864-Rv3876 | member of the CBXX/CFQX family; member of the PE and PPE families; ESAT-6; CFP10; unknown |

TABLE 3

Sequence at the junction of the deleted regions in *M. microti* OV254

| Junction Position | ORFs | Sequences at the junction | Flanking primers |
|---|---|---|---|
| RD1$^{mic}$ (SEQ ID No 23) | 4340,421- 4354,533 | Rv3864- Rv3876 | CAAGACGAGGTTGTAAAACCTCGACG CAGGATCGGCGATGAAATGCCAGTCG GCGTCGCTGAGCGCGCGCTGCGC_CGA_ _G_TCCCATTTTGTCGCTGATTTGTTTGAACA GCGACGAACCGGTGTTGAAAATGTCGCCT GGGTCGGGGATTCCCT | 4340,209F (SEQ ID No 19) GCAGTGCAAAGGTGCAGATA 4354,701R (SEQ ID No 20) GATTGAGACACTTGCCACGA |
| RD5$^{mic}$ (SEQ ID No 26) | 2627,831- 2635,581 | Rv2349- Rv2355 | CCTCGATGAACCACCTGACATGACCC CATCCTTTCCAAGAACTGGAGTCTCC GGACATGCCGGGGCGGTTCA_C_TGCCC CAGGTGTCCTGGGTCGTTCCGTTGACCGT CGAGTCCGAACATCCGTCATTCCCGGTGG CAGTCGGTGCGGTGAC | 2627,370F (SEQ ID No 24) GAATGCCGACGTCATATCG 2633,692R (SEQ ID No 25) CGGCCACTGAGTTCGATTAT |
| MiD1 (SEQ ID No 29) | 3121,880- 3126,684 | Rv2815c- Rv2818c | CACCTGACATGACCCCATCCTTTCCA AGAACTGGAGTCTCCGGACATGCCGG GGCGGTTCAG_GG_ACATTCATGTCCATCTT CTGGCAGATCAGCAGATCGCTTGTTCTCAG TGCAGGTGAGTC | 3121,690F (SEQ ID No 27) CAGCCAACACCAAGTAGACG 3126,924R (SEQ ID No 28) TCTACCTGCAGTCGCTTGTG |

TABLE 3-continued

Sequence at the junction of the deleted regions in *M. microti* OV254

| Junction | Position | ORFs | Sequences at the junction | Flanking primers |
|---|---|---|---|---|
| MiD2 (SEQ ID No 32) | 3554,066-3555,259 | Rv3188-Rv3189 | GCTGCCTACTACGCTCAACGCCAGAG ACCAGCCGCCGGCTGAGGTCTCAGAT CAGAGAGTCTCCGGACTCACCGGGGC GGTTCATAAAGGCTTCGAGACCGGACGG GCTGTAGGTTCCTCAACTGTGTGGCGGAT GGTCTGAGCACTTAAC | 3553,880F (SEQ ID No 30) GTCCATCGAGGATGTCGAGT 3555,385R (SEQ ID No 31) CTAGGCCATTCCGTTGTCTG |
| MiD3 (SEQ ID No 35) | 3741,139-3755,777 | Rv3345c-Rv3349d | TGGCGCCGGCACCTCCGTTGCCACCG TTGCCGCCGCTGGTGGGCGCGGTGCC GTTCGCCCCGGCCGAACCGTTCAGGG CCGGGTTCGCCCTCAGCCGCTAAACACG CCGACCAAGATCAACGAGCTACCTGCCCG GTCAAGGTTGAAGAGCCCCCATATCAGCA AGGGCCCGGTGTCGGCG | 3740,950F (SEQ ID No 33) GGCGACGCCATTTCC 3755,988R (SEQ ID No 34) AACTGTCGGGCTTGCTCTT |

In fact, *M. microti* OV254 lacks the genes plcA, plcB, plcC and one specific PPE-protein encoding gene (Rv2352). This was confirmed by the absence of a clear band on a Southern blot of AseI digested genomic DNA from *M. microti* OV254 hybridized with a plcA probe. However, the genes Rv2346c and Rv2347c, members of the esat-6 family, and Rv2348c, that are missing from *M. bovis* and BCG strains (3) are still present in *M. microti* OV254. The presence of an IS6110 element in this segment suggests that recombination between two IS6110 elements could have been involved in the loss of RD5$^{mic}$, and this is supported by the finding that the remaining copy of IS6110 does not show a 3 base-pair direct repeat in strain OV254 (Table 3).

Lack of MiD1 Provides Genomic Clue for *M. microti* OV254 Characteristic Spoligotype.

Figures 7A, 7B:
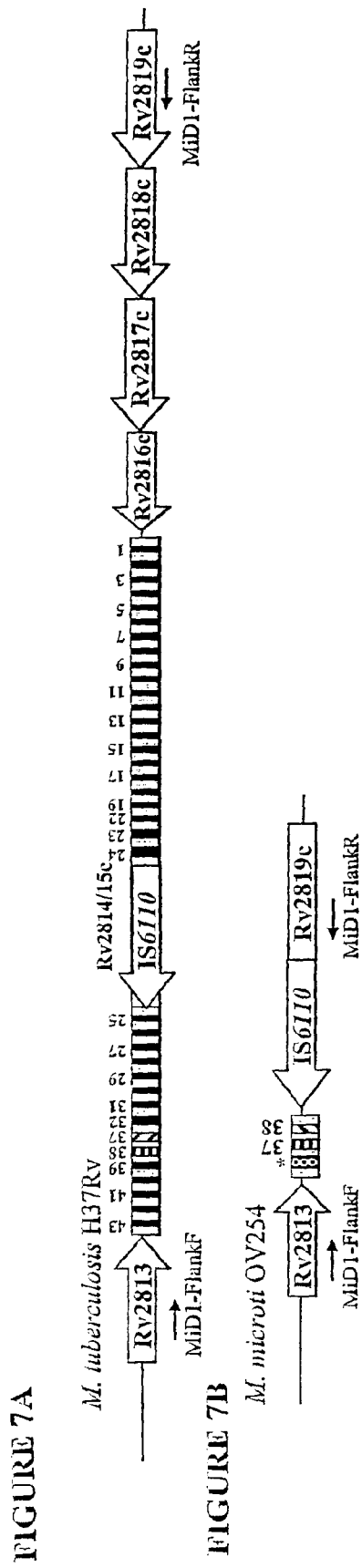
Figure 9:
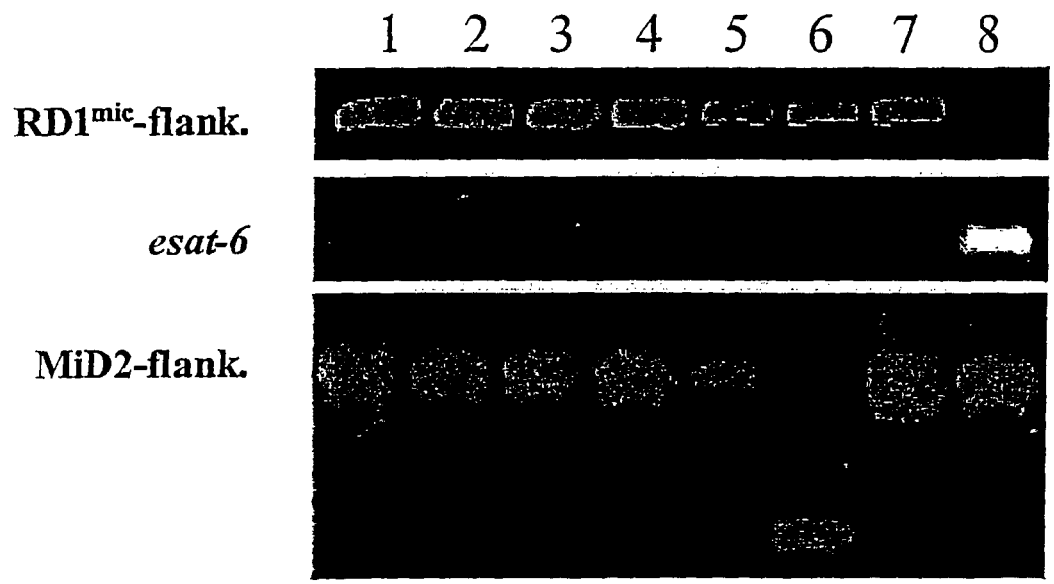

MiD1 encompasses the three ORFs Rv2816, Rv2817 and Rv2818 that encode putative proteins whose functions are yet unknown, and has occurred in the direct repeat region (DR), a polymorphic locus in the genomes of the tubercle bacilli that contains a cluster of direct repeats of 36 bp, separated by unique spacer sequences of 36 to 41 bp (17), (FIG. 7). The presence or absence of 43 unique spacer sequences that intercalate the DR sequences is the basis of spacer-oligo typing, a powerful typing method for strains from the *M. tuberculosis* complex (23). *M. microti* isolates exhibit a characteristic spoligotype with an unusually small DR cluster, due to the presence of only spacers 37 and 38 (43). In *M. microti* OV254, the absence of spacers 1 to 36, which are present in many other *M. tuberculosis* complex strains, appears to result from an 16110 mediated deletion of 636 by of the DR region. Amplification and PvuII restriction analysis of a 2.8 kb fragment obtained with primers located in the genes that flank the DR region (Rv2813c and Rv2819) showed that there is only one copy of IS6110 remaining in this region (FIG. 7). This 16110 element is inserted into ORF Rv2819 at position 3,119,932 relative to the *M. tuberculosis* H37Rv genome. As for other IS6110 elements that result from homologous recombination between two copies (7), no 3 base-pair direct repeat was found for this copy of IS6110 in the DR region. Concerning the absence of spacers 39-43 (FIG. 7), it was found that *M. microti* showed a slightly different organization of this locus than *M. bovis* strains, which also characteristically lack spacers 39-43. In *M. microti* OV254 an extra spacer of 36 bp was found that was not present in *M. bovis* nor in *M. tuberculosis* H37Rv. The sequence of this specific spacer was identical to that of spacer 58 reported by van Embden and colleagues (42). In their study of the DR region in many strains from the *M. tuberculosis* complex this spacer was only found in *M. microti* strain NLA000016240 (AF189828) and in some ancestral *M. tuberculosis* strains (3, 42). Like MiD1, MiD2 most probably results from an IS6110-mediated deletion of two genes (Rv3188. Rv3189) that encode putative proteins whose function is unknown (Table 3 above and Table 4 below),

TABLE 4

Presence of the RD and MiD regions in different *M. microti* strains

| | HOST | | | | | | | | |
|---|---|---|---|---|---|---|---|---|---|
| | VOLES | | | | HUMAN | | | | |
| Strain | OV 254 | OV183 | OV216 | ATCC 35782 | Myc 94-2272 | B3 type mouse | B4 type mouse | B1 type llama | B2 type llama |
| RD1$^{mic}$ | absent | absent | absent | absent | absent | absent | absent | absent | absent |
| RD 3 | absent | absent | absent | absent | absent | absent | absent | absent | absent |
| RD 7 | absent | absent | absent | absent | absent | absent | absent | absent | absent |
| RD8 | absent | absent | absent | absent | absent | absent | absent | absent | absent |
| RD 9 | absent | absent | absent | absent | absent | absent | absent | absent | absent |
| RD 10 | absent | absent | absent | absent | absent | absent | absent | absent | absent |
| MiD3 | absent | ND | ND | absent | absent | absent | absent | absent | absent |
| MiD1 | absent | ND | ND | present | partial | partial | partial | present | present |
| RD5$^{mic}$ | absent | absent | absent | present | present | present | present | present | present |
| MiD2 | absent | ND | ND | present | present | present | present | present | present |

ND, not determined

Absence of Some Members of the PPE Family in *M. microti*.

MiD3 was identified by the absence of two HindIII sites in BAC Mi4B9 that exist at positions 3749 kb and 3754 kb in the *M. tuberculosis* H37Rv chromosome. By PCR and sequence analysis, it was determined that MiD3 corresponds to a 12 kb deletion that has truncated or removed five genes orthologous to Rv3345c-Rv3349c. Rv3347c encodes a protein of 3157 amino-acids that belongs to the PPE family and Rv3346c a conserved protein that is also present in *M. leprae*. The function of both these putative proteins is unknown while Rv3348 and Rv3349 are part of an insertion element (Table 2). At present, the consequences of the MiD3 deletions for the biology of *M. microti* remains entirely unknown.

Extra-DNA in *M. microti* OV254 Relative to *M. tuberculosis* H37Rv.

*M. microti* OV254 possesses the 6 regions RvD1 to RvD5 and TBD1 that are absent from the sequenced strain *M. tuberculosis* H37Rv, but which have been shown to be present in other members of the *M. tuberculosis* complex, like *M. canettii, M. africanum, M. bovis*, and *M. bovis* BCG (3, 7, 13). In *M. tuberculosis* H37Rv, four of these regions (RvD2-5) contain a copy of IS6110 which is not flanked by a direct, repeat, suggesting that recombination of two IS6110 elements was involved in the deletion of the intervening genomic regions (7). In consequence, it seems plausible that these regions were deleted from the *M. tuberculosis* H37Rv genome rather than specifically acquired by *M. microti*. In addition, three other small insertions have also been found and they are due to the presence of an IS6110 element in a different location than in *M. tuberculosis* H37Rv and *M. bovis* AF2122/97. Indeed, PvuII RFLP analysis of *M. microti* OV254 reveals 13 IS6110 elements (data not shown).

Genomic Diversity of *M. microti* Strains.

In order to obtain a more global picture of the genetic organization of the taxon *M. microti* we evaluated the presence or absence of the variable regions found in strain OV254 in eight other *M. microti* strains. These strains which were isolated from humans and voles have been designated as *M. microti* mainly on the basis of their specific spoligotype (26, 32, 43) and can be further divided into subgroups according to the host such as voles, llama and humans (Table 3). As stated in, the introduction, *M. microti* is rarely found in humans unlike *M. tuberculosis*. So the availability of 9 strains from variable sources for genetic characterization is an exceptional resource. Among them was one strain (Myc 94-2272) from a severely immuno-compromised individual (43), and four strains were isolated from HIV-positive or HIV-negative humans with spoligotypes typical of llama and mouse isolates. For one strain, ATCC 35872/M.P. Prague, we could not identify with certainty the original host from which the strain was isolated, nor if this strain corresponds to *M. microti* OV166, that was received by Dr. Sula from Dr. Wells and used thereafter for the vaccination program in Prague in the 1960's (38).

First, we were interested if these nine strains designated as *M. microti* on the basis of their spoligotypes also resembled each other by other molecular typing criteria. As RFLP of pulsed-field gel separated chromosomal DNA represents probably the most accurate molecular typing strategy for bacterial isolates, we determined the AseI profiles of the available *M. microti* strains, and found that the profiles resembled each other closely but differed significantly from the macro-restriction patterns of *M. tuberculosis, M. bovis* and *M. bovis*. BCG strains used as controls. However, as depicted in FIG. 8A, the patterns were not identical to each other and each *M. microti* strain showed subtle differences, suggesting that they were not epidemiologically related. A similar observations was made with other rare cutting restriction enzymes, like DraI or XbaI (data not shown).

Common and Diverging Features of *M. microti* Strains.

Two strategies were used to test for the presence or absence of variable regions in these strains for which we do not have ordered BAC libraries. First, PCRs using internal and flanking primers of the variable regions were employed and amplification products of the junction regions were sequenced. Second, probes from the internal portion of variable regions absent from *M. microti* OV254 were obtained by amplification of *M. tuberculosis* H37Rv DNA using specific primers. Hybridization with these radio-labeled probes was carried out on blots from PFGE separated AseI restriction digests of the *M. microti* strains. In addition, we confirmed the findings obtained by these two techniques by using a focused macro-array, containing some of the genes identified in variable regions of the tubercle bacilli to date (data not shown).

This Led to the Finding that the $RD1^{mic}$ Deletion is Specific for all M. Microti Strains Tested.

Indeed, none of the *M. microti* DNA-digests hybridized with the radio-labeled esat-6 probe (FIG. 8B) but with the $RD1^{mic}$ flanking region (FIG. 8C). In addition, PCR amplification using primers flanking the $RD1^{mic}$ region (Table 2) yielded fragments of the same size for *M. microti* strains whereas no products were obtained for *M. tuberculosis, M. bovis* and *M. bovis* BCG strains (FIG. 9). Furthermore, the sequence of the junction region was found identical among the strains which confirms that the genomic organization of the $RD1^{mic}$ locus was the same in all tested *M. microti* strains (Table 3). This clearly demonstrates that *M. microti* lacks the conserved ESAT-6 family core region stretching in other members of the *M. tuberculosis* complex from Rv3864 to Rv3876 and, as such, represents a taxon of naturally occurring ESAT-6/CFP-10 deletion mutants.

Like $RD1^{mic}$, MiD3 was found to be absent from all nine *M. microti* strains tested and, therefore, appears to be a specific genetic marker that is restricted to *M. microti* strains (Table 3). However, PCR amplification showed that $RD5^{mic}$ is absent only from the vole isolates OV254, OV216 and OV183, but present in the *M. microti* strains isolated from human and other origins (Table 3). This was confirmed by the presence of single bands but of differing sizes on a Southern blot hybridized with a plcA probe for all *M. microti* tested strains except OV254 (FIG. 5D). Interestingly, the presence or absence of $RD5^{mic}$ correlated with the similarity of IS6110 RFLP profiles. The profiles of the three *M. microti* strains isolated from voles in the UK differed considerably from the IS6110 RFLP patterns of humans isolates (43). Taken together; these results underline the proposed involvement of IS6110 mediated deletion of the RD5 region and further suggest that RD5 may be involved in the variable potential of *M. microti* strains to cause disease in humans. Similarly, it was found that MID1 was missing only from the vole isolates OV254, OV216 and OV183, which display the same spoligotype (43), confirming the observations that MiD1 confers the particular spoligotype of a group of *M. microti* strains isolated from voles. In contrast, PCR analysis revealed that MiD1 is only partially deleted from strains B3 and B4 both characterized by the mouse spoligotype and the human isolate *M. microti* Myc 94-2272 (Table 3). For strain ATCC 35782 deletion of the MiD1 region was not observed. These findings correlate with the described spoligotypes of the different isolates, as strains that had intact or partially deleted MiD1 regions had more spacers present than the vole isolates that only showed spacers 37 and 38.

2.3 Comments and Discussion

We have searched for major genomic variations, due to insertion-deletion events, between the vole pathogen, *M. microti*, and the human pathogen, *M. tuberculosis*. BAC based comparative genomics led to the identification of 10 regions absent from the genome of the vole bacillus *M. microti* OV254 and several insertions due to IS6110. Seven of these deletion regions were also absent from eight other *M. microti* strains, isolated from voles or humans, and they account for more than 60 kb of genomic DNA.

Of these regions, RD1$^{mic}$ is of particular interest, because absence of part of this region has been found to be restricted to the BCG vaccine strains to date. As *M. microti* was originally described as non pathogenic for humans, it is proposed here that RD1 genes are involved in the pathogenicity for humans. This is reinforced by the fact that RD1$^{bcg}$ (29) has lost putative ORFs belonging to the esat-6 gene cluster including the genes encoding ESAT-6 and CFP-10 (FIG. 6) (40). Both polypeptides have been shown to act as potent stimulators of the immune system and are antigens recognized during the early stages of infection (8, 12, 20, 34). Moreover, the biological importance of this RD1 region for mycobacteria is underlined by the fact that it is also conserved in *M. leprae*, where genes ML0047-ML0056 show high similarities in their sequence and operon organization to the genes in the esat-6 core region of the tubercle bacilli (11). In spite of the radical gene decay observed in *M. leprae* the esat-6 operon apparently has kept its functionality in this organism.

However, the RD1 deletion may not be the only reason why the vole bacillus is attenuated for humans. Indeed, it remains unclear why certain *M. microti* strains included in the present study that show exactly the same RD1$^{mic}$ deletion as vole isolates, have been found as causative agents of human tuberculosis. As human *M. microti* cases are extremely rare, the most plausible explanation for this phenomenon would be that the infected people were particularly susceptible for mycobacterial infections in general. This could have been due to an immunodeficiency (32, 43) or to a rare genetic host predisposition such as interferon gamma- or IL-12 receptor modification (22).

In addition; the finding that human *M. microti* isolates differed from vole isolates by the presence of region RD5$^{mic}$ may also have an impact on the increased potential of human *M. microti* isolates to cause disease. Intriguingly, BCG and the vole bacillus lack overlapping portions of this chromosomal region that encompasses three (plcA, plcB, plcC) of the four genes encoding phospholipase C (PLC) in *M. tuberculosis*. PLC has been recognized as an important virulence factor in numerous bacteria, including *Clostridium perfringens*, *Listeria monocytogenes* and *Pseudomonas aeruginosa*, where it plays a role in cell to cell spread of bacteria, intracellular survival, and cytolysis (36, 41). To date, the exact role of PLC for the tubercle bacilli remains unclear. plcA encodes the antigen mtp40 which has previously been shown to be absent from seven tested vole and hyrax isolates (28). Phospholipase C activity in *M. tuberculosis*, *M. microti* and *M. bovis*, but not in *M. bovis* BCG, has been reported (21, 47). However; PLC and sphingomyelinase activities have been found associated with the most virulent mycobacterial species (21). The levels of phospholipase C activity detected in *M. bovis* were much lower than those seen in *M. tuberculosis* consistent with the loss of plcABC. It is likely, that plcD is responsible for the residual phospholipase C activity in strains lacking RD5, such as *M. bovis* and *M. microti* OV254. Indeed, the plcD gene is located in region RvD2 which is present in some but not all tubercle bacilli (13, 18). Phospholipase encoding genes have been recognized as hotspots for integration of IS6110 and it appears that the regions RD5 and RvD2 undergo independent deletion processes more frequently than any other genomic regions (44). Thus, the virulence of some *M. microti* strains may be due to a combination of functional phospholipase C encoding genes (7, 25, 26, 29).

Another intriguing detail revealed by this study is that among the deleted genes seven code for members of the PPE family of Gly-, Ala-, Asn-rich proteins. A closer look at the sequences of these genes showed that in some cases they were small proteins with unique sequences, like for example Rv3873, located in the RD1$^{mic}$ region, or Rv2352c and Rv2353c located in the RD5$^{mic}$ region. Others, like Rv3347c, located in the MiD3 region code for a much larger PPE protein (3157 aa). In this case a neighboring gene (Rv3345c), belonging to another multigene family, the PE-PGRS family, was partly affected by the MID3 deletion. While the function of the PE/PPE proteins is currently unknown, their predicted abundance in the proteome of *M. tuberculosis* suggests that they may play an important role in the life cycle of the tubercle bacilli. Indeed, recently some of them were shown to be involved in the pathogenicity of *M. tuberculosis* strains (9). Complementation of such genomic regions in *M. microti* OV254 should enable us to carry out proteomics and virulence studies in animals in order to understand the role of such ORFs in pathogenesis.

In conclusion, this study has shown that *M. microti*, a taxon originally named after its major host *Microtus agrestis*, the common vole, represents a relatively homogenous group of tubercle bacilli. Although all tested strains showed unique PFGE macro-restriction patterns that differed slightly among each other, deletions that were common to all *M. microti* isolates (RD7-RD10, MiD3, RD1$^{mic}$) have been identified. The conserved nature of these deletions suggests that these strains are derived from a common precursor that has lost these regions, and their loss may account for some of the observed common phenotypic properties of *M. microti*, like the very slow growth on solid media and the formation of tiny colonies. This finding is consistent with results from a recent study that showed that *M. microti* strains carry a particular mutation in the gyrB gene (31).

Of Particular Interest, Some of these Common Features (e.g. The Flanking Regions of RD1$^{Mic}$, or MiD3) could be Exploited for an Easy-to-Perform PCR Identification Test, Similar to the One Proposed for a Range of Tubercle Bacilli (33).

This test enables unambiguous and rapid identification of *M. microti* isolates in order to obtain a better estimate of the overall rate of *M. microti* infections in humans and other mammalian species.

EXAMPLE 3

Recombinant BCG Exporting ESAT-6 Confers Enhanced Protection Against Tuberculosis 3.1 Complementation of the RD1 Locus of BCG Pasteur and *M. microti*

Figure 10:
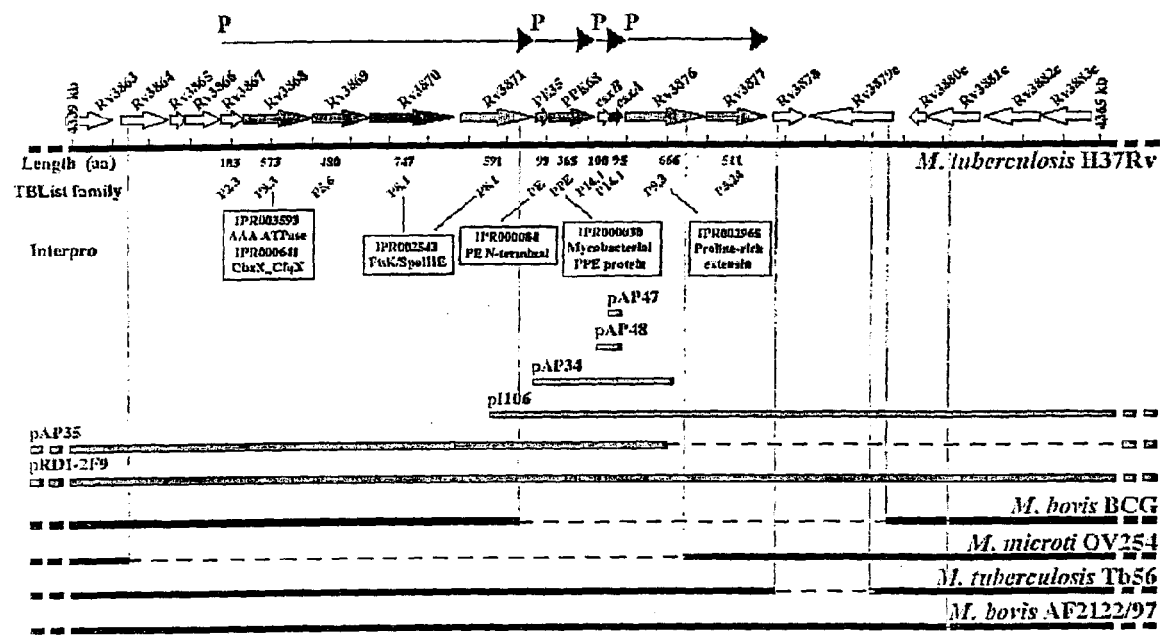

To construct a recombinant vaccine that secretes both ESAT-6 and CFP-10, we complemented BCG Pasteur for the RD1 region using genomic fragments spanning variable sections of the esxBA (or ESAT-6) locus from *M. tuberculosis* (FIG. 10). The RD1 deletion in BCG interrupts or removes nine CDS and affects all four transcriptional units: three are removed entirely while the fourth (Rv3867-Rv3871) is largely intact apart from the loss of 112 codons from the 3'-end of Rv3871 (FIG. 10). Transcriptome analysis of BCG, performed using cDNA probes obtained from early log phase cultures with oligonucleotide-based microarrays, was able to detect signals at least two fold greater than background for the probes corresponding to Rv3867 to 3871 inclusive, but not for the RD1-deleted genes Rv3872 to Rv3879. This suggests that the Rv3867-3871 transcriptional unit is still active in BCG which, like M. bovis, also has frameshifts in the neighbouring gene, Rv3881 (FIG. 10). The RD1$^{mic}$ deletion of M. microti removes three transcriptional units completely with only gene Rv3877 remaining from the fourth. The M. tuberculosis clinical isolate MT56 has lost genes Rv3878-Rv3879 (Brosch, R., et al. A new evolutionary scenario for the Mycobacterium tuberculosis complex. Proc Natl Acad Sci USA 99, 3684-9. (2002)) but still secretes ESAT-6 and CFP-10 (FIG. 10).

To test the hypothesis that a dedicated export machinery exists and to establish which genes were essential for creating an ESAT-6-CFP-10 secreting vaccine we assembled a series of integrating vectors carrying fragments spanning different portions of the RD1 esx gene cluster (FIG. 10). These integrating vectors stably insert into the attB site of the genome of tubercle bacilli. pAP34 was designed to carry only the antigenic core region encoding ESAT-6 and CFP-10, and the upstream PE and PPE genes, whereas RD1-1106 and RD1-pAP35 were selected to include the core region and either the downstream or upstream portion of the gene cluster, respectively. The fourth construct RD1-2F9 contains a ~32 kb segment from M. tuberculosis that stretches from Rv3861 to Rv3885 covering the entire RD1 gene cluster. We adopted this strategy of complementation with large genomic fragments to avoid polar effects that might be expected if a putative protein complex is only partially complemented in trans. In addition, a set of smaller expression constructs (pAP47, pAP48) was established in which individual genes are transcribed from a heat shock promoter (FIG. 10). Using appropriate antibodies all of these constructs were found to produce the corresponding proteins after transformation of BCG or M. microti (see below).

3.2 Several Genes of the esx Cluster are Required for Export of ESAT-6 and CFP-10

Figure 11:
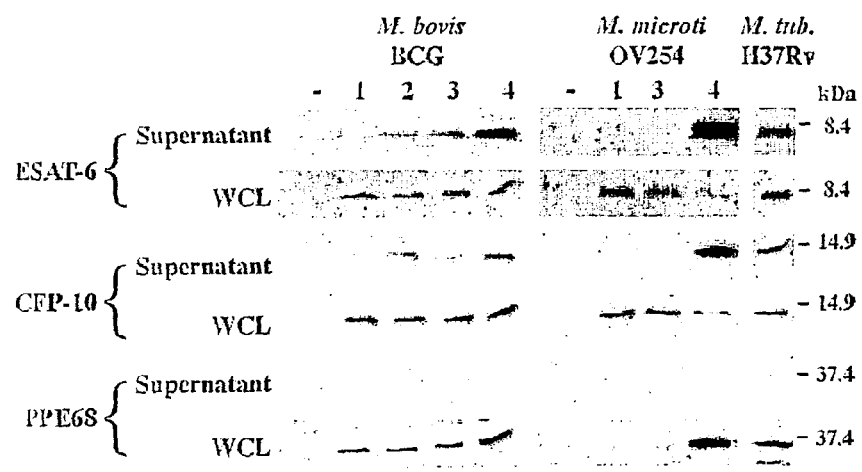

The four BCG::RD1 recombinants (BCG::RD1-pAP34, BCG::RD1-pAP35, BCG::RD1-2F9 and 13CG::RD1-I106) (FIG. 11) were initially tested to ensure that ESAT-6 and CFP-10 were being appropriately expressed from the respective integrated constructs. Immunoblotting of whole cell protein extracts from mid-log phase cultures of the various BCG::RD1 recombinants using an ESAT-6 monoclonal antibody or polyclonal sera for CFP-10 and the PPE68 protein Rv3373 demonstrated that all three proteins were expressed from the four constructs at levels comparable to those of M. tuberculosis (FIG. 11). However, striking differences were seen when the supernatants from early log-phase cultures of each recombinant were screened by Western blot for the two antigens. Although low levels of ESAT-6 and CFP-10 could be detected in the concentrated supernatant protein fractions of BCG::RD1-pAP34, BCG::RD1-pAP35 and BCG::RD1-I106 it was only with the integrated construct encompassing the entire esx gene cluster (BCG::RD1-2F9) that the two antigens accumulated in significant amounts. The high concentrations of ESAT-6 and CFP-10 seen in the supernatant of the recombinant BCG::RD1-2F9 were not due to a non-specific increase in permeability, or loss of cell wall material, because when the same whole cell and supernatant protein fractions were immunoblotted with serum raised against Rv3873, this protein was only localized in the cell wall of the various recombinants. As expected, when constructs were used containing esxA or esxBA alone, ESAT-6 did not accumulate in the culture supernatant (data not shown).

To assess the effect of the RD1$^{mic}$ deletion of M. microti on the export of ESAT-6 and CFP-10 and subsequent antigen handling, the experiments were replicated in this genomic background. As with BCG, ESAT-6 and CFP-10 were only exported into the supernatant fraction in significant amounts if expressed in conjunction with the entire esx cluster (FIG. 11). The combined findings demonstrate that complementation with esxA or esxB alone is insufficient to produce a recombinant vaccine that secretes these two antigens. Rather, secretion requires expression of genes located both upstream and downstream of the antigenic core region confirming our hypothesis[20] that the conserved esx gene cluster does indeed encode functions essential for the export of ESAT-6 and CFP-10.

3.3 Secretion of ESAT-6 is Needed to Induce Antigen Specific T-Cell Responses

Figure 12A:
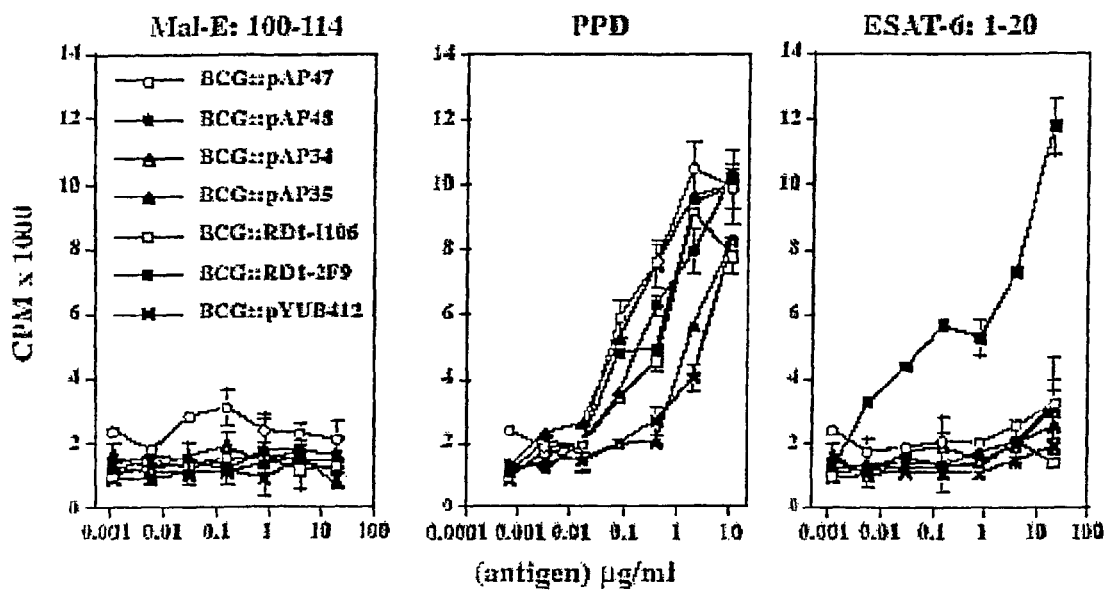
Figure 12B:
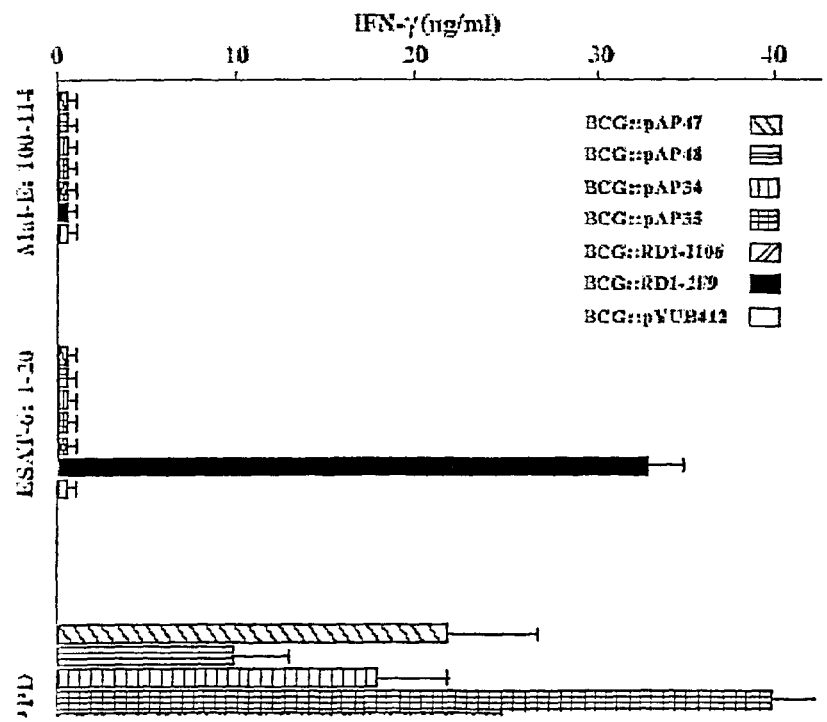

Since the classical observation that inoculation with live, but not dead BCG, confers protection against tuberculosis in animal models it has been considered that secretion of antigens is critical for maximizing protective T-cell immunity. Using our panel of recombinant vaccines we were able to test if antigen secretion was indeed essential for eliciting ESAT-6 specific T-cell responses. Groups of C57/BL6 mice were inoculated subcutaneously with one of six recombinant vaccines (BCG-pAP47, BCG-pAP48, BCG::RD1-pAP34, BCG::RD1-pAP35, BCG::RD1-I106, BCG::RD1-2F9) or with BCG transformed with the empty vector pYUB412. Three weeks following vaccination, T-cell immune responses to the seven vaccines were assessed by comparing antigen-specific splenocyte proliferation and gamma interferon (IFN-γ production (FIG. 12A). As anticipated all of the vaccines generated splenocyte proliferation and IFN-γ production in response to PPD (partially purified protein derivative) but not against an unrelated MalE control peptide indicating successful vaccination in each case. However, only splenocytes from the mice inoculated with BCG::RD1-2F9 proliferated markedly in response to the immunodominant ESAT-6 peptide (FIG. 12A). Furthermore, IFN-γ was only detected in culture supernatants of splenocytes from mice immunized with BCG::RD1-2F9 following incubation with the ESAT-6 peptide (FIG. 12B) or recombinant CFP-10 protein (data not shown). These data demonstrate that export of the antigens is essential for stimulating specific Th1-oriented T-cells.

Figure 13A:
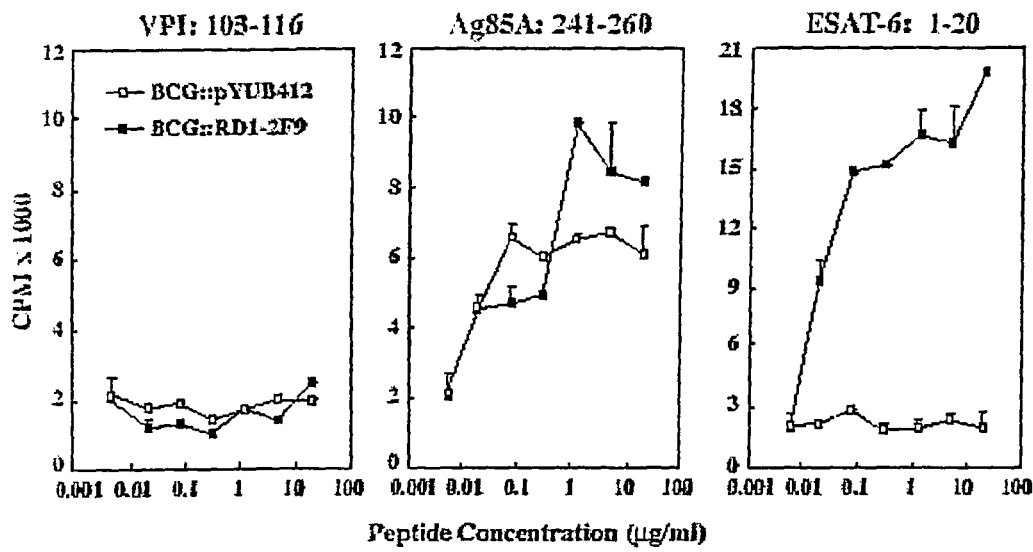
Figure 13B:
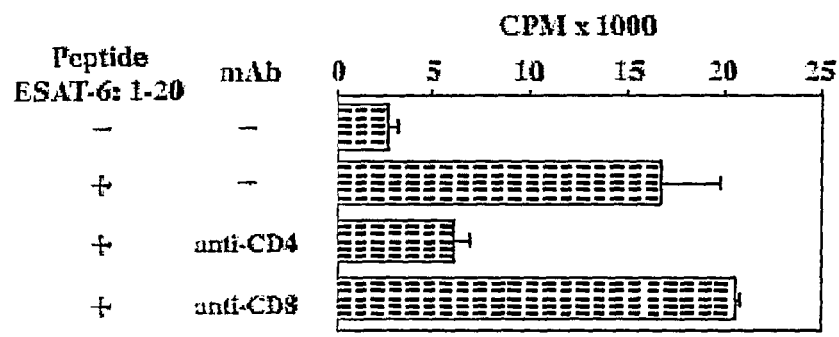
Figure 13C:
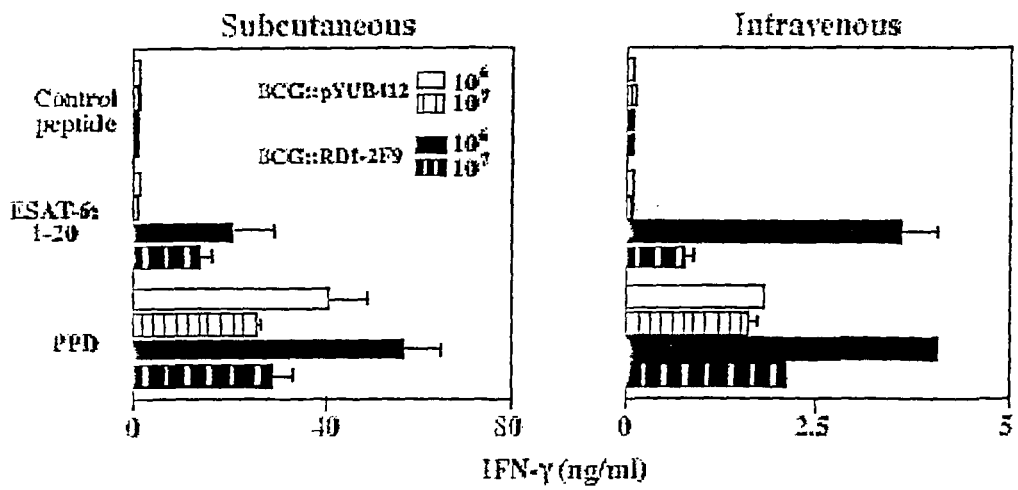

Further characterization of the immune responses was carried out. Splenocytes from mice immunized with BCG::RD1-2F9 or control BCG both proliferated in response to the immunodominant antigen 85A peptide (FIG. 13A). The strong splenocyte proliferation in the presence of ESAT-6 was abolished by an anti-CD4 monoclonal antibody but not by anti-CD8 indicating that the CD4$^+$ T-cell subset was involved (FIG. 13B). Interestingly, as judged by in vitro IFN-γ response to PPD and the ESAT peptide, subcutaneous immunization generated much stronger T-cell responses (FIG. 13C) compared to intravenous injection. After subcutaneous immunisation with BCG::RD1-2F9 strong ESAT-6 specific responses were also detected in inguinal lymph nodes (data not shown). These experiments demonstrated that the ESAT-6 T-cell immune responses to vaccination with BCG::RD1-2F9 were potent, reproducible and robust making this recombinant an excellent candidate for protection studies.

3.4 Protective Efficacy of BCG::RD1-2F9 in Immuno-Competent Mice

When used alone as a subunit or DNA vaccine, ESAT-6 induces levels of protection weaker than but akin to those of BCG (Brandt, L., Elbay, M., Rosenkrands, L., Lindblad, E. B. & Andersen, P. ESAT-6 subunit vaccination against Mycobacterium tuberculosis. Infect. Immun. 68, 791-795 (2000)).

Figure 14A:
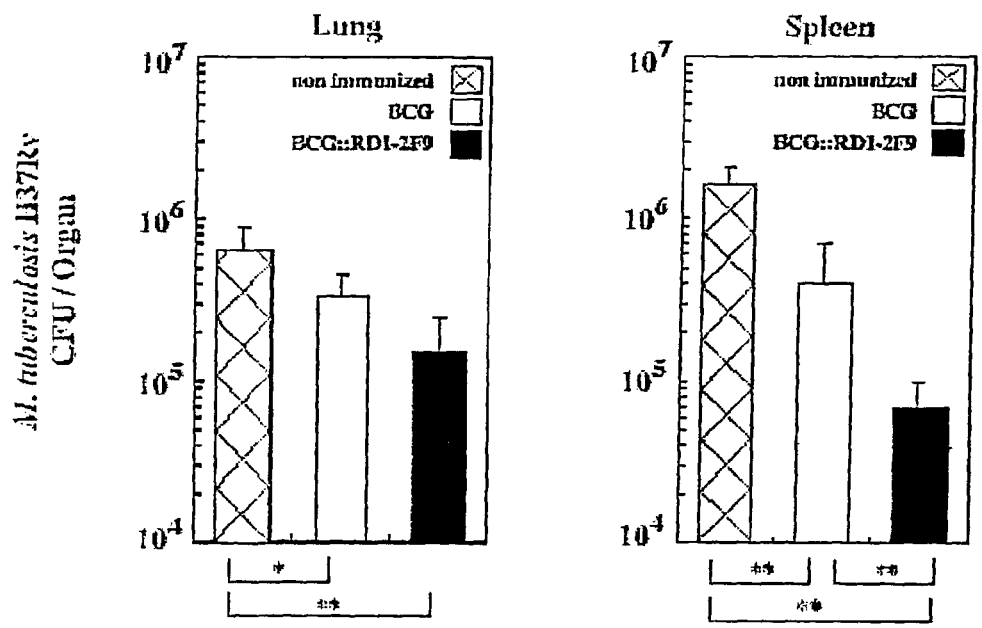

Thus, it was of interest to determine if the presentation to the immune system of ESAT-6 and/or CFP-10 in the context of recombinant BCG, mimicking the presentation of the antigens during natural infection, could increase the protective efficiency of BCG. The BCG::RD1-2F9 recombinant was therefore selected for testing as a vaccine, since it was the only ESAT-6 exporting BCG that elicited vigorous antigen specific T-cell immune responses. Groups of C57BL/6 mice were inoculated intravenously with either BCG::RD1-2F9 or BCG::pYUB412 and challenged intravenously after eight weeks with M. tuberculosis H31Rv. Growth of M. tuberculosis H37Rv in spleens and Bungs of each vaccinated cohort was compared with that of unvaccinated controls two months after infection (FIG. 14A). This demonstrated that, compared to vaccination with BCG, the BCG::RD1-2F9 vaccine inhibited growth of M. tuberculosis H37Rv in the spleens by 0.4 log 10 CFU and was of comparable efficacy at protecting the lungs.

Figure 14B:
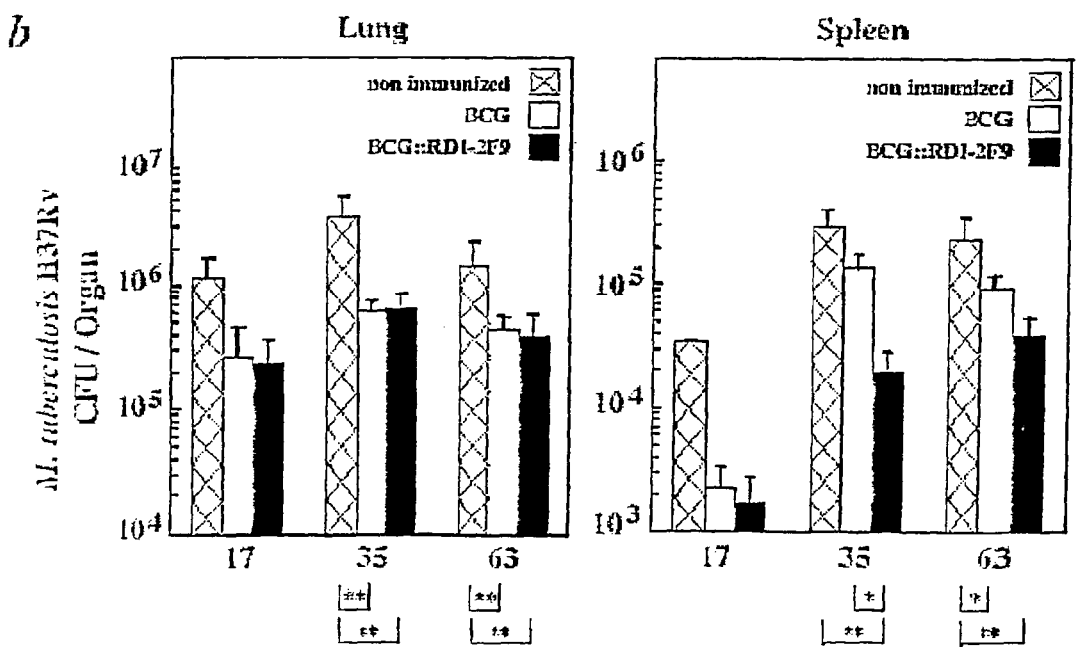

To investigate this enhanced protective effect against tuberculosis further we repeated the challenge experiment using the aerosol route. In this experiment antibiotic treatment was employed to clear persisting BCG from mouse organs prior to infection with M. tuberculosis. Two months following vaccination C57BL/6 Mice were treated with daily rifampicin/izoniazid for three weeks and then infected with 1000 CFU of M. tuberculosis H37Rv by the respiratory route. Mice were then sacrificed after 17, 35 and 63 days and bacterial enumeration carried out on the lungs and spleen. This demonstrated that, even following respiratory infection, vaccination with BCG::RD1-2F9 was superior to vaccination with the control strain of BCG (FIG. 14B). However; growth of M. tuberculosis was again only inhibited strongly in the mouse spleens.

EXAMPLE 4

Protective Efficacy of BCG::RD1-2F9 in Guinea Pigs 4.1 Animal Models

M. tuberculosis H37Rv and the different recombinant vaccines were prepared in the same Manner as for the immunological assays. For the guinea pig assays, groups of outbred female Dunkin-Hartley guinea pigs (David Hall, UK) were inoculated with $5\times10^4$ CFUs by the subcutaneous route. Aerosol challenge was performed 8 weeks after vaccination using a contained Henderson apparatus and an H37Rv (NCTC 7416) suspension in order to obtain an estimated retained inhaled dose of approximately 1000 CFU/lung (Williams, A., Davies, A., Marsh, P. D., Chambers, M. A. & Hewinson, R. G. Comparison of the protective efficacy of bacille calmette-Guerin vaccination against aerosol challenge with *Mycobacterium tuberculosis* and *Mycobacterium bovis*. *Clin Infect Dis* 30 Suppl 3, S299-301. (2000)). Organs were homogenized and dilutions plated out on 7H11 agar, as for the mice experiments. Guinea pig experiments were carried out in the framework of the European Union TB vaccine development program.

4.2 Results

Although experiments in mice convincingly demonstrated a superior protective efficacy of BCG::RD1 over BCG it was important to establish a similar effect in the guinea pig model of tuberculosis. Guinea pigs are exquisitely sensitive to tuberculosis, succumbing rapidly to low dose infection with *M. tuberculosis*, and develop a necrotic granulomatous pathology closer to that of human tuberculosis. Immunization of guinea pigs with BCG:RD1-2F9 was therefore compared to conventional BCG vaccination. Groups of six guinea pigs were inoculated subcutaneously with saline, BCG or BCG::RD1-2F9. Eight weeks following inoculation the three guinea pig cohorts were challenged with *M. tuberculosis* H37Rv via the aerosol route. Individual animals were weighed weekly and were killed 17 weeks after challenge or earlier if they developed signs of severe tuberculosis. Whereas all unvaccinated guinea pigs failed to thrive and were euthanised before the last time-point because of overwhelming disease, both the BCG- and recombinant BCG::RD1-2F9-vaccinated animals progressively gained weight and were clinically well when killed on termination of the experiment (FIG. 15A). This indicated that although the BCG::RD1-2F9 recombinant is more virulent in severely immunodeficient mice (Pym, A. S., Brodin, P., Brosch, R., Huerre, M. & Cole, S.T. Loss of RD1 contributed to the attenuation of the live tuberculosis vaccines *Mycobacterium bovis* BCG and *Mycobacterium microti. Mol. Microbiol.* 46, 709-717 (2002)). There is no increased pathogenesis in the highly susceptible guinea pig model of tuberculosis. Moreover, when the bacterial loads in the spleens of the vaccinated animals were compared there was a greater than ten-fold reduction in the number of CFU recovered from the animals immunized with BCG::RD1-2F9 when compared to BCG (FIG. 15B). Interestingly, there was no significant difference between the number of CFU obtained from the lungs of the two vaccinated groups indicating that the organ-specific enhanced protection observed in mice vaccinated with BCG::RD1-2F9 was also seen with guinea pigs. This marked reduction of bacterial loads in the spleens of BCG::RD1-2F9 immunized animals was also reflected in the gross pathology. Visual examination of the spleens showed that tubercules were much larger and more numerous on the surface of the BCG-vaccinated guinea pigs (FIG. 15C). These results demonstrate that the recombinant vaccine BCG::RD1-2F9 conveys enhanced protection to an aerosol challenge with *M. tuberculosis* in two distinct animal models.

GENERAL CONCLUSION

Tuberculosis is still one of the leading infectious causes of death in the world despite a decade of improving delivery of treatment and control strategies (Dye, C., Scheele, S., Dolin, P., Pathania, V. & Raviglione, M. C. Consensus statement. Global burden of tuberculosis: estimated incidence, prevalence, and mortality by country. WHO Global Surveillance and Monitoring Project. *Jama* 282, 677-86, (1999)). Reasons for the recalcitrance of this pandemic are multi-factorial but include the modest efficacy of the widely used vaccine, BCG. Two broad approaches can be distinguished for the development of improved tuberculosis vaccines (Baldwin, S. L., et al. Evaluation of new vaccines in the mouse and guinea pig model of tuberculosis. *Infection & Immunity* 66, 2951-9 (1998), Kaufmann, S. H., How can immunology contribute to the control of tuberculosis, *Nature Rev Immunol* 1, 20-30. (2001) and Young, D. B. & Fruth, U. in *New Generation Vaccines* (eds. Levine, M., Woodrow, G., Kaper, J. & Cobon G S) 631-645 (Marcel Dekker, 1997)). These are the development of subunit vaccines based on purified protein antigens or new live vaccines that stimulate a broader range of immune responses. Although a growing list of individual or combination subunit vaccines, and hybrid proteins, have been tested none has yet proved superior to BCG in animal models (Baldwin, S. L., et al., 1998). Similarly, new attenuated vaccines derived from virulent *M. tuberculosis* have yet to out-perform BCG (Jackson, M., et al. Persistence and protective efficacy of a *Mycobacterium tuberculosis* auxotroph vaccine. *Infect. Immun.* 67, 2867-73. (1999) and Hondalus, M. K., et al., Attenuation of and protection induced by a leucine auxotroph of *Mycobacterium tuberculosis. Infect. Immun.* 68, 2888-98. (2000)). Interestingly, the only vaccine that appears to surpass BCG is a BCG recombinant over expressing antigen 85A (Horwitz, M. A., Harth, G., Dillon, B. J. & Maslesa-Galic, S., Recombinant bacillus calmette-guerin (BCG) vaccines expressing the *Mycobacterium tuberculosis* 30-kDa major secretory protein induce greater protective immunity against tuberculosis than conventional BCG vaccines in a highly susceptible animal model. *Proc Natl Aced Sci USA* 97, 13853-8. (2000)). The basis for this vaccine was the notion that over-expression of an immunodominant T-cell antigen could quantitatively enhance the BCG-elicited immune response.

In frame with the invention, we were able to show that restoration of the RD1 locus did indeed improve the protective efficacy of BCG and defines a genetic modification that should be included in new recombinant BCG vaccines. Moreover, we were able to demonstrate two further findings that will be crucial for the development of a live vaccine against tuberculosis. First, we have identified the genetic basis of secretion for the ESAT-6 family of immunodominant T-cell antigens, and second, we show that export of these antigens from the cytosol is essential for maximizing their antigenicity.

The extra-cellular proteins of *M. tuberculosis* have been extensively studied and shown to be a rich source of protective antigens (Sorensen, A. L., Nagai, S., Houen, G., Andersen, P. & Andersen, A. B., Purification and characterization of a low-molecular-mass T-cell antigen secreted by *Mycobacterium tuberculosis. Infect. Immun.* 63, 1710-7 (1995), SkjØt, R. L. V., et al., Comparative evaluation of low-molecular-mass proteins from *Mycobacterium tuberculosis* identifies members of the ESAT-6 family as immunodominant T-cell antigens. *Infect. Immun.* 68, 214-220 (2000), Horwitz, M. A., Lee, B. W., Dillon, B. J. & Harth, G., Protective immunity against tuberculosis induced by vaccination with major extra-cellular proteins of *Mycobacterium tuberculosis. Proc Natl Acad Sci USA* 92, 1530-4 (1995) and Boesen, H., Jensen, B. N., Wilcke, T. & Andersen, P. Human T-cell responses to secreted antigen fractions of *Mycobacterium tuberculosis. Infect. Immun.* 63, 1491-7 (1995)). Despite this it remains a mystery how some of these proteins, that lack conventional secretion signals, are exported from the cytosol, a unique problem in *M. tuberculosis* given the impermeability and waxy nature of the mycobacterial cell envelope. Although two secA orthologues were identified in the genome sequence of *M. tuberculosis* (Cole, S.T., et al., Deciphering the biology of *Mycobacterium tuberculosis* from the complete genome sequence. *Nature* 393, 537-544 (1998)), no genes for obvious type I, II, or III protein secretion systems were detected, like those that mediate the virulence of many Gram-negative bacterial pathogens (Finlay, B. B. & Falkow, S., Common themes in microbial pathogenicity revisited. *Microbiol. Mol. Biol. Rev.* 61, 136-169 (1997)). This suggested that novel secretion systems might exist. An in silico analysis of the *M. tuberculosis* proteome identified a set of proteins and genes whose inferred functions, genomic organization and strict association with the esx gene family suggested that they could constitute such a system (Tekaia, F., et al., Analysis of the proteome of *Mycobacterium tuberculosis* in silico. *Tubercle Lung Disease* 79, 329-342 (1999)). Our results provide the first empirical evidence that this gene cluster is essential for the normal export of ESAT-6 and CFP-10.

The antigen genes, esxBA, lie at the center of the conserved gene cluster. Bioinformatics and comparative genomics predicted that both the conserved upstream genes Rv3868-Rv3871, as well as the downstream genes Rv3876-Rv3877, would be required for secretion (FIG. 1) and strong experimental support for this prediction is provided here. Our experiments show that only when BCG or *M. microti* are complemented with the entire cluster is maximal export of ESAT-6 and CFP-10 obtained. This suggests that at least Rv3871 and either Rv3876 or Rv3877 are indeed essential for the normal secretion of ESAT-6 as these are the only conserved genes absent or disrupted in BCG which are not complemented by RD1-I106 or RD1-pAP35. These genes encode a large transmembrane protein with ATPase activity, an ATP-dependent chaperone and an integral membrane protein, functional predictions compatible with them being part of a multi-protein complex involved in the translocation of polypeptides. Amongst the proteins encoded by the esx cluster Rv3871 and Rv3877 are highly conserved, as orthologues have been identified in the more streamlined clusters found in other actinomycetes, further supporting their direct role in secretion (Gey Van Pittius, N. C., et al. The ESAT-6 gene cluster of *Mycobacterium tuberculosis* and other high G+C Gram-positive bacteria. *Genome Biol* 2, 44.1-44.18 (2001)). It has been shown recently that ESAT-6 and CFP-10 form a heterodimer in vitro (Renshaw, P. S. at al. Conclusive evidence that the major T-cell antigens of the *M. tuberculosis* complex ESAT-6 and CFP-10 form a tight, 1:1 complex and characterisation of the structural properties of ESAT-6, CFP-10 and the ESAT-6-CFP-10 complex: implications for pathogenesis and virulence. *J Biol Chem* 8,8 (2002)) but it is not known whether dimerization precedes translocation across the cell membrane or occurs at a later stage in vivo. In either case, chaperone or protein clamp activity is likely to be required to assist dimer formation or to prevent premature complexes arising as is well documented for type III secretion systems (Page, A. L. & Parsot, C. Chaperones of the type III secretion pathway: jacks of all trades. *Mol Microbiol* 46, 1-11. (2002)). These, and other questions concerning the precise roles of the individual components of the ESAT-6 secretory apparatus, can now be addressed experimentally using the tools developed here.

The second major finding of the invention is that the secretion of ESAT-6 (and probably CFP-10) is critical for inducing maximal T-cell responses although other RD1-encoded proteins may also contribute such as the PPE68 protein (Rv3873) which is located in the cell envelope. We show that even though whole cell expression levels of ESAT-6 are comparable amongst our vaccines (FIG. 2), only the vaccine strain exporting ESAT-6, via an intact secretory apparatus, elicits powerful T-cell responses. Surprisingly, even the recombinants RD1-pAP47 and RD1-pAP48, that overexpress ESAT-6 intracellularly, did not generate detectable ESAT-6 specific T-cell responses. Although antigen secretion has long been recognized as, important for inducing immunity against *M. tuberculosis*, and is often used to explain why killed BCG offers no protection, this is one of the first formal demonstrations of its importance. BCG, like *M. tuberculosis* resides in the phagosome, where secreted antigens have ready access to the MHC class II antigen processing pathway, essential for inducing IFN-γ producing CD4 T-cells considered critical for protection against tuberculosis. Further understanding of the mechanism of ESAT-6 secretion could allow the development of BCG recombinants that deliver other antigens in the same way:

The main aim of the present invention was to qualitatively enhance the antigenicity of BCG. So, having assembled a recombinant vaccine that secreted the T-cell antigens ESAT-6 and CFP-10, and shown that it elicited powerful CD4 T-cell immunity against at least ESAT-6 and CFP-10, the next step was to rigorously test its efficacy in animal models of tuberculosis. In three distinct models, including two involving respiratory challenge, we were able to demonstrate that the ESAT-6-CFP-10 secreting recombinant improved protection when compared to a BCG control, although this effect was restricted to the spleen. This is probably due to the fact that the enhanced immunity induced by the two additional antigens is insufficient to abort the primary infection but does significantly reduce the dissemination of bacteria from the lung. The lack of protection afforded to the lung, the portal of entry for *M. tuberculosis*, does not prevent BCG::RD1-2F9 from being a promising vaccine candidate. Primary tuberculosis occurs in the middle and lower lobes and is rarely symptomatic (Garay, S. M. in *Tuberculosis* (eds. Rom, W. N. & Garay, S. M.) 373-413 (Little, Brown and Company, Boston, 1996)). The bacteria need to reach the upper lobes, the commonest site of disease, by haematogenous spread. Therefore, a vaccine that inhibits dissemination of *M. tuberculosis* from the primary site of infection would probably have major impact on the outcome of tuberculosis.

Recombinant BCG vaccines have definite advantages over other vaccination strategies in that they are inexpensive, easy to produce and convenient to store. However, despite an unrivalled and enviable safety record concerns remain and BCG is currently not administered to individuals with HIV infection. As shown above, the recombinant BCG::RD1-2F9 grows more rapidly in Severe Combined Immunodeficient (SCID) mice, an extreme model of immunodeficiency, than its parental BCG strain. However, in both immunocompetent mice and guinea pigs we have not observed any increased pathology only a slight increase in persistence which may be beneficial, since the declining efficacy of BCG with serial passage has been attributed to an inadvertent increase in its attenuation (Behr, M A. & Small, P. M., Has BCG attenuated to impotence *Nature* 389, 133-4. (1997)).

Ultimately, the robust enhancement in protection we have observed with the reincorporation of the RD1 locus is a compelling reason to include this genetic modification in any recombinant BCG vaccine, even if this may require the need for a balancing attenuating mutation.

In summary, the data presented here show that, in addition to its increased persistence, BCG::RD1-2F9 induces specific T-cell memory and enhances immune responses to other endogenous Th1 antigens such as the mycoloyl transferase, antigen 85A.

REFERENCES

1. Behr, M. A., M. A. Wilson, W. P. Gill, H. Salamon, G. K. Schoolnik, S. Rane, and P. M. Small. 1999. Comparative genomics of BCG vaccines by whole-genome DNA microarray. Science 284:1520-1523.
2. Berthet, F.-X., P. B. Rasmusse, I. Rosenkrands, P. Andersen, and B. Gicquel. 1998. A *Mycobacterium tuberculosis* operon encoding ESAT-6 and a novel low-molecular-mass culture filtrate protein (CFP-10). Microbiology 144:3195-3203.
3. Brosch, R., S. V. Gordon, M. Marmiesse, P. Brodin, C. Buchrieser, K. Eiglmeier, T. Garnier, C. Gutierrez, G. Hewinson; K. Kremer, L. M. Parsons, A. S. Pym, S. Samper, D. van Soolingen, and S. T. Cole. 2002. A new evolutionary scenario for the *Mycobacterium tuberculosis* complex. Proc. Natl. Acad. Sci. USA 99:3684-3689.
4. Brosch, R., S. V. Gordon, A. Billault, T. Garnier, K. Eiglmeier, C. Soravito, B. G. Barrell, and S. T. Cole. 1998. Use of a *Mycobacterium tuberculosis* H37Rv bacterial artificial chromosome library for genome mapping, sequencing, and comparative genomics. Infect. Immun. 66:2221-2229.
5. Brosch, R., S. V. Gordon, C. Buchrieser, A. S. Pym, T. Garnier, and S. T. Cole. 2000. Comparative genomics uncovers large tandem chromosomal duplications in *Mycobacterium bovis* BCG Pasteur. Comp. Funct. Genom. (Yeast) 17:111-123.
6. Brosch, R., S. V. Gordon, A. Pym, K. Eiglmeier, T. Garnier, and S. T. Cole. 2000. Comparative genomics of the mycobacteria. Int. J. Med. Microbiol. 290:143-152.
7. Brosch, R., W. J. Philipp, E. Stavropoulos, M. J. Colston, S. T. Cole, and S. V. Gordon. 1999. Genomic analysis reveals variation between *Mycobacterium tuberculosis* H37Rv and the attenuated *M. tuberculosis* H37Ra strain. Infect. Immun. 67:5768-5774.
8. Brusasca, P. N., R. Colangeli, K. P. Lyashchenko, X. Zhao, M. Vogelstein, J. S. Spencer, D. N. McMurray, and M. L. Gennaro. 2001. Immunological characterization of antigens encoded by the RD1 region of the *Mycobacterium tuberculosis* genome. Scand. J. Immunol. 54:448-452.
9. Camacho, L. R., D. Ensergueix, E. Perez, B. Gicquel, and C. Guilhot 1999. Identification of a virulence gene cluster of *Mycobacterium tuberculosis* by signature-tagged transposon mutagenesis. Mol. Microbiol. 34:257-267.
10. Cole, S. T., R. Brosch, J. Parkhill, T. Garnier, C. Churcher, D. Harris, S. V. Gordon, K. Eiglmeier, S. Gas, Barry C E, III, F. Tekaia, K. Badcock, D. Basham, D. Brown, T. Chillingworth, R. Connor, R. Davies, K. Devlin, T. Feltwell, S. Gentles, N. Hamlin, S. Holroyd, T. Hornsby, K. Jagels, A. Krogh, J. McLeah, S. Moule, L. Murphy, K. Oliver, J. Osborne, M. A. Quail, M. A. Rajandream, J. Rogers, S. Rutter, K. Soeger, J. Skelton, R. Squares, S. Squares, J. E. Sulston, K. Taylor, S. Whitehead, and B. G. Barrell. 1998. Deciphering the biology of *Mycobacterium tuberculosis* from the complete genome sequence. Nature 393:537-544.
11. Cole, S. T., K. Eiglmeier, J. Parkhill, K. D. James, N. R. Thomson, P. R. Wheeler, N. Honore, T. Garnier, C. Churches, D. Harris, K. Mungall, D. Basham, D. Brown, T. Chillingworth, R. Connor, R. M. Davies, K. Devlin, S. Duthoy, T. Feltwell, A. Fraser, N. Hamlin, S. Holroyd, T. Hornsby, K. Jagels, C. Lacroix, J. Maclean, S. Moule, L. Murphy, K. Oliver, M. A. Quail, M. A. Rajandream, K. M. Rutherford, S. Rutter, K. Seeger, S. Simon, M. Simmonds, J. Skelton, R. Squares, S. Squares, K. Stevens, K. Taylor, S. Whitehead, J. R. Woodward, and B. G. Barrel. 2001. Massive gene decay in the leprosy bacillus. Nature 409:1007-1011.
12. Elhay, M. J., T. Oettinger, and P. Andersen. 1998. Delayed-type hypersensitivity responses to ESAT-6 and MPT64 from *Mycobacterium tuberculosis* in the guinea pig. Infect. Immun. 66:3454-3456.
13. Gordon, S. V., R Brosch, A. Billault, T. Garnier, K. Eiglmeier, and S. T. Cole. 1999. Identification of variable regions in the genomes of tubercle bacilli using bacterial artificial chromosome arrays. Mol. Microbiol. 32:643-655.
14. Gordon, S. V., K. Eiglmeier, T. Garnier, R. Brosch, J. Parkhill, B. Barrell, S. T. Cole, and R. G. Hewinson. 2001. Genomics of *Mycobacterium bovis*. Tuberculosis (Edinb) 81:157-163.
15. Harboe, M., A. S. Malin, H. S. Dockrell, H. G. Wiker, G. Ulvund, A. Holm, M. C. Jorgensen, and P. Andersen. 1998. B-cell epitopes and quantification of the ESAT-6 protein of *Mycobacterium tuberculosis*. Infect. Immun. 66:717-723.

16. Hart, P. D. a., and I. Sutherland. 1977. BCG and vole bacillus vaccines in the prevention of tuberculosis in adolescence and early adult life. British Medical Journal 2:293-295.
17. Hermans, P. W. M., D. Van Soolingen, E. M. Bik, P. E. W. De Haas, J. W. Dale, and J. D. A. van Embden. 1991. Insertion element IS987 from *Mycobacterium bovis* BCG is located in a hot-spot integration region for insertion elements in *Mycobacterium tuberculosis* complex strains. Infect. Immun. 59:2695-2705.
18. Ho, T. B., B. D. Robertson, G. At Taylor, R. J. Shaw, and D. B. Young. 2000. Comparison of *Mycobacterium tuberculosis* genomes reveals frequent deletions in a 20 kb variable region in clinical isolates. Comp. Funct. Genom. (Yeast) 17:272-282.
19. Horstkotte, M. A., I. Sobottka, K. Schewe Carl, P. Schaefer, R. Laufs, S. Ruesch-Gerdes, and S. Niemann. 2001. *Mycobacterium microti* llama-type infection presenting as pulmonary tuberculosis in a human immunodeficiency virus-positive patient. J. Clin. Microbiol. 39:406-407.
20. Horwitz, M. A., B. W. Lee, B. J. Dillon, and G. Harth. 1995. Protective immunity against tuberculosis induced by vaccination with major extracellular proteins of *Mycobacterium tuberculosis*. Proc. Natl. Acad. Sci. USA 92:1530-1534.
21. Johansen, K. A., R. E. Gill, and M. L. Vasin. 1996. Biochemical and molecular analysis of phospholipase C and phospholipase D activity in mycobacteria. Infect. Immun. 64:3259-3266.
22. Jouanguy, E., R. Doffinger, S. Dupuis, A. Pallier, F. Altare, and J. L. Casanova. 1999. IL-12 and IFN-gamma in host defense against mycobacteria and *salmonella* in mice and men. Curr. Opin. Immunol. 11:346-351.
23. Kamerbeek, J., L. Schouls, A. Kolk, M. Van Agterveld, D. Van Soolingen, S. Kuijper, A. Bunschoten, H. Molhuizen, R. Shaw, M. Goyal, and J. Van Embden. 1997. Simultaneous detection and strain differentiation of *Mycobacterium tuberculosis* for diagnosis and epidemiology. J. Clin. Microbiol. 35:907-914.
24. Kato-Maeda, M., J. T. Rhee, T. R. Gingeras, H. Salamon, J. Drenkow, N. Smittipat, and P. M. Small. 2001. Comparing genomes within the species *Mycobacterium tuberculosis*. Genome Res. 11:547-554.
25. Kremer, K., van Soolingen, D., van Embden, J., Hughes, S., Inwald, J., and G. Hewinson. 1998. *Mycobacterium microti*: more widespread than previously thought. J. Clin. Microbiol. 36:2793-2794.
26. Kremer, K., D. van Soolingen, R. Frothingham, W. H. Haas, P. W. Hermans, C. Martin, P. Palittapongarnpim, B. B. Plikaytis, L. W. Riley, M. A. Yakrus, J. M. Musser, and J. D. van Embden. 1999. Comparison of methods based on different molecular epidemiological markers for typing of *Mycobacterium tuberculosis* complex strains: interlaboratory study of discriminatory power and reproducibility. J. Clin. Microbiol. 37:2607-2618.
27. Levy Frebault, V., and F. Portaels. 1992. Proposed minimal standards for the genus *Mycobacterium* and for description of new slowly growing *Mycobacterium* spp. Int. J. Syst. Bact. 42:315-323.
28. Liebana, E., A. Aranaz, B. Francis, and D. Cousins. 1996. Assessment of genetic markers for species differentiation within the *Mycobacterium tuberculosis* complex. J. Clin. Microbiol. 34:933-938.
29. Mahairas, G. G., P. J. Sabo, M. J. Hickey, D. C. Singh, and C. K. Stover. 1996. Molecular analysis of genetic differences between *Mycobacterium bovis* BCG and virulent *M. bovis*. J. Bact. 178:1274-1282.
30. Manabe, Y. C., Scott, C. P., and W. R. Bishai. 2002 Naturally attenuated, orally administered *Mycobacterium microti* as a tuberculosis vaccine is better than subcutaneous *Mycobacterium bovis* BCG. Infect Immun. 70:1566-1570.
31. Niemann, S., Harmsen, D., Rusch-Gerdes, S., and E. Richter. 2000. Differentiation of clinical *Mycobacterium tuberculosis* complex isolates by gyrB DNA Sequence polymorphism analysis. J. Clin. Microbiol. 38:3231-3234.
32. Niemann, S., E. Richter, H. Daluegge-Tamm, H. Schlesinger, D. Graupner, B. Koenigstein, G. Gurath, U. Greinert, and S. Ruesch-Gerdes. 2000. Two cases of *Mycobacterium microti*-derived tuberculosis in HIV-negative immunocompetent Patients. Emerg. Infect. Dis. 6:539-542.
33. Parsons, L. M., Brosch, R., Cole, S. T., Somoskovi, A., Loder, A., Britzel, G., van Soolingen, D., Hale, Y., Salfinger, M. 2002. Rapid and easy-to-perform identification of *Mycobacterium tuberculosis* complex isolates using PCR-based genomic deletion analysis. J. Clin. Microbiol. submitted and disclosure of the European Patent Application No 02 290 458.2 filed on Feb. 25, 2002 (Institut Pasteur).
34. Rosenkrands, I., P. B. Rasmussen, M. Carnio, S. Jacobsen, M. Theisen, and P. Andersen. 1998. Identification and characterization of a 29-kilodalton protein from *Mycobacterium tuberculosis* culture filtrate recognized by mouse memory effector cells. Infect. Immun. 66:2728-2735.
35. Salamon, H., M. Kato-Maeda, P. M. Small, J. Drenkow, and T. R. Gingeras. 2000. Detection of deleted genomic DNA using a semiautomated computational analysis of GeneChip data. Genome Res. 10:2044-2054.
36. Songer, J. G., 1997. Bacterial phospholipases and their role in virulence. Trends Microbiol. 5:156-161.
37. Staden, R. 1996. The Staden sequence analysis package. Mol. Biotechnol. 5:233-241.
38. Sula, L., and I. Radkovsky. 1976. Protective effects of *M. microti* vaccine against tuberculosis. J. Hyg. Epid. Microbiol. Immunol. 20:1-6.
39. Talbot, E. A., D. L. Williams, and R. Frothingham. 1997. PCR identification of *Mycobacterium bovis* BCG. J. Clin. Microbiol. 35:566-569.
40. Tekaia, F., S. V. Gordon, T. Garnier, R. Brosch, B. G. Barrell, and S. T. Cole. 1999. Analysis of the proteome of *Mycobacterium tuberculosis* in silico. Tubercle & Lung Disease 79:329-342.
41. Titball, R. W. 1998. Bacterial phospholipases. Soc. Appl. Bacteriol. Symp. Ser. 27:127-137.
42. van Embden, J. D., T. van Gorkom, K. Kremer, R. Jansen, B. A. van Der Zeijst, and L. M. Schouls. 2000. Genetic variation and evolutionary origin of the direct repeat locus of *Mycobacterium tuberculosis* complex bacteria. J. Bacteriol. 182:2393-2401.
43. van Soolingen, D., A. G. M. Van Der Zanden, P. E. W. De Haas, G. T. Noordhoek, A. Kiers, N. A. Foudraine, F. Portaels, A. H. J. Kolk, K. Kremer, and J. D. A. Van Embden. 1998. Diagnosis of *Mycobacterium microti* infections among humans by using novel genetic markers. J. Clin. Microbiol. 36:1840-1845.
44. Vera-Cabrera, L., M. A. Hernandez-Vera, O. Welsh; W. M. Johnson, and J. Castro-Garza. 2001. Phospholipase region of *Mycobacterium tuberculosis* is a preferential locus for IS6110 transposition. J. Clin. Microbiol. 39:3499-3504.
45. Wells, A. Q. 1937. Tuberculosis in wild voles. Lancet 1221.
46. Wells, A. Q. 1946. The murine type of tubercle bacillus. Medical Research council special report series 259:1-42.
47. Wheeler, P. R., and C. Ratledge. 1992. Control and location of acyl-hydrolysing phospholipase activity in pathogenic mycobacteria. J. Gen. Microbiol. 138:825-830.

The invention claimed is:

1. A strain of *M. microti*, wherein said strain has integrated all or part of the fragment, named RD1-2F9, of 31808 pb of DNA originating from *Mycobacterium tuberculosis* or any virulent member of the *Mycobacterium tuberculosis* complex (*M. africanum, M. bovis, M. canettii*), designated as SEQ ID NO: 1 and which is responsible for enhanced immunogenicity and increased persistence of BCG to the tubercle bacilli.

2. A strain of *M. microti* according to claim 1, wherein said strain has integrated all or part of the fragment of DNA originating from *Mycobacterium tuberculosis* or any virulent member of the *Mycobacterium tuberculosis* complex (*M. africanum, M. bovis, M. canettii*) designated as SEQ ID NO: 2 responsible for enhanced immunogenicity and increased persistence of BCG to the tubercle bacilli.

3. A strain of *M. microti* according to claim 1, wherein said strain has integrated all or part of the fragment of DNA originating from *Mycobacterium tuberculosis* or any virulent member of the *Mycobacterium tuberculosis* complex (*M. africanum, M. bovis, M. canettii*) designated as SEQ ID NO: 3 responsible for enhanced immunogenicity and increased persistence of BCG to the tubercle bacilli.

4. A strain according to claim 1, which has integrated a portion of DNA originating from *Mycobacterium tuberculosis* or any virulent member of the *Mycobacterium tuberculosis* complex (*M. africanum, M. bovis, M. canettii*), which comprises at least one, two, three or more gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28).

5. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises at least one, two, three or more gene(s) selected from Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19) and Rv3877 (SEQ ID No 20).

6. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises at least one; two, three or more gene(s) selected from Rv3872 (SEQ ID No 15, mycobacterial PE), Rv3873 (SEQ ID No 16, PPE), Rv3874 (SEQ ID No 17, CFP-10) and Rv3875 (SEQ ID No 18, ESAT-6).

7. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises at least four genes selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3871 (SEQ ID No 14), Rv3872 (SEQ ID No 15, mycobacterial PE), Rv3873 (SEQ ID No 16, PPE), Rv3874 (SEQ ID No 17, CFP-10), Rv3875 (SEQ ID No 18, ESAT-6), Rv3876 (SEQ ID No 19), Rv3877 (SEQ ID No 20), Rv3878 (SEQ ID No 21), Rv3879 (SEQ ID No 22), Rv3880 (SEQ No 23), Rv3881 (SEQ ID No 24), Rv3882 (SEQ ID No 25), Rv3883 (SEQ ID No 26), Rv3884 (SEQ ID No 27) and Rv3885 (SEQ ID No 28), provided that it comprises Rv3874 (SEQ ID No 17, CFP-10) and/or Rv3875 (SEQ ID No 18, ESAT-6).

8. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises at least Rv3871 (SEQ ID No 14), Rv3875 (SEQ ID No 18, ESAT-6) and Rv3876 (SEQ ID No 19).

9. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises at least Rv3871 (SEQ ID No 14), Rv3875 (SEQ ID No 18, ESAT-6) and Rv3877 (SEQ ID No 20).

10. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises at least Rv3871 (SEQ ID No 14), Rv3875 (SEQ ID No 18, ESAT-6), Rv3876 (SEQ ID No 19) and Rv3877 (SEQ ID No 20).

11. A strain according to claim 8 which has integrated a portion of DNA originating from *Mycobacterium tuberculosis* or any virulent member of the *Mycobacterium tuberculosis* complex (*M. africanum, M. bovis, M. canettii*), which further comprises Rv3874 (SEQ ID No 17, CFP-10).

12. A strain according to claim 8 which has integrated a portion of DNA originating from *Mycobacterium tuberculosis* or any virulent member of the *Mycobacterium tuberculosis* complex (*M. africanum, M. bovis, M. canettii*), which further comprises Rv3872 (SEQ ID No 15, mycobacterial PE).

13. A strain according to claim 8 which has integrated a portion of DNA originating from *Mycobacterium tuberculosis* or any virulent member of the *Mycobacterium tuberculosis* complex (*M. africanum, M. bovis, M. canettii*), which further comprises Rv3873 (SEQ ID No 16, PPE).

14. A strain according to claim 8 which has integrated a portion of DNA originating from *Mycobacterium tuberculosis* or any virulent member of the *Mycobacterium tuberculosis* complex (*M. africanum, M. bovis, M. canettii*), which further comprises at least one, two, three or four gene(s) selected from Rv3861 (SEQ ID No 4), Rv3862 (SEQ ID No 5), Rv3863 (SEQ ID No 6), Rv3864 (SEQ ID No 7), Rv3865 (SEQ ID No 8), Rv3866 (SEQ ID No 9), Rv3867 (SEQ ID No 10), Rv3868 (SEQ ID No 11), Rv3869 (SEQ ID No 12), Rv3870 (SEQ ID No 13), Rv3878 (SEQ ID No 21), Rv3879 (SEQ ID No 22), Rv3880 (SEQ ID No 23), Rv3881 (SEQ ID No 24), Rv3882 (SEQ ID No 25), Rv3883 (SEQ ID No 26), Rv3884 (SEQ ID No 27) and Rv3885 (SEQ ID No 28).

15. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises Rv3875 (SEQ ID No 18, ESAT-6).

16. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises Rv3874 (SEQ ID No 17, CFP-10).

17. A strain according to claim 1 which has integrated a portion of DNA originating from *Mycobacterium tuberculosis* or any virulent member of the *Mycobacterium tuberculosis* complex (*M. africanum, M. bovis, M. canettii*), which comprises both Rv3875 (SEQ ID No 18, ESAT-6) and Rv3874 (SEQ ID No 17, CFP-10).

18. A strain according to claim 4, wherein the coding sequence of the integrated gene is in frame with its natural promoter or with an exogenous promoter, such as a promoter capable of directing high level of expression of said coding sequence.

19. A strain according to claim 4, wherein the said integrated gene is mutated so as to maintain the improved immunogenicity while decreasing the virulence of the strain.

20. A strain according to claim 18, wherein said strain only carries parts of the genes coding for ESAT-6 or CFP-10 in a mycobacterial expression vector under the control of a promoter, more particularly an hsp60 promoter.

21. A strain according to claim 18, wherein said strain carries at least one portion of the esat-6 gene that codes for immunogenic 20-mer peptides of ESAT-6 active as T-cell epitopes.

22. A strain according to claim 19, wherein the esat-6 encoding gene is altered by directed mutagenesis in a way that most of the immunogenic peptides of ESAT-6 remain intact, but the biological functionality of ESAT-6 is lost.

23. A strain according to claim 19, wherein the CFP-10 encoding gene is altered by directed mutagenesis in a way that most of the immunogenic peptides of CFP-10 remain intact, but the biological functionality of CFP-10 is lost.

24. *M. microti*::RD1 strain which has integrated the insert of the cosmid RD1-AP34 which corresponds to the 3909 by fragment of the *M. tuberculosis* H37Rv genome from region 4350459 by to 4354367 bp of SEQ ID No: 3.

25. *M. microti*::RD1 strain which has integrated the insert of the cosmid RD1-2F9 (~32 kb) of the region of the *M. tuberculosis* genome AL123456 from ca 4337 kb to ca 4369 kb of SEQ ID No: 1.

26. A method for preparing and selecting *M. microti* strains defined in any one of claims 1 to 25 comprising a step consisting of modifying said strains by insertion, deletion or mutation in the integrated portion of DNA originating from *Mycobacterium tuberculosis* or any virulent member of the *Mycobacterium tuberculosis* complex (*M. africanum, M. bovis, M. canettii*), more particularly in the esat-6 or CFP-10 gene, said method leading to strains that are less virulent for immuno-depressed individuals.

27. A pharmaceutical composition comprising a strain according to claim 1 and a pharmaceutically acceptable carrier.

28. A pharmaceutical composition according to claim 27 containing suitable pharmaceutically-acceptable carriers comprising excipients and auxiliaries which facilitate processing of the living vaccine into preparations which can be used pharmaceutically.

29. A pharmaceutical composition according to claim 27 which is suitable for intravenous or subcutaneous administration.

30. A vaccine comprising a strain according to claim 1 and a suitable carrier.

31. A product comprising a strain according to claim 1 and at least one protein selected from ESAT-6 and CFP-10 or epitope of ESAT-6 and CFP-10 for a separate, simultaneous or sequential use for treating tuberculosis.

32. A strain of *M. microti*, wherein said strain has integrated the DNA fragment RD1-2F9, which comprises 31808 bp of DNA originating from *Mycobacterium tuberculosis* or any virulent member of the *Mycobacterium tuberculosis* complex (*M. africanum, M. bovis, M. canettii*), and having SEQ ID NO: 1, and which is responsible for enhanced immunogenicity and increased persistence of BCG to the tubercule bacilli.

33. A transformed *M. microti* strain, wherein the strain has integrated a portion of DNA originating from *Mycobacterium tuberculosis* or any virulent member of the *Mycobacterium tuberculosis* complex (*M. africanum, M. bovis, M. canettii*), wherein the integrated DNA comprises the genes Rv3874 (SEQ ID NO: 17, CFP-10), Rv3875 (SEQ ID NO: 18, ESAT-6), Rv3868 (SEQ ID NO: 11), Rv3869 (SEQ ID NO: 12), Rv3870 (SEQ ID NO: 13), Rv3871 (SEQ ID NO: 14), Rv3876 (SEQ ID NO: 19), and Rv3877 (SEQ ID NO: 20).

34. A strain according to claim 33, wherein said strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least nine genes selected from the group consisting of Rv3861 (SEQ ID NO:4), Rv3862 (SEQ ID NO:5), Rv3863 (SEQ ID NO:6), Rv3864 (SEQ ID NO:7), Rv3865 (SEQ ID NO:8), Rv3866 (SEQ ID NO:9), Rv3867 (SEQ ID NO:10), Rv3872 (SEQ ID NO:15, mycobacterial PE), Rv3873 (SEQ ID NO:16, PPE), Rv3878 (SEQ ID NO:21), Rv3879 (SEQ ID NO:22), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28).

35. A strain according to claim 33, wherein said strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least the gene Rv3867 (SEQ ID NO:10), combined with at least one gene selected from the group consisting of: Rv3872 (SEQ ID NO:15, mycobacterial PE); and Rv3873 (SEQ ID NO:16, PPE).

36. A strain according to claim 33, wherein said strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises the gene Rv3872 (SEQ ID NO: 15, mycobacterial PE).

37. A strain according to claim 36, wherein said strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises the gene Rv3873 (SEQ ID NO:16, PPE).

38. A strain according to claim 37, wherein said strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least one gene selected from the group consisting of: Rv3861 (SEQ ID NO:4), Rv3862 (SEQ ID NO:5), Rv3863 (SEQ ID NO:6), Rv3864 (SEQ ID NO:7), Rv3865 (SEQ ID NO:8), Rv3866 (SEQ ID NO:9), Rv3867 (SEQ ID NO: 10), Rv3878 (SEQ ID NO:21), Rv3879 (SEQ ID NO:22), Rv3880 (SEQ ID NO:23), 35 Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28).

39. A strain according to claim 33, wherein the coding sequence of the integrated gene is in frame with its natural promoter or with an exogenous promoter, such as a promoter capable of directing a high level of expression of said coding sequence.

40. A strain according to claim 39, wherein said strain carries genes coding for ESAT-6 or CFP-10 in a mycobacterial expression vector under the control of a promoter, more particularly an hsp60 promoter.

41. A strain according to claim 39, wherein the coding sequence of the integrated gene codes for immunogenic polymer peptides of ESAT 6 which are active as T-cell epitopes.

42. A pharmaceutical composition comprising a strain according to claim 33 and a pharmaceutically acceptable carrier.

43. A pharmaceutical composition according to claim 42, wherein the pharmaceutically-acceptable carrier comprises excipients and auxiliaries which facilitate processing of the living vaccine into preparations which can be used pharmaceutically.

44. A pharmaceutical composition according to claim 42, which is suitable for oral, intravenous, or subcutaneous administration.

45. A vaccine comprising a strain according to claim 33 and a suitable carrier.

46. A product comprising a strain according to claim 33 and at least one protein selected from ESAT-6 and CFP-10 for a separate, simultaneous, or sequential use for treating tuberculosis.

47. A strain according to claim 33, which has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least one gene selected from the group consisting of: Rv3878 (SEQ ID NO:21), Rv3879 (SEQ ID NO:22), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28), in combination with at least one gene selected from the group consisting of: Rv3872 (SEQ ID NO:15, mycobacterial PE) and Rv3873 (SEQ ID NO:16, PPE).

48. A strain according to claim 33, wherein the strain has integrated a portion of DNA originating from *Mycobacterium tuberculosis* or any virulent member of the *Mycobacterium tuberculosis* complex (*M. africanum, M. bovis, M. canettii*), wherein the integrated DNA further comprises at least one gene selected from the group consisting of: Rv3861 (SEQ ID NO:4), Rv3862 (SEQ ID NO:5), Rv3863 (SEQ ID NO:6), Rv3864 (SEQ ID NO:7), Rv3865 (SEQ ID NO:8), Rv3866 (SEQ ID NO:9), Rv3867 (SEQ ID NO: 10), Rv3880 (SEQ ID NO:23), Rv3881 (SEQ ID NO:24), Rv3882 (SEQ ID NO:25), Rv3883 (SEQ ID NO:26), Rv3884 (SEQ ID NO:27), and Rv3885 (SEQ ID NO:28), in combination with at least one gene selected from the group consisting of: Rv3872 (SEQ ID NO:15, mycobacterial PE) and Rv3873 (SEQ ID NO:16, PPE).

\* \* \* \* \*